US009744213B2

(12) United States Patent
Wieczorek et al.

(10) Patent No.: US 9,744,213 B2
(45) Date of Patent: Aug. 29, 2017

(54) FGF21 DERIVATIVES AND USES THEREOF

(71) Applicant: Novo Nordisk A/S, Bagsvaerd (DK)

(72) Inventors: Birgit Wieczorek, Copenhagen (DK); Tina Moeller Tagmose, Bellerup (DK); Kristian Sass-Oerum, Copenhagen (DK); Birgitte Andersen, Maaloev (DK); Joergen Olsen, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/453,617

(22) Filed: Mar. 8, 2017

(65) Prior Publication Data
US 2017/0182124 A1   Jun. 29, 2017

Related U.S. Application Data

(63) Continuation of application No. PCT/EP2015/080969, filed on Dec. 22, 2015.

(30) Foreign Application Priority Data

Dec. 23, 2014  (EP) .................................. 14199935

(51) Int. Cl.
A61K 38/00    (2006.01)
A61K 38/18    (2006.01)
A61K 47/48    (2006.01)

(52) U.S. Cl.
CPC .... A61K 38/1825 (2013.01); A61K 47/48038 (2013.01)

(58) Field of Classification Search
None
See application file for complete search history.

(56) References Cited

U.S. PATENT DOCUMENTS

| | | | |
|---|---|---|---|
| 5,424,286 A | 6/1995 | Eng | |
| 2007/0237768 A1 | 10/2007 | Glaesner et al. | |
| 2010/0216715 A1 | 8/2010 | Tagmose et al. | |
| 2012/0035099 A1 | 2/2012 | Garibay et al. | |
| 2013/0252884 A1 | 9/2013 | Garibay et al. | |

FOREIGN PATENT DOCUMENTS

| | | | |
|---|---|---|---|
| CN | 1802386 A | 7/2006 | |
| CN | 101250547 A | 8/2008 | |
| CN | 101663046 A | 3/2010 | |
| JP | 2007-535306 A | 12/2007 | |
| JP | 2008507477 | 3/2008 | |
| WO | 9808871 A1 | 3/1998 | |
| WO | 03/011213 A2 | 2/2003 | |
| WO | 03/061712 A1 | 7/2003 | |
| WO | 2005/027978 A2 | 3/2005 | |
| WO | 2005/028516 A2 | 3/2005 | |
| WO | 2005/058958 A2 | 6/2005 | |
| WO | 2005/061712 A1 | 7/2005 | |
| WO | 2005/091944 | 10/2005 | |
| WO | 2005/113606 A2 | 12/2005 | |
| WO | 2005/117984 A2 | 12/2005 | |
| WO | 2006/028595 A2 | 3/2006 | |
| WO | 2006/028714 A1 | 3/2006 | |
| WO | 2006/050247 | 5/2006 | |
| WO | 2006/065582 A2 | 6/2006 | |
| WO | 2006/078463 A2 | 7/2006 | |
| WO | 2006/097537 A2 | 9/2006 | |
| WO | 2008/087190 A2 | 7/2008 | |
| WO | 2008/121563 A2 | 10/2008 | |
| WO | 2009/020802 A2 | 2/2009 | |
| WO | 2009/030771 A1 | 3/2009 | |
| WO | 2009/083549 A1 | 7/2009 | |
| WO | 2009149171 A2 | 12/2009 | |
| WO | 2010/042747 A2 | 4/2010 | |
| WO | 2010/065439 A1 | 6/2010 | |
| WO | 2010/084169 A2 | 7/2010 | |
| WO | WO2010/084169 | * | 7/2010 |
| WO | 2010129503 A1 | 11/2010 | |
| WO | 2010129600 A2 | 11/2010 | |
| WO | 2010/142665 A1 | 12/2010 | |
| WO | 2011154349 A2 | 12/2011 | |
| WO | 2012010553 A1 | 1/2012 | |

OTHER PUBLICATIONS

Cuevas-Ramos D. et al., Exercise Increases Serum Fibroblast Growth Factor 21 (FGF21) Levels, Public Library of Science One, 2012, vol. 7, No. 5 e3/8022, pp. 1-8.
Database Geneseq, Mar. 15, 2012, "Human fibroblast growth factor 21 mature protein analog #5", retrieved from EBI accession No. GSP:AZS97428, Database accession No. AZS97428, WO2012010553-A1, Filing Date Jul. 18, 2011, Publication Date Jan. 26, 2012.
Ding X. et al., BetaKlotho is Required for Fibroblast Growth Factor 21 Effects on Growth and Metabolism, Cell Metabolism, 2012, vol. 16, No. 3, pp. 387-393.
Fon Tacer K. et al., Research Resource: Comprehensive Expression Atlas of the Fibroblast Growth Factor System in Adult Mouse, Molecular Endocrinology, 2010, vol. 24, No. 10, pp. 2050-2064.
Galman C. et al., The circulating metabolic regulator FGF21 is induced by prolonged fasting and PPARalpha activation in man, Cell Metabolism, 2008, vol. 8, No. 2, pp. 169-174.
Gimeno R., Secreted proteins as therapeutic targets for metabolic disorders. Challenges and opportunities in diabetes research and treatment. Keystone symposium, Vancouver 2014, Speaker Abstracts—Thrusday Jan. 16, 2014 p. 67.
Hecht R. et al., Rationale-Based Engineering of a Potent Long-Acting FGF21 Analog for the Treatment of Type 2 Diabetes, Public Library of Science One, 2012, vol. 7, No. 11, e49345, pp. 1-14 XP055192704.
Kharitonenkov A. et al., FGF-21 as a novel metabolic regulator, The Journal of Clinical Investigation, 2005, vol. 115, No. 6, pp. 1627-1635.

(Continued)

Primary Examiner — Jeanette Lieb
(74) Attorney, Agent, or Firm — Leon Y. Lum

(57) ABSTRACT

The invention relates to a derivative of a FGF21 protein having a cysteine residue at a position corresponding to position 167, 169, 170, 171, 172, 173, 174, 175 and in particular position 180 or position 181 of mature human FGF21 and derivatives thereof having a side chain attached to this cysteine. The FGF21 derivatives of the invention display high potency towards the FGF receptors. The invention also relates to pharmaceutical compositions comprising such FGF21 derivatives and pharmaceutically acceptable excipients, as well as the medical use of the FGF21 derivatives.

20 Claims, No Drawings

(56) References Cited

OTHER PUBLICATIONS

Kliewer S. A. et al., Fibroblast growth factor 21: from pharmacology to physiology1-4, The American Journal of Clinical Nutrition, 2010, vol. 91, No. Suppl, pp. 254S-257S.
Lee P. et al., Mild Cold Exposure Modulates Fibroblast Growth Factor 21 (FGF21) Diurnal Rhythm in Humans: Relationship between FGF21 Levels, Lipolysis, and Cold-Induced Thermogenesis, The Journal of Clinical Endocrinology & Metabolism, 2013, vol. 98, No. 1, pp. E98-E102.
Micanovic R. et al., Different roles of N- and C-termini in the functional activity of FGF21, Journal of Cellular Physiology, Wiley Subscription Services Inc US., 2009, vol. 219, No. 2, pp. 227-234, XP008118374.
Murata Y. et al., FGF21 as an Endocrine Regulator in Lipid Metabolism: From Molecular Evolution to Physiology and Pathophysiology, Journal of Nutrition and Metabolism, 2011, vol. 2011, Article ID 981315, pp. 1-8.
Nishimura T. et al., Identification of a novel FGF, FGF-21, preferentially expressed in the liver, Biochimia et Biophysica Acta vol. 1492 No. 1, 2000, pp. 203-206.
Suzuki M. et al., Beta-Klotho Is Required for Fibroblast Growth Factor (FGF) 21 Signaling through FGF Receptor (FGFR) 1c and FGFR3c, Molecular Endocrinology, 2008, vol. 22, No. 4, pp. 1006-1014.
Vienberg S. G. et al., Impact of short-term high-fat feeding and insulin-stimulated FGF21 levels in subjects with low birth weight and controls, European Journal of Endocrinology, 2012, vol. 167, pp. 49-57.
Ku J. et al., Polyethylene Glycol Modified FGF21 Engineered to Maximize Potency and Minimize Vacuole Formation, Bioconjugate Chemistry, 2013, vol. 24, No. 6, pp. 915-925, XP055192703.
Yie J et al., FGF21 N- and C-termini play different roles in receptor interaction and activation, The Federation of European Biochemical Societies Letters, Elsevier Amsterdam NL, 2009, vol. 583, No. 1, pp. 19-24, XP026194363.
Zhang Y et al., The starvation hormone, fibroblast growth factor-21, extends lifespan in mice, eLife, 2012, vol. 1, e00065, pp. 1-14.
Yie et al., "FGF21 N- and C-termini play different roles in receptor interaction and activation," FEBS Letters, 583 (2009), pp. 19-24. CN Abstract 101250547.
Coskun, T. et al., "Fibroblast Growth Factor 21 Corrects Obesity in Mice", Endocrinology, 2008, vol. 149, No. 12, pp. 6018-6027.
Dennis, M.S. et al., "Albumin Binding as a General Strategy for Improving the Pharmacokinetics of Proteins", The Journal of Biological Chemistry, 2002, vol. 277, No. 38, pp. 35035-35043.
Erickson et al., Journal of Lipid Research, 2009, pp. S412-S416.
Grundy, S.M. et al., "Definition of Metabolic Syndrome", Circulation, 2004, vol. 109, pp. 433-438.
Kharitonenkov, A. et al., "The Metabolic State of Diabetic Monkeys is Regulated by Fibroblast Growth Factor-21", Endocrinology, 2007, vol. 148, No. 2, pp. 774-781.
Kharitonenkov, A. et al., "FGF-21 as a Novel Metabolic Regulator", The Journal of Clinical Investigation, 2005, vol. 115, No. 6, pp. 1627-1635.
Kratz, F., "Albumin as a Drug Carrier: Design of Prodrugs, Drug Conjugates and Nanoparticles", Journal of Controlled Release, 2008, vol. 132, No. 3, pp. 171-183.
Ku, J. et al., "Fibroblast Growth Factor 21 Reverses Hepatic Steatosis, Increases Energy Expenditure, and Improves Insulin Sensitivity in Diet-Induced Obese Mice", Diabetes, 2009, vol. 58, No. 1, pp. 250-259.
Knudsen, L.B., Journal of Medicinal Chemistry, "Glucagon-Like Peptide-1: The Basis of a New Class of Treatment for Type 2 Diabetes", 2004, vol. 47, No. 17, pp. 4128-4134.
Micanovic et al., Journal of Cellular Physiology, "Different Roles of N- and C-Termini in the Functional Activity of FGF21", Wiley Liss, New York, NY, US, vol. 219, No. 2, May 1, 2009, pp. 227-234.
Nauck, M.A et al., Regulatory Peptides, "Glucagon-Like Peptide 1 and . . . ", 2005, vol. 128, No. 2, pp. 135-148.
Kharitonenkov A et al. "Fibroblast growth factor-21 as a therapeutic agent for metabolic diseases." BioDrugs 2008 vol. 22(1): 37-44.
Makrides S C et al: "Extended in vivo half-life of Human Soluble Complement Receptor Type 1 Fused to a Serum Albumin-Binding Receptor", Journal of Pharmacology and Experimental Therapeutics, 1996 American Society for Pharmacology and Experimental Therapeutics, vol. 277, No. 1, pp. 534-542.
Sjolander A et al: "The serum albumin-binding region of streptococcal protein G: a bacterial fusion partner with carrier-related properties", 1997 Journal of Immunological Methods, vol. 201, No. 1, pp. 115-123.
Kurtzhals P. et al: "Albumin Binding of Insulins Acylated With Fatty Acids: Characterization of the Ligand-Protein Interaction and Correlation Between Binding Affinity and Timing of the Insulin Effect in Vivo", Biochemical Journal, 1995 vol. 312, No. 3, pp. 725-731.

\* cited by examiner

SEQUENCE LISTING

<160> NUMBER OF SEQ ID NOS: 20

<210> SEQ ID NO 1
<211> LENGTH: 181
<212> TYPE: PRT
<213> ORGANISM: HOMO SAPIENS

<400> SEQUENCE: 1

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 2
<211> LENGTH: 182
<212> TYPE: PRT
<213> ORGANISM: Artificial Sequence
<220> FEATURE:
<223> OTHER INFORMATION: Synthetic

<400> SEQUENCE: 2

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125
```

```
Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 3
<211> LENGTH: 182
<212> TYPE: PRT
<213> ORGANISM: Artificial Sequence
<220> FEATURE:
<223> OTHER INFORMATION: Synthetic

<400> SEQUENCE: 3

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Gly Arg
                165                 170                 175

Ser Pro Ser Tyr Ala Ser
            180

<210> SEQ ID NO 4
<211> LENGTH: 182
<212> TYPE: PRT
<213> ORGANISM: Artificial Sequence
<220> FEATURE:
<223> OTHER INFORMATION: Synthetic

<400> SEQUENCE: 4

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
```

```
                50                  55                  60
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Gln Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Gly Arg
                165                 170                 175

Cys Pro Ser Tyr Ala Ser
                180

<210> SEQ ID NO 5
<211> LENGTH: 182
<212> TYPE: PRT
<213> ORGANISM: Artificial Sequence
<220> FEATURE:
<223> OTHER INFORMATION: Synthetic

<400> SEQUENCE: 5

Ala His Pro Ile Pro Asp Ser Ser Pro Leu Leu Gln Phe Gly Gly Gln
  1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
                 35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Gln Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Gly Arg
                165                 170                 175

Ser Cys Ser Tyr Ala Ser
                180

<210> SEQ ID NO 6
<211> LENGTH: 182
<212> TYPE: PRT
<213> ORGANISM: Artificial Sequence
<220> FEATURE:
<223> OTHER INFORMATION: Synthetic
```

<400> SEQUENCE: 6

```
Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Gly Arg
                165                 170                 175

Ser Pro Cys Tyr Ala Ser
            180
```

<210> SEQ ID NO 7
<211> LENGTH: 182
<212> TYPE: PRT
<213> ORGANISM: Artificial Sequence
<220> FEATURE:
<223> OTHER INFORMATION: Synthetic

<400> SEQUENCE: 7

```
Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160
```

Val Gly Ser Ser Asp Pro Leu Ser Leu Val Gly Pro Ser Gln Gly Arg
                165                 170                 175

Ser Pro Ser Cys Ala Ser
            180

<210> SEQ ID NO 8
<211> LENGTH: 182
<212> TYPE: PRT
<213> ORGANISM: Artificial Sequence
<220> FEATURE:
<223> OTHER INFORMATION: Synthetic

<400> SEQUENCE: 8

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Gln Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Gly Arg
                165                 170                 175

Ser Pro Ser Tyr Cys Ser
            180

<210> SEQ ID NO 9
<211> LENGTH: 181
<212> TYPE: PRT
<213> ORGANISM: Artificial Sequence
<220> FEATURE:
<223> OTHER INFORMATION: Synthetic

<400> SEQUENCE: 9

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

```
Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Gly Arg
                165                 170                 175

Ser Pro Ser Tyr Cys
            180

<210> SEQ ID NO 10
<211> LENGTH: 182
<212> TYPE: PRT
<213> ORGANISM: Artificial Sequence
<220> FEATURE:
<223> OTHER INFORMATION: Synthetic

<400> SEQUENCE: 10

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Gly Arg
                165                 170                 175

Ser Pro Ser Tyr Ala Cys
            180

<210> SEQ ID NO 11
<211> LENGTH: 182
<212> TYPE: PRT
<213> ORGANISM: Artificial Sequence
<220> FEATURE:
<223> OTHER INFORMATION: Synthetic

<400> SEQUENCE: 11

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
```

```
                    20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
     50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Cys
            180

<210> SEQ ID NO 12
<211> LENGTH: 182
<212> TYPE: PRT
<213> ORGANISM: Artificial Sequence
<220> FEATURE:
<223> OTHER INFORMATION: Synthetic

<400> SEQUENCE: 12

Ala His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
     50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Gln Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Cys Leu Val Gly Pro Ser Gln Gly Arg
                165                 170                 175

Ser Pro Ser Tyr Ala Ser
            180
```

-continued

```
<210> SEQ ID NO 13
<211> LENGTH: 182
<212> TYPE: PRT
<213> ORGANISM: Artificial Sequence
<220> FEATURE:
<223> OTHER INFORMATION: Synthetic

<400> SEQUENCE: 13

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Gln Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Cys Val Gly Pro Ser Gln Gly Arg
                165                 170                 175

Ser Pro Ser Tyr Ala Ser
            180

<210> SEQ ID NO 14
<211> LENGTH: 182
<212> TYPE: PRT
<213> ORGANISM: Artificial Sequence
<220> FEATURE:
<223> OTHER INFORMATION: Synthetic

<400> SEQUENCE: 14

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Gln Lys Ser Pro His Arg Asp
            115                 120                 125
```

```
Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Cys Gly Pro Ser Gln Gly Arg
                165                 170                 175

Ser Pro Ser Tyr Ala Ser
            180

<210> SEQ ID NO 15
<211> LENGTH: 182
<212> TYPE: PRT
<213> ORGANISM: Artificial Sequence
<220> FEATURE:
<223> OTHER INFORMATION: Synthetic

<400> SEQUENCE: 15

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Cys Pro Ser Gln Gly Arg
                165                 170                 175

Ser Pro Ser Tyr Ala Ser
            180

<210> SEQ ID NO 16
<211> LENGTH: 182
<212> TYPE: PRT
<213> ORGANISM: Artificial Sequence
<220> FEATURE:
<223> OTHER INFORMATION: Synthetic

<400> SEQUENCE: 16

Ala His Pro Ile Pro Asp Ser Ser Pro Leu Leu Gln Phe Gly Gly Gln
1               5                   10                  15
```

```
Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Cys Ser Gln Gly Arg
                165                 170                 175

Ser Pro Ser Tyr Ala Ser
            180

<210> SEQ ID NO 17
<211> LENGTH: 182
<212> TYPE: PRT
<213> ORGANISM: Artificial Sequence
<220> FEATURE:
<223> OTHER INFORMATION: Synthetic

<400> SEQUENCE: 17

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125
```

```
Pro Ala Pro Arg Gly Pro Ala Arg Phe Leu Pro Leu Pro Gly Leu Pro
            130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Cys Gln Gly Arg
                165                 170                 175

Ser Pro Ser Tyr Ala Ser
            180

<210> SEQ ID NO 18
<211> LENGTH: 182
<212> TYPE: PRT
<213> ORGANISM: Artificial Sequence
<220> FEATURE:
<223> OTHER INFORMATION: Synthetic

<400> SEQUENCE: 18

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gln Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Cys Gly Arg
                165                 170                 175

Ser Pro Ser Tyr Ala Ser
            180

<210> SEQ ID NO 19
<211> LENGTH: 182
<212> TYPE: PRT
<213> ORGANISM: Artificial Sequence
<220> FEATURE:
<223> OTHER INFORMATION: Synthetic

<400> SEQUENCE: 19

Ala His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30
```

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Gln Lys Ser Pro His Arg Asp
             115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Cys Arg
                165                 170                 175

Ser Pro Ser Tyr Ala Ser
            180

<210> SEQ ID NO 20
<211> LENGTH: 182
<212> TYPE: PRT
<213> ORGANISM: Artificial Sequence
<220> FEATURE:
<223> OTHER INFORMATION: Synthetic

<400> SEQUENCE: 20

Ala His Pro Ile Pro Asp Ser Ser Pro Leu Leu Gln Phe Gly Gly Gln
1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Gln Lys Ser Pro His Arg Asp
             115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Leu Val Gly Pro Ser Gln Gly Cys
                165                 170                 175

Ser Pro Ser Tyr Ala Ser
            180

FGF21 DERIVATIVES AND USES THEREOF

CROSS-REFERENCE TO RELATED APPLICATIONS

This application is a Continuation application of International Application PCT/EP2015/080969 (WO 2016/102562), filed Dec. 22, 2015, which claims priority to European Patent Application 14199935.9, filed Dec. 23, 2014; the contents of which are incorporated herein by reference.

TECHNICAL FIELD

The present invention relates to derivatives of analogues of FGF21, more in particular to analogues of FGF21 having a side chain in position 167, 169, 170, 171, 172, 173, 174, 175, 180 or 181, and their pharmaceutical use.

INCORPORATION-BY-REFERENCE OF THE SEQUENCE LISTING

In accordance with 37 C.F.R. §1.52(e)(5), Applicants enclose herewith the Sequence Listing for the above-captioned application entitled "140109US01_SeqListing", created on Dec. 21, 2015 and Modified on Mar. 8, 2017. The Sequence Listing is made up of 33,477 bytes, and the information contained in the attached "SEQUENCE LISTING" is identical to the information in the specification as originally filed. No new matter is added.

BACKGROUND

FGF21 belongs to the FGF19 subfamily of atypical fibroblast growth factors (FGFs) with metabolic rather than mitogenic effects. FGF21 binds and activates FGF receptors (FGFR1c, FGFR2c and FGFR3c) but only in the presence of the non-signaling co-receptor beta-klotho (BKL). Tissue specific expression of BKL determines the metabolic activity of FGF21. FGF21 transgenic mice are resistant towards diet-induced obesity and have increased longevity. FGF21 is a metabolic regulator of energy expenditure, glucose and lipid metabolism, with a great potential to reverse bodyweight, hyperglycaemia and dyslipidaemia in obese patients with diabetes and dyslipidaemia.

FGF21 suffers from in vivo instability due to proteolysis, and as much as half of the endogenous circulating human FGF21 is inactive. The loss of activity is due to degradation of the C-terminal, the majority of these metabolites terminate at P171 rather than S181. Protection against metabolic breakdown in the C-terminal region is therefore desirable for a therapeutic FGF21 molecule. Engineering of the C-terminal region may protect against degradation, however so far such engineering has come at the cost of lowered or lost potency of the engineered FGF21 compound. The N-terminal region of FGF21 binds to FGFRs while the C-terminal region of FGF21 binds to BKL. Truncations of C-terminal amino acids lead to significant loss of potency.

PEGylation in position 180 of [180C]FGF21 results in dramatic reduction in in vitro activity (J. Xu et al, Bioconjugate Chemistry (2013), 24, 915-925). The Fc fusion protein resulting from attaching Fc to the C-terminus of FGF21 is much less potent than native FGF21 and the N-terminal Fc fusion of FGF21 (Hecht et al, PLoS One 2012, 7(11), e49345).

SUMMARY

The present invention relates to FGF21 derivatives having a side chain in a position corresponding to one of positions 167, 169, 170, 171, 172, 173, 174, 175, 180 or 181 as compared to mature human FGF21 (SEQ ID NO; 1). The present invention relates to FGF21 derivatives having a side chain in a position corresponding to one of positions 180 or 181 as compared to mature human FGF21 (SEQ ID NO:1). More in particular the side chain is covalently attached to the position of a FGF21 analogue that corresponds to position 180 of mature human FGF21 (SEQ ID NO:1), or covalently attached to the position of a FGF21 analogue that corresponds to position 181 of mature human FGF21 (SEQ ID NO:1).

More in particular the side chain is covalently attached to the position of a FGF21 analogue that corresponds to position 170, 174 or 175 of mature human FGF21 (SEQ ID NO:1), or covalently attached to the position of a FGF21 analogue that corresponds to position 167, 171, 172 or 173 of mature human FGF21 (SEQ ID NO:1).

A cysteine is present in the FGF21 analogue in the position of attachment of the side chain. The side chain is covalently attached to the sulfur atom of the cysteine residue to which the side chain is attached. The side chain comprises a linker and a protractor. The protractor may be a fatty di-acid.

The linker may comprise several linker elements, such as one or more gGlu residues, and/or one or more Ado residues (Ado is 8-amino-3,6-dioxaoctanoic acid), and/or one or more other di-radicals incorporating a *—NH group and a *—CO group. The protractor and the linker are connected via an amide bond. The linker is connected to the sulfur atom of 180Cys or 181Cys of the FGF21 protein, via a thioether bond.

The linker may comprise several linker elements, such as one or more gGlu residues, and/or one or more Ado residues (Ado is 8-amino-3,6-dioxaoctanoic acid), and/or one or more Trx element (Trx is tranexamic acid), and/or one or more *—NH—S(=O)$_2$—(CH$_2$)$_3$—CO—* and/or one or more other di-radicals incorporating a *—NH group and a *—CO group. The protractor and the linker are connected via an amide bond, while the linker is connected to the FGF21 protein through a thioether bond via the sulfur atom of the cysteine in position 167, 169, 170, 171, 172, 173, 174, 175, 180 or 181.

The FGF21 protein incorporated in the FGF21 derivative of the invention is an analogue of mature human FGF21 (SEQ ID NO:1), the analogue which comprises a cysteine residue in one of the positions corresponding to position 180 or position 181 of mature human FGF21 (SEQ ID NO:1).

The FGF21 analogue of the derivative of the invention may have up to 30 amino acid changes in total as compared to mature human FGF21 (SEQ ID NO:1), of which the cysteine residue in one of positions 180 or 181 counts for one amino acid change. The maximum 29 additional changes may be, independently, one or more extensions, one or more insertions, one or more deletions, and/or one or more substitutions.

In particular the invention relates, in a first aspect, to a derivative of a FGF21 protein, wherein said protein comprises a Cys residue at a position corresponding to position 167, 169, 170, 171, 172, 173, 174, 175, 180 or position 181 of mature human FGF21 (SEQ ID NO:1), wherein said derivative comprises a protractor attached to said Cys residue via a linker; wherein the protractor is selected from the group of

 HOOC—(CH$_2$)$_x$—CO—*,      Chem. 1A:

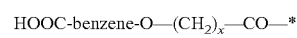 HOOC-benzene-O—(CH$_2$)$_x$—CO—*      Chem. 1B:

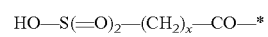 HO—S(=O)$_2$—(CH$_2$)$_x$—CO—*      Chem. 1C:

wherein x is an integer in the range of 8-18; and wherein the linker comprises at least one of each of Chem. 2, Chem. 3 and Chem. 4;
wherein Chem. 2 is selected from:

*—NH—CH(COOH)—(CH$_2$)$_2$—CO—*,    Chem. 2A:

*—NH—S(=O)$_2$—(CH$_2$)$_3$—CO—* and    Chem. 2B:

*—NH—CH$_2$-cyclohexane-CO—*,    Chem. 2C:

wherein Chem. 3 is *—NH—(CH$_2$)$_2$—[O—(CH$_2$)$_2$]$_k$—O—[CH$_2$]n-CO—*, wherein k is an integer in the range of 1-5, n is an integer in the range of 1-5, and
wherein Chem. 4 is selected from

*—NH—(CH$_2$)$_m$—NH—CO—CH$_2$—* and

*—NH—CH(COOH)—(H$_2$)$_m$—NH—CO—CH$_2$—* wherein m is an integer in the range of 1-5 and
wherein Chem. 2, Chem. 3, and Chem. 4 are interconnected via amide bonds and in the sequence indicated, connected at its *—NH end to the CO—* end of the protractor, and at its CH$_2$—* end to the sulfur atom of the Cys residue at a position corresponding to position 167, 169, 170, 171, 172, 173, 174, 175, 180 or 181 of mature human FGF21 (SEQ ID NO:1), or a pharmaceutically acceptable salt, amide, or ester thereof.

More in particular the invention relates, in a first aspect, to a derivative of a FGF21 protein, wherein said protein comprises a Cys residue at a position corresponding to position 180 or position 181 of mature human FGF21 (SEQ ID NO:1), and a maximum of 30 amino acid modifications as compared to mature human FGF21 (SEQ ID NO:1); wherein said derivative comprises a protractor attached to said Cys residue via a linker; wherein the protractor is Chem. 1: HOOC—(CH$_2$)$_x$—CO—*, wherein x is an integer in the range of 10-18; and wherein the linker comprises at least one of each of Chem. 2, Chem. 3 and Chem. 4:

*—NH—CH(COOH)—(CH$_2$)$_2$—CO—*,    Chem. 2:

*—NH—(CH$_2$)$_2$—[O—(CH$_2$)$_2$]$_k$—O—[CH$_2$]$_n$—CO—*, and    Chem. 3:

*—NH—(CH$_2$)$_m$—NH—CO—CH$_2$—*,    Chem. 4:

wherein k is an integer in the range of 1-5, n is an integer in the range of 1-5, and m is an integer in the range of 1-5. Chem. 2, Chem. 3, and Chem. 4 are interconnected via amide bonds and in the sequence indicated, connected at its *—NH end to the CO—* end of the protractor, and at its CH$_2$—* end to the sulfur atom of the Cys residue at a position corresponding to position 180 or position 181 of mature human FGF21 (SEQ ID NO:1).

Preferred FGF21 derivatives of the invention designated Compound 13 to Compound 24 are disclosed in the experimental section.

Further preferred FGF21 derivatives of the invention designated Compound 13 to Compound 18 are disclosed in the experimental section.

Further preferred FGF21 derivatives of the invention designated Compound 35 to Compound 41 are disclosed in the experimental section.

Further preferred FGF21 derivatives of the invention designated Compound 43 to Compound 56 are disclosed in the experimental section.

In a further aspect, the invention relates to a FGF21 analogue comprising a Cys residue at a position corresponding to position 167, 169, 170, 171, 172, 173, 174, 175, 180 or 181 of mature human FGF21 (SEQ ID NO:1). The analogues preferably have a high degree of identity to human FGF21 (SEQ ID NO:1). The degree of identity may be described by the number of amino acid substitution or modification compared to human FGF21 (SEQ ID NO:1).

In a further aspect, the invention relates to a FGF21 analogue comprising a Cys residue at a position corresponding to position 180 or position 181 of mature human FGF21 (SEQ ID NO:1), and a maximum of 30 amino acid modifications as compared to mature human FGF21 (SEQ ID NO:1).

In a third aspect, the invention relates to the pharmaceutical use of the FGF21 derivatives and analogues of the invention, for example for use in the treatment and/or prevention of all forms of diabetes and related diseases, such as eating disorders, cardiovascular diseases, diabetic complications; and/or for improving lipid parameters, improving β-cell function; and/or for delaying or preventing diabetic disease progression; and/or for of treatment and/or prevention of hepatic steatosis and non-alcoholic fatty liver disease (NAFLD).

The FGF21 derivatives of the invention are biologically active. For example they are very potent, and, also or alternatively, they bind very well to FGF receptors. Also, or alternatively, they have a protracted pharmacokinetic profile. For example they have a very long terminal half-life when administered i.v. to mice and/or mini pigs. The particular combination of good potency and long half-life may be highly desirable.

It is of interest that FGF21 derivatives comprising a side chain in a position corresponding to one of positions 167, 169, 170, 171, 172, 173, 174, 175, 180 and 181 of mature human FGF21 all retain potency.

Also, or alternatively, it is noticed that FGF21 derivatives comprising a side chain in a position corresponding to one of positions 180 and 181, and in particular position 180, of mature human FGF21 have retain high potency.

DESCRIPTION

In what follows, Greek letters may be represented by their symbol or the corresponding written name, for example: α=alpha; β=beta; ϵ=epsilon; γ=gamma; ω=omega; etc. Also, the Greek letter of μ may be represented by "u", e.g. in μl=ul, or in μM=uM.

An asterisk (*) in a chemical formula designates a point of attachment.

The invention relates in a first aspect to a derivative of a FGF21 protein, wherein said protein comprises a Cys residue at a position corresponding to position 167, 169, 170, 171, 172, 173, 174, 175, 180 or position 181 of mature human FGF21 (SEQ ID NO:1), wherein said derivative comprises a protractor attached to said Cys residue via a linker; wherein the protractor is selected from the group of HOOC—(CH$_2$)$_x$—CO—*,    Chem. 1A:

HOOC-benzene-O—(CH$_2$)$_x$—CO—*    Chem. 1B:

HO—S(=O)$_2$—(CH$_2$)$_x$CO—*    Chem. 1C:

wherein x is an integer in the range of 8-18; and wherein the linker comprises at least one of each of Chem. 2, Chem. 3 and Chem. 4;
wherein Chem. 2 is selected from:

*—NH—CH(COOH)—(CH$_2$)$_m$—CO—*,

*—NH—S(=O)$_2$—(CH$_2$)$_m$—CO—* and

*—NH—(CH$_2$)$_m$-cyclohexane-CO—*, wherein m is individually selected as an integer in the range of 1-5, wherein Chem. 3 is *—NH—(CH$_2$)$_2$—[O—(CH$_2$)$_2$]$_k$—O—[CH$_2$]$_n$—CO—*, wherein k is an integer in the range of 1-5, n is an integer in the range of 1-5, and wherein Chem. 4 is selected from

*—NH—(CH$_2$)$_m$—NH—CO—CH$_2$—* and

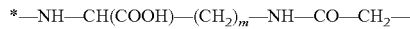

*—NH—CH(COOH)—(CH$_2$)$_m$—NH—CO—CH$_2$— wherein m is an integer in the range of 1-5.

In further embodiments Chem. 2 is selected from:

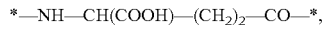

*—NH—CH(COOH)—(CH$_2$)$_2$—CO—*,

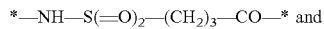

*—NH—S(=O)$_2$—(CH$_2$)$_3$—CO—* and

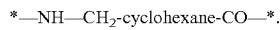

*—NH—CH$_2$-cyclohexane-CO—*.

In a further embodiment Chem. 2 is *—NH—CH(COOH)—(CH$_2$)$_2$—CO—*.

In a further embodiment Chem. 2 is *—NH—S(=O)$_2$—(CH$_2$)$_3$—CO—*.

In a further embodiment Chem. 2 is *—NH—CH$_2$-cyclohexane-CO—*.

As mentioned above the derivative includes at least one of each of Chem. 2, Chem. 3, and Chem. 4 interconnected via amide bonds. Furthermore the linker elements are linked in the sequence indicated. Chem. 2 is connected at its *—NH end to the CO—* end of the protractor, and Chem. 4 is at its CH$_2$—* end linked to the sulfur atom of the Cys residue at a position corresponding to position 167, 169, 170, 171, 172, 173, 174, 175, 180 or 181 of mature human FGF21 (SEQ ID NO:1), or a pharmaceutically acceptable salt, amide, or ester thereof.

In a further aspect, the invention relates to a derivative of a FGF21 protein, wherein said protein comprises a Cys residue at a position corresponding to position 180 or position 181 of mature human FGF21 (SEQ ID NO:1), and a maximum of 30 amino acid modifications as compared to mature human FGF21 (SEQ ID NO:1); wherein said derivative comprises a protractor attached to said Cys residue via a linker; wherein the protractor is Chem. 1: HOOC—(CH$_2$)$_x$—CO—*, wherein x is an integer in the range of 10-18; and wherein the linker comprises at least one of each of Chem. 2, Chem. 3 and Chem. 4:

| *—NH—CH(COOH)—(CH$_2$)$_2$—CO—*, | Chem. 2: |
|---|---|
| *—NH—(CH$_2$)$_2$—[O—(CH$_2$)$_2$]$_k$—O—[CH$_2$]$_n$—CO—*, and | Chem. 3: |
| *—NH—(CH$_2$)$_m$—NH—CO—CH$_2$—*, | Chem. 4: | wherein k is an integer in the range of 1-5, n is an integer in the range of 1-5, and m is an integer in the range of 1-5. Chem. 2, Chem. 3, and Chem. 4 are interconnected via amide bonds and in the sequence indicated, connected at its *—NH end to the CO—* end of the protractor, and at its CH$_2$—* end to the thiol group of the Cys residue at a position corresponding to position 180 or position 181 of mature human FGF21 (SEQ ID NO:1).

FGF21 Proteins and Analogues

In nature the native FGF21 protein is synthesised with a signal peptide of 28 amino acids for secretion. The mature FGF21 polypeptide consisting of the remaining 181 amino acids is included in the sequence listing as SEQ ID NO:1.

The FGF21 protein of the derivative of the invention may now and then be referred to as the "backbone" or the "protein backbone" of the derivative or as a "FGF21 analogue".

The term "FGF21 protein" as used herein refers to an analogue or variant of the human FGF21 (FGF21(1-181)), the sequence of which is included in the sequence listing as SEQ ID NO:1. The protein having the sequence of SEQ ID NO:1 may also be designated "native" FGF21, "mature" FGF21, and/or "mature human" FGF21.

In the sequence listing, the first amino acid residue of mature human FGF21 of SEQ ID NO:1 (histidine) is assigned no. 1.

An example of an FGF21 analogue is the protein of SEQ ID NO:1, which has an N-terminal methionine, also designated MetFGF21 (SEQ ID NO:2). An N-terminal Met is added when mature human FGF21 is expressed in *E. coli*, see e.g. WO 2006/050247, Table 6. An additional N-terminal amino acid residue, preceding the histidine in position 1 of mature human FGF21 (SEQ ID NO:1) is assigned position no. −1. Non-limiting examples of suitable nomenclature for MetFGF21 of SEQ ID NO:2 are MetFGF21, [Met]FGF21 or [−1M]FGF21.

MetFGF21 shows comparable biological activity to mature human FGF21 of SEQ ID NO:1, and is for practical reasons often used as reference compound instead of mature human FGF21 of SEQ ID NO:1. The amino acid sequence of MetFGF21 is included in the sequence listing as SEQ ID NO:2.

Herein, the FGF21 proteins of the invention may be described by reference to i) the number of the amino acid residue in mature human FGF21(1-181) which corresponds to the amino acid residue which is changed (i.e., the corresponding position in mature human FGF21), and to ii) the actual change.

An aspect of the invention relates to an FGF21 protein (FGF21 analogue) comprising an amino acid substitution where a wild type amino acid residue is substituted by a cysteine residue. In one embodiment the FGF21 protein comprises a Cys residue in a position corresponding to one of the positions 167, 169, 170, 171, 172, 173, 174, 175, 180 and 181 of FGF21 (1-181) (SEQ ID NO:1). In one embodiment the FGF21 protein comprises a Cys residue in a position corresponding to one of the positions 167, 169, 170, 171, 172, 173, 174 and 175 of FGF21 (1-181) (SEQ ID NO:1). In one embodiment the FGF21 protein comprises a Cys residue in a position corresponding to one of the positions 167, 170, 171, 172, 173, 174, 175 and 180 of FGF21 (1-181) (SEQ ID NO:1).

In one embodiment the FGF21 protein comprises a Cys residue in a position corresponding to one of the positions 169, 170, 173, 174, 175, 180 and 181 of FGF21 (1-181) (SEQ ID NO:1). In one embodiment the FGF21 protein comprises a Cys residue in a position corresponding to one of the positions 170, 173, 174, 175 and 180 of FGF21 (1-181) (SEQ ID NO:1). In one embodiment the FGF21 protein comprises a Cys residue in a position corresponding to one of the positions 170, 173, 174, 175, 180 and 181 of FGF21 (1-181) (SEQ ID NO:1). In one embodiment the FGF21 protein comprises a Cys residue in a position corresponding to one of the positions 170, 173, 174, 175 and 180 of FGF21 (1-181) (SEQ ID NO:1). In one embodiment the FGF21 protein comprises a Cys residue in a position corresponding to one of the positions 170, 173, 174 and 175 of FGF21 (1-181) (SEQ ID NO:1).

In one embodiment the FGF21 protein comprises a Cys residue in a position corresponding to one of the positions 170, 173, 174, 180 and 181 of FGF21 (1-181) (SEQ ID NO:1). In one embodiment the FGF21 protein comprises a Cys residue in a position corresponding to one of the positions 170, 173, 174 and 180 of FGF21 (1-181) (SEQ ID NO:1). In one embodiment the FGF21 protein comprises a Cys residue in a position corresponding to one of the positions 170, 173 and 174 of FGF21 (1-181) (SEQ ID NO:1). In one embodiment the FGF21 protein comprises a Cys residue in a position corresponding to one of the positions 180 and 181 of FGF21 (1-181) (SEQ ID NO:1).

For example, the FGF21 protein of the invention is defined so as to comprise a Cys residue either at the position corresponding to position 180 of FGF21(1-181) (SEQ ID NO:1) or at the position corresponding to position 181 of FGF21(1-181) (SEQ ID NO:1). In one embodiment the FGF21 protein comprises a Cys residue in a position corresponding to position 180 or 181 of FGF21 (1-181) (SEQ ID NO: 1). In one embodiment the FGF21 protein comprises a Cys residue in a position corresponding to position 180 of FGF21 (1-181) (SEQ ID NO:1).

These Cys residues of the FGF21 protein of the invention may be designated Cys180 and Cys181, respectively. For example, a FGF21 protein of the invention having a Cys residue in the position corresponding to position 181 of mature human FGF21 (SEQ ID NO:1) may be referred to as Cys181 FGF21 and/or as 181C FGF21, alternatively [Cys181]FGF21 and/or as [181C]FGF21.

The following is a non-limiting example of suitable analogue nomenclature.

Ala[Gln121,Leu168,Cys180]FGF21 designates an analogue of mature human FGF21, wherein an alanine has been added to the N-terminal (i.e. Ala in the position corresponding to position −1 of mature human FGF21 (SEQ ID NO:1)), the naturally occurring asparagine in position 121 has been substituted with glutamine, the naturally occurring methionine in position 168 has been substituted with leucine, and the naturally occurring alanine in position 180 has been substituted with cysteine.

The following is a non-limiting example of suitable nomenclature for a derivative of a FGF21 analogue. S{Beta-180}-[2-[2-[[2-[2-[2-[[2-[2-[2-[[(4S)-4-carboxy-4-(17-carboxyheptadecanoylamino)butanoyl]amino]ethoxy]ethoxy] acetyl]amino]ethoxy]ethoxy]acetyl]amino]ethylamino]-2-oxoethyl]-Ala[Gln121,Leu168,Cys180]FGF21 designates a derivative of an analogue of mature human FGF21 (SEQ ID NO:1), wherein Ala[Gln121,Leu168,Cys180]designate the amino acid changes as compared to mature human FGF21 (SEQ ID NO:1) with the numbers referring to the corresponding positions of mature FGF21, and wherein the substituent [2-[2-[[2-[2-[2-[[2-[2-[2-[[(4S)-4-carboxy-4-(17-carboxyheptadecanoylamino)butanoyl]amino]ethoxy] ethoxy]acetyl]-amino]ethoxy]ethoxy]acetyl]amino]ethyl-amino]-2-oxoethyl]- is covalently attached to the sulfur atom of the cysteine in the position corresponding to position 180 in mature human FGF21 (SEQ ID NO:1).

The FGF21 protein of the invention may have additional amino acid changes as compared to FGF21 (SEQ ID NO:1), however limited to a maximum of 30 amino acid changes. These changes are also as compared to mature human FGF21(1-181) (SEQ ID NO:1), and they may represent, independently, one or more amino acid substitutions, insertions, extensions, and/or deletions.

In a particular embodiment the amino acid changes are at one or more positions corresponding to one or more of positions −1, 121, and 168 of FGF21 (SEQ ID NO:1).

In one embodiment the FGF21 protein of the invention comprises—1Ala, 121Gln and 168Leu in addition to the cysteine amino acid substitution.

In an embodiment the FGF21 protein of the invention comprises—1Ala, 121Gln, and 168Leu in addition to either of 167Cys, 170Cys, 171Cys, 172Cys, 173Cys, 174Cys, 175Cys, 180Cys and 181Cys. Particular FGF21 proteins of the invention, which are also incorporated in the particular derivatives of the invention disclosed in the experimental section, are SEQ ID NO: 8, 10, 12, 14, 15, 16, 17, 18, 19 and 20 of the sequence listing.

In another particular embodiment the FGF21 protein of the invention comprises—1Ala, 121Gln, and 168Leu in addition to either of 180Cys or 181Cys.

Particular FGF21 proteins of the invention, which are also incorporated in the particular derivatives of the invention disclosed in the experimental section, are SEQ ID NO:8 and SEQ ID NO:10 of the sequence listing.

A protein "comprising" certain specified changes may comprise further changes, when compared to mature human FGF21 (SEQ ID NO:1).

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a variant FGF21 sequence by reference to mature human FGF21 (SEQ ID NO:1). Equivalent or corresponding positions, as well as the number of changes, are easily deduced, e.g. by simple handwriting and eyeballing; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted herein below, in which sequence no. 1 is mature human FGF21 (SEQ ID NO:1), and sequence no. 2 is the analogue Ala[121Q, 168L, 181C]FGF21 (SEQ ID NO:10). The calculated identity is thus 97.8%.

1: FGF21
2: Ala[121Q, 168L, 181C]FGF21
Matrix: EBLOSUM62
Gap_penalty: 10.0
Extend_penalty: 0.5
Length: 182
Identity: 178/182 (97.8%)
Similarity: 179/182 (98.4%)
Gaps: 1/182 (0.5%)
Score: 952.0

```
1      1 -HPIPDSSPLLQFGGQVRQRYLYTDDAQQTEAHLEIREDGTVGGAADQSP  49
         |||||||||||||||||||||||||||||||||||||||||||||||||
2      1 AHPIPDSSPLLQFGGQVRQRYLYTDDAQQTEAHLEIREDGTVGGAADQSP  50

1     50 ESLLQLKALKPGVIQILGVKTSRFLCQRPDGALYGSLHFDPEACSFRELL  99
         |||||||||||||||||||||||||||||||||||||||||||||||||
```

```
2   51 ESLLQLKALKPGVIQILGVKTSRFLCQRPDGALYGSLHFDPEACSFRELL 100

1  100 LEDGYNVYQSEAHGLPLHLPGNKSPHRDPAPRGPARFLPLPGLPPALPEP 149
        ||||||||||||||||||||||||.|||||||||||||||||||||||||
2  101 LEDGYNVYQSEAHGLPLHLPGQKSPHRDPAPRGPARFLPLPGLPPALPEP 150

1  150 PGILAPQPPDVGSSDPLSMVGPSQGRSPSYAS                  181
        |||||||||||||||||||||:|||||||||.
2  151 PGILAPQPPDVGSSDPLSLVGPSQGRSPSYAC                  182
```

In further embodiments the FGF21 protein or analogue or FGF21 backbone of the FGF derivatives has at least 80% identity with human FGF21 (SEQ ID NO:1), such as at least 85% identity, such as at least 90% identity, such as at least 92, 93, 94, 95, 96, 97, 98 or 99% identity to human FGF21 (SEQ ID NO:1).

The term "protein" refers to a compound which comprises a series of amino acids interconnected by amide (or peptide) bonds.

The proteins of the invention comprise at least 151 constituent amino acids connected by peptide bonds. In particular embodiments the protein comprises at least 160, preferably at least 170, more preferably at least 180, even more preferably at least 181, or most preferably at least 182. In additional particular embodiments, the protein is a) composed of, or b) consists of, 181 or 182 amino acids.

In a still further particular embodiment the protein consists of amino acids interconnected by peptide bonds.

An amino acid may be defined as a compound which comprises an amine group and a carboxylic acid group, and optionally one or more additional groups often referred to as a side chain. The amine group may, e.g., be a primary or secondary amino group.

An amino acid residue is a radical of an amino acid as incorporated into a peptide or protein.

In a particular embodiment the amino acids of the protein of the invention are alpha-amino acids where the nitrogen atom of the primary or secondary amino group is bonded to the alpha-carbon atom.

In another particular embodiment the amino acids of the protein of the invention are selected from coded amino acids and non-coded amino acids.

In one embodiment all amino acids of the protein of the invention are coded amino acids.

Coded amino acids may be defined as in Table 1 in section 3AA-1 of the Recommendations by IUPAC (INTERNATIONAL UNION OF PURE AND APPLIED CHEMISTRY; see http://www.chem.qmul.ac.uk/iupac/), where structure, trivial name, systematic name, one- and three-letter symbols for 20 coded amino acids are given.

The term "non-coded amino acids" refers to all other amino acids. Non-limiting examples of non-coded amino acids are the D-isomers of the coded amino acids such as D-alanine and D-leucine.

In what follows, all specific amino acids for which the optical isomer is not stated is to be understood to mean the L-isomer (unless otherwise specified), e.g. when reference is made to the specific amino acid of glutamine, this is intended to refer to L-glutamine, unless otherwise is stated. On the other hand, where amino acids are described by more general formulas such as brutto formulas or structural formulas and when no stereo chemistry is shown, these formulas are intended to cover all stereo isomers.

According to general practice in the art the N-terminus of the FGF21 proteins of the invention is shown to the left and the C-terminus to the right.

FGF21 Derivatives

The term "derivative" as used herein in the context of a FGF21 protein or analogue means a chemically modified FGF21 protein or analogue, in which a well-defined number of substituents have been covalently attached to one or more specific amino acid residues of the protein. The substituent(s) may be referred to as (a) side chain(s).

In a particular embodiment, the side chain is capable of forming non-covalent associations with albumin, thereby promoting the circulation of the derivative with the blood stream, and also having the effect of protracting the time of action of the derivative, due to the fact that the association of the FGF21 derivative and albumin is only slowly disintegrated to release the active pharmaceutical ingredient.

The side chain comprises a portion which is referred to herein as a protractor.

The protractor may be at, or near, the distant end of the side chain, relative to its point of attachment to the protein.

In a still further particular embodiment the side chain comprises a portion in between the protractor and the point of attachment to the protein, which portion may be referred to as a linker. The linker may consist of one or more linker elements.

In particular embodiments, the side chain and/or the protractor is lipophilic, and/or negatively charged at physiological pH (7.4).

The side chain may be covalently attached to a cysteine residue of the FGF21 protein by alkylation.

In a preferred embodiment, the side chain is synthesised as and activated with a haloacetamide group, which reacts with the thiol group of a cysteine residue, under formation of a covalent thiol-carbon bond (this process being referred to as Cys-alkylation) which is also referred to as a thio-ether bond. The thiol group is thus not present in the derivatives, and the sidechain is linked through the sulfur atom. In cases where the thiol group is mentioned in relation to a derivative it must be understood as the sulfur atom which is part of the thiol group of the cysteine prior to Cys-alkylation.

In another embodiment, the side chain is activated with a maleimide group, which reacts with the thiol group of a cysteine residue, under formation of a covalent thiol-carbon bond.

For the present purposes, the terms protractor, and linker may include the unreacted as well as the reacted forms of these molecules. Whether or not one or the other form is meant is clear from the context in which the term is used.

In one aspect, each protractor comprises, or consists of, a protractor of formula Chem. 1:

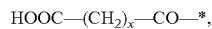
$$\text{HOOC—(CH}_2)_x\text{—CO—*,} \qquad \text{Chem. 1:}$$

wherein x is an integer in the range of 10-18.

In alternative embodiments the protractor Chem. 1 is selected from the group of protractors defined by Chem. 1A, Chem. 1B and Chem. 1C

$$\text{HOOC—(CH}_2)_x\text{—CO—*,} \qquad \text{Chem. 1A:}$$

wherein x is an integer in the range of 8-18,

HOOC-benzene-O—(CH$_2$)$_x$—CO—*    Chem. 1B:

wherein x is an integer in the range of 8-18, and

HO—S(=O)$_2$—(CH$_2$)$_x$—CO—*    Chem. 1C;

wherein x is an integer in the range of 8-18.

The length of the carbon chain defined by x may vary from 8-18 for each of the different Chem. 1 structures, while as described below shorter or longer version may be favoured for different types of protractor elements.

In a particular embodiment of 1A, *—(CH$_2$)$_x$—* refers to straight alkylene in which x is an integer in the range of 10-18, such as 14-18 or such as 14-16.

In another particular embodiment of 1A, *—(CH$_2$)$_x$—* refers to straight alkylene in which x is 16. This protractor may be briefly referred to as C18 diacid, i.e. a fatty dicarboxylic acid with 18 carbon atoms. When x=16 the structure of this linker element corresponds to Chem. 1a:

HOOC—(CH$_2$)$_{16}$—CO—*.    Chem. 1a:

In one embodiment the protractor is Chem. 1B. In an embodiment of 1B *—(CH$_2$)$_x$—* refers to a straight alkylene in which x is an integer in the range of 8-14. In particular embodiment when x=9 the structure of this linker element corresponds to Chem. 1b.

HOOC-benzene-O—(CH$_2$)$_9$—CO*    Chem. 1b:

In one embodiment the protractor is Chem. 1C. In an embodiment of 1C, *—(CH$_2$)$_x$—* refers to a straight alkylene in which x is an integer in the range of 10-18, such as 12-18 or 14-18. In a particular embodiment of 1C, when x=15 the structure of this linker element corresponds to Chem. 1c HO—S(=O)$_2$—(CH$_2$)$_{15}$—CO—*    Chem. 1c:

The nomenclature is as is usual in the art, for example in the above formulas *—CO—* refers to carbonyl (*—C(=O)—*). For example, in any formula (R—CO—*) herein (where R is as defined by each formula), R—CO—* refers to R—C(=O)—*. Benzene refers to the ring structure which in Chem. 1B is substituted at C1 and C4 by O—(CH$_2$)x-* and —COOH, respectively. HO—S(=O)$_2$ describes sulfonic acid.

The linker of the derivative of the invention comprises at least one of the following linker elements Chem. 2, Chem. 3 and Chem. 4. The elements Chem. 2 and chem3 both holds a —NH— and CO— end allowing them to be linked by amid bonds to each other and to either —CO— or —NH— of the protractor or Chem. 4.

Chem. 4 has a —NH— end (capable of forming an amide bond with Chem. 2 or Chem. 3, and a —NH—CO—CH$_2$— end, which in the unreacted form is a haloacetamide capable of reacting with the thiol group of the cysteine of the FGF21 analogue.

The linker of the derivative of the invention comprises at least one of the following linker elements Chem. 2, Chem. 3 and Chem. 4, wherein Chem. 2 is selected from:

*—NH—CH(COOH)—(CH$_2$)$_m$—CO—*,

*—NH—S(=O)$_2$—(CH$_2$)$_m$—CO—*,

*—NH—(CH$_2$)$_m$-cyclohexane-CO—*, and wherein m is individually selected as an integer in the range of 1-5.
wherein Chem. 3 is: *—NH—(CH$_2$)$_2$—[O—(CH$_2$)$_2$]$_k$—O—[CH$_2$]n-CO—*, wherein k is an integer in the range of 1-5, n is an integer in the range of 1-5, and wherein Chem. 4 is selected from:

*—NH—(CH$_2$)$_m$—NH—CO—CH$_2$—* and

*—NH—CH(COOH)—(H$_2$)$_m$N H—CO—CH$_2$—* wherein m is individually selected as an integer in the range of 1-5.

In one embodiment Chem. 2 is *—NH—CH(COOH)—(CH$_2$)$_m$—CO—*, wherein m is 1, 2 or 3.

In one embodiment m is 2 or 3.

In the embodiment where m is 2, the linker element Chem. 2 may be referred to as Chem. 2a that is *—NH—CH(COOH)—(CH$_2$)$_2$—CO—*. The linker element *—NH—CH(COOH)—(CH$_2$)$_2$—CO—* may be briefly referred to as gGlu, gamma Glu, or γ-Glu. In gGlu it is the gamma carboxy group of the amino acid glutamic acid which is used for connection to another linker element. In one particular embodiment the (each) gGlu linker element is in the L-form.

In one embodiment Chem. 2 is *—NH—S(=O)$_2$—(CH$_2$)$_m$—CO—*, wherein m is 1, 2 or 3. In one embodiment m is 2 or 3. The linker element *—NH—S(=O)$_2$—(CH$_2$)$_m$—CO—*, is a sulfonic acid derivative, where the carboxy group is used for connection to another linker element. In one embodiment m is 3 and linker element Chem. 2 may be referred to as Chem. 2b: *—NH—S(=O)$_2$—(CH$_2$)$_3$—CO—*.

In one embodiment Chem. 2 is *—NH—(CH$_2$)$_m$-cyclohexane-CO—*, wherein m is 1, 2 or 3. In one embodiment m is 2 or 3. In the Chem. 2 structure, the cyclohexane ring is thus substituted at C1 and C4 with NH—CH2 and CO respectively.

In one embodiment m is 1 and linker element Chem2 may be referred to as Chem. 2c; *—NH—CH$_2$-cyclohexane-CO—*. This linker element may further be referred to as Trx.

In the linker element of Chem. 3, "k" and "n" may both vary between 1 and 5. When k=n=1 the structure of this linker element corresponds to Chem. 3a:

In one embodiment Chem. 3 is Chem. 3a: *—NH—(CH$_2$)$_2$—O—(CH$_2$)$_2$—O—CH$_2$—CO—*. The linker element of Chem. 3a may be briefly referred to as Ado (8-amino-3,6-dioxaoctanoic acid) as it is a di-radical thereof.

In the linker element of Chem. 4, "m" may vary between 1 and 5. In one embodiment Chem. 4 is *—NH—(CH$_2$)$_m$—NH—CO—CH$_2$—*, wherein m is 1, 2, 3 or 4. In one embodiment m is 2 or 3.

In one embodiment when Chem. 4 is *—NH—(CH$_2$)$_m$—NH—CO—CH$_2$—* and m=2 the structure of this linker element corresponds to Chem. 4a:*—NH—(CH$_2$)$_2$—NH—CO—CH$_2$—*.

In one embodiment Chem. 4 is *—NH—CH(COOH)—(CH$_2$)$_m$—NH—CO—CH$_2$—* wherein m is 1, 2, 3 or 4. In one embodiment m is 2 or 3. In one embodiment m is 4 or 5.

When Chem. 4 is *—NH—CH(COOH)—(CH$_2$)$_m$—NH—CO—CH$_2$—* and m=4 the structure of this linker element corresponds to Chem. 4b: *—NH—CH(COOH)—(CH$_2$)$_4$—NH—CO—CH$_2$—*.

The linker of the derivative of the invention may comprise one or more of these three different types of linker elements, and it may also comprise one or more of each individual linker element. In one embodiment the linker comprises only one Chem. 4 element. In one embodiment the linker comprises one or more of each of Chem2 and Chem. 3 and only one Chem. 4 element.

As a non-limiting example, the linker may consist of one Chem. 2 element, two Chem. 3a elements, and one Chem. 4 element, interconnected via amide bonds and in the sequence indicated, connected at its *—NH end to the CO—* end of the protractor, and at its CO—* end to the sulfur atom of the Cys residue in either position 180 or 181 of the FGF21 protein. The Chem. 4 elements thus links the —CO—* end of the Chem.2/Chem.3 elements to the sulfor atom of the FGF21 cysteine analogue.

In a further example, the linker may consist of two Chem. 2 elements, such as two Chem. 2a elements, two Chem. 3a elements, and one Chem. 4 element, interconnected via amide bonds and in the sequence indicated. The Chem. 2 element being connected at there *—NH end to the CO—* end of the protractor, and the Chem4 at its $CH_2$—* end to the sulfur atom of the Cys residue of the FGF21 protein.

In one embodiment the linker is connected to the thiol group of the cys in position 167, 169, 170, 171, 172, 173, 173, 174, 175, 180 or 181 of the FGF21 protein. In further embodiments the linker is connected to the sulfur atom of the Cys in position 180 or 181.

Needless to say, just for the sake of good order: The phrase "in the sequence indicated" means, that the *—NH end of the first-mentioned linker element (here the Chem. 2) is connected to the CO—* end of the protractor, and the CO—* end of the last-mentioned linker element (here Chem. 4) is connected to the thiol group of the Cys residue in question of the FGF21 protein.

In one embodiment the derivative of the invention is selected from the groups consisting of:
  a. Compound 13-24
  b. Compound 35-41 and/or
  c. Compound 43-56.

In a further embodiment the derivative is selected from compound 13-24.

In one embodiment the derivative is selected from compound 13-18. In one embodiment the derivative is selected from compound 20-24.

In one embodiment the derivative is selected from compound 35-41.

In one embodiment the derivative is selected from compound 43-56. In one embodiment the derivative is selected from compound 43-44 and 46-54. In one embodiment the derivative is selected from compound 44, 47 and 50-54.

Instead of Chem. 4, a maleimide derived linker element can be used where p and q may vary between 1 and 5:

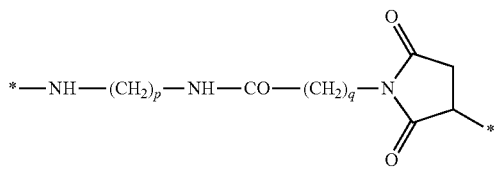

When p=q=2 the structure of this linker element corresponds to N-(2-aminoethyl)-3-(-2,5-dioxo-pyrrolidin-1-yl)propanamide:

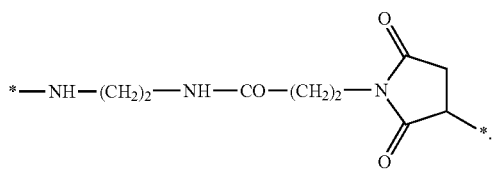

The derivatives of the invention may exist in different stereo-isomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

Functional Properties

The FGF21 derivatives of the invention are biologically active. For example they are very potent, and, also or alternatively, they bind very well to FGF receptors. Also, or alternatively, they have a protracted pharmacokinetic profile. For example they have a very long terminal half-life when administered i.v. to mice and/or mini pigs. The particular combination of good potency and long half-life may be highly desirable.

Also, or alternatively, it is surprising that FGF21 derivatives comprising a side chain of the invention in a position corresponding to one of positions 167, 169, 170, 171, 172, 173, 173, 174, 175, 180 and 181 of mature human FGF21 have high potency.

According to a first aspect, the FGF21 derivatives have FGF21 activity. For example, the FGF21 derivatives of the invention have a surprisingly good potency towards human FGF receptors.

In a first particular embodiment, potency and/or activity refer to in vitro potency, i.e. performance in a functional FGF receptor assay, more in particular to the capability of activating human FGF receptors.

The in vitro potency may, e.g., be determined in an assay with whole cells expressing human FGF receptors (FGFR1c, FGFR2c or FGFR3c) and BKL. For example, the response of the human FGF receptors may be measured using HEK (Human Embryonic Kidney cells) overexpressing human beta-klotho (BKL). HEK293 cells endogenously express several FGF receptors, including FGFR1c and FGFR3c. These cells are unresponsive to FGF21 until transfected with the co-receptor BKL. Activation of the FGF receptor/BKL complex leads to activation of the MAPK/ERK signalling pathway and phosphorylation of ERK. The level of phosphorylated ERK (pERK) at a given time point increases with increasing concentrations of FGF21. One non-limiting example of such an assay is described in Example 6.

The in vitro potency may also be determined in an assay with mouse 3T3-L1 adipocytes. For example, the FGF21 analogues and derivatives can be tested for their ability to increase glucose uptake into adipocytes. Differentiated 3T3-L1 adipocytes endogenously express FGFR1c and BKL. The 3T3-L1 cells are unresponsive to FGF21 until after differentiated as differentiation lead to expression of the co-receptor BKL. Activation of the FGFR1c receptor/BKL complex increase the expression of glucose transporter 1 (GLUT1) and therefore FGF21 analogues will lead to increased amount of glucose taken into the adipocytes in a dose responsive manner.

The EC50 value is commonly used as a measure of potency of a drug. It refers to the concentration of the compound in question which induces a response halfway between the baseline and maximum, by reference to the dose-response curve. Popularly speaking EC50 represents the concentration where 50% of the maximal effect is observed. The in vitro potency of the derivatives of the invention may be determined as described above, and the EC50 of the derivative in question determined. The lower the EC50 value, the better the potency.

As a non-limiting example, the FGF21 derivative of the invention has a potency measured using HEK293 cells overexpressing human beta-klotho corresponding to an EC50 at 0% HSA of below 60 nM, preferably below 20 nM, or more preferably below 10 nM (e.g. determined as described in Example 6).

As a non-limiting example, the FGF21 derivative of the invention has a potency measured using glucose uptake in 3T3-L1 adipocytes corresponding to an EC50 of below 60 nM, preferably below 20 nM, or more preferably below 10 nM (e.g. determined as described in Example 7).

As a non-limiting example, the FGF21 derivative of the invention has an efficacy Emax measured using glucose uptake in 3T3-L1 adipocytes of at least 50%, preferably at least 80%, or more preferably at least 90% (e.g. determined as described in Example 7).

As a non-limiting example, the FGF21 derivative of the invention has a potency measured using glucose uptake in 3T3-L1 adipocytes corresponding to an EC50 of below 60 nM, preferably below 20 nM, or more preferably below 10 nM (e.g. determined as described in Example 7) and an efficacy Emax measured using glucose uptake in 3T3-L1 adipocytes of at least 80%, or more preferably at least 90% (e.g. determined as described in Example 7).

In a second particular embodiment, potency and/or activity refer to in vivo potency. The proteins and derivatives of the invention are potent in vivo, which may be determined as is known in the art in any suitable animal model, as well as in clinical trials.

It has previously been shown that the weight loss induced by FGF21 in lean mice is predictive of the effect in obese mice and therefore lean mice are considered a good screening model. Lean C57BL mice is one example of a suitable animal model, and the body weight lowering effect may be determined in such mice in vivo (determined, e.g., as described in Example 9).

According to a second aspect, the derivatives of the invention are protracted. Protraction may be estimated in vitro, and/or determined from pharmacokinetic in vivo studies. An increase of the in vitro potency, EC50 value, in the presence of serum albumin indicates an affinity to serum albumin and represents a method to predict a protracted pharmacokinetic profile of the test substance in animal models. Protraction may be determined, e.g., as terminal half-life (t ½) after i.v. administration to, e.g., mice or mini pigs.

As a non-limiting example, the derivative of the invention has a terminal half-life after i.v. administration to mice of at least 1 hour, more preferably at least 3 hours, or most preferably at least 10 hours (determined, e.g., as described in Example 8).

As another non-limiting example, the derivative of the invention has a terminal half-life after i.v. administration to mini pigs of at least 2 hours, more preferably at least 10 hours, even more preferably at least 20 hours or most preferably at least 50 hours (determined, e.g., as described in Example 8).

According to a third aspect, the derivatives of the invention are protracted and at the same time have a very good potency. The particular combination of good potency/binding and long half-life may be highly desirable.

According to a fourth aspect, the derivatives of the invention have good biophysical properties. These properties include but are not limited to physical stability and/or solubility. These and other biophysical properties may be measured using standard methods known in the art of protein chemistry. In a particular embodiment, these properties are improved as compared to mature human FGF21.

Additional particular embodiments of the derivatives of the invention are described in the sections headed "PARTICULAR EMBODIMENTS" before the experimental section.

Production and Purification of FGF21 Compound

The production of proteins, e.g., FGF21, is well known in the art. FGF21 analogues may be produced by a method which comprises culturing a host cell containing a DNA sequence encoding the molecule and capable of expressing FGF21 analogues in a suitable nutrient medium under conditions permitting the expression of the FGF21 analogue. Several recombinant methods may be used in the production of FGF21 and analogues thereof. Examples of methods which may be used in the production of FGF21 in microorganisms such as, e.g., *Escherichia coli* and *Saccharomyces cerevisiae* are, e.g., disclosed in WO12010553.

Specific examples of methods of preparing a number of the derivatives of the invention are included in the experimental part. In short, the FGF21 analogues are derivatized at the cysteine residue by alkylation. Thiol reactive side chains, such as side chains prepared with a haloacetamide may thus be reacted with the FGF21 analogue. The FGF analogue may be prepared with a cystamine protecting the thiol group of the cysteine. If so the analogue is reduced with e.g. a reducing agent such as a phosphine prior to reacting the analogue with the thiol reactive side chain.

The FGF21 analogues and derivatives of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989).

Mode of Administration

The term "treatment" is meant to include both the prevention and minimization of the referenced disease, disorder, or condition (i.e., "treatment" refers to both prophylactic and therapeutic administration of the FGF21 derivatives of the invention or composition comprising the FGF21 derivatives of the invention) unless otherwise indicated or clearly contradicted by context.

The route of administration may be any route which effectively transports a compound of this invention to the desired or appropriate place in the body, such as parenteral, for example, subcutaneous, intramuscular or intravenous. Alternatively, a compound of this invention can be administered orally, pulmonary, rectally, transdermally, buccally, sublingually, or nasally.

Pharmaceutical Compositions

Pharmaceutical compositions comprising a derivative of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19$^{th}$ edition (1995), and any later editions).

Injectable compositions comprising FGF21 compounds of the present invention can be prepared using the conventional techniques of the pharmaceutical industry which involve dissolving and mixing the ingredients as appropriate to give the desired end product. Thus, according to one procedure, a FGF21 compound of this invention is dissolved in a suitable buffer at a suitable pH so precipitation is minimised or avoided. The injectable composition is made sterile, for example, by sterile filtration. Antimicrobial agents may also be added to the composition.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to physical state and changes hereof without altering covalent bonds and hence the tendency of the protein to form biologically inactive and/or insoluble aggregates and/or fibrillates as a result of exposure to thermo-mechanical stress, and/or interaction with destabilising interfaces and surfaces (such as hydrophobic surfaces). The physical stability of an aqueous protein formulation may be evaluated by means of visual inspection, and/or by turbidity measurements and/or by concentration measurements after exposure to mechanical/physical stress (e.g. agitation) at different temperatures for various time periods. Alternatively, the physical stability may be evaluated using a spectroscopic agent or probe of the conformational status of the protein such as e.g. Thioflavin T or "hydrophobic patch" probes.

The term "chemical stability" refers to chemical (in particular covalent) changes of covalent bonds in the protein structure leading to formation of chemical degradation products potentially having a reduced biological potency, and/or increased immunogenic effect as compared to the intact protein. The chemical stability can be evaluated by measuring the amount of chemical degradation products at various time-points after exposure to different environmental conditions, e.g. by SEC-HPLC, RP-HPLC, LCMS, and/or peptide mapping.

In one aspect, the invention provides FGF21 derivatives with improved physical stability. In one aspect, the invention provides FGF21 derivatives with improved chemical stability.

Combination Treatment

The treatment with a FGF21 derivative according to the present invention may also be combined with one or more additional pharmacologically active substances, e.g. selected from anti-diabetic agents, anti-obesity agents, appetite regulating agents, antihypertensive agents, agents for the treatment and/or prevention of complications resulting from or associated with diabetes and agents for the treatment and/or prevention of complications and disorders resulting from or associated with obesity.

Examples of these pharmacologically active substances are: GLP-1 receptor agonists, insulin, DPP-IV (dipeptidyl peptidase-IV) inhibitors, amylin agonists and leptin receptor agonists.

Pharmaceutical Indications

The present invention also relates to a derivative of the invention, for use as a medicament.

In particular embodiments, the derivative of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of eating disorders, such as obesity, e.g. by decreasing food intake, increasing energy expenditure, reducing body weight, suppressing appetite, inducing satiety; treating or preventing binge eating disorder, bulimia nervosa, and/or obesity induced by administration of an antipsychotic or a steroid; and/or prevention and/or treatment of comorbidities to obesity, such as osteoarthritis and/or urine incontinence;

(v) prevention and/or treatment of diabetic complications, such as nephropathy;

(vi) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(vii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(viii) prevention and/or treatment of hepatic steatosis and non-alcoholic fatty liver disease (NAFLD); and/or (ix) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation.

In a particular embodiment the indication is selected from the group consisting of (i)-(vii). In another particular embodiment, the indication is selected from the group consisting of (i), (iv), (vi) and/or (vii). The following indications are particularly preferred: Type 2 diabetes, and/or obesity. In one embodiment the compounds of the invention are for treatment of Type 2 diabetes. In one embodiment the compounds of the invention are for treatment of obesity.

Particular Embodiments

The following are particular embodiments of the invention:

1. A derivative of a FGF21 protein,
wherein said protein comprises a Cys residue at a position corresponding to position 167, 169, 170, 171, 172, 173, 174, 175, 180 or position 181 of mature human FGF21 (SEQ ID NO:1)
wherein said derivative comprises a protractor attached to said Cys residue via a linker;
wherein the protractor is selected from the group of HOOC—(CH$_2$)$_x$—CO—*,      Chem. 1A:

HOOC-benzene-O—(CH$_2$)$_x$—CO—* and      Chem. 1B:

HO—S(=O)$_2$—(CH$_2$)$_x$CO—*      Chem. 1C:

wherein x is an integer in the range of 8-18; and
wherein the linker comprises at least one of each of Chem. 2, Chem. 3 and Chem. 4:
wherein Chem. 2 is selected from:

*—NH—CH(COOH)—(CH$_2$)$_m$—CO—*,

*—NH—S(=O)$_2$—(CH$_2$)$_m$—CO—* and

*—NH—(CH$_2$)$_m$-cyclohexane-CO—*, wherein m is an integer in the range of 1-5,
wherein Chem. 3 is *—NH—(CH$_2$)$_2$—[O—(CH$_2$)$_2$]$_k$—O—[CH$_2$]$_n$—CO—*, wherein k is an integer in the range of 1-5 and n is an integer in the range of 1-5, and
wherein Chem. 4: is selected from

*—NH—(CH$_2$)$_m$—NH—CO—CH$_2$—* and

*—NH—CH(COOH)—(H$_2$)$_m$—NH—CO—CH$_2$—* wherein m is an integer in the range of 1-5; and wherein Chem. 2, Chem. 3, and Chem. 4 are interconnected via amide bonds and in the sequence indicated, connected at its *—NH end to the CO—* end of the protractor, and at its CH2-* end to the sulfur atom of the Cys residue at a position corresponding to position 167, 169, 170, 171, 172, 173, 174, 175, 180 or position 181 of mature human FGF21 (SEQ ID NO:1), or a pharmaceutically acceptable salt, amide, or ester thereof.

2. The derivative according to embodiment 1, wherein said protein comprises a Cys residue at position 170, 171, 172, 173, 174, 175, 180 or position 181.

3. The derivative according to embodiment 1, wherein said protein comprises a Cys residue at position 170, 173, 174, 175, 180 or position 181.

4. The derivative according to any of the previous embodiments, wherein Chem. 2 is selected from the group of:

*—NH—CH(COOH)—(CH$_2$)$_2$—CO—*,      Chem. 2a:

*—NH—S(=O)$_2$—(CH$_2$)$_3$—CO—* and      Chem. 2b:

*—NH—CH$_2$-cyclohexane-CO—*.      Chem. 2c:

5. The derivative according to embodiment 1, wherein Chem. 4 is selected from:

*—NH—(CH$_2$)$_2$—NH—CO—CH$_2$—*.      Chem. 4a:

*—NH—CH(COOH)—(CH$_2$)$_4$—NH—CO—CH$_2$—*.      Chem. 4b:

6. A derivative of a FGF21 protein, wherein said protein comprises a Cys residue at a position corresponding to position 180 or position 181 of mature human FGF21 (SEQ ID NO:1), and a maximum of 30 amino acid modifications as compared to mature human FGF21 (SEQ ID NO:1);
wherein said derivative comprises a protractor attached to said Cys residue via a linker;
wherein the protractor is selected from the group of HOOC—(CH$_2$)$_x$—CO—*,      Chem. 1A:

wherein x is an integer in the range of 10-18,

HOOC-benzene-O—(CH$_2$)$_x$      Chem. 1B:

wherein x is an integer in the range of 8-18, and

HO—S(=O)$_2$—(CH$_2$)$_x$      Chem. 1C;

wherein x is an integer in the range of 10-18,
wherein the linker comprises at least one of each of Chem. 2, Chem. 3 and Chem. 4:

*—NH—CH(COOH)—(CH$_2$)$_2$—CO—*,      Chem. 2:

*—NH—(CH$_2$)$_2$—[O—(CH$_2$)$_2$]$_k$—O—[CH$_2$]$_n$—CO—*, and      Chem. 3:

*—NH—(CH$_2$)$_m$—NH—CO—CH$_2$—*,      Chem. 4:

wherein k is an integer in the range of 1-5, n is an integer in the range of 1-5, and m is an integer in the range of 1-5;
and
wherein Chem. 2, Chem. 3, and Chem. 4 are interconnected via amide bonds and in the sequence indicated, connected at its *—NH end to the CO—* end of the protractor, and at its —CH$_2$-* end to the sulfur atom of the Cys residue at a position corresponding to position 180 or position 181 of mature human FGF21 (SEQ ID NO:1), or a pharmaceutically acceptable salt, amide, or ester thereof.

7. The derivative according to any of the previous embodiments, wherein Chem. 1 is selected from the group of:

HOOC—(CH$_2$)$_{16}$—CO—*,      Chem. 1a:

HOOC-benzene-O—(CH$_2$)$_9$—CO—* and      Chem. 1b:

HO—S(=O)$_2$—(CH$_2$)$_{15}$—CO—*      Chem. 1c:

8. A derivative of a FGF21 protein,
wherein said protein comprises a Cys residue at a position corresponding to position 180 or position 181 of mature human FGF21 (SEQ ID NO:1), wherein said derivative comprises a protractor attached to said Cys residue via a linker;
wherein the protractor is HOOC—(CH$_2$)$_x$—CO—*,      Chem. 1:

wherein x is an integer in the range of 10-18; and wherein the linker comprises at least one of each of Chem. 2, Chem. 3 and Chem. 4:

*—NH—CH(COOH)—(CH$_2$)$_2$—CO—*,      Chem. 2:

*—NH—(CH$_2$)$_2$—[O—(CH$_2$)$_2$]$_k$—O—[CH$_2$]$_n$—CO—*, and      Chem. 3:

*—NH—(CH$_2$)$_m$—NH—CO—CH$_2$—*,      Chem. 4:

wherein k is an integer in the range of 1-5, n is an integer in the range of 1-5, and m is an integer in the range of 1-5;
wherein Chem. 2, Chem. 3, and Chem. 4 are interconnected via amide bonds and in the sequence indicated, connected at its *—NH end to the CO—* end of the protractor, and at its CH$_2$—* end to the sulfur atom of the Cys residue at a position corresponding to position 180 or position 181 of mature human FGF21 (SEQ ID NO:1), or a pharmaceutically acceptable salt, amide, or ester thereof.

9. A derivative of a FGF21 protein,
wherein said protein comprises a Cys residue at a position corresponding to position 180 or position 181 of mature human FGF21 (SEQ ID NO:1), and a maximum of 30 amino acid modifications as compared to mature human FGF21 (SEQ ID NO:1);
wherein said derivative comprises a protractor attached to said Cys residue via a linker;
wherein the protractor is $$HOOC-(CH_2)_x-CO-*, \quad \text{Chem. 1:}$$

wherein x is an integer in the range of 10-18; and
wherein the linker comprises at least one of each of Chem. 2, Chem. 3 and Chem. 4:

$$*-NH-CH(COOH)-(CH_2)_2-CO-*, \quad \text{Chem. 2:}$$

$$*-NH-(CH_2)_2-[O-(CH_2)_2]_k-O-[CH_2]_n-CO-*, \text{ and} \quad \text{Chem. 3:}$$

$$*-NH-(CH_2)_m-NH-CO-CH_2-*, \quad \text{Chem. 4:}$$

wherein k is an integer in the range of 1-5, n is an integer in the range of 1-5, and m is an integer in the range of 1-5;
wherein Chem. 2, Chem. 3, and Chem. 4 are interconnected via amide bonds and in the sequence indicated, connected at its *—NH end to the CO—* end of the protractor, and at its $CH_2$—* end to the thiol group of the Cys residue at a position corresponding to position 180 or position 181 of mature human FGF21 (SEQ ID NO:1), or a pharmaceutically acceptable salt, amide, or ester thereof.

10. The derivative according to any of the preceding embodiments, wherein said protein comprises a Cys residue at the position corresponding to position 180 of mature human FGF21 (SEQ ID NO:1).

11. The derivative according to any one of the preceding embodiments, wherein said protein has a maximum of 30, such as 25, such as 20, such as 15, such as 10, such as 8, such as a maximum of 5 amino acid modifications as compared to mature human FGF21 (SEQ ID NO:1).

12. The derivative according to any one of the preceding embodiments, wherein said protein has 4 or 5 amino acid modifications as compared to mature human FGF21 (SEQ ID NO:1).

13. The derivative according to any one of the preceding embodiments, wherein said protein has 4 amino acid modifications as compared to mature human FGF21 (SEQ ID NO:1).

14 The derivative according to any one of the preceding embodiments, wherein said FGF protein has at least 80%, such as 85%, such as 90%, such as 95% identity to mature human FGF21 (SEQ ID NO:1).

15 The derivative according to any one of the preceding embodiments, wherein said FGF protein has at least 96%, such as 97%, such as 98%, such as 99% identity to mature human FGF21 (SEQ ID NO:1).

16. The derivative according to any one of the preceding embodiments, wherein the amino acid changes are at one or more of positions corresponding to one or more of positions 121, 168, 180, or 181 of mature human FGF21 (SEQ ID NO:1).

17. The derivative according to any one of the preceding embodiments, wherein one of the amino acid changes is the addition of an Ala residue at a position corresponding to the N-terminal of mature human FGF21 (SEQ ID NO:1).

18. The derivative according to any one of the preceding embodiments, wherein the protein comprises an Ala in the N-terminal end of said protein.

19. The derivative according to any one of the preceding embodiments, wherein the protein comprises 121Q.

20. The derivative according to any one of the preceding embodiments, wherein the protein comprises 168L.

21. The derivative according to any one of the preceding embodiments, wherein the protein comprises the amino acid sequence of SEQ ID NO:8 or 10.

22. The derivative according to any one of the preceding embodiments, wherein the protein has the amino acid sequence of SEQ ID NO: 8, 10, 12, 15, 16, 17, 18, 19 or 20.

23. The derivative according to any one of the preceding embodiments, wherein Chem. 1 is 1A or 1C and x is an integer in the range of 12-18.

24. The derivative according to any one of the preceding embodiments, wherein Chem. 1 is 1A or 1C and x is an integer in the range of 14-16.

25. The derivative according to any one of the preceding embodiments, wherein Chem. 1 is 1B and x is an integer in the range of 8-12.

26. The derivative according to any one of the preceding embodiments, wherein x is 16.

27. The derivative according to any one of the preceding embodiments, wherein k is an integer in the range of 1-2.

28. The derivative according to any one of the preceding embodiments, wherein k is 1.

29. The derivative according to any one of the preceding embodiments, wherein n is an integer in the range of 1-2.

30. The derivative according to any one of the preceding embodiments, wherein n is 1.

31. The derivative according to any one of the preceding embodiments, wherein m of Chem. 4 is an integer in the range of 1-5.

32. The derivative according to any one of the preceding embodiments, wherein m of Chem4 is 2.

33. The derivative according to any one of the preceding embodiments, wherein the protractor comprises Chem. 1a: $HOOC-(CH_2)_{16}-CO-*$.

34. The derivative according to any one of the preceding embodiments, wherein the protractor consists of Chem. 1a: $HOOC-(CH_2)_{14}-CO-*$.

35. The derivative according to any one of the preceding embodiments, wherein the linker comprises Chem. 3a: $*-NH-(CH_2)_2-O-(CH_2)_2-O-CH-CO-*$ 36. The derivative according to any one of the preceding embodiments, wherein the linker comprises Chem. 4a: $*-NH-(CH_2)_2-NH-CO-CH_2-*$ 37. The derivative according to any one of the preceding embodiments, wherein the linker consists of at least one Chem. 2 element, two Chem. 3 elements, and one Chem. 4 element.

38 The derivative according to any one of the preceding embodiments, wherein the linker consists of one Chem. 2 element, two Chem. 3 elements, and one Chem. 4 element.

39 The derivative according to any one of the preceding embodiments, wherein the linker consists of two Chem. 2 element, two Chem. 3 elements, and one Chem. 4 element.

40. The derivative according to any one of the preceding embodiments, wherein the linker consists of one Chem. 2 element, two Chem. 3a elements, and one Chem. 4a element.

41. The derivative according to any one of the preceding embodiments, wherein the derivative is one of the following:

S{Beta-180}-[2-[2-[[2-[2-[2-[[2-[2-[2-[[(4S)-4-carboxy-4-(11-carboxyundecanoyl-amino)butanoyl]amino]ethoxy]ethoxy]acetyl]amino]ethoxy]ethoxy]acetyl]amino]-ethyl-amino]-2-oxoethyl]-Ala[Gln121,Leu168,Cys180]FGF21 (Compound 13)

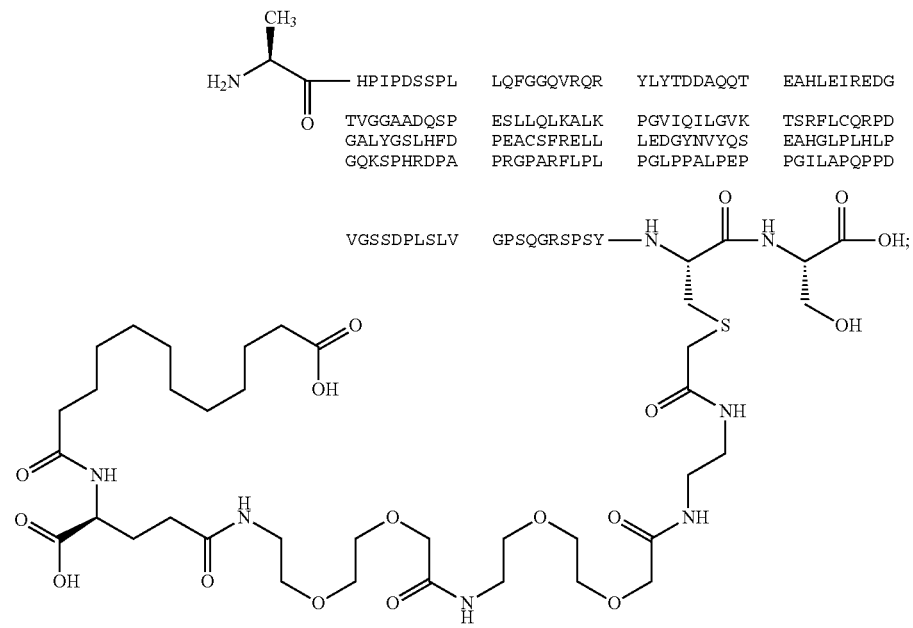

S{Beta-180}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethyl-amino]-2-oxoethyl]-Ala[Gln121,Leu168,Cys180]FGF21 (Compound 14)

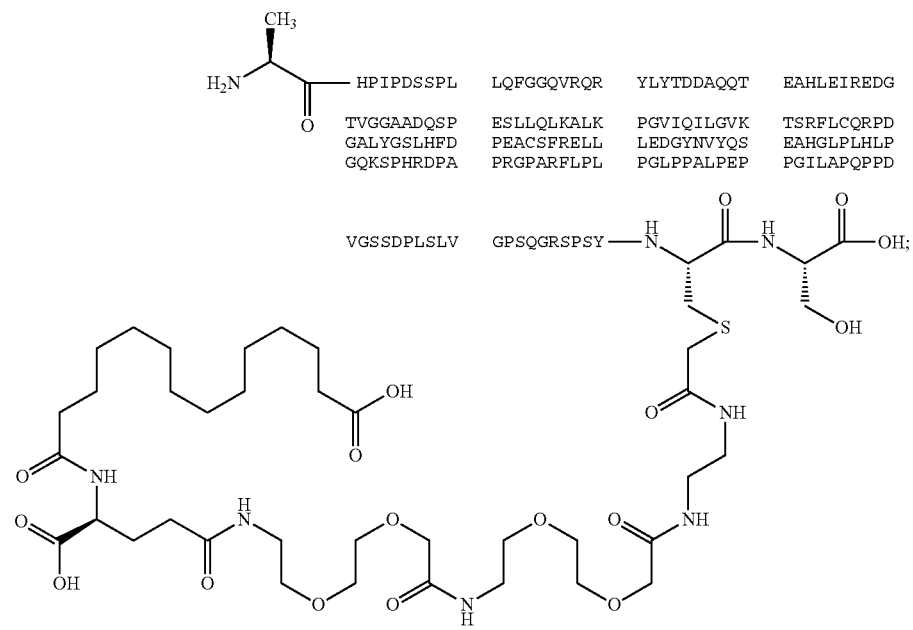

S{Beta-180}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 15)
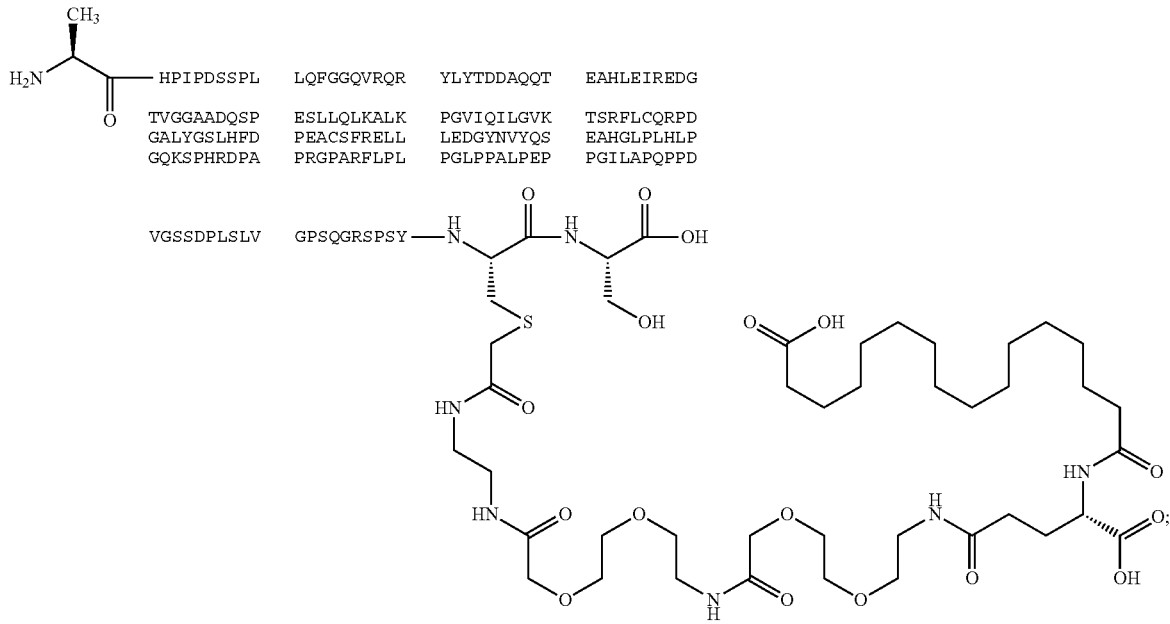
S{Beta-180}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys180]FGF21 (Compound 16)
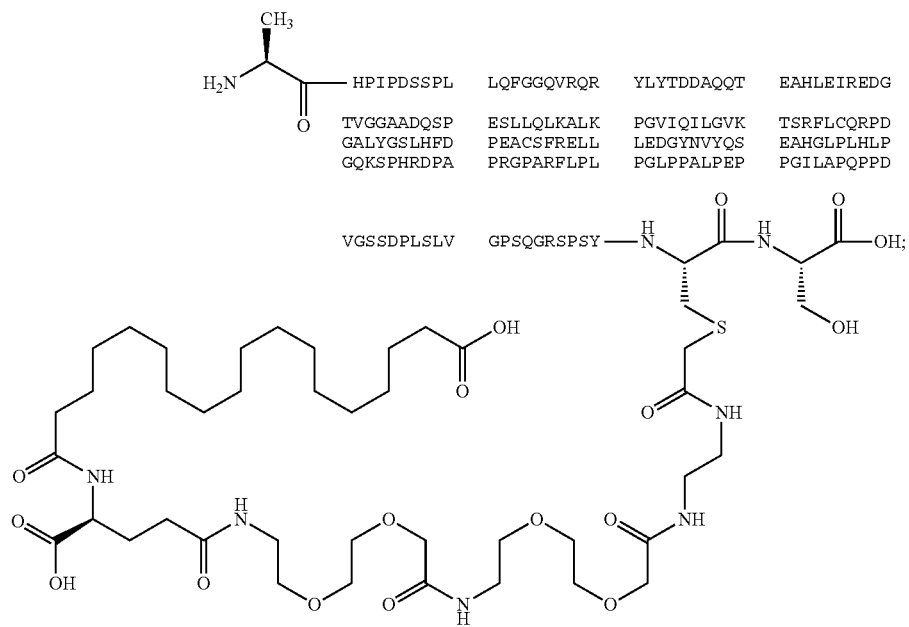

S{Beta-180}-[2-[2-[[2-[2-[2-[[2-[2-[2-[[(4S)-4-carboxy-4-(19-carboxynonadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 17)
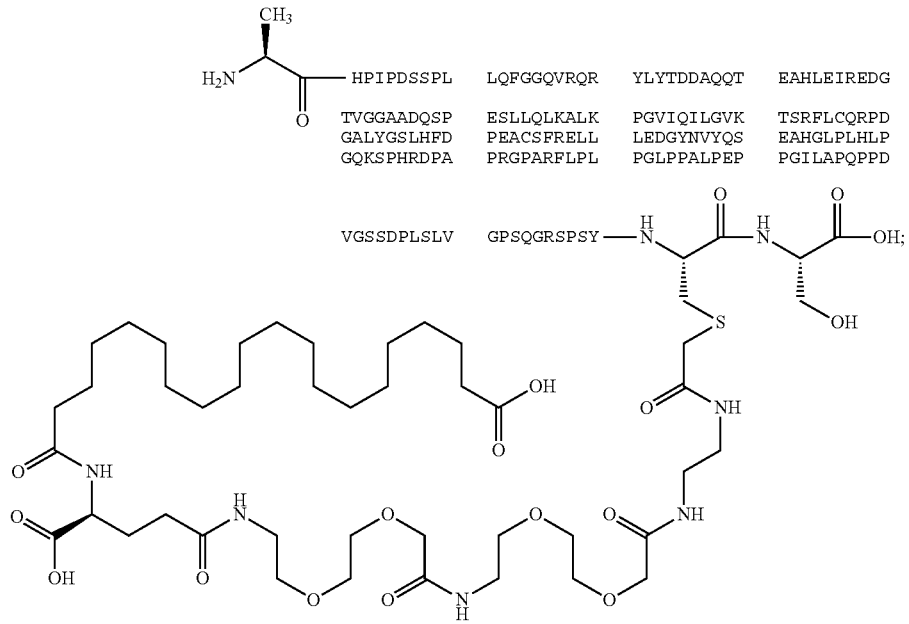
S{Beta-180}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180,des181]FGF21 (Compound 18)
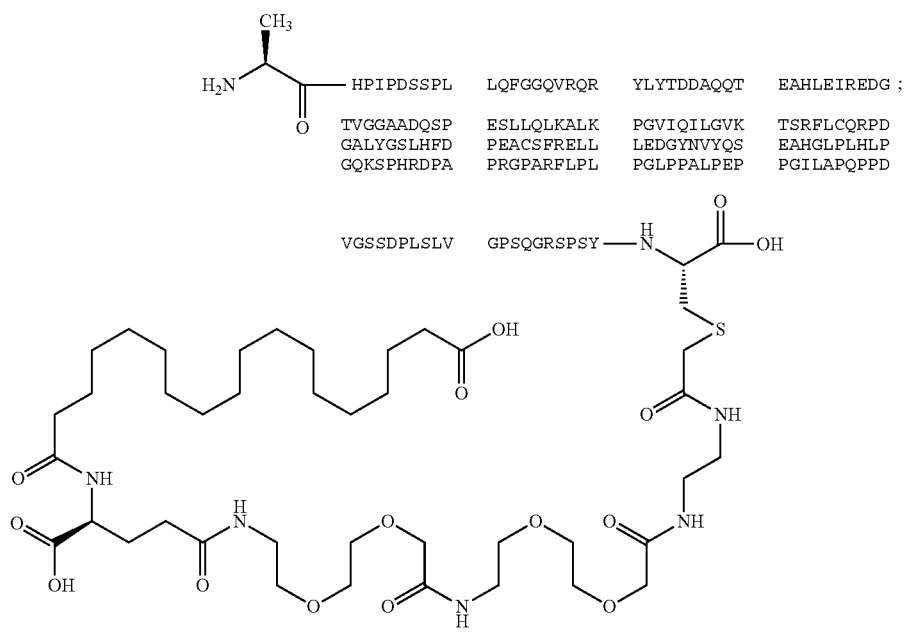

S{Beta-181}-[2-[2-[[2-[2-[2-[[2-[2-[2-[[(4S)-4-carboxy-4-(11-carboxyundecanoyl-amino)butanoyl]amino]ethoxy]ethoxy]acetyl]amino]ethoxy]ethoxy]acetyl]amino]-ethyl-amino]-2-oxoethyl]-Ala[Gln121,Leu168,Cys181]FGF21 (Compound 19)
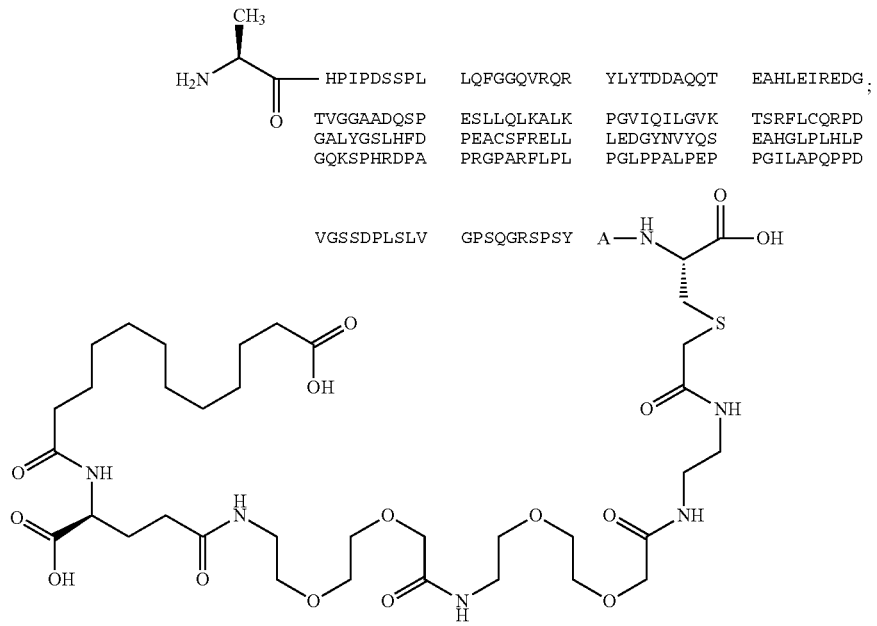
S{Beta-181}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethyl-amino]-2-oxoethyl]-Ala[Gln121,Leu168,Cys181]FGF21 (Compound 20)
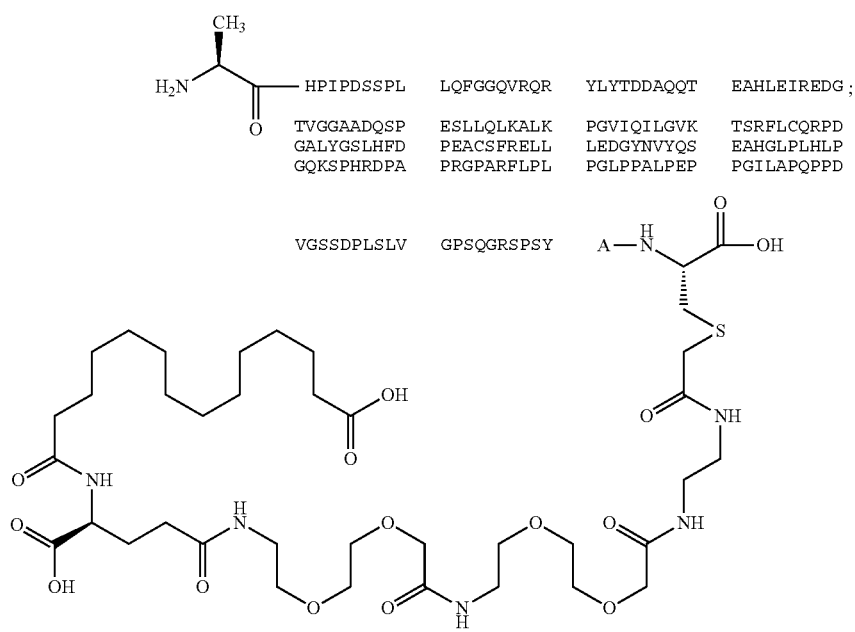

S{Beta-181}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 21)
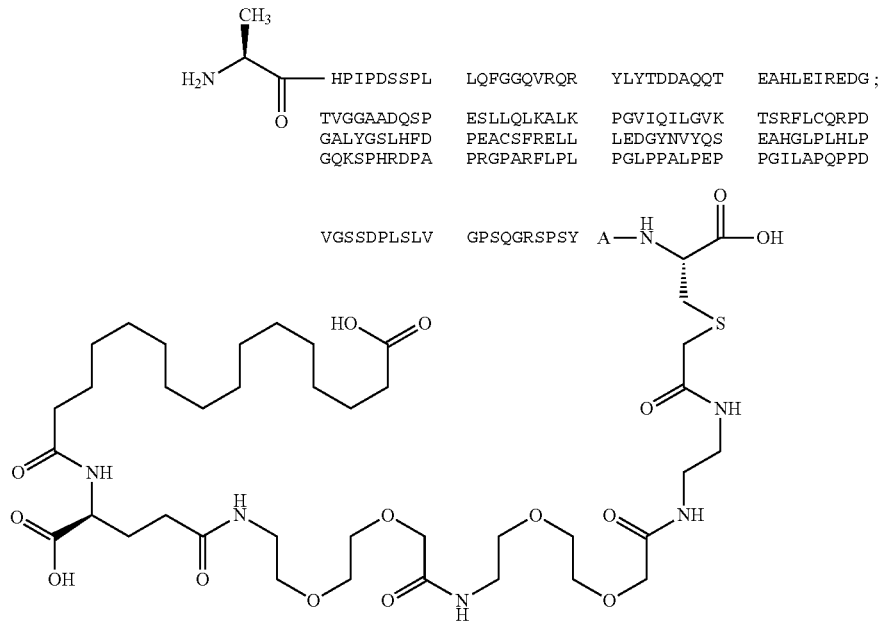
S{Beta-181}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 22)
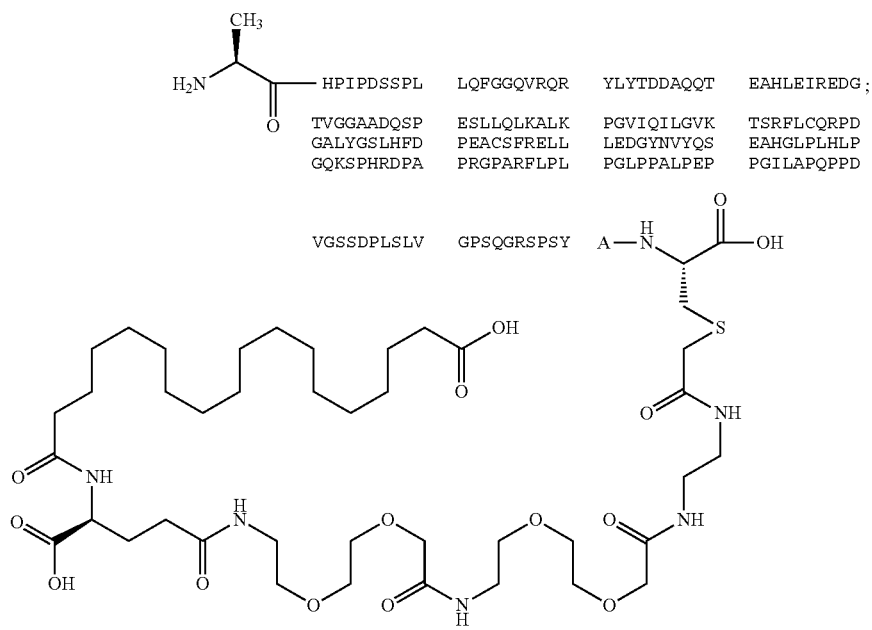

S{Beta-181}-[2-[2-[[2-[2-[2-[[2-[2-[2-[[(4S)-4-carboxy-4-(19-carboxynonadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 23)
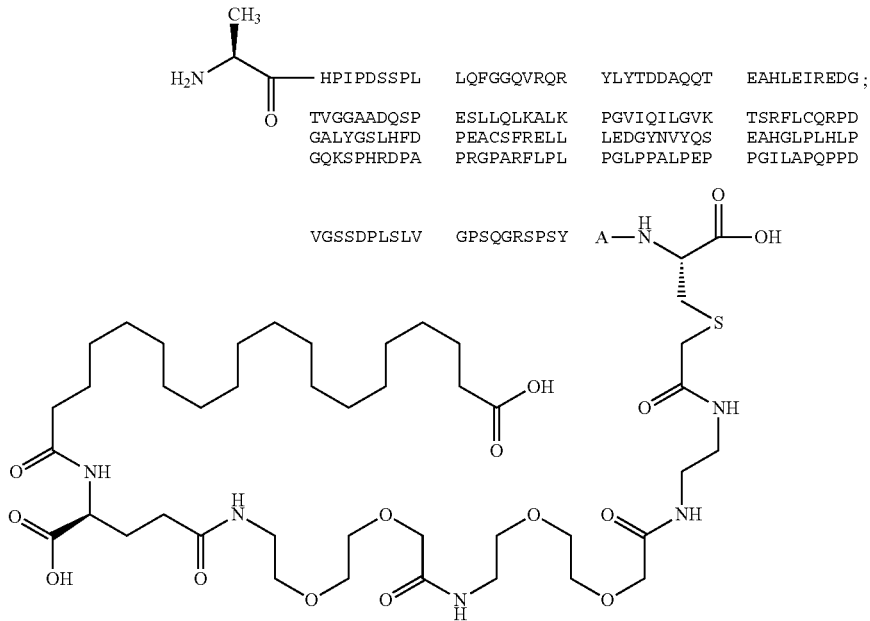
S{Beta-181}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Met[Cys181]FGF21 (Compound 24)
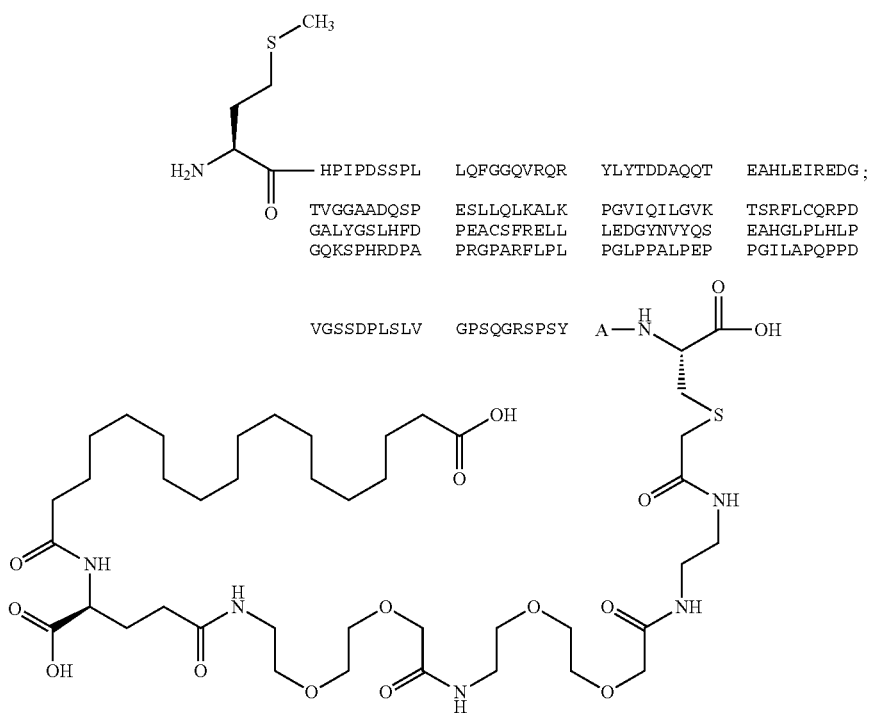

42. The derivative according to any one of the preceding embodiments, wherein the derivative is one of the following:

S{Beta-180}-[2-[2-[[2-[2-[2-[[2-[2-[2-[[(4S)-4-carboxy-4-(11-carboxyundecanoyl-amino)butanoyl]amino]ethoxy]ethoxy]acetyl]amino]ethoxy]ethoxy]acetyl]amino]-ethyl-amino]-2-oxoethyl]-Ala[Gln121,Leu168,Cys180]FGF21 (Compound 13)

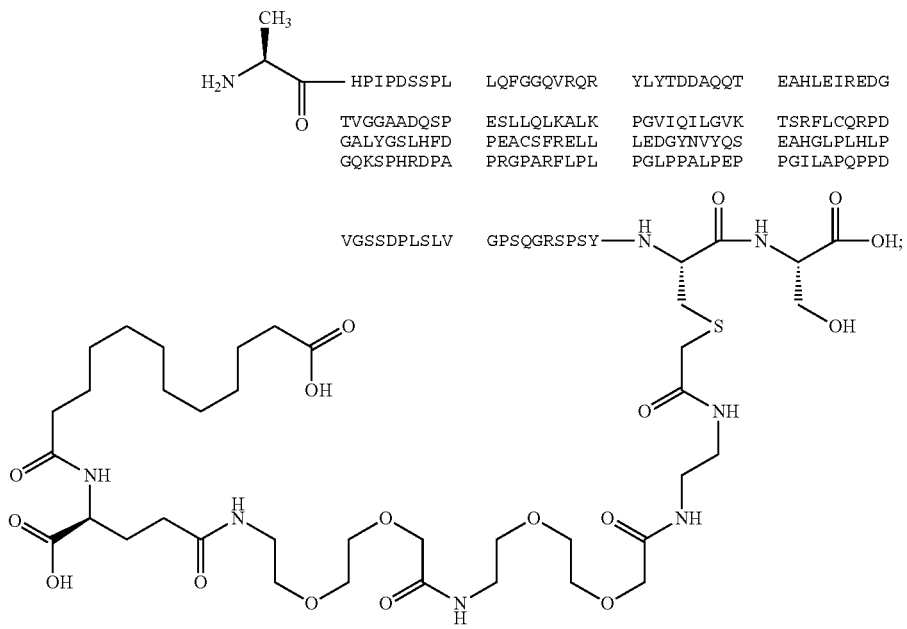

S{Beta-180}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethyl-amino]-2-oxoethyl]-Ala[Gln121,Leu168,Cys180]FGF21 (Compound 14)

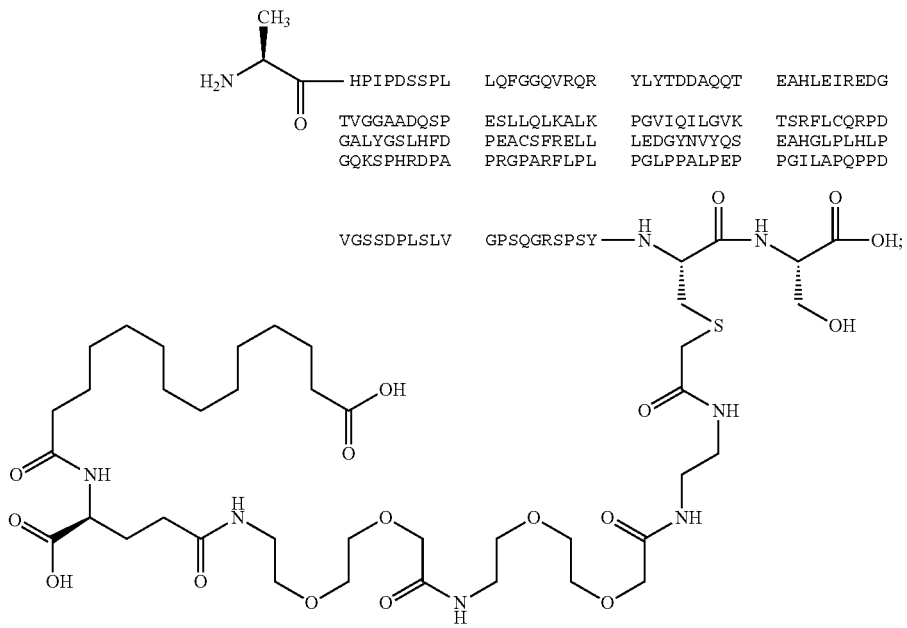

S{Beta-180}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 15)
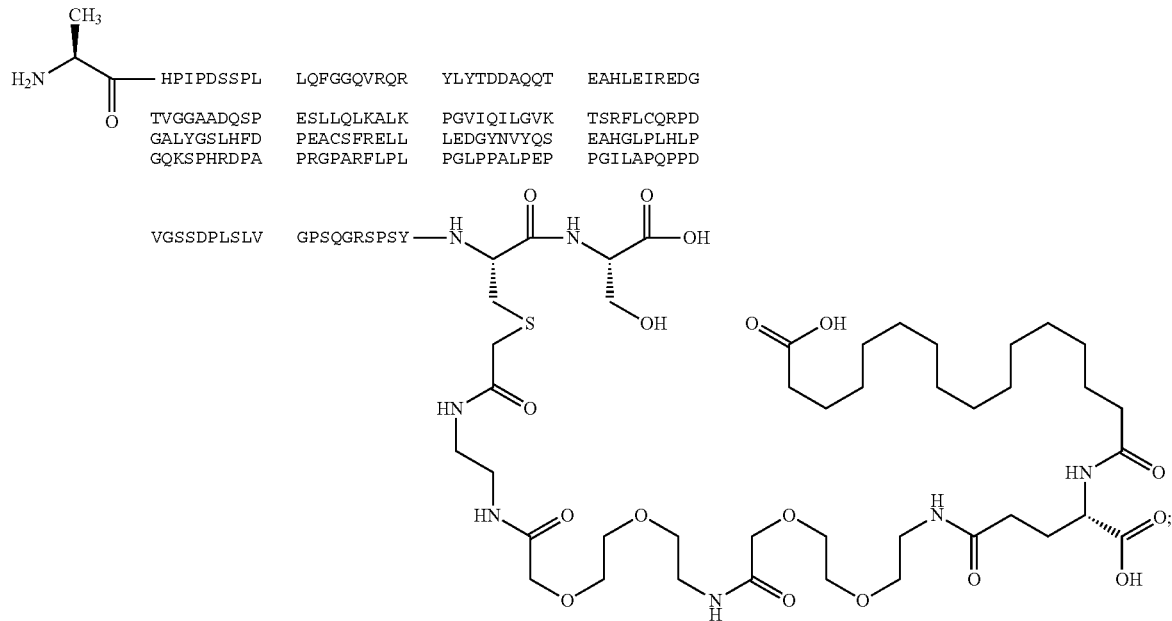
S{Beta-180}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys180]FGF21 (Compound 16)
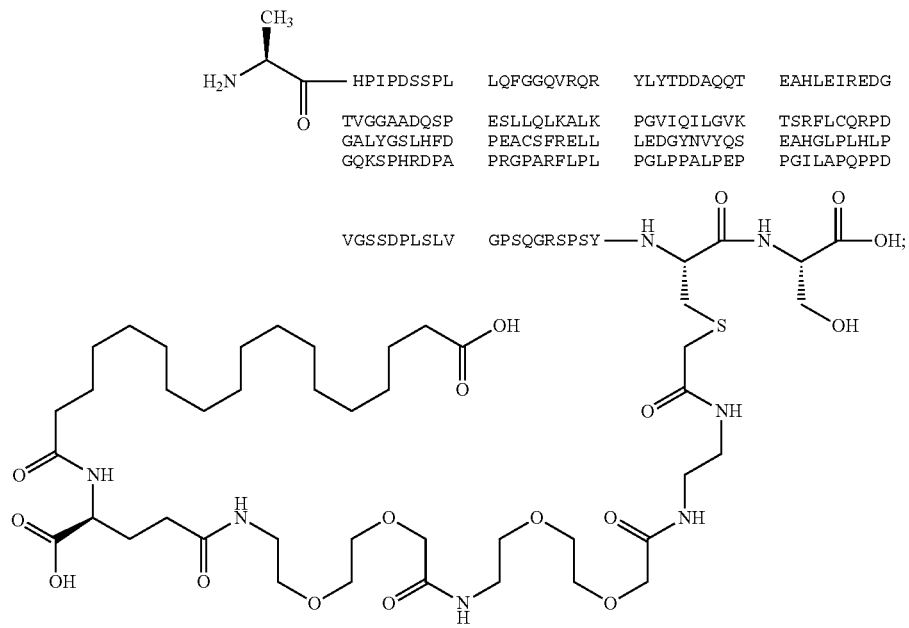

S{Beta-180}-[2-[2-[[2-[2-[2-[[2-[2-[2-[[(4S)-4-carboxy-4-(19-carboxynonadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 17)

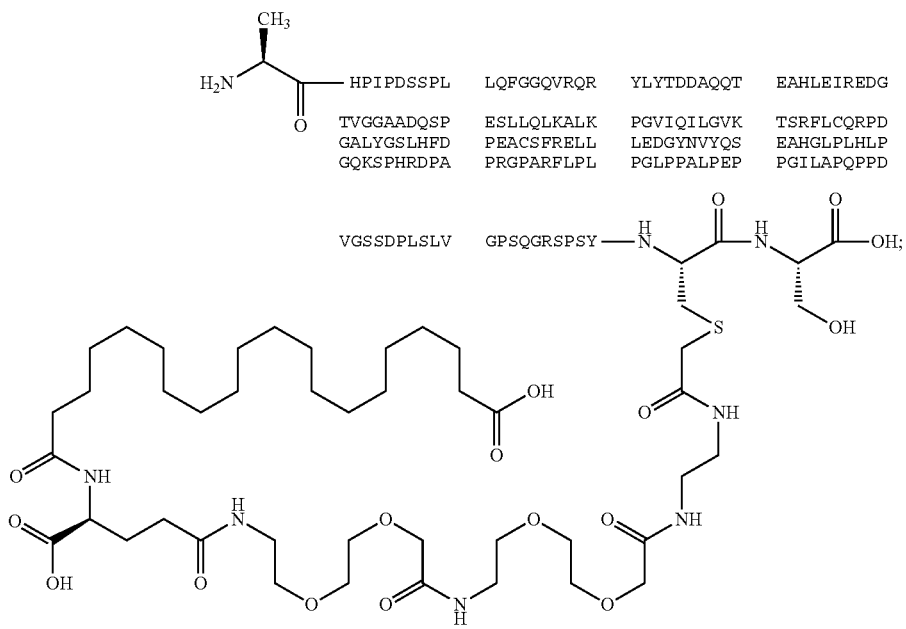

S{Beta-180}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180,des181]FGF21 (Compound 18)

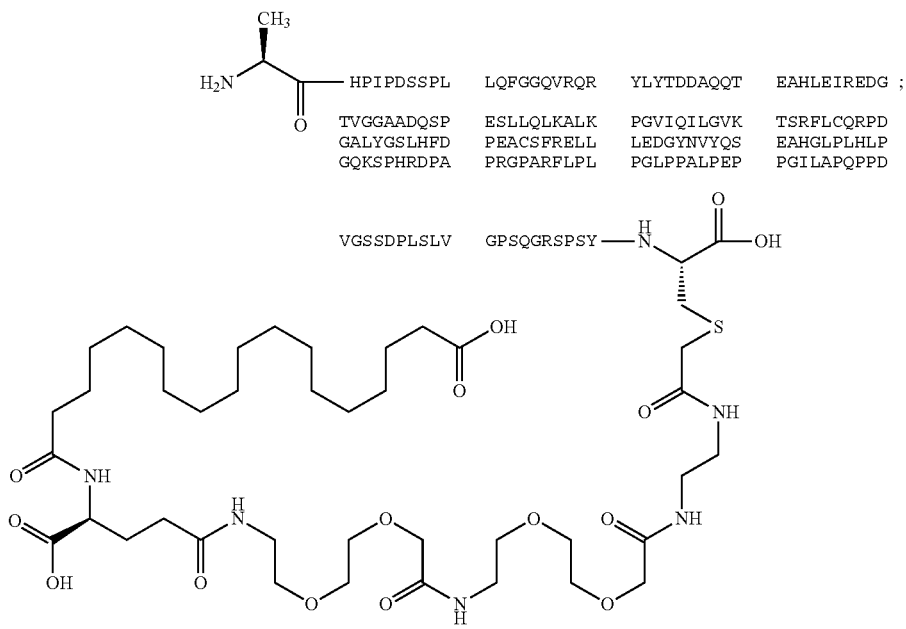

43. The derivative according to any one of the preceding embodiments, wherein the derivative is selected from the group of compound 13-24 and 43 to 56.

44. The derivative according to any one of the preceding embodiments, wherein the derivative is selected from the group of compound 35-41.

45. The derivative according to any one of the preceding embodiments, wherein the derivative is selected from the group of compound 13-24, 35-41 and 43 to 56.

46. The derivative according to any one of the preceding embodiments, wherein the derivative is Compound 13.

47. The derivative according to any one of the preceding embodiments, wherein the derivative is Compound 14.
48. The derivative according to any one of the preceding embodiments, wherein the derivative is Compound 15. The derivative according to any one of the preceding embodiments, wherein the derivative is Compound 16.
49. The derivative according to any one of the preceding embodiments, wherein the derivative is Compound 17.
50. The derivative according to any one of the preceding embodiments, wherein the derivative is Compound 18.
51. The derivative according to any one of the preceding embodiments, wherein the derivative is Compound 19.
52. The derivative according to any one of the preceding embodiments, wherein the derivative is Compound 20.
53. The derivative according to any one of the preceding embodiments, wherein the derivative is Compound 21.
54. The derivative according to any one of the preceding embodiments, wherein the derivative is Compound 22.
55. The derivative according to any one of the preceding embodiments, wherein the derivative is Compound 23.
56. The derivative according to any one of the preceding embodiments, wherein the derivative is Compound 24.
57. The derivative according to any one of the preceding embodiments, wherein the derivative is Compound 35.
58. The derivative according to any one of the preceding embodiments, wherein the derivative is Compound 36.
59. The derivative according to any one of the preceding embodiments, wherein the derivative is Compound 37.
60. The derivative according to any one of the preceding embodiments, wherein the derivative is Compound 38.
61. The derivative according to any one of the preceding embodiments, wherein the derivative is Compound 39.
62. The derivative according to any one of the preceding embodiments, wherein the derivative is Compound 40.
63. The derivative according to any one of the preceding embodiments, wherein the derivative is Compound 41.
64. The derivative according to any one of the preceding embodiments, wherein the derivative is Compound 43.
65. The derivative according to any one of the preceding embodiments, wherein the derivative is Compound 44.
66. The derivative according to any one of the preceding embodiments, wherein the derivative is Compound 45.
67. The derivative according to any one of the preceding embodiments, wherein the derivative is Compound 46.
68. The derivative according to any one of the preceding embodiments, wherein the derivative is Compound 47.
69. The derivative according to any one of the preceding embodiments, wherein the derivative is Compound 48.
70. The derivative according to any one of the preceding embodiments, wherein the derivative is Compound 49.
71. The derivative according to any one of the preceding embodiments, wherein the derivative is Compound 50.
72. The derivative according to any one of the preceding embodiments, wherein the derivative is Compound 51.
73. The derivative according to any one of the preceding embodiments, wherein the derivative is Compound 53.
74. The derivative according to any one of the preceding embodiments, wherein the derivative is Compound 54.
75. The derivative according to any one of the preceding embodiments, wherein the derivative is Compound 55.
76. The derivative according to any one of the preceding embodiments, wherein the derivative is Compound 56.
77. The derivative according to any one of the preceding embodiments, wherein the derivative has FGF21 activity.
78. The derivative according to any one of the preceding embodiments, wherein the derivative is capable of activating FGF receptors.
79. The derivative according to any one of the preceding embodiments, wherein the terminal half-life (t ½) after i.v. administration to mini pigs is at least 20 times higher than the terminal half-life (t ½) of mature human FGF21.
80. A derivative according to any one of embodiments 1-79 for use as a medicament.
81. A derivative according to any one of embodiments 1-79 for use in a method for treatment and/or prevention any one of all forms of diabetes and related diseases, such as obesity, eating disorders, cardiovascular diseases, diabetic complications; and/or for improving lipid parameters, improving 3-cell function; and/or for delaying or preventing diabetic disease progression; and/or for of treatment and/or prevention of hepatic steatosis and non-alcoholic fatty liver disease (NAFLD).
82. Use of a derivative according to any one of embodiments 1-79 in the manufacture of a medicament for the treatment and/or prevention of all forms of diabetes and related diseases, such as obesity, eating disorders, cardiovascular diseases, diabetic complications; and/or for improving lipid parameters, improving β-cell function; and/or for delaying or preventing diabetic disease progression; and/or for of treatment and/or prevention of hepatic steatosis and non-alcoholic fatty liver disease (NAFLD).
83. A method for treating or preventing all forms of diabetes and related diseases, such as obesity, eating disorders, cardiovascular diseases, diabetic complications; and/or for improving lipid parameters, improving β-cell function; and/or for delaying or preventing diabetic disease progression; and/or for of treatment and/or prevention of hepatic steatosis and non-alcoholic fatty liver disease (NAFLD) by administering a pharmaceutically active amount of a derivative according to any of embodiments 1-79.
84. An FGF21 protein comprising an amino acid substitution of a wild type amino acid by a cysteine residue in a position corresponding to one of position 167, 169, 170, 171, 172, 173, 174, 175, 180 and 181 of FGF21 (1-181) (SEQ ID NO:1).
85. The FGF21 protein according to embodiment 83, wherein the FGF21 protein comprises a Cys residue in a position corresponding to one of position 170, 173, 174, 180 and 181 of FGF21 (1-181) (SEQ ID NO:1).
86. The FGF21 protein according to embodiment 83, wherein the FGF21 protein comprises a Cys residue in a position corresponding to one of position 170, 173 and 174 of FGF21 (1-181) (SEQ ID NO:1).
87. The FGF21 protein according to embodiment 83, wherein the FGF21 protein comprises a Cys residue in a position corresponding to one of position 180 and 181 of FGF21 (1-181) (SEQ ID NO:1).
88. The FGF21 protein according to embodiment 83 wherein the FGF21 protein comprises—1Ala, 121Gln and/or 168Leu in addition to a variant Cys residue.
89. The FGF21 protein according to embodiment 83 wherein the FGF21 protein comprises—1Ala, 121Gln and/or 168Leu in addition to a cysteine in one of position 167, 169, 170, 171, 172, 173, 174, 175, 180 and 181 of FGF21 (1-181) (SEQ ID NO:1).

EXAMPLES

List of Abbreviations
AcOD: deuterated acetone
Ado: 8-amino-3,6-dioxaoctanic acid
BSPP: Bis(p-sulfonatophenyl)phenylphosphine dihydrate dipotassium salt DCM: dichloromethane
DMSO: Dimethylsulfoxide
DPBS: Dulbecco's Phosphate-Buffered Saline
EDAC: (3-dimethylaminopropyl) ethyl carbodiimide
ELSD: Evaporating Light Scattering Detector
Fmoc: 9H-fluoren-9-ylmethoxycarbonyl
Fc: Fragment, crystallizable
GLP-1: glucagon-like peptide-1
gGlu: gamma glutamic acid
GLUT1: glucose transporter 1
HATU: 2-(7-Aza-1H-benzotriazole-1-yl)-1, 1,3,3-tetramethyluronium hexafluorophosphate
HEPES: 4-(2-hydroxyethyl)-1-piperazineethanesulfonic acid
HPLC: High Performance Liquid Chromatography
IgG4: Immunoglobulin G4
IBMX: 3-isobutyl-1-methylxanthine
IPTG: isopropyl β-D-1-thiogalactopyranoside
LCMS: Liquid Chromatography Mass Spectroscopy
Mtt: 4-methyltrityl
NMR: Nuclear Magnetic resonance
OtBu: tert-butyl ester
PBS: phosphate buffered saline
RF: retardation factor
Rt: retention time
RT: room temperature
tBu: t-butyl
TCTU: O-(6-chloro-benzotriazol-1-yl)-N,N,N',N'-tetramethyluronium tetrafluoroborate
TFA: trifluoroacetic acid
Tris: tris(hydroxymethyl)aminomethane or 2-amino-2-hydroxymethylpropane-1,3-diol
Trx: tranexamic acid
UPLC: Ultra Performance Liquid Chromatography
ZOSu: N-(benzyloxycarbonyloxy)succinimide Materials and Methods General Methods of Detection and Characterisation LCMS Method 1

Sample is diluted to approx. 0.2 mg/ml and injected to a LCMS system, e.g. 3-5 uL. The LCMS instrument consists of a UPLC system and a mass spectrometer. The analogues are desalted and maybe separated at an reverse phase column (e.g. a C4, C8, C18 column or precolumn) and analysed using a linear gradient of acetonitrile in 0.02-0.05% TFA (trifluoroacetic acid). The instrument should be calibrated and if possible by use of lock mass spray. MS spectrum over main chromatographic peak is generated and the intact mass is reconstructed using a deconvolution algorithm.

Example of LCMS instrument settings (Synapt):
positive ion mode
3000 V capillary potential,
30V cone voltage
110° C. source temperature,
250° C. desolvation temperature
cone gas flow (N2) of 25 L/h.
m/z range 200-3000
Deconvoluted mass is given LCMS method 2
System: Agilent 1290 infinity series UPLC Column: Aeris WIDEPORE 3.6p XB—C18 2, 1×50 mm
Detector: Agilent Technologies LC/MSD TOF 6230 (G6230A) Detector setup Ionisation method: Agilent Jet Stream source Scanning range: m/z min. 100, m/z max. 3200 linear reflector mode positive mode
Conditions: Linear gradient: 5% to 95% B Gradient run-time: 10 minutes 0-8 min 5-95% B, 8-9 min 95% B, 9-9.5 min 95-5% B 9.5-10 min 5% B Flow rate: 0.40 ml/min fixed Column temperature: 40° C.
Eluents Solvent A: 99.90% H2O, 0.02% TFA Solvent B: 99.90% CH3CN, 0.02% TFA Solvent
C: NA
Results specification and validation: Mass found is either m/z ((m+z)/z) of the compound for compounds with m<4000 or mass (average) as the result of a deconvolution using Masshunter Workstation Software Version B.05.00 Build 5.0.519.13 SP1 (Agilent). Calculated Mass is the average molecular weight of the desired compound Calculated m/z is the molecular weight (m+z)/z of the desired compound.

LCMS Method 3
System: Agilent 1290 infinity series UPLC Column: Phenomenex Aeris widepore 3.6μ C4 50×2.1 mm Detector: Agilent Technologies LC/MSD TOF 6230 (G6230A)
Detector setup Ionisation method: Agilent Jet Stream source Scanning range: m/z min. 100, m/z max. 3200 linear reflector mode positive mode
Conditions: Step gradient: 5% to 90% B Gradient run-time: 10 minutes: 0-1 min 5-20% B, 1-7 min 20-90% B, 7-8 min 90% B 8-8.5 min 90-5% B 8.5-10 min 5% B Flow rate: 0.40 ml/min fixed Column temperature: 40° C.
Eluents Solvent A: 99.90% H2O, 0.02% TFA Solvent B: 99.90% CH3CN, 0.02% TFA Solvent C: NA
Results specification and validation: Mass found is either m/z ((m+z)/z) of the compound for compounds with m<4000 or mass (average) as the result of a deconvolution using Masshunter Workstation Software Version B.05.00 Build 5.0.519.13 SP1 (Agilent). Calculated Mass is the average molecular weight of the desired compound Calculated m/z is the molecular weight (m+z)/z of the desired compound.

LCMS Method 4
System: Waters autopurification system
Column: Kinetex C18 4.6 mm×50 mm
Detector: UV: PDA, ELSD, MS Micromass Quatro micro Detector setup: Ionisation method: ES+, scanning range 100-1000, Cone 30 V, Capillary 300 kV, scantime 1.3 s; PDA: 210-400 nm; ELSD: Nebulizer heater-cooler 70%, drift tube 57.0° C.
Conditions: Linear gradient acetonitrile/water 20:80 to 100:0+0.1% FA, gradient run-time: 4.0 min, total run-time: 6.0 min, flow rate: 1.1 ml/min, column temperature: 23° C.

Preparation of the Compounds of the Invention

Example 1: Cloning and Expression of Human Mature FGF21

The DNA and amino acid sequences for human FGF21 have been disclosed by, e.g., Nishimura et al. in *Biochim. Biophys. Acta* 1492(1):203-206 (2000). The sequences are also available from public databases with accession nos. EMBL:AB021975 and UNIPROT:Q9NSA1, respectively.

The mature human FGF21 protein was cloned and expressed as an intracellular protein in *E. coli*, without the signal peptide, but with an added N-terminal methionine. More in particular, gene sequence coding for mature human FGF21 (with a Met added at the N-terminus) was codon-optimized for *E. coli* expression and cloned between the Ndel and BamHI site of vector pET11c. This put FGF21 gene under control of the phage T7 promoter. The expression construct was transformed into *E. coli* BL21(DE3). Single colony was picked and grown in LB+Amp 100 ug/mL to $OD_{450}$ of 0.5. Expression was induced with 0.3 mM IPTG for 4 hours at 37° C. Crude extracts of cells were made by sonication for analysis of FGF21 expression. A Coomassie stained SDS-PAGE showed successful expression of FGF21 which was identified mainly in the pellet fraction. Although the calculated MW of the thus expressed MetFGF21 is 19.5 kD, it migrated on the gel as a 25 kD protein, which is likely due to the high content of prolines, delaying the movement of the protein.

In the present application, MetFGF21 is used as reference compound. When FGF21 is produced by the use of *E. Coli* expression systems, a methionine is introduced at the N-terminal of FGF21. However, this is not considered to affect the biological activity, and both FGF21 and MetFGF21 are thus commonly used as reference compounds.

Example 2: Cloning and Expression of FGF21 Analogues

The expression constructs for analogues in table 1 (example 3) were made by mutagenesis on FGF21 mature expression construct described in example 1. Stratagene multiple-site mutagenesis kit was used. The same expression condition as described in example 1 was also applied. A coomassie blue stained SDS-PAGE showed successful expression of the analogues. The analogues were expressed including the di-peptide Met-Ala N-terminal to FGF21 sequences which allows for expression of a FGF21 analogue with Ala as N-terminal amion acid residue due to cleavage of the Met by *E. coli* enzymes.

Example 3: Purification of Mature FGF21 and FGF21 Analogues

In order to purify mature FGF21 and FGF21 analogues described in Examples 1-2, the following process or similar techniques were used:

The *E. coli* cell pellet was resuspended in 10 mM potassium phosphate pH 6.0, and was disrupted by homogenizer under 800 bar twice. The inclusion bodies were pelleted by centrifugation (10,000×g, for 30 minutes), re-solubilised in 50 mM Tris pH 8.0, and optionally 2M urea and/or 5 mM cysteamine were added, and the slurry stirred over night at 4° C. Before column application, the slurry was centrifuged again at 10,000× g for 30 minutes. The supernatant was applied onto anion exchange chromatography (Q Sepharose Fast Flow resin, GE Healthcare) and was eluted with 50-250 mM NaCl. 0.4M ammonium sulphate was added to the elution pool, which was then applied to a Phenyl FF column (GE Healthcare) equilibrated in 20 mM Tris pH 8.0, 0.4M ammonium sulphate. The column was washed with 20 mM Tris pH 8.0, 1.5 M sodium chloride before elution with 10% Tris-chloride buffer (20 mM Tris pH 8.0, 1.5M sodium chloride). A 30Q column can be used for further purity polishing. The final product was analysed by SDS-PAGE or other relevant techniques. For compounds 3 and 5-10, cysteamine protection of introduced cysteines was retained during pharmacological testing.

The FGF21 analogues were prepared as described above. Intact mass was determined by LCMS (using LCMS method 1) are given for the compounds.

TABLE 1A

FGF21 analogues 1 to 10.

| Compound | Compound Name | SEQ ID NO of the protein backbone | Mol Weight | LCMS Mass intact (average) (Da) |
|---|---|---|---|---|
| 1 | MetFGF21 | 2 | 19540.0 | 19540.5 |
| 2 | Ala[Gln121,Leu168]FGF21 | 3 | 19475.9 | 19476.4 |
| 3 | S{Beta-176}-2-aminoethylsulfanyl-Ala[Gln121,Leu168,Cys176]FGF21 | 4 | 19567.1 | 19567.0 |
| 4 | Ala[Gln121,Leu168,Cys177]FGF21 | 5 | 19481.9 | 19481.6 |
| 5 | S{Beta-178}-2-aminoethylsulfanyl-Ala[Gln121,Leu168,Cys178]FGF21 | 6 | 19567.1 | 19568.0 |
| 6 | S{Beta-179}-2-aminoethylsulfanyl-Ala[Gln121,Leu168,Cys179]FGF21 | 7 | 19491.0 | 19492.0 |
| 7 | S{Beta-180}-2-aminoethylsulfanyl-Ala[Gln121,Leu168,Cys180]FGF21 | 8 | 19583.1 | 19583.96 |
| 8 | S{Beta-180}-2-aminoethylsulfanyl-Ala[Gln121,Leu168,Cys180,des181]FGF21 | 9 | 19496.0 | 19496.1 |
| 9 | S{Beta-181}-2-aminoethylsulfanyl-Ala[Gln121,Leu168,Cys181]FGF21 | 10 | 19567.1 | 19567.8 |
| 10 | S{Beta-181}-2-aminoethylsulfanyl-Met[Cys181]FGF21 | 11 | 19631.0 | 19630.6 |

TABLE 1B

FGF21 analogues 25 to 32

| Compound | Compound Name | SEQ ID NO of the protein backbone | Mol Weight | LCMS Mass intact (average) (Da) |
|---|---|---|---|---|
| 25 | -1A, 121Q, 167C, 168L | 12 | 19491.9 | 19491.7 |
| 26 | -1A, 121Q, 168C | 13 | 19465.9 | 19466.2 |
| 27 | -1A, 121Q, 168L, 169C | 14 | 19479.9 | 19479.7 |
| 28 | -1A, 121Q, 168L, 170C | 15 | 19522.0 | 19521.9 |
| 29 | -1A, 121Q, 168L, 172C | 17 | 19491.9 | 19492.0 |
| 30 | -1A, 121Q, 168L, 173C | 18 | 19450.9 | 19450.5 |
| 31 | -1A, 121Q, 168L, 174C | 19 | 19522.0 | 19522.1 |
| 32 | -1A, 121Q, 168L, 175C | 20 | 19422.8 | 19422.4 |

Example 4: Preparation of Reagents for Derivatisation of FGF21 Analogues

The preparation of a representative reagent for derivatisation is given in Example 4.1. The reagents of Examples 4.2-4.4 are prepared by the method provided in Example 4.1. Reagents of examples 4.5-4.17 were prepared by similar methods as described below.

Example 4.1: Preparation of 15-{(S)-1-carboxy-3-[2-(2-{[2-(2-{[2-(2-Bromoacetylamino)ethylcarbamoyl]methoxy}-ethoxy)ethyl-carbamoyl]methoxy}ethoxy)ethylcarbamoyl]propylcarbamoyl}pentadecanoic acid

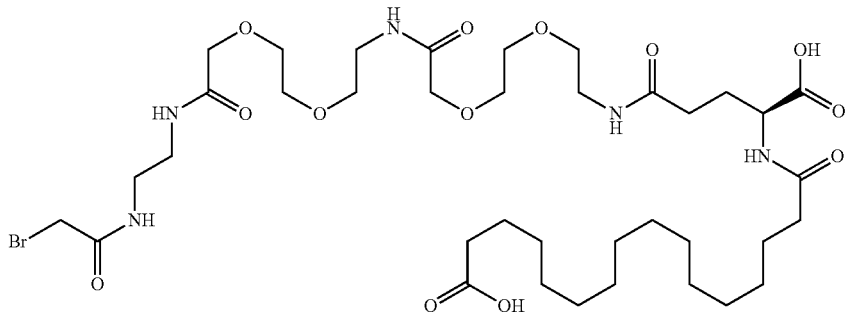 [SMILES: O=C(O)CCCCCCCCCCCCCCC(=O)N[C@@H](CCC(=O)NCCOCCOCC(=O)NCCOCCOCC(=O)NCCNC(=O)CBr)C(=O)O]

Solid Phase Synthetic Protocol:

A solution of N-(benzyloxycarbonyloxy)succinimide (ZOSu, 100 g, 401 mmol) in dichloromethane (500 mL) was added dropwise over 2 hours to a solution of ethylenediamine (1, 189 mL, 2.81 mol) in dichloromethane (750 mL). After 30 minutes the suspension was filtered and solids washed with dichloromethane. The filtrate was evaporated to dryness and the residue diluted with toluene (1.00 L) and water (0.50 L). The resulting mixture was filtered and the filtrate was separated to afford two phases. The aqueous phase contained the product; therefore it was extracted with dichloromethane (2×250 mL). All organic phases were combined, dried over anhydrous sodium sulfate, filtered and concentrated in vacuo. The residue was diluted with toluene (750 mL) and extracted with 2 M aqueous hydrochloric acid (500 mL) and 1 M aqueous hydrochloric acid (100 mL). Acidic aqueous phases were combined and basified with a solution of sodium hydroxide (60.0 g, 1.50 mol) in water (90 mL). The resulting mixture was extracted with dichloromethane (4×200 mL), dried over anhydrous sodium sulfate, filtered, concentrated in vacuo and diluted with hexanes (200 mL). 4 M Solution of hydrogen chloride in ether (100 mL, 400 mmol) was added to the solution, the resulting suspension was concentrated in vacuo and diluted with hexanes (1.00 L). The precipitated solid was filtered, washed with hexanes and dried in vacuo to give (2-amino-ethyl)-carbamic acid benzyl ester hydrochloride as white powder.

Yield: 62.62 g (68%).

RF (SiO2, dichloromethane/methanol 4:1): 0.25 (free base).

1H NMR spectrum (300 MHz, AcOD-d4, 80° C., dH): 7.42-7.26 (m, 5H); 5.16 (s, 2H); 3.60 (t, J=5.7 Hz, 2H); 3.32 (t, J=5.7 Hz, 2H).

2-Chlorotrityl resin 100-200 mesh 1.7 mmol/g (3, 40.1 g, 68.1 mmol) was left to swell in dry dichloromethane (250 mL) for 20 minutes. A solution of {2-[2-(9H-fluoren-9-ylmethoxycarbonylamino)-ethoxy]-ethoxy}-acetic acid (Fmoc-Ado-OH, 17.5 g, 45.4 mmol) and N,N-diisopropylethylamine (30.1 mL, 173 mmol) in dry dichloromethane (50 mL) was added to resin and the mixture was shaken for 5 hours. Resin was filtered and treated with a solution of N,N-diisopropylethylamine (15.8 mL, 90.8 mmol) in methanol/dichloromethane mixture (4:1, 250 mL, 2×5 min). Then resin was washed with N,N-dimethylformamide (2×250 mL), dichloromethane (2×250 mL) and N,N-dimethylformamide (3×250 mL). Fmoc group was removed by treatment with 20% piperidine in dimethylformamide (1×5 min, 1×10 min, 1×30 min, 3×250 mL). Resin was washed with N,N-dimethylformamide (3×250 mL), 2-propanol (2×250 mL) and dichloromethane (300 mL, 2×250 mL). Solution of {2-[2-(9H-fluoren-9-ylmethoxycarbonylamino)-ethoxy]-ethoxy}-acetic acid (Fmoc-Ado-OH, 26.3 g, 68.1 mmol), O-(6-chloro-benzotriazol-1-yl)-N,N,N',N'-tetramethyluronium tetrafluoroborate (TCTU, 24.2 g, 68.1 mmol) and N,N-diisopropylethylamine (21.4 mL, 123 mmol) in N,N-dimethylformamide (140 mL) was added to resin and mixture was shaken for 1 hour. Resin was filtered and washed with N,N-dimethylformamide (2×250 mL), dichloromethane (2×250 mL) and N,N-dimethylformamide (250 mL). Fmoc group was removed by treatment with 20% piperidine in dimethylformamide (1×5 min, 1×10 min, 1×30 min, 3×250 mL). Resin was washed with N,N-dimethylformamide (3×250 mL), 2-propanol (2×250 mL) and dichloromethane (300 mL, 2×250 mL). Solution of (S)-2-(9H-fluoren-9-ylmethoxycarbonylamino)-pentanedioic acid 1-tert-butyl ester (Fmoc-Glu-OtBu, 29.0 g, 68.1 mmol), O-(6-chloro-benzotriazol-1-yl)-N,N,N',N'-tetramethyluronium tetrafluoroborate (TCTU, 24.2 g, 68.1 mmol) and N,N-diisopropylethylamine (21.4 mL, 123 mmol) in N,N-dimethylformamide (140 mL) was added to resin and mixture was shaken for 1 hour. Resin was filtered and washed with N,N-dimethylformamide (2×250 mL), dichloromethane (2×250 mL) and N,N-dimethylformamide (250 mL). Fmoc group was removed by treatment with 20% piperidine in dimethylformamide (1×5 min, 1×10 min, 1×30 min, 3×250 mL). Resin was washed with N,N-dimethylformamide (3×250 mL), 2-propanol (2×250 mL) and dichloromethane (300 mL, 2×250 mL). Solution of 16-(tert-butoxy)-16-oxohexadecanoic acid (23.3 g, 68.1 mmol), O-(6-chloro-benzotriazol-1-yl)-N,N,N',N'-tetramethyluronium tetrafluoroborate (TCTU, 24.2 g, 68.1 mmol) and N,N-diisopropylethylamine (21.4 mL, 123 mmol) in N,N-dimethylformamide/dichloromethane mixture (4:1, 200 mL) was added to resin. Resin was shaken for 1 hour, filtered and washed with N,N-dimethylformamide (3×250 mL), dichloromethane (2×250 mL), methanol (2×250 mL) and dichloromethane (350, 6×250 mL). The product was cleaved from resin by treatment with 2,2,2-trifluoethanol (250 mL) for 18 hours. Resin was filtered off and washed with dichloromethane (2×250 mL), 2-propanol/dichloromethane mixture (1:1, 2×250 mL), 2-propanol (250 mL) and dichloromethane (3×250 mL). Solutions were combined; solvent evaporated and crude product was purified by flash column chromatography (Silicagel 60, 0.040-0.060 mm; eluent: dichloromethane/methanol 1:0-9:1). Pure (S)-22-(tert-butoxycarbonyl)-41,41-dimethyl-10,19,24,39-tetraoxo-3,6,12,15,40- pentaoxa-9,18,23-triazadotetracontanoic acid was dried in vacuo and obtained as pale yellow thick yellow oil.

Yield: 30.88 g (83%).

RF (SiO2, dichloromethane/methanol 4:1): 0.30.

1H NMR spectrum (300 MHz, CDCl3, dH): 7.36 (t, J=5.7 Hz, 1H); 7.02 (t, J=5.4 Hz, 1H); 6.55 (d, J=7.7 Hz, 1H); 4.46 (m, 1H); 4.18 (s, 2H); 4.02 (s, 2H); 3.83-3.36 (m, 16H); 2.44-2.12 (m, 7H); 2.02-1.86 (m, 1H); 1.60 (m, 4H); 1.47 (s, 9H); 1.45 (s, 9H); 1.36-1.21 (m, 20H).

LC-MS method 4:

Purity: 100%

Rt (Kinetex 4.6 mm×50 mm, acetonitrile/water 50:50 to 100:0+0.1% FA): 3.60 min.

Found m/z, z=1: 818.7 (M+H)+

2-(7-Aza-1H-benzotriazole-1-yl)-1, 1,3,3-tetramethyluronium hexafluorophosphate (HATU, 11.4 g, 30.1 mmol) and triethylamine (8.77 mL, 62.9 mmol) were subsequently added to a solution of (S)-22-(tert-butoxycarbonyl)-41,41-dimethyl-10,19,24,39-tetraoxo-3,6,12,15,40-pentaoxa-9,18,23-triazadotetracontanoic acid (22.4 g, 27.4 mmol) in dry dichloromethane (110 mL). Triethylamine (5.72 mL, 41.0 mmol) was added to a suspension of (2-amino-ethyl)-carbamic acid benzyl ester hydrochloride (6.94 g, 30.1 mmol) in dry dichloromethane (165 mL) and the resulting mixture was added to the above solution. The mixture was stirred at room temperature overnight, and then it was evaporated to dryness. The residue was re-dissolved in ethyl acetate (500 mL); washed with 1 M aqueous hydrochloric acid (2×200 mL), 5% aqueous solution of sodium carbonate (2×200 mL, very slow separation of phases), 1 M aqueous hydrochloric acid (8×200 mL) and brine; dried over anhydrous sodium sulfate and evaporated to dryness in vacuo. The residue was purified by flash column chromatography (Silicagel 60, 0.040-0.060 mm; eluent: dichloromethane/methanol 95:5) to afford 15-[(S)-3-(2-{2-[(2-{2-[(2-benzyloxycarbonylamino-ethylcarbamoyl)-methoxy]-ethoxy}-ethylcarbamoyl)-methoxy]-ethoxy}-ethylcarbamoyl)-1-tert-butoxycarbonyl-propylcarbamoyl]-pentadecanoic acid tert-butyl ester as pale yellow thick oil.

Yield: 23.84 g (88%)

RF (SiO2, dichloromethane/methanol 9:1): 0.35

1H NMR spectrum (300 MHz, CDCl3, dH): 7.39-7.26 (m, 6H); 7.19 (t, J=6.3 Hz, 1H); 6.91 (t, J=5.7 Hz, 1H); 6.52 (d, J=7.5 Hz, 1H); 5.83 (t, J=5.5 Hz, 1H); 5.09 (s, 2H); 4.41 (ddd, J=12.3, 4.6 and 4.3 Hz, 1H); 3.99 (s, 2H); 3.97 (s, 2H); 3.71-3.30 (m, 20H); 2.33-2.08 (m, 7H); 1.97-1.83 (m, 1H); 1.67-1.51 (m, 4H); 1.45 (s, 9H); 1.44 (s, 9H); 1.35-1.20 (m, 20H).

LCMS method 4

Purity: 100%

Rt (Kinetex 4.6 mm×50 mm, acetonitrile/water 50:50 to 100:0+0.1% FA): 4.18 min

Found m/z, z=1: 994.9 (M+H)+

Palladium on carbon (10%, 1.27 g, 1.20 mmol) was added to a solution of the above compound (23.8 g, 24.0 mmol) in methanol (350 mL) and the resulting mixture was hydrogenated at normal pressure for 4 hours. The catalyst was filtered off and the filtrate evaporated to dryness. The residue was evaporated several times from dichloromethane in order to remove residues of methanol and dried in vacuo to yield tert-butyl (S)-1-amino-25-(tert-butoxycarbonyl)-4,13,22,27-tetraoxo-6,9,15,18-tetraoxa-3,12,21,26-tetraazadotetracontan-42-oate as thick colourless oil.

Yield: 20.50 g (99%).

RF (SiO2, dichloromethane/methanol 9:1): 0.05.

1H NMR spectrum (300 MHz, CDCl3, dH): 7.54 (t, J=5.7 Hz, 1H); 7.41 (t, J=5.6 Hz, 1H); 7.14 (t, J=5.5 Hz, 1H); 6.68 (d, J=7.5 Hz, 1H); 5.25 (bs, 2H); 4.39 (td, J=8.3 and 4.2 Hz, 1H); 4.01 (s, 4H); 3.74-3.39 (m, 18H); 2.96 (t, J=5.7 Hz, 2H); 2.34-2.06 (m, 7H); 1.97-1.83 (m, 1H); 1.68-1.50 (m, 4H); 1.45 (s, 9H); 1.43 (s, 9H); 1.37-1.19 (m, 20H).

LCMS method 4

Purity: 100%

Rt (Kinetex 4.6 mm×50 mm, acetonitrile/water 50:50 to 100:0+0.1% FA): 1.43 min

Found m/z, z=1: 860.8 (M+H)+

N,N-Diisopropylethylamine (4.98 mL, 28.6 mmol) was added to a solution of the above amine (6, 20.5 g, 23.8 mmol) in dry dichloromethane (290 mL) at −30° C. under argon. Bromoacetyl bromide (2.48 mL, 28.6 mmol) was added dropwise and the resulting solution was stirred at −30° C. for additional 3 hours. The cooling bath was removed, the mixture was stirred at room temperature for 1 hour, and then the solvent was removed in vacuo. The residue was re-dissolved in ethyl acetate (450 mL) and washed with 5% aqueous solution of citric acid (300 mL). The phases were separated within 1 hour. The organic layer was washed with water (300 mL) and the resulting emulsion was left to separate overnight to give 3 phases. The clear aqueous layer was removed and the residual 2 phases were shaken with saturated aqueous solution of potassium bromide (100 mL) was added. The phases were left to separate overnight, the aqueous one was then removed and the organic one dried over anhydrous sodium sulfate. The solvent was removed in vacuo and the residue was purified by flash column chromatography (Silicagel 60, 0.040-0.060 mm; eluent: dichloromethane/methanol 95:5) to afford tert-butyl (S)-1-bromo-28-(tert-butoxycarbonyl)-2,7,16,25,30-pentaoxo-9,12,18,21-tetraoxa-3,6,15,24,29-pentaazapentatetracontan-45-oate as colorless solid.

Yield: 19.46 g (83%).

RF (SiO2, dichloromethane/methanol 9:1): 0.25

1H NMR spectrum (300 MHz, CDCl3, dH): 7.46 (m, 1H); 7.33 (t, J=5.9 Hz, 1H); 7.21 (t, J=5.1 Hz, 1H); 6.92 (t, J=5.2 Hz, 1H); 6.50 (d, J=7.5 Hz, 1H); 4.41 (ddd, J=12.2, 4.5 and 4.2 Hz, 1H); 4.01 (s, 4H); 3.85 (s, 2H); 3.75-3.40 (m, 20H), 2.36-2.08 (m, 7H); 1.99-1.84 (m, 1H); 1.68-1.51 (m, 4H); 1.46 (s, 9H); 1.44 (s, 9H); 1.38-1.19 (m, 20H)

LCMS method 4

Purity: 100%

Rt (Kinetex 4.6 mm×50 mm, acetonitrile/water 50:50 to 100:0+0.1% FA): 3.51 min.

Found: m/z, z=1: 980.9, 982.9 (M+H)+

The above compound (19.5 g, 19.8 mmol) was dissolved in trifluoroacetic acid (120 mL) and the resulting solution was stirred at room temperature for 1.5 hours. Trifluoroacetic acid was removed in vacuo and the residue was evaporated from dichloromethane (6×200 mL).

Diethyl ether (200 mL) was added to the oily residue and the mixture was stirred overnight to give a suspension. Solid product was filtered, washed with diethyl ether and hexanes and dried in vacuo to afford the title product 15-{(S)-1-carboxy-3-[2-(2-{[2-(2-{[2-(2-Bromoacetylamino)ethylcarbamoyl]methoxy}-ethoxy)ethyl-carbamoyl]methoxy}ethoxy)ethylcarbamoyl]propylcarbamoyl}pentadecanoic acid as white powder.

Yield: 16.74 g (97%).

1H NMR spectrum (300 MHz, AcOD-d4, dH): 4.61 (dd, J=8.8 and 4.8 Hz, 1H); 4.12 (s, 2H), 4.10 (s, 2H); 3.96 (s, 2H); 3.77-3.39 (m, 20H), 2.49-2.18 (m, 7H); 2.16-1.04 (m, 1H); 1.71-1.56 (m, 4H), 1.30 (bs, 20H)

LCMS method 4:

Purity: 100%

Rt (Kinetex 4.6 mm×50 mm, acetonitrile/water 50:50 to 100:0+0.1% FA): 3.51 min Theoretical m/z, z=1: 869.8. Found: m/z, z=1: 868.7, 870.7

Example 4.2: Preparation of 11-{(S)-1-carboxy-3-
[2-(2-{[2-(2-{[2-(2-Bromoacetylamino)ethylcarbam-
oyl]methoxy}-ethoxy)ethyl-carbamoyl]
methoxy}ethoxy)ethylcarbamoyl]
propylcarbamoyl}undecanoic acid

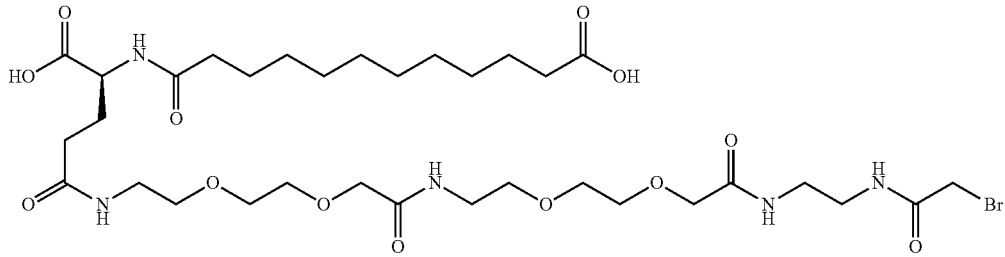 [SMILES: O=C(O)CCCCCCCCCCC(=O)N[C@@H](CCC(=O)NCCOCCOCC(=O)NCCOCCOCC(=O)NCCNC(=O)CBr)C(=O)O]

11-{(S)-1-carboxy-3-[2-(2-{[2-(2-{[2-(2-Bromoacety-
lamino)ethylcarbamoyl]methoxy}-ethoxy)ethylcarbam-
oyl]methoxy}ethoxy)ethylcarbamoyl]
propylcarbamoyl}undecanoic acid was prepared by the
same method as described in Example 4.1 resulting in a
thick orange oil.

1H NMR spectrum (300 MHz, AcOD-d4, dH): 4.61 (dd,
J=8.9 and 4.9 Hz, 1H); 4.13 (s, 2H); 4.10 (s, 2H); 3.96 (s,
2H); 3.79-3.38 (m, 20H); 2.50-2.16 (m, 7H); 2.16-2.00 (m,
1H); 1.72-1.56 (m, 4H); 1.42-1.24 (m, 12H)

LCMS method 4:
Purity: 100% (ELSD)
Rt (Kinetex, 4.6 mm×50 mm, acetonitrile/water 20:80 to
100:0+0.1% FA): 2.74 min
Theoretical, m/z, z=1:813.8. Found m/z, z=1: 812.0,
814.0

Example 4.3: Preparation of 13-{(S)-1-carboxy-3-
[2-(2-{[2-(2-{[2-(2-Bromoacetylamino)ethylcarbam-
oyl]methoxy}-ethoxy)ethyl-carbamoyl]
methoxy}ethoxy)ethylcarbamoyl]
propylcarbamoyl}tridecanoic acid

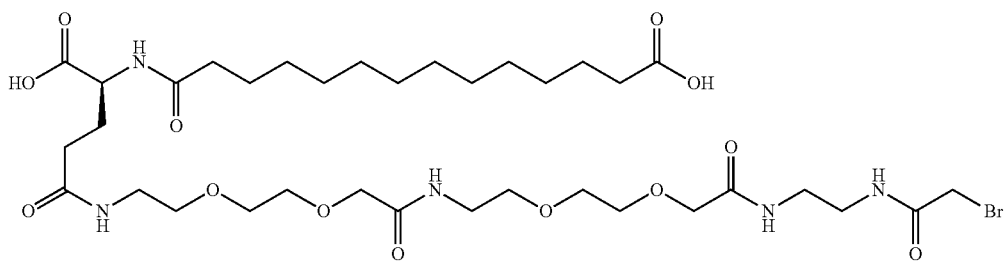 [SMILES: O=C(O)CCCCCCCCCCCCC(=O)N[C@@H](CCC(=O)NCCOCCOCC(=O)NCCOCCOCC(=O)NCCNC(=O)CBr)C(=O)O]

13-{(S)-1-carboxy-3-[2-(2-{[2-(2-{[2-(2-Bromoacety-
lamino)ethylcarbamoyl]methoxy}-ethoxy)ethylcarbam-
oyl]methoxy}ethoxy)ethylcarbamoyl]
propylcarbamoyl}tridecanoic acid was prepared by the
same method as described in Example 4.1 resulting in a
thick yellow oil.

1H NMR spectrum (300 MHz, AcOD-d4, dH): 4.61 (dd,
J=8.9 and 4.9 Hz, 1H); 4.13 (s, 2H); 4.11 (s, 2H); 3.96 (s,
2H); 3.77-3.40 (m, 20H); 2.49-2.18 (m, 7H); 2.16-2.07 (m,
1H); 1.70-1.56 (m, 4H); 1.31 (bs, 16H).

LCMS method 4:
Purity: 100% (ELSD)
Rt (Kinetex, 4.6 mm×50 mm, acetonitrile/water 20:80 to
100:0+0.1% FA): 2.94 min
Theoretical m/z, z=1: 841.9. Found: m/z, z=1: 841.7,
843.7

Example 4.4: Preparation of 19-{(S)-1-carboxy-3-[2-(2-{[2-(2-{[2-(2-Bromoacetyl-amino)ethylcarbamoyl]methoxy}ethoxy)ethylcarbamoyl]methoxy}ethoxy)-ethylcarbamoyl]propylcarbamoyl}nonadecanoic acid

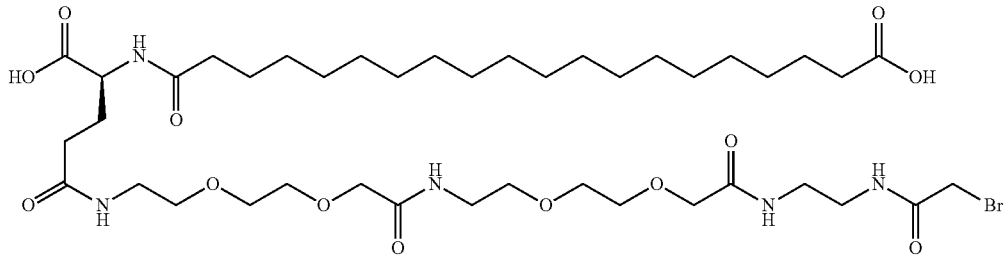 [SMILES: O=C(O)CCCCCCCCCCCCCCCCCCC(=O)N[C@@H](CCC(=O)NCCOCCOCC(=O)NCCOCCOCC(=O)NCCNC(=O)CBr)C(=O)O]

19-{(S)-1-carboxy-3-[2-(2-{[2-(2-{[2-(2-Bromoacetylamino)ethylcarbamoyl]methoxy}-ethoxy)ethylcarbamoyl]methoxy}ethoxy)ethylcarbamoyl]propylcarbamoyl}nonadecanoic acid was prepared by the same method as described in Example 4.1 resulting in a beige powder.

1H NMR spectrum (300 MHz, AcOD-d4, dH): 4.65-4.57 (m, 1H); 4.13 (s, 2H); 4.10 (s, 2H); 3.96 (s, 2H); 3.77-3.43 (m, 20H); 2.49-2.40 (t, J=7.3 Hz, 2H); 2.39-2.23 (m, 5H); 2.17-2.07 (m, 1H); 1.68-1.57 (m, 4H); 1.30 (bs, 28H)

LCMS method 4:
Purity: 100% (ELSD)
Rt (Kinetex, 4.6 mm×50 mm, acetonitrile/water 50:50 to 100:0+0.1% FA): 2.17 min
Theoretical mass: 926.0. Found m/z: 926 (M+H)+

Example 4.5: Preparation of 18-[[(1 S)-4-[2-[2-[2-[2-[2-[2-[2-[(2-bromoacetyl)amino]ethylamino]-2-oxo-ethoxy]ethoxy]ethylamino]-2-oxo-ethoxy]ethoxy]ethylamino]-1-carboxy-4-oxo-butyl]amino]-18-oxo-octadecanoic acid

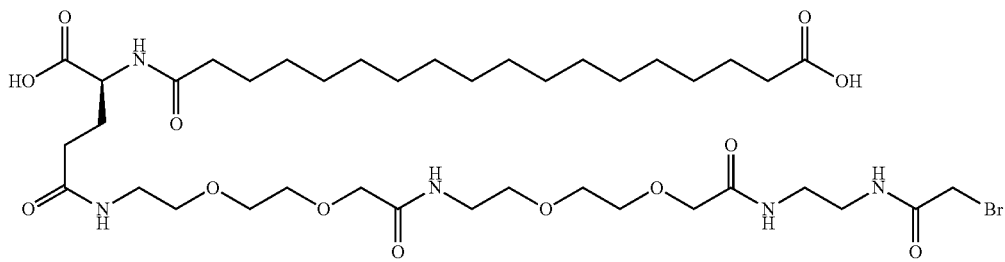 [SMILES: O=C(O)CCCCCCCCCCCCCCCCC(=O)N[C@@H](CCC(=O)NCCOCCOCC(=O)NCCOCCOCC(=O)NCCNC(=O)CBr)C(=O)O]

Solution Phase Synthetic Protocol

Step 1: benzyl 18-[[(1 S)-4-[2-[2-[2-[2-[2-[2-(2-aminoethylamino)-2-oxo-ethoxy]ethoxy]ethylamino]-2-oxo-ethoxy]ethoxy]ethylamino]-1-benzyloxycarbonyl-4-oxo-butyl]amino]-18-oxo-octadecanoate To a solution of ethylenediamine (8.5 ml) in DCM (80 ml) and triethylamine (5.2 ml) at 0° C. was added a solution of benzyl 18-[[(1S)-1-benzyloxycarbonyl-4-[2-[2-[2-[2-[2-[2-(2,5-dioxopyrrolidin-1-yl)oxy-2-oxo-ethoxy]ethoxy]ethylamino]-2-oxo-ethoxy]ethoxy]ethylamino]-4-oxo-butyl]amino]-18-oxo-octadecanoate (26 g), prepared as described in WO10029159, in DCM (320 ml) dropwise over 75 min.

After stirring for 2 h the precipitate was filtered off. To the filtrate was added water (200 ml) and isopropanol (50 ml). The mixture was extracted. The organic layer was dried using MgSO4. The MgSO4 was removed by filtration and the filtrate was dried in vacuo to give the title compound 20.07 g (81%) LCMS: Theoretical mass: 956.2. Found m/z, z=1: 957.0

Step 2: benzyl 18-[[(1S)-1-benzyloxycarbonyl-4-[2-[2-[2-[2-[2-[2-[(2-chloroacetyl)amino]ethylamino]-2-oxo-ethoxy]ethoxy]ethylamino]-2-oxo-ethoxy]ethoxy]ethylamino]-4-oxo-butyl]amino]-18-oxo-octadecanoate Chloroacetic acid (0.19 g) was dissolved in DCM (15 ml). N-hydroxysuccinimide (0.22 g) and EDAC HCl (0.42 g)

was added. After stirring for 2.5 h benzyl 18-[[(1S)-4-[2-[2-[2-[2-[2-[2-(2-aminoethylamino)-2-oxo-ethoxy]ethoxy]ethylamino]-2-oxo-ethoxy]ethoxy]ethylamino]-1-benzyloxycarbonyl-4-oxo-butyl]amino]-18-oxo-octadecanoate (1.5 g) in DCM (5 ml) was added. After stirring over night at RT the mixture was extracted with 1M HCl (2×20 ml) and water/brine 2:1 (30 ml). The organic layer was dried (MgSO4), filtered and concentrated in vacuo to give a clear oil, 1.37 g (84%) LCMS: Theoretical mass: 1032.7. Found m/z, z=1: 1033.1

Step 3: 18-[[(1S)-1-Carboxy-4-[2-[2-[2-[2-[2-[2-[2-[(2-chloroacetyl)amino]ethylamino]-2-oxo-ethoxy]ethoxy]ethylamino]-2-oxo-ethoxy]ethoxy]ethylamino]-4-oxo-butyl]amino]-18-oxo-octadecanoic acid To a solution of benzyl 18-[[(1S)-1-benzyloxycarbonyl-4-[2-[2-[2-[2-[2-[2-[2-[(2-chloroacetyl)amino]ethylamino]-2-oxo-ethoxy]ethoxy]ethylamino]-2-oxo-ethoxy]ethoxy]ethylamino]-4-oxo-butyl]amino]-18-oxo-octadecanoate (10.5 g) in acetone (140 ml) was added 10% PD/C (1.0 g) after Nitrogen aeration. After hydrogenation for 6 h, the mixture was heated to 40-50° C. before filtration. The precipitate in the cold filtrate was isolated and washed with acetone and dried to give the title compound, 7.42 g (85%).

Step 4: 8-[[(1 S)-4-[2-[2-[2-[2-[2-[2-[2-[(2-Bromoacetyl)amino]ethylamino]-2-oxo-ethoxy]ethoxy]ethylamino]-2-oxo-ethoxy]ethoxy]ethylamino]-1-carboxy-4-oxo-butyl]amino]-18-oxo-octadecanoic acid To a suspension of 18-[[(1S)-1-Carboxy-4-[2-[2-[2-[2-[2-[2-[(2-chloroacetyl)amino]ethylamino]-2-oxo-ethoxy]ethoxy]ethylamino]-2-oxo-ethoxy]ethoxy]ethylamino]-4-oxo-butyl]amino]-18-oxo-octadecanoic acid in acetone (60 ml) was added sodium bromide (5 eq, 1.21 g). The mixture was stirred at RT in the dark. After 2 h more sodium bromide (10 eq, 2.41 g) was added. After 2 days more sodium bromide (5 eq, 1.21 g) was added. After 5 days the mixture was concentrated. To half the residue was added DCM (30 ml), 10% ascorbic acid (20 ml) and water 30 ml. To the emulsion was added isopropanol (50 ml) and water (30 ml). The organic phase was separated and washed twice with a mixture of 10% ascorbic acid (20 ml) and isopropanol (10 ml). The organic layer was dried (MgSO4), filtered and concentrated to give a solid oil, which was crystalised in acetone and isolated by filtration to give the title compound contaminated with starting material, 0.80 g (72%).

LCMS: Theoretical mass: 896.9. Found m/z, z=1: 898.9 (M+1)

Example 4.6: Preparation of 12-[[4-[[(1S)-4-[2-[2-[2-[2-[2-[2-[2-[(2-bromoacetyl)amino]ethylamino]-2-oxo-ethoxy]ethoxy]ethylamino]-2-oxo-ethoxy]ethoxy]ethylamino]-1-carboxy-4-oxo-butyl]carbamoyl]cyclohexyl]methylamino]-12-oxo-dodecanoic acid

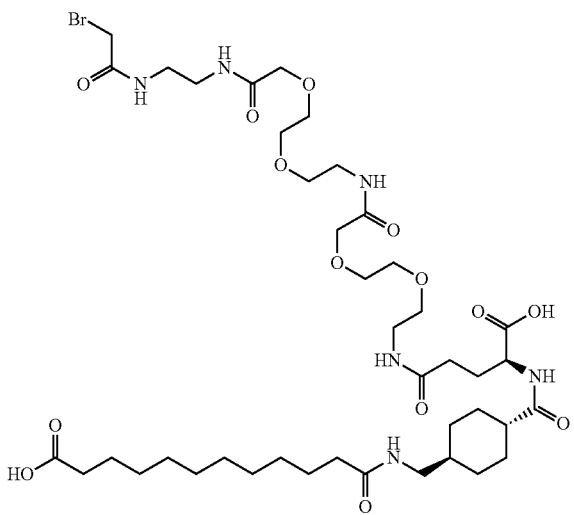 [SMILES: O=C(O)CCCCCCCCCCC(=O)NC[C@H]1CC[C@H](C(=O)N[C@@H](CCC(=O)NCCOCCOCC(=O)NCCOCCOCC(=O)NCCNC(=O)CBr)C(=O)O)CC1]

Solid Phase Synthetic Protocol:
2-Chlorotrityl resin 100-200 mesh 1.8 mmol/g (1, 11.9 g, 21.4 mmol) was left to swell in dry dichloromethane (80 mL) for 20 minutes. A solution of {2-[2-(9H-fluoren-9-ylmethoxycarbonylamino)-ethoxy]-ethoxy}-acetic acid (Fmoc-OEG-OH, 5.50 g, 14.3 mmol) and N,N-diisopropylethylamine (9.44 mL, 54.2 mmol) in dry dichloromethane (70 mL) was added to resin and the mixture was shaken for 4 hours. Resin was filtered and treated with a solution of N,N-diisopropylethylamine (4.97 mL, 28.5 mmol) in methanol/dichloromethane mixture (4:1, 2×5 min, 2×57 mL). Then resin was washed with N,N-dimethylformamide (2×80 mL), dichloromethane (2×80 mL) and N,N-dimethylformamide (3×80 mL). Fmoc group was removed by treatment with 20% piperidine in N,N-dimethylformamide (1×5 min, 1×30 min, 2×80 mL). Resin was washed with N,N-dimethylformamide (3×80 mL), 2-propanol (2×80 mL) and dichloromethane (100 mL, 2×80 mL). Solution of {2-[2-(9H-fluoren-9-ylmethoxycarbonylamino)-ethoxy]-ethoxy}-acetic acid (Fmoc-OEG-OH, 11.0 g, 28.5 mmol), O-(6-chloro-benzotriazol-1-yl)-N,N,N',N'-tetramethyluronium tetrafluoroborate (TCTU, 10.1 g, 28.5 mmol) and N,N-diisopropylethylamine (9.93 mL, 57.0 mmol) in N,N-dimethylformamide (80 mL) was added to resin and mixture was shaken for 2 hours. Resin was filtered and washed with N,N-dimethylformamide (2×80 mL), dichloromethane (2×80 mL) and N,N—N,N-dimethylformamide (3×80 mL). Fmoc group was removed by treatment with 20% piperidine in N,N-dimethylformamide (1×5 min, 1×30 min, 2×80 mL). Resin was washed with N,N-dimethylformamide (3×80 mL), 2-propanol (2×80 mL) and dichloromethane (100 mL, 2×80 mL). Solution of (S)-2-(9H-fluoren-9-ylmethoxycarbonylamino)-pentanedioic acid 1-tert-butyl ester (Fmoc-LGlu-OtBu, 9.11 g, 21.4 mmol), O-(6-chloro-benzotriazol-1-yl)-N,N,N',N'-tetramethyluronium tetrafluoroborate (TCTU, 7.60 g, 21.4 mmol) and N,N-diisopropylethylamine (6.71 mL, 38.5 mmol) in N,N-dimethylformamide (80 mL)

was added to resin and mixture was shaken for 1 hour. Resin was filtered and washed with N,N-dimethylformamide (2×80 mL), dichloromethane (2×80 mL) and N,N-dimethylformamide (2×80 mL). Fmoc group was removed by treatment with 20% piperidine in N,N-dimethylformamide (1×5 min, 1×30 min, 2×80 mL). Resin was washed with N,N-dimethylformamide (3×80 mL), 2-propanol (2×80 mL) and dichloromethane (100 mL, 2×80 mL). Solution of 4-[(9H-fluoren-9-ylmethoxycarbonylamino)methyl]cyclohexanecarboxylic acid (Fmoc-Trx-OH, 9.11 g, 21.4 mmol), O-(6-chloro-benzotriazol-1-yl)-N,N,N',N'-tetramethyluronium tetrafluoroborate (TCTU, 7.60 g, 21.4 mmol) and N,N-diisopropylethylamine (6.71 mL, 38.5 mmol) in N,N-dimethylformamide (80 mL) was added to resin and mixture was shaken for 1 hour. Resin was filtered and washed with N,N-dimethylformamide (2×80 mL), dichloromethane (2×80 mL) and N,N-dimethylformamide (2×80 mL). Fmoc group was removed by treatment with 20% piperidine in N,N-dimethylformamide (1×5 min, 1×30 min, 2×80 mL). Resin was washed with N,N-dimethylformamide (3×80 mL), 2-propanol (2×80 mL) and dichloromethane (100 mL, 2×80 mL). Solution of dodecanedioic acid mono-tert-butyl ester (C12(OtBu)-OH, 6.13 g, 21.4 mmol), O-(6-chloro-benzotriazol-1-yl)-N,N,N',N'-tetramethyluronium tetrafluoroborate (TCTU, 7.61 g, 21.4 mmol) and N,N-diisopropylethylamine (6.71 mL, 38.5 mmol) in dichloromethane/N,N-dimethylformamide mixture (4:1, 80 mL) was added to resin and mixture was shaken for 1.5 hour. Resin was filtered and washed with N,N-dimethylformamide (6×80 mL), dichloromethane (4×80 mL), methanol (4×80 mL) and dichloromethane (7×80 mL). The product was cleaved from resin by treatment with 2,2,2-trifluoroethanol (80 mL) for 18 hours. Resin was filtered off and washed with dichloromethane (4×80 mL), dichloromethane/2-propanol mixture (1:1, 4×80 mL), 2-propanol (2×80 mL) and dichloromethane (6×80 mL). Solutions were combined; solvent evaporated and crude product was purified by column chromatography (Silicagel 60, 0.040-0-063 mm; eluent: dichloromethane/methanol 1:0-9:1). The pure product (2) was dried in vacuo and obtained as oil.

Yield: 5.40 g (42%).

RF (SiO2, dichloromethane/methanol 9:1): 0.30.

1H NMR spectrum (300 MHz, CDCl3, dH): 7.45-7.31 (m, 1H); 7.10-6.97 (m, 1H); 6.71-6.60 (m, 1H); 5.70-5.58 (m, 1H); 4.43-4.31 (m, 1H); 4.15 (s, 2H); 4.01 (s, 2H); 3.79-3.31 (m, 16H); 3.13-3.08 (m, 2H); 2.28-1.79 (m, 11H); 1.71-1.51 (m, 4H); 1.46 (s, 9H); 1.44 (s, 9H); 1.25 (bs, 12H); 1.05-0.88 (m, 2H).

LC-MS purity: 100%.

LC-MS Rt (Sunfire 4.6 mm×100 mm, acetonitrile/water 50:50 to 100:0+0.1% FA): 2.16 min.

LC-MS m/z: 903.0 (M+H)+.

2-(7-Aza-1H-benzotriazole-1-yl)-1,1,3,3-tetramethyluronium hexafluorophosphate (HATU, 2.46 g, 6.48 mmol) and triethylamine (1.89 mL, 13.6 mmol) were subsequently added to a solution of the oil from above (2, 5.31 g, 5.89 mmol) in dry dichloromethane (23 mL). Triethylamine (1.36 mL, 9.72 mmol) was added to a suspension of (2-aminoethyl)-carbamic acid benzyl ester hydrochloride (3, 1.49 g, 6.48 mmol) in dry dichloromethane (35 mL) and the resulting mixture was added to the above solution. The mixture was stirred overnight at room temperature, and then it was evaporated in dryness. The residue was redissolved in ethyl acetate (70 mL); washed with 1 M aqueous hydrochloric acid (1×70 mL), 5% aqueous solution of sodium carbonate (2×70 mL), 1 M aqueous hydrochloric acid (4×70 mL) and brine (70 mL); dried over anhydrous sodium sulfate and evaporated. The residue was purified by flash column chromatography (Silicagel 60, 0.040-0-063 mm; eluent: dichloromethane/methanol 95:5 to 92:8) to afford a thick yellow oil.

Yield: 2.81 g (44%).

RF (SiO2, dichloromethane/methanol 9:1): 0.25.

1H NMR spectrum (300 MHz, CDCl3, dH): 7.41-7.29 (m, 6H); 7.22-7.13 (m, 1H); 6.93-6.81 (m, 1H); 6.62-6.58 (m, 1H); 5.90-5.81 (m, 1H); 5.68-5.55 (m, 1H); 5.09 (s, 2H); 4.42-4.33 (m, 1H); 4.01-3.95 (m, 4H); 3.75-3.30 (m, 20H); 3.14-3.06 (m, 2H); 2.31-2.01 (m, 11H); 1.97-1.76 (m, 1H); 1.65-1.52 (m, 4H); 1.46 (s, 9H); 1.44 (s, 9H); 1.27 (bs, 12H); 1.04-0.87 (m, 2H).

Palladium on carbon (10%, 0.15 g, 0.13 mmol) was added to a solution of the above compound (2.81 g, 2.60 mmol) in methanol (43 mL) and the resulting mixture was hydrogenated at normal pressure for 2.5 hours. The catalyst was filtered off and the filtrate evaporated to dryness. The residue was co-evaporated four times with toluene and dried in vacuo to yield compound 5.

Yield: 2.01 g (81%).

1H NMR spectrum (300 MHz, CDCl3, dH): 7.51-7.36 (m, 2H); 7.04-6.96 (m, 1H); 6.76-6.66 (m, 1H); 5.93-5.85 (m, 1H); 4.41-4.29 (m, 1H); 4.03-3.99 (m, 4H); 3.73-3.25 (m, 18H); 3.13-2.97 (m, 4H); 2.34-1.78 (m, 11H); 1.67-1.51 (m, 4H); 1.46 (s, 9H); 1.44 (s, 9H); 1.30 (m, 12H); 1.04-0.88 (m, 2H).

LC-MS purity: 100% (ELSD).

LC-MS Rt (Kinetex, 4.6 mm×50 mm, acetonitrile/water 70:30 to 100:0+0.1% TFA): 0.67 min.

LC-MS m/z: 945.0 (M+H)+.

N,N-Diisopropylethylamine (0.40 mL, 2.28 mmol) was added to a solution of the above amine (5, 1.79 g, 1.90 mmol) in dry dichloromethane (30 mL) at −30° C. under argon. Bromoacetyl bromide (0.20 mL, 2.28 mmol) was added dropwise and the resulting solution was stirred at −30° C. for 3 hours. The cooling bath was removed, the mixture was stirred at room temperature for additional 1 hour and then it was evaporated to dryness. The residue was redissolved in ethyl acetate (50 mL), washed with 5% aqueous solution of citric acid (3×50 mL, very slow separation of phases), 1 M aqueous hydrochloric acid (4×50 mL) and brine (50 mL). The organic layer was dried over anhydrous sodium sulfate, filtered and evaporated. The residue was purified by flash column chromatography (Silicagel 60, 0.040-0-063 mm; eluent: dichloromethane/methanol 95:5 to 93:7) to afford a yellow oil.

Yield: 1.63 g (80%).

RF (SiO2, dichloromethane/methanol 95:5): 0.25.

1H NMR spectrum (300 MHz, CDCl3, dH): 7.56-7.48 (m, 1H); 7.43-7.34 (m, 1H); 7.04-6.95 (m, 1H); 6.62 (d, J=7.9 Hz, 1H); 5.74-5.63 (m, 1H); 4.43-4.33 (m, 1H); 4.02 (s, 4H); 3.85 (s, 2H); 3.73-3.40 (m, 20H); 3.14-3.09 (m, 2H); 2.34-2.04 (m, 9H); 1.97-1.76 (m, 4H); 1.68-1.51 (m, 7H); 1.46 (s, 9H); 1.44 (s, 9H); 1.27 (m, 12H); 1.07-0.90 (m, 2H).

LC-MS purity: 100% (ELSD).

LC-MS Rt (Kinetex, 4.6 mm×50 mm, acetonitrile/water 50:50 to 100:0+0.1% FA): 2.16 min.

LC-MS m/z: 1066.0 (M+H)+.

The above compound (1.53 g, 1.44 mmol) was dissolved in trifluoroacetic acid (25 mL) and left to stay for 1.5 hour. Trifluoroacetic acid was removed in vacuo and the residue was co-evaporated with toluene three times and dichloromethane ten times to afford a yellow oily solid.

Yield: 810 mg (59%).

1H NMR spectrum (300 MHz, AcOD-d4, dH): 4.64-4.54 (m, 1H); 4.13 (s, 2H); 4.11 (s, 2H); 3.96 (s, 2H); 3.78-3.40

(m, 20H); 3.13-3.10 (d, J=6.6 Hz, 2H); 2.51-2.19 (m, 9H); 1.94-1.77 (m, 4H); 1.68-1.41 (m, 7H); 1.31 (bs, 12H); 1.10-0.92 (m, 2H).

LC-MS purity: 100% (ELSD).

LC-MS Rt (Kinetex, 4.6 mm×50 mm, acetonitrile/water 20:80 to 100:0+0.1% FA): 2.82 min.

LC-MS m/z: 952.0 (M+H)+.

Example 4.7: Preparation of 16-[[4-[[(1S)-4-[2-[2-[2-[2-[2-[2-[(2-bromoacetyl)amino]ethylamino]-2-oxo-ethoxy]ethoxy]ethylamino]-2-oxo-ethoxy]ethoxy]ethylamino]-1-carboxy-4-oxo-butyl]carbamoyl]cyclohexyl]methylamino]-16-oxo-hexadecanoic acid was shaken for 2 hours. Resin was filtered and washed with N,N-dimethylformamide (2×80 mL), dichloromethane (2×80 mL) and N,N—N,N-dimethylformamide (3×80 mL). Fmoc group was removed by treatment with 20% piperidine in N,N-dimethylformamide (1×5 min, 1×30 min, 2×80 mL). Resin was washed with N,N-dimethylformamide (3×80 mL), 2-propanol (2×80 mL) and dichloromethane (100 mL, 2×80 mL). Solution of (S)-2-(9H-fluoren-9-ylmethoxycarbonylamino)-pentanedioic acid 1-tert-butyl ester (Fmoc-LGlu-OtBu, 9.11 g, 21.4 mmol), O-(6-chloro-benzotriazol-1-yl)-N,N,N',N'-tetramethyluronium tetrafluoroborate (TCTU, 7.60 g, 21.4 mmol) and N,N-diisopropylethylamine (6.71 mL, 38.5 mmol) in N,N-dimethylformamide (80 mL) was added to resin and mixture was shaken for 1 hour. Resin

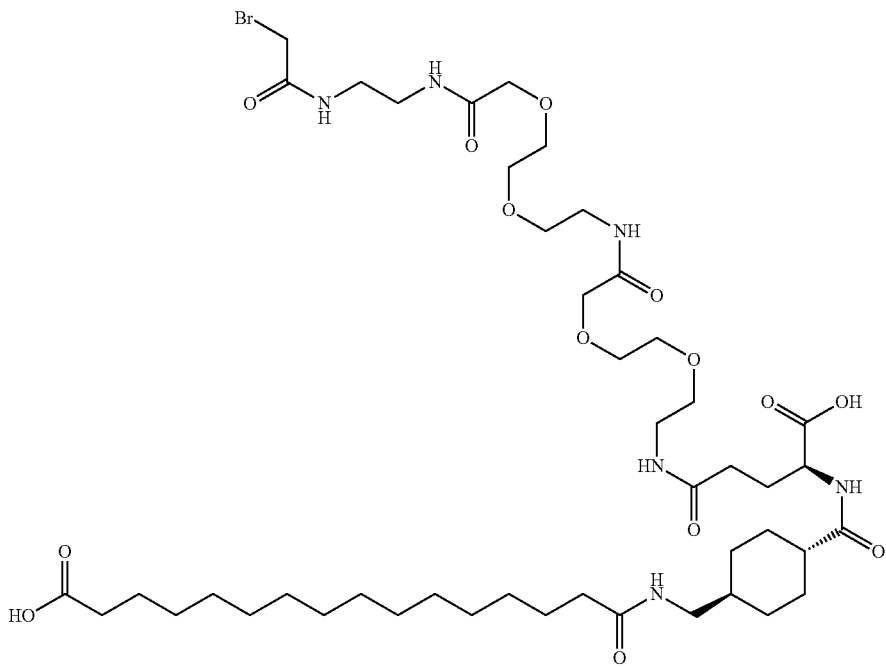 [SMILES: O=C(O)CCCCCCCCCCCCCCC(=O)NC[C@H]1CC[C@H](C(=O)N[C@@H](CCC(=O)NCCOCCOCC(=O)NCCOCCOCC(=O)NCCNC(=O)CBr)C(=O)O)CC1]

Solid Phase Synthetic Protocol:

2-Chlorotrityl resin 100-200 mesh 1.8 mmol/g (1, 11.9 g, 21.4 mmol) was left to swell in dry dichloromethane (80 mL) for 20 minutes. A solution of {2-[2-(9H-fluoren-9-ylmethoxycarbonylamino)-ethoxy]-ethoxy}-acetic acid (Fmoc-OEG-OH, 5.50 g, 14.3 mmol) and N,N-diisopropylethylamine (9.44 mL, 54.2 mmol) in dry dichloromethane (70 mL) was added to resin and the mixture was shaken for 4 hours. Resin was filtered and treated with a solution of N,N-diisopropylethylamine (4.97 mL, 28.5 mmol) in methanol/dichloromethane mixture (4:1, 2×5 min, 2×57 mL). Then resin was washed with N,N-dimethylformamide (2×80 mL), dichloromethane (2×80 mL) and N,N-dimethylformamide (3×80 mL). Fmoc group was removed by treatment with 20% piperidine in N,N-dimethylformamide (1×5 min, 1×30 min, 2×80 mL). Resin was washed with N,N-dimethylformamide (3×80 mL), 2-propanol (2×80 mL) and dichloromethane (100 mL, 2×80 mL). Solution of {2-[2-(9H-fluoren-9-ylmethoxycarbonylamino)-ethoxy]-ethoxy}-acetic acid (Fmoc-OEG-OH, 11.0 g, 28.5 mmol), O-(6-chloro-benzotriazol-1-yl)-N,N,N',N'-tetramethyluronium tetrafluoroborate (TCTU, 10.1 g, 28.5 mmol) and N,N-diisopropylethylamine (9.93 mL, 57.0 mmol) in N,N-dimethylformamide (80 mL) was added to resin and mixture was filtered and washed with N,N-dimethylformamide (2×80 mL), dichloromethane (2×80 mL) and N,N-dimethylformamide (2×80 mL). Fmoc group was removed by treatment with 20% piperidine in N,N-dimethylformamide (1×5 min, 1×30 min, 2×80 mL). Resin was washed with N,N-dimethylformamide (3×80 mL), 2-propanol (2×80 mL) and dichloromethane (100 mL, 2×80 mL). Solution of Fmoc-tranexamic acid (Fmoc-Trx-OH, 9.11 g, 21.4 mmol), O-(6-chloro-benzotriazol-1-yl)-N,N,N',N'-tetramethyluronium tetrafluoroborate (TCTU, 7.60 g, 21.4 mmol) and N,N-diisopropylethylamine (6.71 mL, 38.5 mmol) in N,N-dimethylformamide (80 mL) was added to resin and mixture was shaken for 1 hour. Resin was filtered and washed with N,N-dimethylformamide (2×80 mL), dichloromethane (2×80 mL) and N,N-dimethylformamide (2×80 mL). Fmoc group was removed by treatment with 20% piperidine in N,N-dimethylformamide (1×5 min, 1×30 min, 2×80 mL). Resin was washed with N,N-dimethylformamide (3×80 mL), 2-propanol (2×80 mL) and dichloromethane (100 mL, 2×80 mL). Solution of hexadecanedioic acid mono-tert-butyl ester (C16(OtBu)-OH, 7.33 g, 21.4 mmol), O-(6-chloro-benzotriazol-1-yl)-N,N,N',N'-tetramethyluronium tetrafluoroborate (TCTU, 7.61 g, 21.4 mmol) and N,N-diisopropylethylamine (6.71 mL, 38.5 mmol) in dichloromethane/N,N-dimethylformamide mixture (4:1, 80 mL) was added to resin and mixture was shaken for 1.5 hour. Resin was filtered and washed with N,N-dimethylformamide (6×80 mL), dichloromethane (4×80 mL), methanol (4×80 mL) and dichloromethane (7×80 mL). The product was cleaved from resin by treatment with 2,2,2-trifluoroethanol (80 mL) for 18 hours. Resin was filtered off and washed with dichloromethane (4×80 mL), dichloromethane/2-propanol mixture (1:1, 4×80 mL), 2-propanol (2×80 mL) and dichloromethane (6×80 mL). Solutions were combined; solvent evaporated and crude product was purified by column chromatography (Silicagel 60, 0.040-0-063 mm; eluent: dichloromethane/methanol 1:0-9:1). Intermediate (2) was dried in vacuo and obtained as oil.

Yield: 8.20 g (80%).

RF (SiO2, dichloromethane/methanol 9:1): 0.20.

1H NMR spectrum (300 MHz, CDCl3, dH): 7.44-7.33 (m, 1H); 7.07-6.97 (m, 1H); 6.72-6.63 (m, 1H); 5.70-5.59 (m, 1H); 4.44-4.33 (m, 1H); 4.15 (s, 2H); 4.01 (s, 2H); 3.76-3.32 (m, 16H); 3.14-3.07 (m, 2H); 2.38-1.77 (m, 11H); 1.71-1.50 (m, 4H); 1.46 (s, 9H); 1.44 (s, 9H); 1.25 (bs, 20H); 1.05-0.87 (m, 2H).

LC-MS purity: 100%.

LC-MS Rt (Sunfire 4.6 mm×100 mm, acetonitrile/water 50:50 to 100:0+0.1% FA): 3.56 min.

LC-MS m/z: 959.0 (M+H)+.

2-(7-Aza-1H-benzotriazole-1-yl)-1,1,3,3-tetramethyluronium hexafluorophosphate (HATU, 3.55 g, 9.34 mmol) and triethylamine (2.72 mL, 19.5 mmol) were subsequently added to a solution of intermediate 2 (8.13 g, 8.49 mmol) in dry dichloromethane (34 mL). Triethylamine (1.78 mL, 12.7 mmol) was added to a suspension of (2-amino-ethyl)-carbamic acid benzyl ester hydrochloride (2.15 g, 9.34 mmol) in dry dichloromethane (51 mL) and the resulting mixture was added to the above solution. The mixture was stirred overnight at room temperature, and then it was evaporated in dryness. The residue was redissolved in ethyl acetate (150 mL); washed with 1 M aqueous hydrochloric acid (1×100 mL), 5% aqueous solution of sodium carbonate (2×100 mL), 1 M aqueous hydrochloric acid (4×100 mL) and brine; dried over anhydrous sodium sulfate and evaporated. The residue was purified by flash column chromatography (Silicagel 60, 0.040-0-063 mm; eluent: dichloromethane/methanol 95:5 to 92:8) to afford compound 4 as thick yellow oil.

Yield: 5.59 g (58%).

RF (SiO2, dichloromethane/methanol 9:1): 0.20.

1H NMR spectrum (300 MHz, CDCl3, dH): 7.41-7.31 (m, 6H); 7.21-7.12 (m, 1H); 6.92-6.83 (m, 1H); 6.58-6.52 (m, 1H); 5.89-5.79 (m, 1H); 5.62-5.51 (m, 1H); 5.10 (s, 2H); 4.43-4.32 (m, 1H); 4.05-3.92 (m, 4H); 3.75-3.30 (m, 20H); 3.15-3.07 (m, 2H); 2.33-2.03 (m, 11H); 1.97-1.68 (m, 1H); 1.67-1.51 (m, 4H); 1.45 (s, 9H); 1.44 (s, 9H); 1.26 (bs, 20H); 1.05-0.87 (m, 2H).

LC-MS purity: 100% (ELSD).

LC-MS Rt (Kinetex, 4.6 mm×50 mm, acetonitrile/water 70:30 to 100:0+0.1% TFA): 1.41 min.

LC-MS m/z: 1136.0 (M+H)+.

Palladium on carbon (10%, 0.27 g, 0.24 mmol) was added to a solution of the above compound (4, 5.59 g, 4.93 mmol) in methanol (85 mL) and the resulting mixture was hydrogenated at normal pressure for 2.5 hours. The catalyst was filtered off and the filtrate evaporated to dryness. The residue was co-evaporated four times with toluene and dried in vacuo to yield compound 5.

Yield: 3.45 g (70%).

1H NMR spectrum (300 MHz, CDCl3, dH): 7.43-7.33 (m, 2H); 7.05-6.94 (m, 1H); 6.72-6.65 (m, 1H); 5.69-5.59 (m, 1H); 4.44-4.33 (m, 1H); 4.03-3.98 (m, 4H); 3.72-3.39 (m, 18H); 3.15-3.07 (m, 2H); 2.96-2.90 (m, 2H); 2.34-1.78 (m, 13H); 1.71-1.51 (m, 7H); 1.46 (s, 9H); 1.44 (s, 9H); 1.25 (m, 20H); 1.07-0.93 (m, 1H).

LC-MS purity: 100% (ELSD).

LC-MS Rt (Kinetex, 4.6 mm×50 mm, acetonitrile/water 70:30 to 100:0+0.1% TFA): 0.76 min.

LC-MS m/z: 1001.0 (M+H)+.

N,N-Diisopropylethylamine (0.73 mL, 4.14 mmol) was added to a solution of the above amine (5, 3.45 g, 3.45 mmol) in dry dichloromethane (55 mL) at −30° C. under argon. Bromoacetyl bromide (0.36 mL, 4.14 mmol) was added dropwise and the resulting solution was stirred at −30° C. for 3 hours. The cooling bath was removed, the mixture was stirred at room temperature for additional 1 hour and then it was evaporated to dryness. The residue was redissolved in ethyl acetate (100 mL), washed with 5% aqueous solution of citric acid (3×100 mL, very slow separation of phases), 1 M aqueous hydrochloric acid (4×100 mL) and brine. The organic layer was dried over anhydrous sodium sulfate, filtered and evaporated. The residue was purified by flash column chromatography (Silicagel 60, 0.040-0-063 mm; eluent: dichloromethane/methanol 95:5 to 93:7) to afford compound 6 as yellow oil.

Yield: 1.63 g (44%).

RF (SiO2, dichloromethane/methanol 95:5): 0.15.

1H NMR spectrum (300 MHz, CDCl3, dH): 7.55-7.46 (m, 1H); 7.43-7.33 (m, 1H); 6.99-6.89 (m, 1H); 6.58 (d, J=7.5 Hz, 1H); 5.72-5.59 (m, 1H); 4.44-4.32 (m, 1H); 4.02 (s, 4H); 3.85 (s, 2H); 3.74-3.40 (m, 20H); 3.14-3.09 (m, 2H); 2.33-2.05 (m, 9H); 2.01-1.76 (m, 4H); 1.67-1.53 (m, 7H); 1.46 (s, 9H); 1.44 (s, 9H); 1.25 (m, 20H); 1.07-0.89 (m, 2H).

LC-MS purity: 100% (ELSD).

LC-MS Rt (Kinetex, 4.6 mm×50 mm, acetonitrile/water 50:50 to 100:0+0.1% FA): 3.47 min.

LC-MS m/z: 1122.0 (M+H)+.

The above compound (6, 1.63 g, 1.53 mmol) was dissolved in trifluoroacetic acid (25 mL) and left to stay for 1.5 hour. Trifluoroacetic acid was removed in vacuo and the residue was co-evaporated with toluene three times. Diethyl ether (120 mL) was added to the oily residue and the mixture was stirred for 1 hour. Then precipitate was filtered off and the residue dried in vacuo to afford a white powder.

Yield: 1.55 g (90%).

1H NMR spectrum (300 MHz, AcOD-d4, dH): 4.65-4.56 (m, 1H); 4.14 (s, 2H); 4.12 (s, 2H); 3.98 (s, 2H); 3.78-3.44 (m, 20H); 3.14-3.10 (d, J=6.8 Hz, 2H); 2.48-2.21 (m, 8H); 2.18-2.10 (m, 1H); 1.97-1.79 (m, 4H); 1.70-1.46 (m, 7H); 1.32 (bs, 20H); 1.11-0.93 (m, 2H).

LC-MS purity: 100% (ELSD).

LC-MS Rt (Kinetex, 4.6 mm×50 mm, acetonitrile/water 20:80 to 100:0+0.1% FA): 3.32 min.

LC-MS m/z: 1008.0 (M+H)+.

Example 4.8: Preparation of 18-[[4-[[[(1S)-4-[2-[2-[2-[2-[2-[2-[[[(1S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]carbamoyl]cyclohexyl]methylamino]-18-oxo-octadecanoic acid

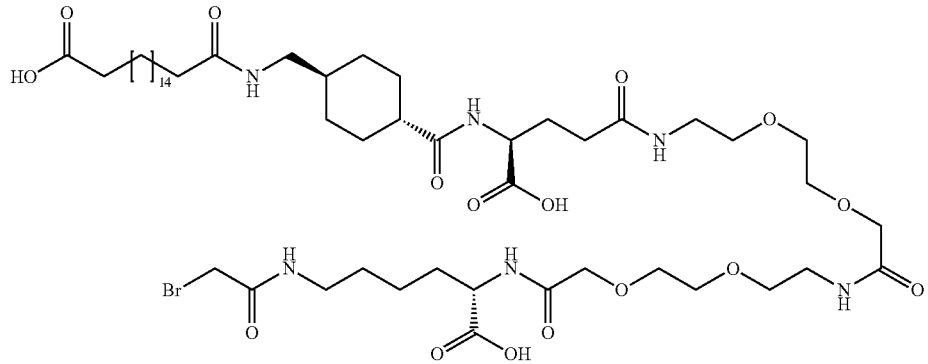

Synthetic Protocol:

Wang Fmoc-Lys(Mtt) resin 0.26 mmol/g (1, 11.7 g, 3.05 mmol) was left to swell in dichloromethane (100 mL) for 45 minutes. Fmoc group was removed by treatment with 20% piperidine in N,N-dimethylformamide (1×5 min, 1×10 min, 1×30 min, 3×90 mL). Resin was washed with N,N-dimethylformamide (3×90 mL), 2-propanol (3×90 mL) and dichloromethane (3×90 mL). A solution of {2-[2-(9H-fluoren-9-ylmethoxycarbonylamino)-ethoxy]-ethoxy}-acetic acid (Fmoc-OEG-OH, 2.35 g, 6.09 mmol), O-(6-chlorobenzotriazol-1-yl)-N,N,N',N'-tetramethyluronium tetrafluoroborate (TCTU, 2.17 g, 6.09 mmol) and N,N-diisopropylethylamine (2.12 mL, 12.2 mmol) in N,N-dimethylformamide (100 mL) was added to resin and the mixture was shaken for 1 hour. Resin was filtered and washed with N,N-dimethylformamide (3×90 mL), dichloromethane (3×90 mL) and N,N-dimethylformamide (3×90 mL). Fmoc group was removed by treatment with 20% piperidine in N,N-dimethylformamide (1×5 min, 1×10 min, 1×30 min, 3×90 mL). Resin was washed with N,N-dimethylformamide (3×90 mL), 2-propanol (3×90 mL) and dichloromethane (3×90 mL). Solution of {2-[2-(9H-fluoren-9-ylmethoxycarbonylamino)-ethoxy]-ethoxy}-acetic acid (Fmoc-OEG-OH, 2.35 g, 6.09 mmol), O-(6-chloro-benzotriazol-1-yl)-N,N,N',N'-tetramethyluronium tetrafluoroborate (TCTU, 2.17 g, 6.09 mmol) and N,N-diisopropylethylamine (2.12 mL, 12.2 mmol) in N,N-dimethylformamide (100 mL) was added to resin and mixture was shaken for 1.5 hour. Resin was filtered and washed with N,N-dimethylformamide (3×90 mL), dichloromethane (3×90 mL) and N,N-dimethylformamide (3×90 mL) to obtain intermediate 1. Fmoc group was removed by treatment with 20% piperidine in N,N-dimethylformamide (1×5 min, 1×10 min, 1×30 min, 3×90 mL). Resin was washed with N,N-dimethylformamide (3×90 mL), 2-propanol (3×90 mL) and dichloromethane (3×90 mL). Solution of (S)-2-(9H-fluoren-9-ylmethoxycarbonylamino)-pentanedioic acid 1-tert-butyl ester (Fmoc-LGlu-OtBu, 1.94 g, 4.57 mmol), O-(6-chloro-benzotriazol-1-yl)-N,N,N',N'-tetramethyluronium tetrafluoroborate (TCTU, 1.62 g, 4.57 mmol) and N,N-diisopropylethylamine (1.43 mL, 8.23 mmol) in N,N-dimethylformamide (100 mL) was added to resin and mixture was shaken for 1.5 hour. Resin was filtered and washed with N,N-dimethylformamide (3×90 mL), dichloromethane (3×90 mL) and N,N-dimethylformamide (3×90 mL). Fmoc group was removed by treatment with 20% piperidine in N,N-dimethylformamide (1×5 min, 1×10 min, 1×30 min, 3×90 mL). Resin was washed with N,N-dimethylformamide (3×90 mL), 2-propanol (3×90 mL) and dichloromethane (3×90 mL). Solution of 4-[(9H-fluoren-9-ylmethoxycarbonylamino)methyl]cyclohexanecarboxylic acid (Fmoc-Trx-OH, 1.73 g, 4.57 mmol), O-(6-chloro-benzotriazol-1-yl)-N,N,N',N'-tetramethyluronium tetrafluoroborate (TCTU, 1.62 g, 4.57 mmol) and N,N-diisopropylethylamine (1.43 mL, 8.23 mmol) in N,N-dimethylformamide (100 mL) was added to resin and mixture was shaken for 1 hour. Resin was filtered and washed with N,N-dimethylformamide (3×90 mL), dichloromethane (3×90 mL) and N,N-dimethylformamide (3×90 mL) to obtain intermediate2. Fmoc group was removed by treatment with 20% piperidine in N,N-dimethylformamide (1×5 min, 1×10 min, 1×30 min, 3×50 mL). Resin was washed with N,N-dimethylformamide (3×50 mL), 2-propanol (3×50 mL) and dichloromethane (3×30 mL). Solution of octadecanedioic acid mono-tert-butyl ester (C18(OtBu)-OH, 0.85 g, 2.28 mmol), O-(6-chloro-benzotriazol-1-yl)-N,N,N',N'-tetramethyluronium tetrafluoroborate (TCTU, 0.81 g, 2.28 mmol) and N,N-diisopropylethylamine (0.72 mL, 4.11 mmol) in N,N-dimethylformamide (50 mL) was added to resin and mixture was shaken for 1.5 hour. Resin was filtered and washed with N,N-dimethylformamide (3×50 mL), dichloromethane (3×50 mL) and N,N-dimethylformamide (3×50 mL). Mtt group was removed by treatment with 80% 1,1,1,3,3,3-hexafluoro-2-propanol in dichloromethane (2×10 min, 2×30 min, 4×50 mL). Resin was washed with dichloromethane (6×50 mL). Solution of bromoacetic acid (4.24 g, 30.5 mmol) and N,N'-diisopropylcarbodiimide (DIC, 4.01 mL, 25.9 mmol) in N,N-dimethylformamide (50 mL) was added to resin and mixture was shaken for 45 minutes. Resin was filtered and washed with N,N-dimethylformamide (5×50 mL) and dichloromethane (10×50 mL). The product was cleaved from resin by treatment with trifluoroacetic acid (50 mL) for 1 hour. Resin was filtered off and washed with trifluoroacetic acid (1×25 mL) and dichloromethane (2×30 mL). Solutions were combined and solvents were evaporated to dryness giving the compound as thick brownish oil.

Yield: 2.18 mg (64%).

1H NMR spectrum (300 MHz, AcOD-d4, 80° C., dH): 4.72-4.55 (m, 2H); 4.16 (s, 2H); 4.12 (s, 2H); 3.80-3.62 (m, 12H); 3.58-3.44 (m, 4H); 3.32 (t, J=6.8 Hz, 2H); 3.15 (d, J=6.8 Hz, 2H); 2.51-2.07 (m, 8H); 2.01-1.77 (m, 6H); 1.72-1.44 (m, 11H); 1.33 (bs, 24H); 1.13-0.95 (m, 2H).

LC-MS purity: 96%.

LC-MS Rt (Kinetex 4.6 mm×50 mm, acetonitrile/water 20:80 to 100:0+0.1% FA): 3.68 min.

LC-MS m/z: 1124.1 (M+H)+.

Example 4.9: Preparation of 16-[[4-[[(1S)-4-[2-[2-[2-[2-[2-[2-[[(1S)-5-[(2-bromoacetyl)amino]-1-carboxy-pentyl]amino]-2-oxo-ethoxy]ethoxy]ethyl-amino]-2-oxo-ethoxy]ethoxy]ethylamino]-1-carboxy-4-oxo-butyl]carbamoyl]cyclohexyl]methylamino]-16-oxo-hexadecanoic acid

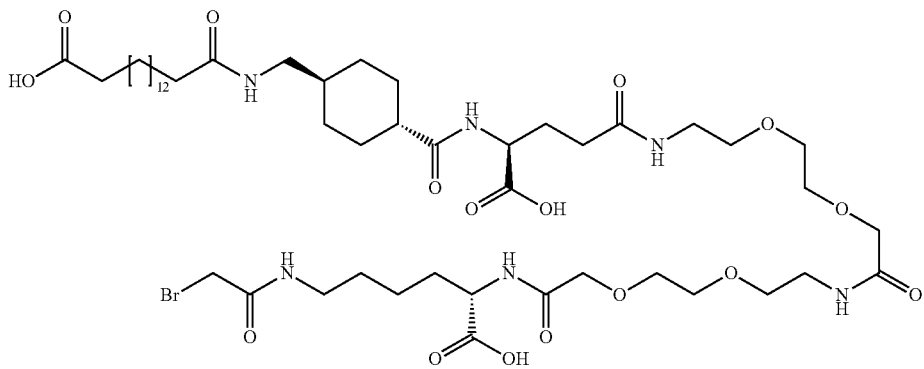

The synthetic procedure was similar to example 4.8, except that in the synthetic steps following intermediate 2 hexadecanedioic acid mono-tert-butyl ester (C16(OtBu)-OH) was used instead of octadecanedioic acid mono-tert-butyl ester (C18(OtBu)-OH). The product was obtained as a thick brownish oil.

Yield: 2.05 mg (62%).

1H NMR spectrum (300 MHz, AcOD-d4, 80° C., dH): 4.71-4.55 (m, 2H); 4.16 (s, 2H); 4.12 (s, 2H); 3.79-3.62 (m, 12H); 3.58-3.44 (m, 4H); 3.32 (t, J=6.7 Hz, 2H); 3.15 (d, J=6.6 Hz, 2H); 2.49-2.07 (m, 8H); 2.01-1.77 (m, 6H); 1.72-1.44 (m, 11H); 1.33 (bs, 20H); 1.13-0.97 (m, 2H).

LC-MS purity: 92%.

LC-MS Rt (Kinetex 4.6 mm×50 mm, acetonitrile/water 20:80 to 100:0+0.1% FA): 3.38 min.

LC-MS m/z: 1096.0 (M+H)+.

Example 4.10: Preparation of 4-[10-[[4-[2-[2-[2-[2-[2-[2-[[(1 S)-5-[(2-bromoacetyl)amino]-1-carboxy-pentyl]amino]-2-oxo-ethoxy]ethoxy]ethylamino]-2-oxo-ethoxy]ethoxy]ethylamino]-4-oxo-butyl]sulfonylamino]-10-oxo-decoxy]benzoic acid

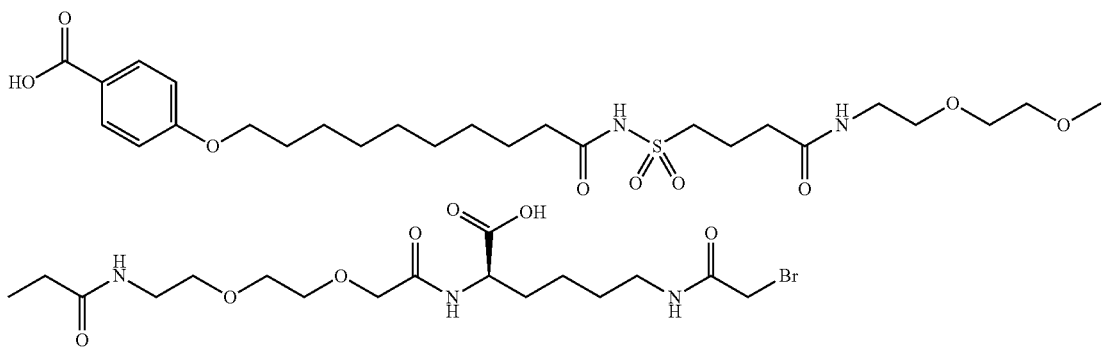

The synthetic procedure was similar to example 4.8, except that in the synthetic steps following intermediate 1 first 3-Carboxypropanesulfonamide and subsequently 10-(4-tert-butoxycarbonylphenoxy)decanoic acid were coupled to resin using standard Fmoc protection/deprotection synthetic procedures. Subsequent synthetic steps, cleavage and work-up as exemplified in example 4.8 gave a white solid.

LC-MS m/z:998.54 (M1+).

UPLC5: method 09_B4_1, Rt=8.3004 min (pH 2.3); 98% purity.

Example 4.11: Preparation of 4-[10-[[(1 S)-4-[2-[2-[2-[2-[2-[2-[[(1 S)-5-[(2-bromoacetyl)amino]-1-carboxy-pentyl]amino]-2-oxo-ethoxy]ethoxy]ethyl-amino]-2-oxo-ethoxy]ethoxy]ethylamino]-1-carboxy-4-oxo-butyl]amino]-10-oxo-decoxy]benzoic acid

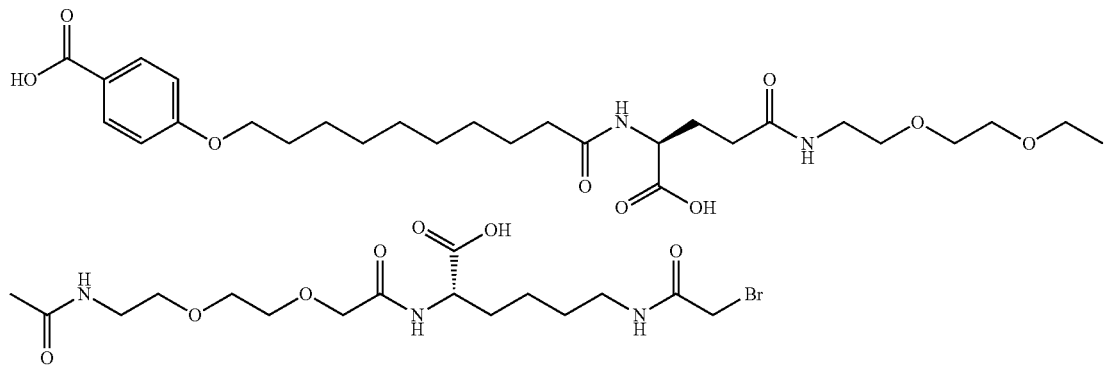

The synthetic procedure was similar to example 4.8, except that in the synthetic steps following intermediate 1 first (S)-2-(9H-fluoren-9-ylmethoxycarbonylamino)-pentanedioic acid 1-tert-butyl ester (Fmoc-LGlu-OtBu) and subsequently 10-(4-tert-butoxycarbonylphenoxy)decanoic acid were coupled to resin using standard Fmoc protection/deprotection synthetic procedures. Subsequent synthetic steps, cleavage and work-up as exemplified in example 4.8 gave a white solid.

LC-MS m/z: 978.55 (M1+).

UPLC5: method 09_B4_1, Rt=7.573 min (pH 2.3); 99% purity.

Example 4.12: Preparation of 20-[[(1S)-4-[[(1S)-4-[2-[2-[2-[2-[2-[2-[[(1S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-1-carboxy-4-oxo-butyl]amino]-20-oxo-icosanoic acid

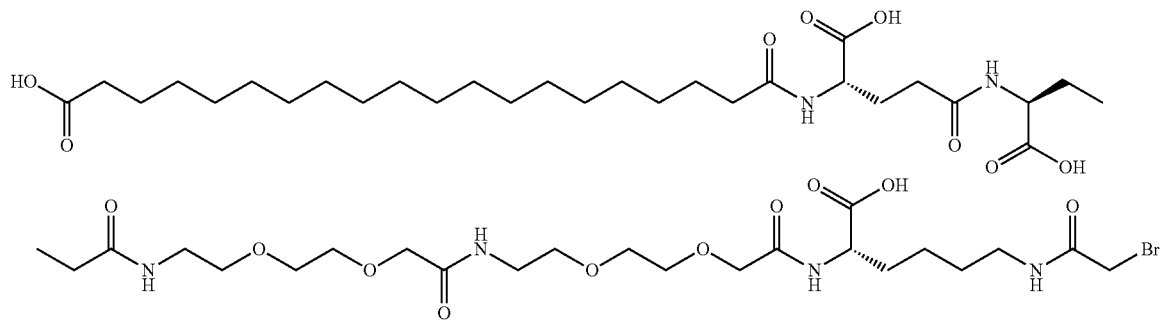

The synthetic procedure was similar to example 4.8, except that in the synthetic steps following intermediate 1 first (S)-2-(9H-fluoren-9-ylmethoxycarbonylamino)-pentanedioic acid 1-tert-butyl ester (Fmoc-LGlu-OtBu) was coupled to the resin twice, after which 20-tert-butoxy-20-oxo-icosanoic acid (C20(OtBu)-OH) was coupled to the resin using standard Fmoc protection/deprotection synthetic procedures. Subsequent synthetic steps, cleavage and work-up as exemplified in example 4.8 gave a white solid.

LC-MS m/z: 1141.2 (M+H)+.

Example 4.13: Preparation of 20-[[(1S)-4-[2-[2-[2-[2-[2-[2-[[(1S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-20-oxo-icosanoic acid

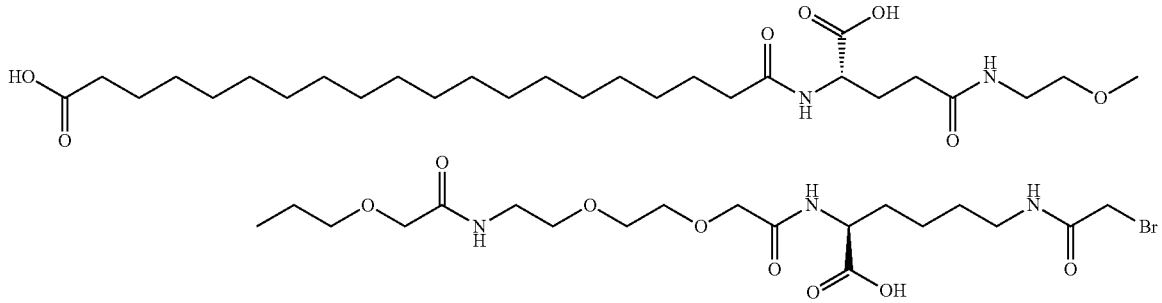

The synthetic procedure was similar to example 4.8, except that in the synthetic steps following intermediate 1 first (S)-2-(9H-fluoren-9-ylmethoxycarbonylamino)-pentanedioic acid 1-tert-butyl ester (Fmoc-LGlu-OtBu) was coupled to the resin, after which 20-tert-butoxy-20-oxo-icosanoic acid (C20(OtBu)-OH) was coupled to the resin using standard Fmoc protection/deprotection synthetic procedures. Subsequent synthetic steps, cleavage and work-up as exemplified in example 4.8 gave a white solid.

LC-MS m/z: 1012.0 (M+H)+.

Example 4.14: Preparation of (2S,25S)-2-(4-(2-Bromoacetamido)butyl)-4,13,22-trioxo-25-(15-sulfo-pentadecanamido)-6,9,15,18-tetraoxa-3,12,21-triaza-hexacosanedioic acid

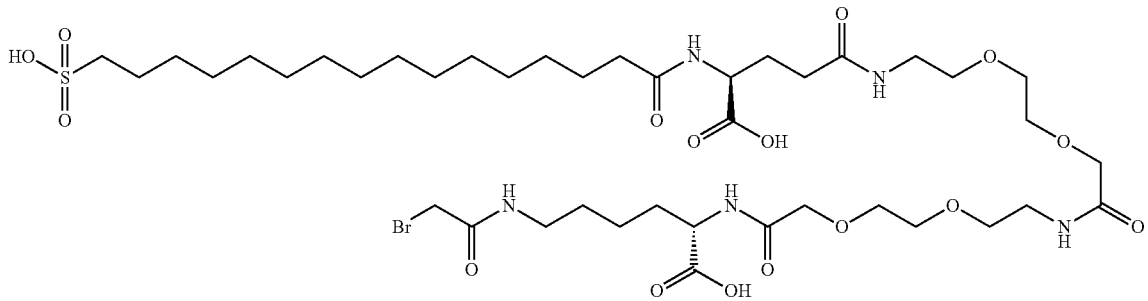 [SMILES: O=C(CBr)NCCCC[C@H](NC(=O)COCCOCCNC(=O)COCCOCCNC(=O)CC[C@H](NC(=O)CCCCCCCCCCCCCCCS(=O)(=O)O)C(=O)O)C(=O)O]

Synthetic Protocol:

Wang Fmoc-Lys(Mtt) resin 0.26 mmol/g (1, 36.7 g, 9.55 mmol) was left to swell in dichloromethane (200 mL) for 45 minutes. Fmoc group was removed by treatment with 20% piperidine in N,N-dimethylformamide (1×5 min, 1×30 min, 2×150 mL). Resin was washed with N,N-dimethylformamide (3×150 mL), 2-propanol (2×150 mL) and dichloromethane (2×150 mL). A solution of {2-[2-(9H-fluoren-9-ylmethoxycarbonylamino)-ethoxy]-ethoxy}-acetic acid (Fmoc-OEG-OH, 7.36 g, 19.1 mmol), O-(6-chlorobenzotri-azol-1-yl)-N,N,N',N'-tetramethyluronium tetrafluoroborate (TCTU, 6.79 g, 19.1 mmol) and N,N-diisopropylethylamine (6.66 mL, 38.2 mmol) in N,N-dimethylformamide (150 mL) was added to resin and the mixture was shaken for 1 hour. Resin was filtered and washed with N,N-dimethylformamide (2×150 mL), dichloromethane (2×150 mL) and N,N-dimethylformamide (2×150 mL). Fmoc group was removed by treatment with 20% piperidine in N,N-dimethylformamide (1×5 min, 1×10 min, 1×30 min, 3×150 mL). Resin was washed with N,N-dimethylformamide (2×150 mL), 2-propanol (2×150 mL) and dichloromethane (2×150 mL). Solution of {2-[2-(9H-fluoren-9-ylmethoxycarbonylamino)-ethoxy]-ethoxy}-acetic acid (Fmoc-OEG-OH, 7.36 g, 19.1 mmol), O-(6-chloro-benzotriazol-1-yl)-N,N,N',N'-tetramethyluronium tetrafluoroborate (TCTU, 6.79 g, 19.1 mmol) and N,N-diisopropylethylamine (6.66 mL, 38.2 mmol) in N,N-dimethylformamide (150 mL) was added to resin and mixture was shaken for 1 hour. Resin was filtered and washed with N,N-dimethylformamide (2×150 mL), dichloromethane (2×150 mL) and N,N-dimethylformamide (150 mL). Fmoc group was removed by treatment with 20% piperidine in N,N-dimethylformamide (1×5 min, 1×30 min, 2×150 mL). Resin was washed with N,N-dimethylformamide (3×150 mL), 2-propanol (2×150 mL) and dichloromethane (2×150 mL). Solution of (S)-2-(9H-fluoren-9-ylmethoxycarbonylamino)-pentanedioic acid 1-tert-butyl ester (Fmoc-LGlu-OtBu, 6.10 g, 14.3 mmol), O-(6-chloro-benzotriazol-1-yl)-N,N,N',N'-tetramethyluronium tetrafluoroborate (TCTU, 5.09 g, 14.3 mmol) and N,N-diisopropylethylamine (4.49 mL, 25.8 mmol) in N,N-dimethylformamide (150 mL) was added to resin and mixture was shaken for 1 hour. Resin was filtered and washed with N,N-dimethylformamide (2×150 mL), dichloromethane (2×150 mL) and N,N-dimethylformamide (150 mL). Fmoc group was removed by treatment with 20% piperidine in N,N-dimethylformamide (1×5 min, 1×30 min, 2×150 mL). Resin was washed with N,N-dimethylformamide (3×150 mL), 2-propanol (2×150 mL) and dichloromethane (2×150 mL). The resin was separated in three portions, solution of sodium 16-sulfo-hexadecanoic acid (3, 2.28 g, 6.37 mmol, (benzotriazol-1-yloxy)tripyrrolidino-phosphonium hexafluorophosphate (PyBOP, 3.31 g, 6.37 mmol) and N,N-diisopropylethylamine (2.22 mL, 12.8 mmol) in dimethyl sulfoxide (80 mL) was added to one sort of above resins and mixture was shaken for 2 hours. Resin was filtered and washed with N,N-dimethylformamide:water mixture (3:1, 3×80 mL), N,N-dimethylformamide (3×80 mL), dichloromethane (3×80 mL) and N,N-dimethylformamide (2×80 mL). Mtt group was removed by treatment with 80% 1,1,1,3,3,3-hexafluoro-2-propanol in dichloromethane (3×10 min, 2×30 min, 5×80 mL). Resin was washed with dichloromethane (6×80 mL). Solution of bromoacetic acid (6.64 g, 47.8 mmol) and N,N'-diisopropylcarbodiimide (DIC, 5.26 mL, 34.0 mmol) in N,N-dimethylformamide (80 mL) was added to resin and mixture was shaken for 45 minutes. Resin was filtered and washed with N,N-dimethylformamide (4×80 mL) and dichloromethane (10×80 mL). The product was cleaved from resin by treatment with trifluoroacetic acid (100 mL) for 1 hour. Resin was filtered off and washed with trifluoroacetic acid (1×40 mL) and dichloromethane (3×50 mL). Solutions were combined and solvents were evaporated to dryness giving a thick brownish oil. The oil was dissolved in water:acetonitrile mixture (4:1, 25 mL) and the solution was passed through a column (7×10 cm) of Dowex 50WX4 in the H+form (50-100 mesh; eluent: water). The fractions with acidic pH were combined and freeze-dried to give a white powder.

Yield: 2.17 g (68%).

1H NMR spectrum (300 MHz, AcOD-d4, 80° C., dH): 4.74-4.56 (m, 2H); 4.16 (d, J=5.3 Hz, 4H); 3.95 (s, 2H); 3.82-3.64 (m, 12H); 3.61-3.47 (m, 4H); 3.33 (t, J=6.9 Hz, 2H); 3.17-3.07 (m, 2H); 2.54 (t, J=7.3 Hz, 2H); 2.38 (t, J=7.5 Hz, 2H); 2.34-2.09 (m, 2H); 2.01-1.93 (m, 1H); 1.93-1.78 (m, 3H); 1.74-1.57 (m, 4H); 1.57-1.29 (m, 24H).

LC-MS purity: 100%.

LC-MS Rt (Kinetex 4.6 mm×50 mm, acetonitrile/water 20:80 to 100:0+0.1% FA): 2.86 min.

LC-MS m/z: 1003.9 (M+H)+.

Example 4.15: Preparation of: 12-[[(1S)-4-[[(1S)-4-[2-[2-[2-[2-[2-[2-[[(1S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-1-carboxy-4-oxo-butyl]amino]-12-oxo-dodecanoic acid (Fmoc-OEG-OH, 7.36 g, 19.1 mmol), O-(6-chlorobenzotriazol-1-yl)-N,N,N',N'-tetramethyluronium tetrafluoroborate (TCTU, 6.79 g, 19.1 mmol) and N,N-diisopropylethylamine (6.66 mL, 38.2 mmol) in N,N-dimethylformamide (150 mL) was added to resin and the mixture was shaken for 1 hour. Resin was filtered and washed with N,N-dimethylformamide (2×150 mL), dichloromethane (2×150 mL) and N,N-dimethylformamide (2×150 mL). Fmoc group was removed by treatment with 20% piperidine in N,N-dimethylformamide (1×5 min, 1×10 min, 1×30 min, 3×150 mL). Resin was washed with N,N-dimethylformamide (2×150 mL), 2-propanol (2×150 mL) and dichloromethane (2×150 mL). Solution of {2-[2-(9H-fluoren-9-ylmethoxycarbonylamino)-ethoxy]-ethoxy}-acetic acid (Fmoc-OEG-OH, 7.36 g, 19.1 mmol), O-(6-chloro-benzotriazol-1-yl)-N,N,N',N'-tetramethyluronium tetrafluoroborate (TCTU, 6.79 g, 19.1 mmol) and N,N-diisopropylethylamine (6.66 mL, 38.2 mmol) in N,N-dimethylformamide (150 mL) was added to resin and mixture was shaken for 1 hour. Resin was filtered and washed with N,N-dimethylformamide (2×150 mL), dichloromethane (2×150 mL) and N,N-dimethylformamide (150 mL). Fmoc group was removed by treatment with 20% piperidine in N,N-dimethylformamide (1×5 min, 1×30 min, 2×150 mL). Resin was washed with N,N-dimethylformamide (3×150 mL), 2-propanol (2×150 mL) and dichloromethane (2×150 mL).

Solution of (S)-2-(9H-fluoren-9-ylmethoxycarbonylamino)-pentanedioic acid 1-tert-butyl ester (Fmoc-LGlu-OtBu, 6.10 g, 14.3 mmol), O-(6-chloro-benzotriazol-1-yl)-N,N,N',N'-tetramethyluronium tetrafluoroborate (TCTU, 5.09 g, 14.3 mmol) and N,N-diisopropylethylamine (4.49 mL, 25.8 mmol) in N,N-dimethylformamide (150 mL) was added to resin and mixture was shaken for 1 hour. Resin was filtered and washed with N,N-dimethylformamide (2×150 mL), dichloromethane (2×150 mL) and N,N-dimethylformamide (150 mL). Fmoc group was removed by treatment with 20% piperidine in N,N-dimethylformamide (1×5 min, 1×30 min, 2×150 mL). Resin was washed with N,N-dimethylformamide (3×150 mL), 2-propanol (2×150 mL) and dichloromethane (2×150 mL). The resin was separated in three portions, solution of (S)-2-(9H-fluoren-9-ylmethoxycarbonylamino)-pentanedioic acid 1-tert-butyl ester (Fmoc-LGlu-OtBu, 2.03 g, 4.78 mmol), O-(6-chloro-benzotriazol-1-yl)-N,N,N',N'-tetramethyluronium tetrafluoroborate (TCTU, 1.70 g, 4.78 mmol) and N,N-diisopropylethylamine (1.50 mL, 8.60 mmol) in N,N-dimethylformamide (70 mL) was added to one sort of above resins (2) and mixture was

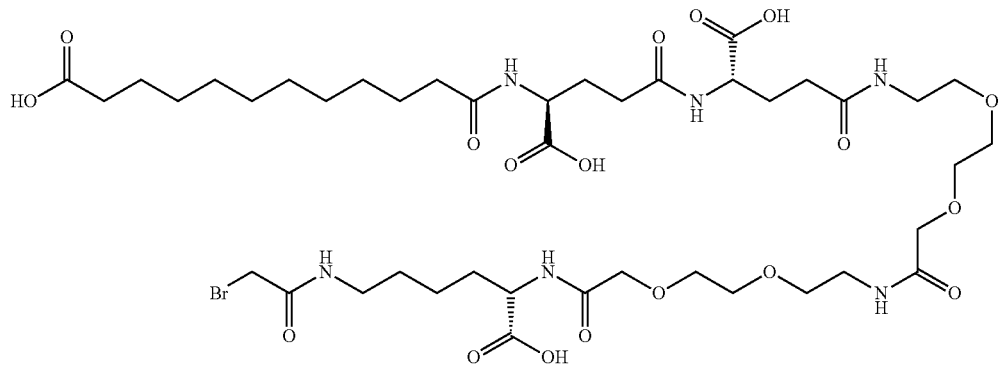

Synthetic Protocol:

Wang Fmoc-Lys(Mtt) resin 0.26 mmol/g (1, 36.7 g, 9.55 mmol) was left to swell in dichloromethane (200 mL) for 45 minutes. ). Fmoc group was removed by treatment with 20% piperidine in N,N-dimethylformamide (1×5 min, 1×30 min, 2×150 mL). Resin was washed with N,N-dimethylformamide (3×150 mL), 2-propanol (2×150 mL) and dichloromethane (2×150 mL). A solution of {2-[2-(9H-fluoren-9-ylmethoxycarbonylamino)-ethoxy]-ethoxy}-acetic acid shaken for 1 hour. Resin was filtered and washed with N,N-dimethylformamide (2×70 mL), dichloromethane (2×70 mL) and N,N-dimethylformamide (70 mL). Fmoc group was removed by treatment with 20% piperidine in N,N-dimethylformamide (1×5 min, 1×30 min, 2×70 mL). Resin was washed with N,N-dimethylformamide (3×70 mL), 2-propanol (2×70 mL) and dichloromethane (2×70 mL). Solution of dodecanedioic acid mono-tert-butyl ester (C12(OtBu)-OH, 1.37 g, 4.78 mmol), O-(6-chloro-benzotriazol-1-yl)-N,N,N',N'-tetramethyluronium tetrafluoroborate (TCTU, 1.70 g, 4.78 mmol) and N,N-diisopropylethylamine (1.50 mL, 8.60 mmol) in dichloromethane/N,N-dimethylformamide mixture (4:1, 70 mL) was added to resin and mixture was shaken for 1.5 hr. Resin was filtered and washed with N,N-dimethylformamide (3×150 mL), dichloromethane (3×150 mL) and N,N-dimethylformamide (3×150 mL). Mtt group was removed by treatment with 80% 1,1,1,3,3,3-hexafluoro-2-propanol in dichloromethane (3×10 min, 2×30 min, 4×70 mL). Resin was washed with dichloromethane (6×70 mL). Solution of bromoacetic acid (6.60 g, 47.8 mmol) and N,N'-diisopropylcarbodiimide (DIC, 5.30 mL, 34.0 mmol) in N,N-dimethylformamide (90 mL) was added to resin and mixture was shaken for 30 minutes. Resin was filtered and washed with N,N-dimethylformamide (4×70 mL) and dichloromethane (10×70 mL). The product was cleaved from resin by treatment with trifluoroacetic acid (100 mL) for 1 hour. Resin was filtered off and washed with trifluoroacetic acid (1×40 mL) and dichloromethane (2×40 mL). Solutions were combined and solvents were evaporated to dryness giving a thick brownish oil.

Yield: 2.94 mg (90%).

1H NMR spectrum (300 MHz, AcOD-d4, dH): 4.74-4.53 (m, 3H); 4.17 (s, 2H); 4.12 (s, 2H); 3.96 (s, 2H); 3.81-3.40 (m, 16H); 3.31 (t, J=6.8 Hz, 2H); 2.57-2.20 (m, 10H); 2.16-2.04 (m, 3H); 1.89-1.75 (m, 1H); 1.72-1.54 (m, 6H); 1.52-1.41 (m, 2H); 1.32 (bs, 12H).

LC-MS purity: 100%.

LC-MS Rt (Kinetex 4.6 mm×50 mm, acetonitrile/water 20:80 to 100:0+0.1% FA): 2.64 min.

LC-MS m/z: 1028.0 (M+H)+.

Example 4.16: Preparation of 12-[[(1 S)-4-[2-[2-[2-[2-[2-[2-[[(1S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-12-oxo-dodecanoic acid

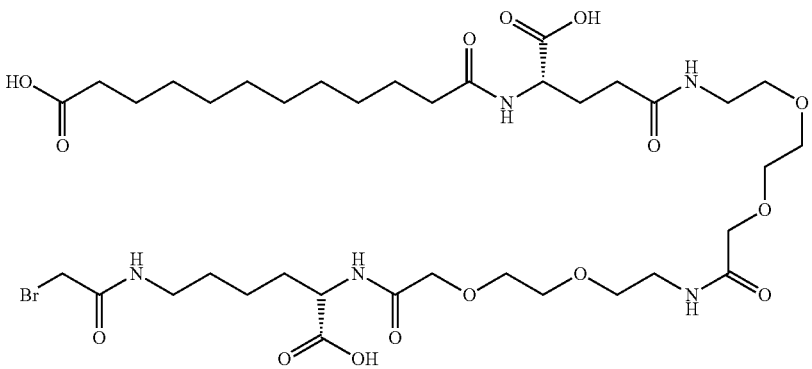

The synthetic procedure was the same as for example 4.8, except that in the synthetic steps following intermediate 1 first (S)-2-(9H-fluoren-9-ylmethoxycarbonylamino)-pentanedioic acid 1-tert-butyl ester (Fmoc-LGlu-OtBu) and subsequently 12-tert-butoxy-12-oxo-dodecanoic acid were coupled to resin using standard Fmoc protection/deprotection synthetic procedures.

Subsequent synthetic steps, cleavage and work-up as exemplified in example 4.8 gave the compound as thick brownish oil.

Yield: 97%

1H NMR spectrum (300 MHz, AcOD-d4, dH): 4.73-4.55 (m, 2H); 4.17 (s, 2H); 4.12 (s, 2H); 3.96 (s, 2H); 3.80-3.42 (m, 16H); 3.31 (t, J=6.78 Hz, 2H); 2.49-2.17 (m, 7H); 2.01-1.92 (m, 2H); 1.87-1.76 (m, 1H); 1.70-1.54 (m, 6H); 1.52-1.41 (m, 2H); 1.32 (bs, 12H).

LC-MS purity: 100%.

LC-MS Rt (Kinetex 4.6 mm×50 mm, acetonitrile/water 20:80 to 100:0+0.1% FA): 2.72 min.

LC-MS m/z: 900.0 (M+H)+.

Example 4.17: Preparation of 20-[[4-[[(1 S)-4-[2-[2-[2-[2-[2-[[(1S)-5-[(2-bromoacetyl)amino]-1-carboxy-pentyl]amino]-2-oxo-ethoxy]ethoxy]ethyl-amino]-2-oxo-ethoxy]ethoxy]ethylamino]-1-carboxy-4-oxo-butyl]carbamoyl]cyclohexyl]methylamino]-20-oxo-icosanoic acid

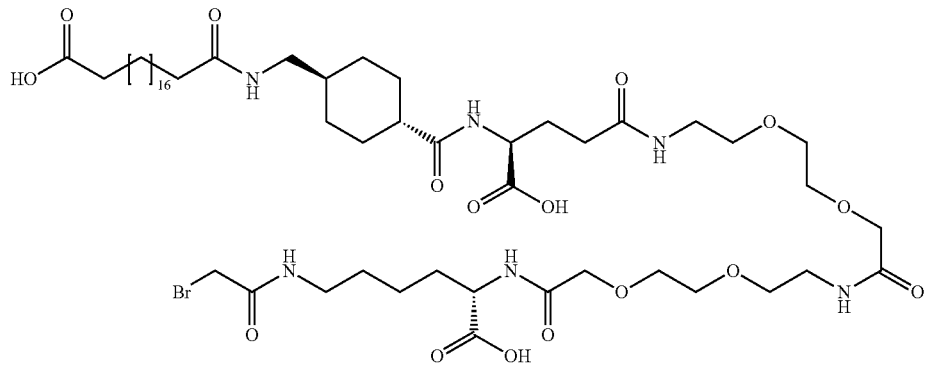

Synthetic Protocol:

Wang Fmoc-Lys(Mtt) resin 0.26 mmol/g (1, 11.2 g, 2.90 mmol) was left to swell in dichloromethane (100 mL) for 45 minutes. Fmoc group was removed by treatment with 20% piperidine in N,N-dimethylformamide (1×5 min, 1×10 min, 1×30 min, 3×100 mL). Resin was washed with N,N-dimethylformamide (3×90 mL), 2-propanol (3×90 mL) and dichloromethane (3×90 mL). A solution of {2-[2-(9H-fluoren-9-ylmethoxycarbonylamino)-ethoxy]-ethoxy}-acetic acid (Fmoc-OEG-OH, 2.23 g, 5.80 mmol), O-(6-chlorobenzotriazol-1-yl)-N,N,N',N'-tetramethyluronium tetrafluoroborate (TCTU, 2.06 g, 5.80 mmol) and N,N-diisopropylethylamine (2.02 mL, 11.6 mmol) in N,N-dimethylformamide (100 mL) was added to resin and the mixture was shaken for 1 hour. Resin was filtered and washed with N,N-dimethylformamide (3×90 mL), dichloromethane (3×90 mL) and N,N-dimethylformamide (3×90 mL). Fmoc group was removed by treatment with 20% piperidine in N,N-dimethylformamide (1×5 min, 1×10 min, 1×30 min, 3×100 mL). Resin was washed with N,N-dimethylformamide (3×90 mL), 2-propanol (3×90 mL) and dichloromethane (3×90 mL). Solution of {2-[2-(9H-fluoren-9-ylmethoxycarbonylamino)-ethoxy]-ethoxy}-acetic acid (Fmoc-OEG-OH, 2.23 g, 5.80 mmol), O-(6-chloro-benzotriazol-1-yl)-N,N,N',N'-tetramethyluronium tetrafluoroborate (TCTU, 2.06 g, 5.80 mmol) and N,N-diisopropylethylamine (2.02 mL, 11.6 mmol) in N,N-dimethylformamide (100 mL) was added to resin and mixture was shaken for 1.5 hour. Resin was filtered and washed with N,N-dimethylformamide (3×90 mL), dichloromethane (3×90 mL) and N,N-dimethylformamide (3×90 mL). Fmoc group was removed by treatment with 20% piperidine in N,N-dimethylformamide (1×5 min, 1×10 min, 1×30 min, 3×100 mL). Resin was washed with N,N-dimethylformamide (3×90 mL), 2-propanol (3×90 mL) and dichloromethane (3×90 mL). Solution of (S)-2-(9H-fluoren-9-ylmethoxycarbonylamino)-pentanedioic acid 1-tert-butyl ester (Fmoc-LGlu-OtBu, 1.85 g, 4.35 mmol), O-(6-chloro-benzotriazol-1-yl)-N,N,N',N'-tetramethyluronium tetrafluoroborate (TCTU, 1.55 g, 4.35 mmol) and N,N-diisopropylethylamine (1.36 mL, 7.82 mmol) in N,N-dimethylformamide (100 mL) was added to resin and mixture was shaken for 1.5 hour. Resin was filtered and washed with N,N-dimethylformamide (3×90 mL), dichloromethane (3×90 mL) and N,N-dimethylformamide (3×90 mL). Fmoc group was removed by treatment with 20% piperidine in N,N-dimethylformamide (1×5 min, 1×10 min, 1×30 min, 3×100 mL). Resin was washed with N,N-dimethylformamide (3×90 mL), 2-propanol (3×90 mL) and dichloromethane (3×90 mL). Solution of 4-[(9H-fluoren-9-ylmethoxycarbonylamino)methyl]cyclohexanecarboxylic acid (Fmoc-Trx-OH, 1.65 g, 4.35 mmol), O-(6-chloro-benzotriazol-1-yl)-N,N,N',N'-tetramethyluronium tetrafluoroborate (TCTU, 1.55 g, 4.35 mmol) and N,N-diisopropylethylamine (1.36 mL, 7.82 mmol) in N,N-dimethylformamide (100 mL) was added to resin and mixture was shaken for 2 hours. Resin was filtered and washed with N,N-dimethylformamide (3×90 mL), dichloromethane (3×90 mL) and N,N-dimethylformamide (3×90 mL). Fmoc group was removed by treatment with 20% piperidine in N,N-dimethylformamide (1×5 min, 1×10 min, 1×30 min, 3×100 mL). Resin was washed with N,N-dimethylformamide (3×90 mL), 2-propanol (3×90 mL) and dichloromethane (3×90 mL). Solution of icosanedioic acid mono-tert-butyl ester (C20(OtBu)-OH, 1.73 g, 4.35 mmol), O-(6-chloro-benzotriazol-1-yl)-N,N,N',N'-tetramethyluronium tetrafluoroborate (TCTU, 1.55 g, 4.35 mmol) and N,N-diisopropylethylamine (1.36 mL, 7.82 mmol) in N,N-dimethylformamide (100 mL) was added to resin and mixture was shaken for 2 hours. Resin was filtered and washed with N,N-dimethylformamide (3×90 mL), dichloromethane (3×90 mL), N,N-dimethylformamide (3×90 mL) and dichloromethane (3×90 mL). Mtt group was removed by treatment with 80% 1,1,1,3,3,3-hexafluoro-2-propanol in dichloromethane (2×10 min, 2×30 min, 4×100 mL). Resin was washed with dichloromethane (6×90 mL) and N,N-dimethylformamide (3×90 mL). Solution of bromoacetic acid (8.06 g, 58.0 mmol) and N,N'-diisopropylcarbodiimide (DIC, 7.60 mL, 49.3 mmol) in N,N-dimethylformamide (100 mL) was added to resin and mixture was shaken for 40 minutes. Resin was filtered and washed with N,N-dimethylformamide (5×90 mL) and dichloromethane (12×90 mL). The product was cleaved from resin by treatment with trifluoroacetic acid (100 mL) for 1 hour. Resin was filtered off and washed with trifluoroacetic acid (1×50 mL) and dichloromethane (7×70 mL). Solutions were combined and solvents were evaporated to dryness giving a thick brownish oil.

Yield: 3.28 g (98%).

1H NMR spectrum (300 MHz, AcOD-d4, 80° C., dH): 4.68 (dd, J=8.0 and 5.4 Hz, 1H); 4.60 (dd, J=7.9 and 5.3 Hz, 1H); 4.16 (s, 2H); 4.12 (s, 2H); 3.94 (s, 2H); 3.81-3.61 (m, 12H); 3.59-3.44 (m, 4H); 3.32 (t, J=6.8 Hz, 2H); 3.14 (d, J=6.8 Hz, 2H); 2.49-1.79 (m, 15H); 1.73-1.43 (m, 11H); 1.33 (s, 28H); 1.11-0.96 (m, 2H).

LC-MS purity: 100% (ELSD).

LC-MS Rt (Kinetex 4.6 mm×50 mm, acetonitrile/water 20:80 to 100:0+0.1% FA): 4.04 min.

LC-MS m/z: 1151.3 (M+H)+.

Example 5: Preparation of FGF21 Derivatives

The preparation of a representative FGF21 derivative is given in Example 5.1 (Compound 21). The FGF21 derivatives of Examples 5.2-5.14 (Compounds 11-20 and 22-14) are prepared by the method provided in Example 5.1. The FGF21 derivative of examples 5.15-5.37 is prepared by the method provided in Example 5.1 or as described here below.

Example 5.1: Compound 21

S{Beta-181}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21

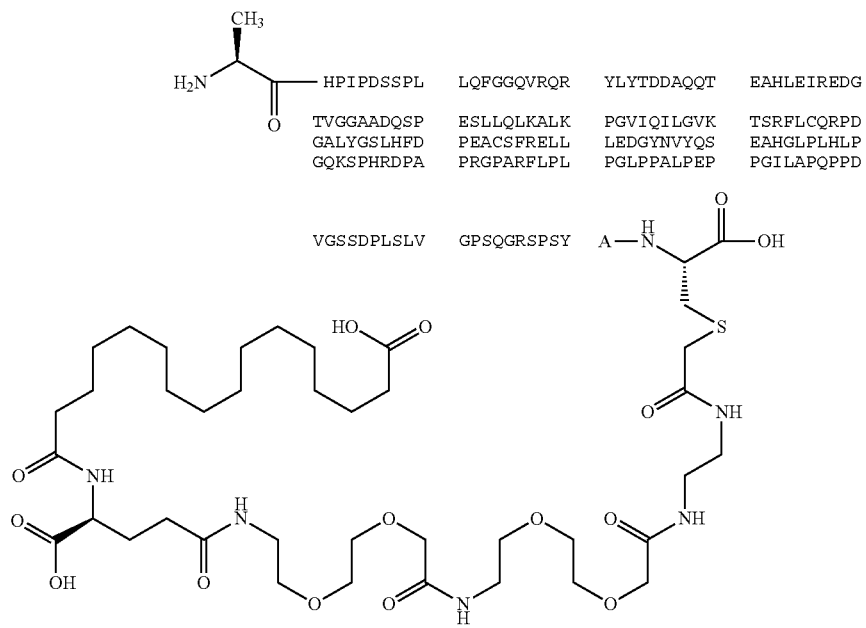

This compound is a derivative of the FGF21 analogue of SEQ ID NO:10 (see example 3).

Compound 21 was Prepared as Follows:

The Cys residue at position 181 in the S{Beta-181}-2-aminoethylsulfanyl-Ala[Gln121,Leu168,Cys181]FGF21 analogue of SEQ NO:10, prepared as generally described in Examples 1-3, was modified at the thiol group of the Cys residue at position 181C with the reagent prepared in example 4.1:

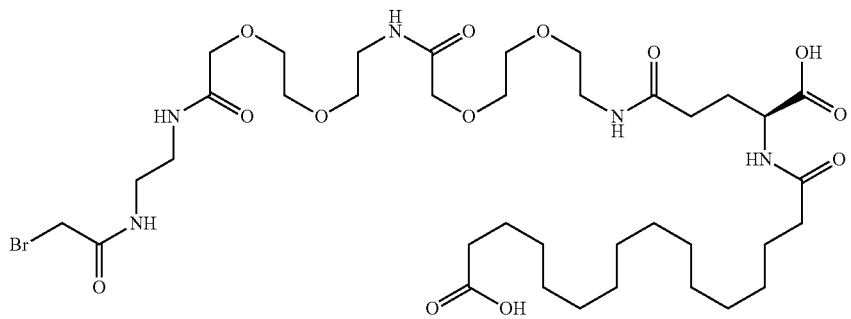 [SMILES: O=C(O)CCCCCCCCCCCCCCC(=O)N[C@@H](CCC(=O)NCCOCCOCC(=O)NCCOCCOCC(=O)NCCNC(=O)CBr)C(=O)O]

To cysteamin protected Ala[Gln121,Leu168,Cys181] FGF21 (70 mg, 0.0036 mmol), in Tris and NaCl-buffer (1.35 mg/ml) was added Tris in water to adjust pH to 8.0. BSPP (Bis(p-sulfonatophenyl)phenylphosphine dihydrate dipotassium salt, 12 mg) dissolved in water was added and stirred gently for 4 hours at room temperature. 15-{(S)-1-Carboxy-3-[2-(2-{[2-(2-{[2-(2-bromoacetylamino)ethylcarbamoyl]methoxy}ethoxy)ethylcarbamoyl]-methoxy}ethoxy)ethylcarbamoyl]propylcarbamoyl}pentadecanoic acid (19 mg, 0.022 mmol) in ethanol (0.5 ml) was added. After stirring gently overnight, MiliQ water (150 ml) was added to lower the conductivity to 2.5 mS/cm. The mixture was purified using anion exchange on a MonoQ 10/100 GL column using A-buffer: 20 mM Tris, pH 8.0; B-buffer: 20 mM Tris, 500 mM NaCl, pH 8.0, flow 6 ml and a gradient of 0-80% B over 60 CV. Yield: 37 mg, 51%.

LCMS method 2:
Theoretical mass: 20279.9. Found: 20280.4

Example 5.2: Compound 11

S{Beta-178}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys178]FGF21

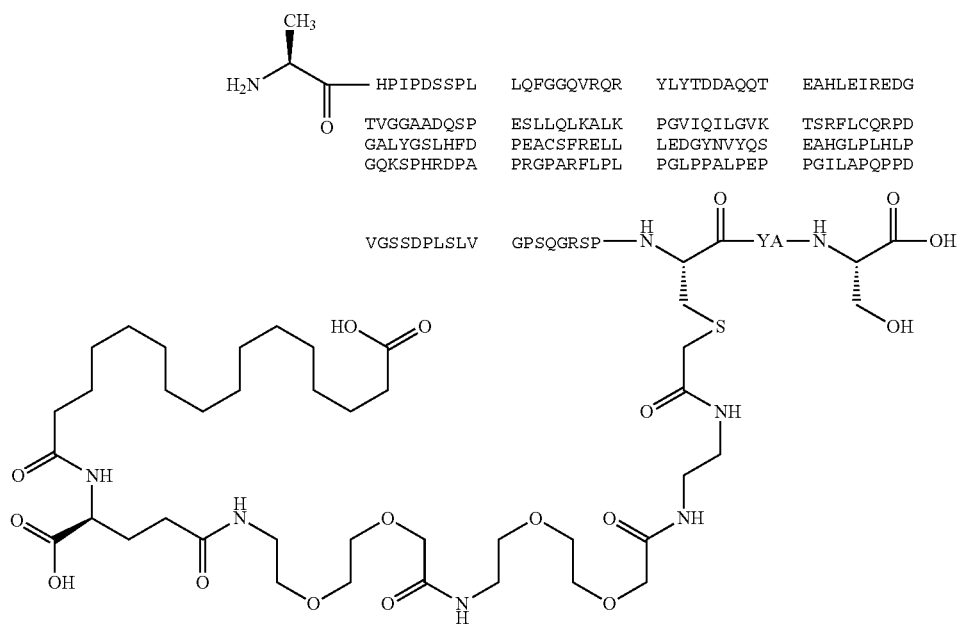

This compound is a derivative of the FGF21 analogue of SEQ ID NO:6 (see example 3) prepared by the method described under Example 5.1 using the reagent 15-{(S)-1-carboxy-3-[2-(2-{[2-(2-{[2-(2-bromoacetylamino)ethylcarbamoyl]methoxy}ethoxy)-ethylcarbamoyl]methoxy}ethoxy)ethylcarbamoyl]-propylcarbamoyl}pentadecanoic acid of Example 4.1.

LCMS method 2
Theoretical mass: 20279.9. Found: 20280.2

Example 5.3: Compound 12

S{Beta-179}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys179]FGF21

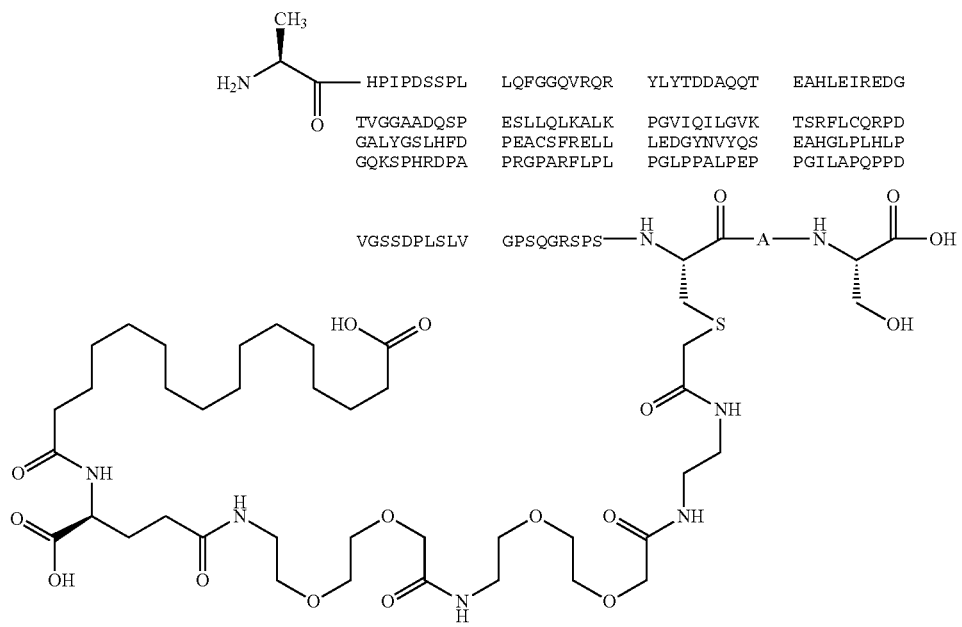

This compound is a derivative of the FGF21 analogue of SEQ ID NO:7 (see example 3) prepared by the method described under Example 5.1 using the reagent 15-{(S)-1-carboxy-3-[2-(2-{[2-(2-{[2-(2-bromoacetylamino)-ethylcarbamoyl]methoxy}ethoxy)-ethylcarbamoyl]methoxy}ethoxy)ethylcarbamoyl]propylcarbamoyl}pentadecanoic acid of Example 4.1.

LCMS method 3

Theoretical mass: 20203.8. Found: 20204.2

Example 5.4: Compound 13

S{Beta-180}-[2-[2-[[2-[2-[2-[[2-[2-[2-[[(4S)-4-carboxy-4-(11-carboxyundecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys180]FGF21

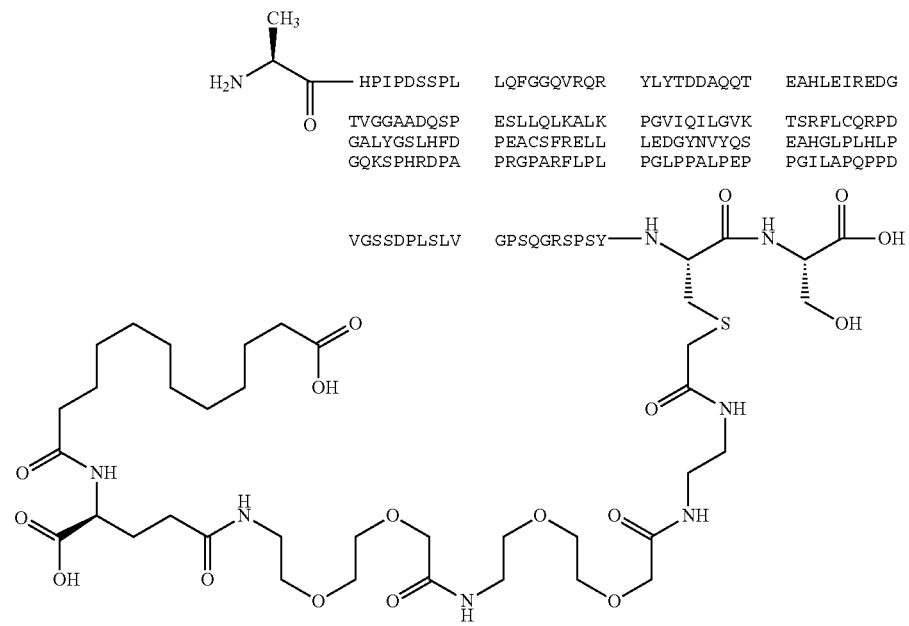

This compound is a derivative of the FGF21 analogue of SEQ ID NO:8 (see example 3) prepared by the method described under Example 5.1 using the reagent 11-{(S)-1-carboxy-3-[2-(2-{[2-(2-{[2-(2-bromoacetylamino)-ethyl-carbamoyl]methoxy}-ethoxy)ethylcarbamoyl]methoxy}ethoxy)ethylcarbamoyl]-propylcarbamoyl}undecanoic acid of Example 4.2.

LCMS method 2
Theoretical mass: 20239.8. Found: 20240.1

Example 5.5: Compound 14

S{Beta-180}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys180]FGF21

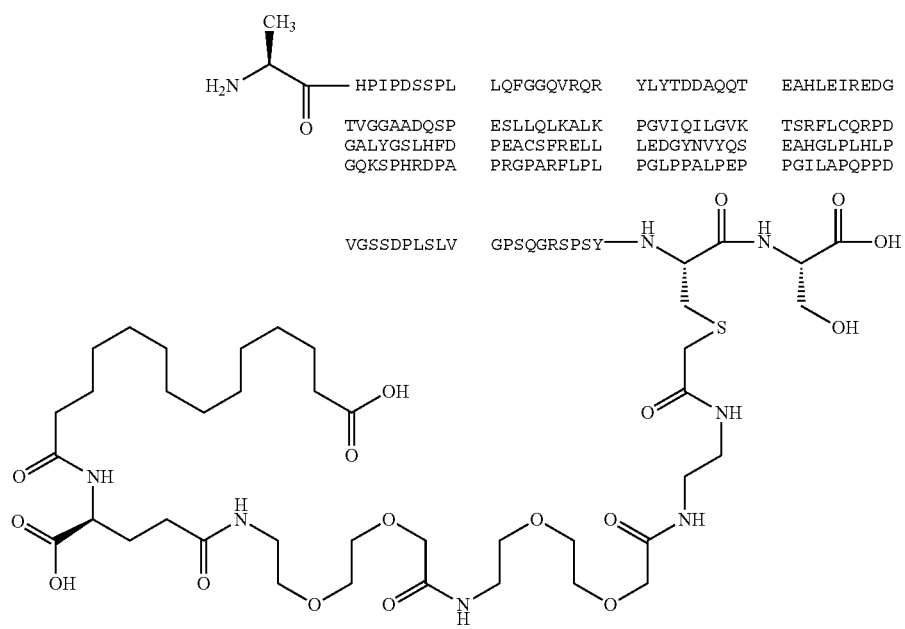

This compound is a derivative of the FGF21 analogue of SEQ ID NO:8 (see example 3) prepared by the method described under Example 5.1 using the reagent 13-{(S)-1-carboxy-3-[2-(2-{[2-(2-{[2-(2-bromoacetylamino)ethylcarbamoyl]methoxy}-ethoxy)ethyl-carbamoyl]methoxy}ethoxy)ethylcarbamoyl]propylcarbamoyl}tridecanoic acid of Example 4.3.

LCMS method 3:
Theoretical mass: 20267.8. Found: 20268.1

Example 5.6: Compound 15

S{Beta-180}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys180]FGF21

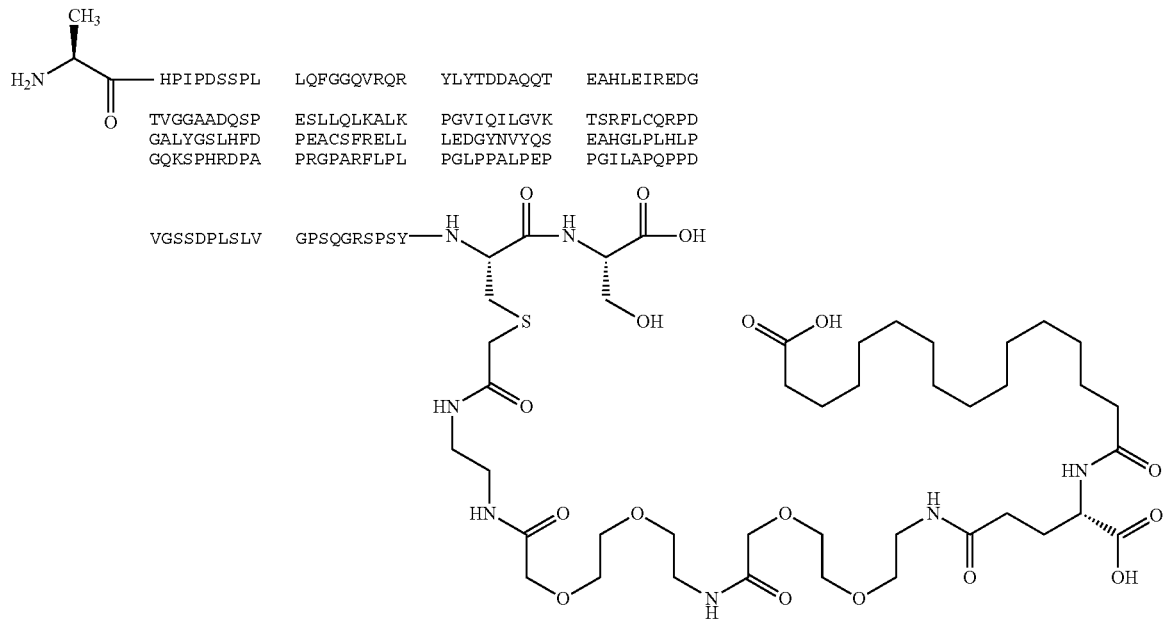

This compound is a derivative of the FGF21 analogue of SEQ ID NO:8 (see example 3) prepared by the method described under Example 5.1 using the reagent 15-{(S)-1-carboxy-3-[2-(2-{[2-(2-{[2-(2-bromoacetylamino)ethylcarbamoyl]methoxy}ethoxy)-ethyl-carbamoyl]methoxy}ethoxy)ethylcarbamoyl]propylcarbamoyl}pentadecanoic acid of Example 4.1.

LCMS method 2:
Theoretical mass: 20295.9. Found: 20296.2

Example 5.7: Compound 16

S{Beta-180}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys180]FGF21

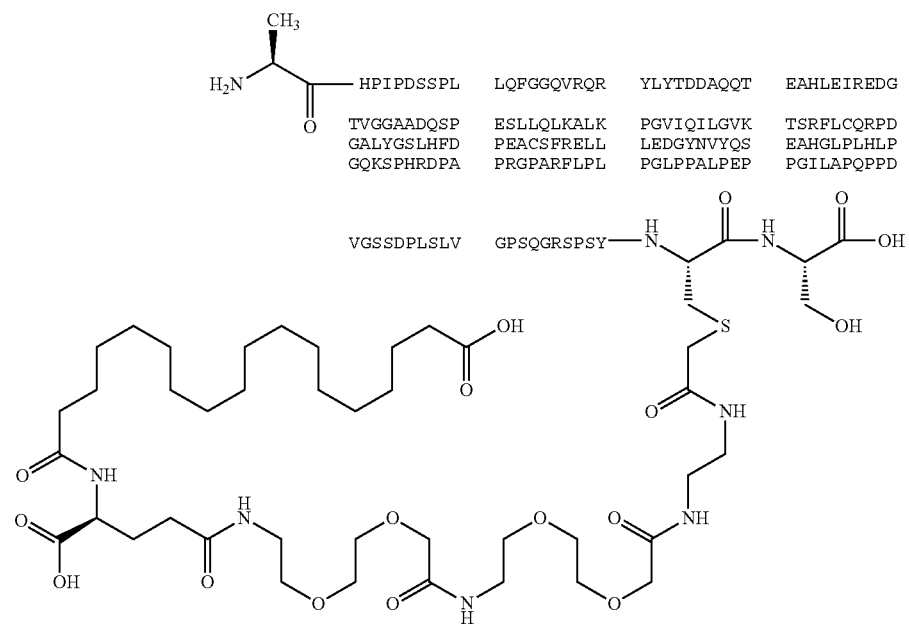

This compound is a derivative of the FGF21 analogue of SEQ ID NO:8 (see example 3) prepared by the method described under Example 5.1 using the reagent 17-{(S)-1-carboxy-3-[2-(2-{[2-(2-{[2-(2-bromoacetylamino)ethylcarbamoyl]methoxy}ethoxy)-ethyl-carbamoyl]methoxy}ethoxy)ethylcarbamoyl]propylcarbamoyl}heptadecanoic acid of Example 4.5.

LCMS method 3
Theoretical mass: 20323.9. Found: 20324.5

Example 5.8: Compound 17

S{Beta-180}-[2-[2-[[2-[2-[2-[[2-[2-[2-[[(4S)-4-carboxy-4-(19-carboxynonadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys180]FGF21

|  |  |  |  |
|---|---|---|---|
| HPIPDSSPL | LQFGGQVRQR | YLYTDDAQQT | EAHLEIREDG |
| TVGGAADQSP | ESLLQLKALK | PGVIQILGVK | TSRFLCQRPD |
| GALYGSLHFD | PEACSFRELL | LEDGYNVYQS | EAHGLPLHLP |
| GQKSPHRDPA | PRGPARFLPL | PGLPPALPEP | PGILAPQPPD |
| VGSSDPLSLV | GPSQGRSPSY |  |  |

This compound is a derivative of the FGF21 analogue of SEQ ID NO:8 (see example 3) prepared by the method described under Example 5.1 using the reagent 19-{(S)-1-carboxy-3-[2-(2-{[2-(2-{[2-(2-bromoacetylamino)-ethylcarbamoyl]methoxy}-ethoxy)ethylcarbamoyl]methoxy}ethoxy)ethylcarbamoyl]-propylcarbamoyl}nonadecanoic acid of Example 4.4.

LCMS method 3
Theoretical mass: 20352.0. Found: 20352.0

Example 5.9: Compound 18

S{Beta-180}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168,Cys180,des181]FGF21

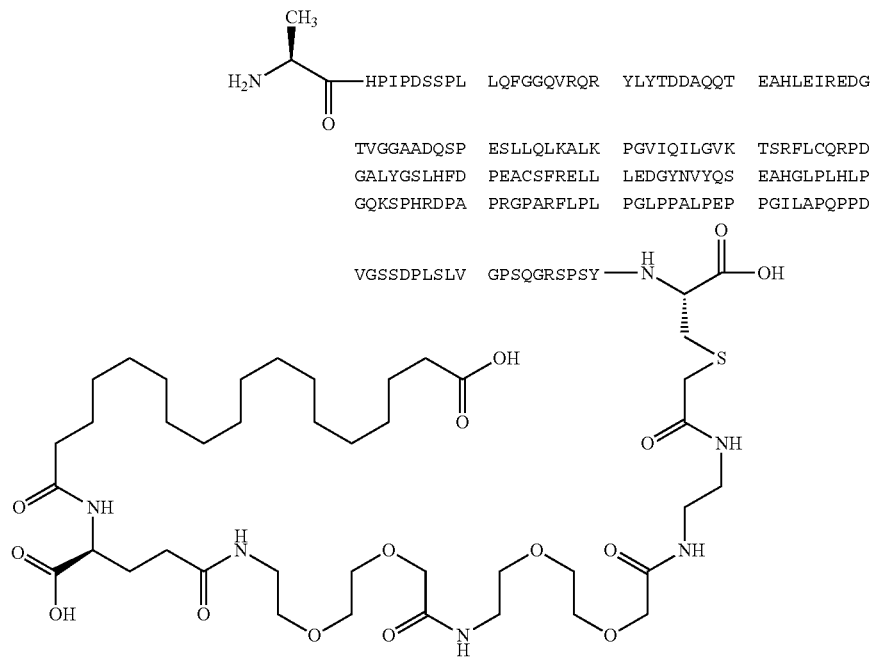

This compound is a derivative of the FGF21 analogue of SEQ ID NO:9 (see example 3) prepared by the method described under Example 5.1 using the reagent 17-{(S)-1-carboxy-3-[2-(2-{[2-(2-{[2-(2-bromoacetylamino)-ethyl-carbamoyl]methoxy}ethoxy)-ethylcarbamoyl]methoxy}ethoxy)ethylcarbamoyl]-propylcarbamoyl}heptadecanoic acid of Example 4.5.

LCMS method 2:
Theoretical mass: 20236.8. Found: 20237.0

Example 5.10: Compound 19

S{Beta-181}-[2-[2-[[2-[2-[2-[[2-[2-[2-[[(4S)-4-carboxy-4-(11-carboxyundecanoyl-amino)butanoyl]amino]ethoxy]ethoxy]acetyl]amino]ethoxy]ethoxy]acetyl]amino]-ethylamino]-2-oxoethyl]-Ala[Gln121, Leu168,Cys181]FGF21

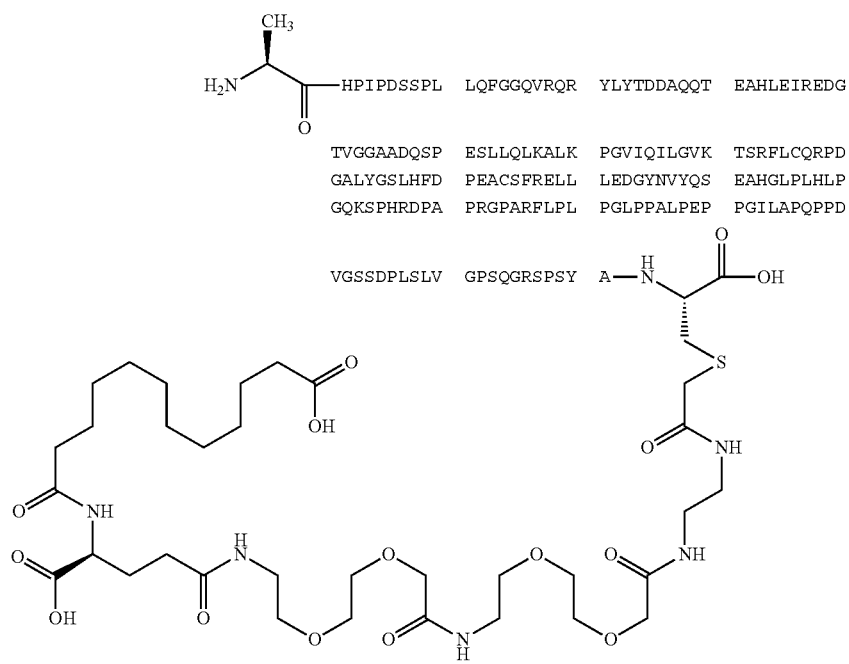

This compound is a derivative of the FGF21 analogue of SEQ ID NO:1 (see example 3) prepared by the method described under Example 5.1 using the reagent 11-{(S)-1-carboxy-3-[2-(2-{[2-(2-{[2-(2-bromoacetylamino)ethylcarbamoyl]methoxy}-ethoxy)ethyl-carbamoyl]methoxy}ethoxy)ethylcarbamoyl]propylcarbamoyl}undecanoic acid of Example 4.2.

LCMS method 2:

Theoretical mass: 20223.8. Found: 20224.4.

Example 5.11: Compound 20

S{Beta-181}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethylamino]-2-oxoethyl]-Ala[Gln121, Leu168,Cys181]FGF21

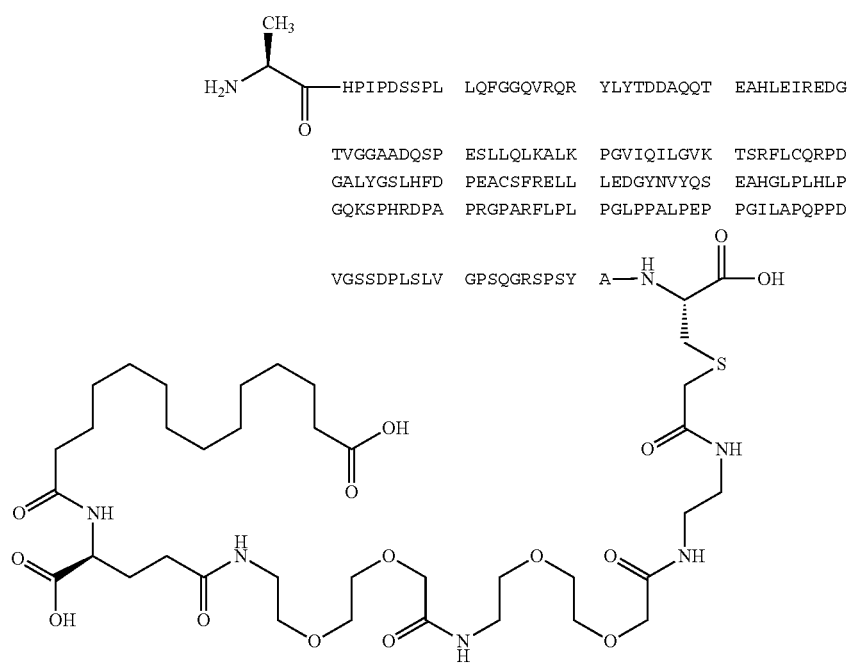

This compound is a derivative of the FGF21 analogue of SEQ ID NO:10 (see example 3) prepared by the method described under Example 5.1 using the reagent 13-{(S)-1-carboxy-3-[2-(2-{[2-(2-{[2-(2-bromoacetylamino)ethylcarbamoyl]methoxy}-ethoxy)ethylcarbamoyl]methoxy}ethoxy)ethylcarbamoyl]-propylcarbamoyl}tridecanoic acid of Example 4.3.

LCMS method 2:

Theoretical mass: 20251.8. Found: 20252.2

Example 5.12: Compound 22

S{Beta-181}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21

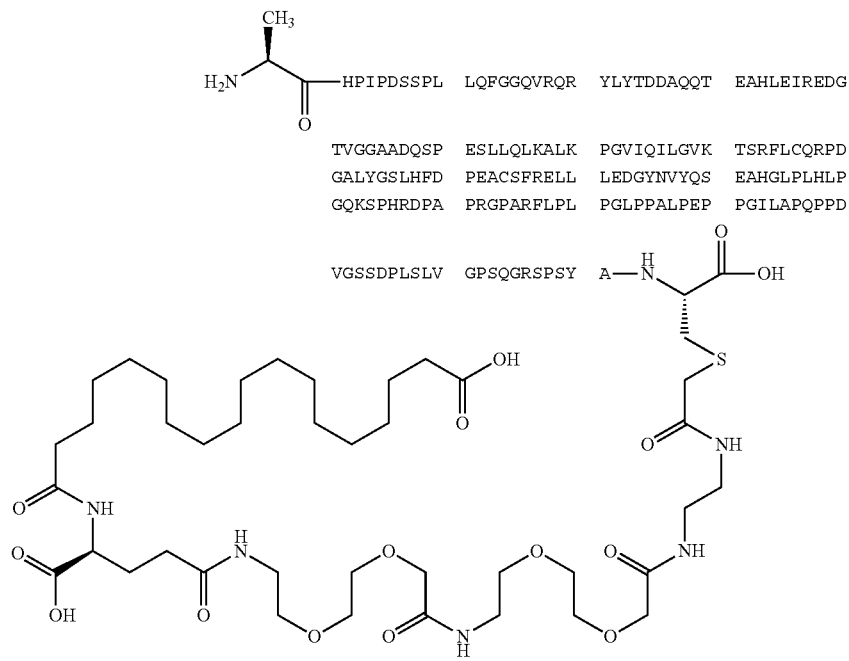

This compound is a derivative of the FGF21 analogue of SEQ ID NO:10 (see example 3) prepared by the method described under Example 5.1 using the reagent 17-{(S)-1-carboxy-3-[2-(2-{[2-(2-{[2-(2-bromoacetylamino)ethylcarbamoyl]methoxy}-ethoxy)ethyl-carbamoyl]methoxy}ethoxy)ethylcarbamoyl]propylcarbamoyl}heptadecanoic acid of Example 4.5.

LCMS method 2:
Theoretical mass: 20307.9. Found: 20308.6.

Example 5.13: Compound 23

S{Beta-181}-[2-[2-[[2-[2-[2-[[2-[2-[2-[[(4S)-4-carboxy-4-(19-carboxynonadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21

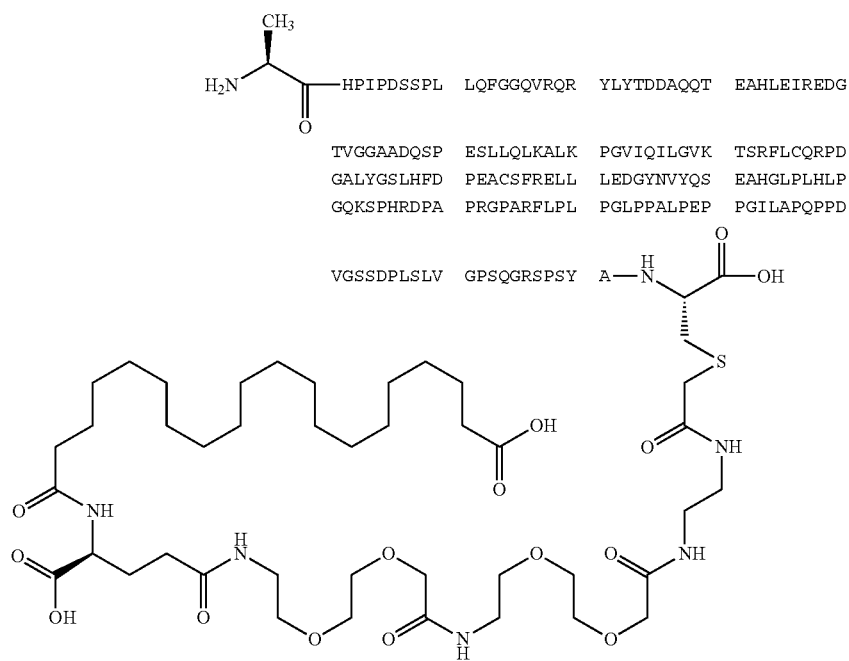

This compound is a derivative of the FGF21 analogue of SEQ ID NO:10 (see example 3) prepared by the method described under Example 5.1 using the reagent 19-{(S)-1-carboxy-3-[2-(2-{[2-(2-{[2-(2-bromoacetylamino)ethyl-carbamoyl]methoxy}ethoxy)-ethylcarbamoyl]methoxy}ethoxy)ethylcarbamoyl]-propylcarbamoyl}nonadecanoic acid of Example 4.4.

LCMS method 2:
Theoretical mass: 20336.0. Found: 20336.2

Example 5.14: Compound 24

S{Beta-181}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Met[Cys181]FGF21

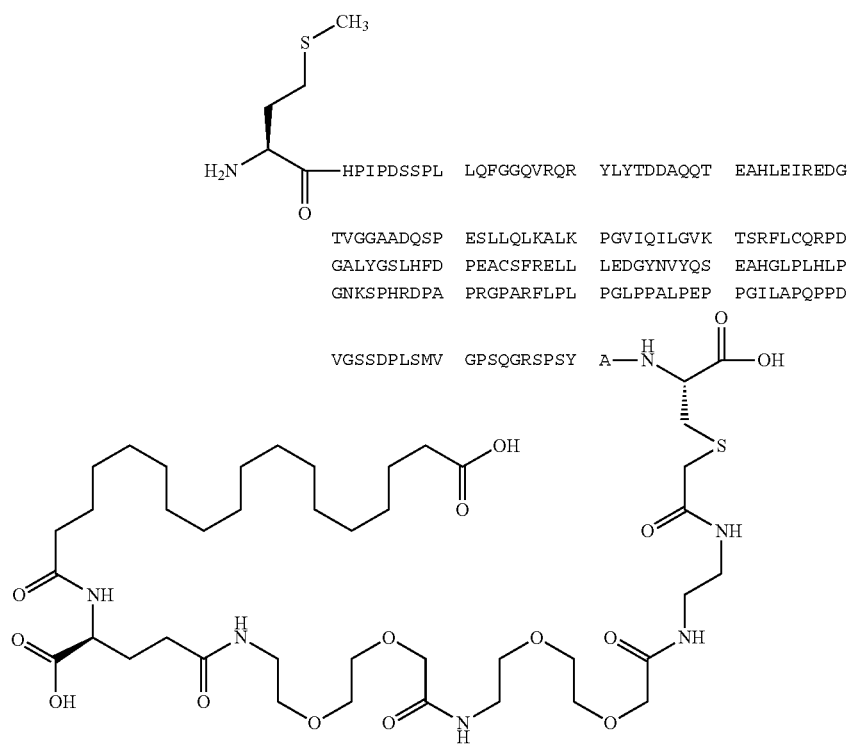

This compound is a derivative of the FGF21 analogue of SEQ ID NO:11 (see example 3) prepared by the method described under Example 5.1 using the reagent 17-{(S)-1-carboxy-3-[2-(2-{[2-(2-{[2-(2-bromoacetylamino)-ethyl-carbamoyl]methoxy}ethoxy)-ethylcarbamoyl]methoxy}ethoxy)ethylcarbamoyl]-propylcarbamoyl}heptadecanoic acid of Example 4.5.

LCMS method 3:
Theoretical mass: 20372.2. Found: 20372.2.

Example 5.15: Compound 34

S{Beta-168}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethylamino]-2-oxoethyl]-Ala[Gln121, Cys168]FGF21

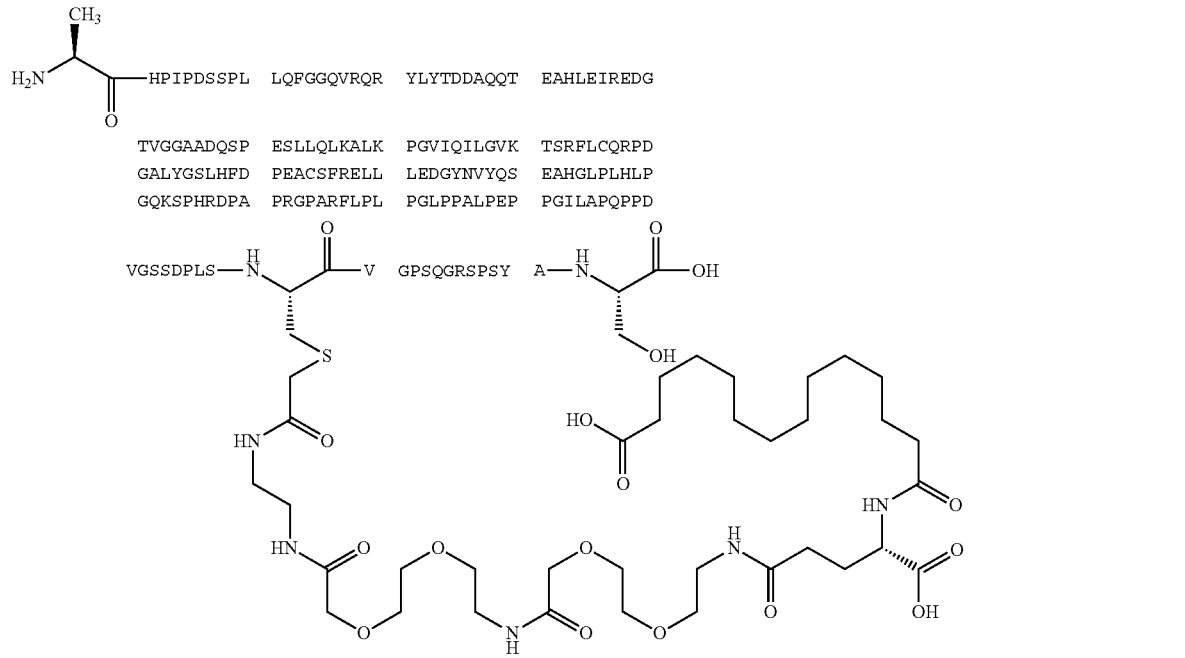

This compound is a derivative of the FGF21 analogue of SEQ ID NO:13 (see example 3) prepared by the method described under Example 5.1 using the reagent 13-{(S)-1-carboxy-3-[2-(2-{[2-(2-{[2-(2-bromoacetylamino)ethylcarbamoyl]methoxy}ethoxy)-ethylcarbamoyl]methoxy}ethoxy)ethylcarbamoyl]-propylcarbamoyl}tridecanoic acid of Example 4.3.

LCMS method 1
Theoretical mass: 20225. Found: 20226.7

Example 5.16: Compound 35

S{Beta-169}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168,Cys169]FGF21

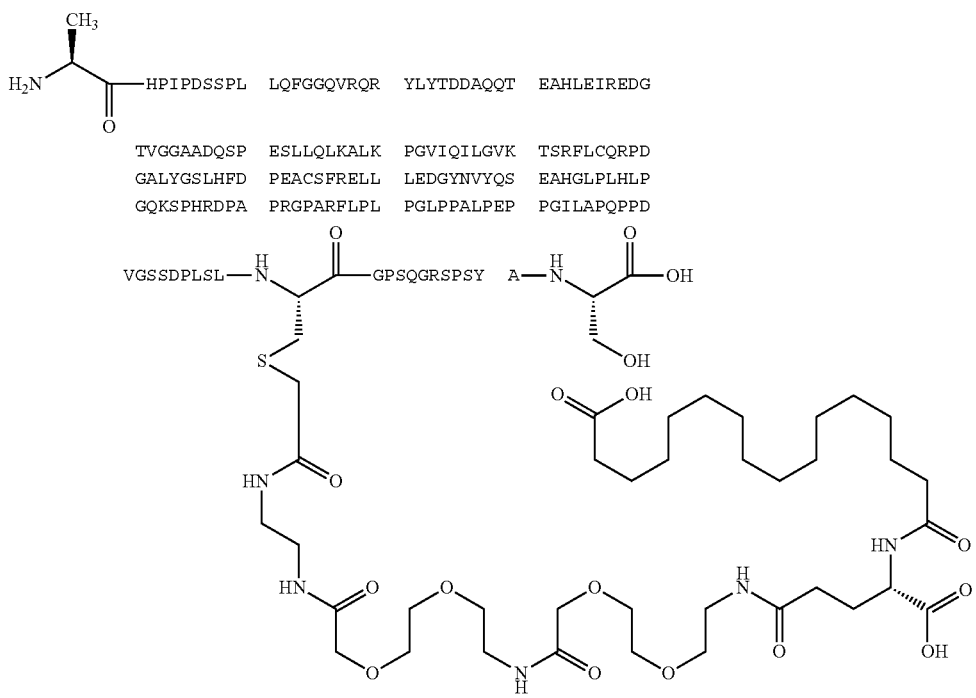

This compound is a derivative of the FGF21 analogue of SEQ ID NO:14 (see example 3) prepared by the method described under Example 5.1 using the reagent 15-{(S)-1-carboxy-3-[2-(2-{[2-(2-{[2-(2-bromoacetylamino)ethylcarbamoyl]methoxy}ethoxy)-ethylcarbamoyl]methoxy}ethoxy)ethylcarbamoyl]-propylcarbamoyl}pentadecanoic acid of Example 4.1.

LCMS method 3

Theoretical mass: 20267.8. Found: 20268.2

Example 5.17: Compound 36

18-[[(1 S)-4-[2-[2-[2-[2-[2-[2-(2-acetamidoethyl-amino)-2-oxo-ethoxy]ethoxy]ethylamino]-2-oxo-ethoxy]ethoxy]ethylamino]-1-carboxy-4-oxo-butyl]amino]-18-oxo-octadecanoic acid-Ala[Gln121, Leu168,Cys170]FGF21

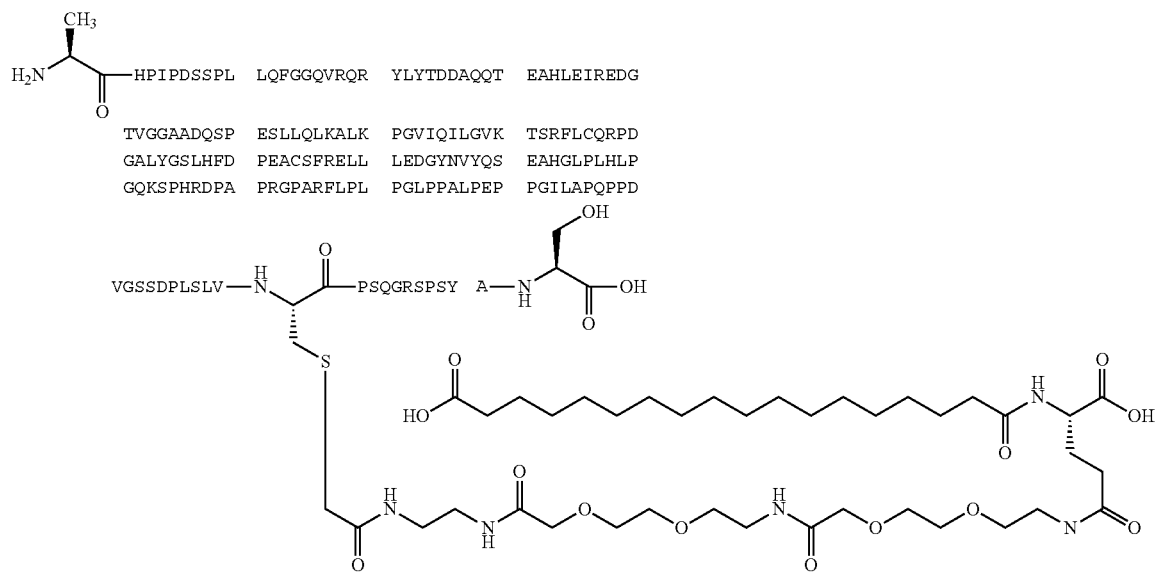

This compound is a derivative of the FGF21 analogue of SEQ ID NO:15 (see example 3) prepared by the method described under Example 5.1 using the reagent 18-[[(1 S)-4-[2-[2-[2-[2-[2-[2-[(2-bromoacetyl)amino]ethyl-amino]-2-oxo-ethoxy]ethoxy]ethylamino]-2-oxo-ethoxy]ethoxy]ethylamino]-1-carboxy-4-oxo-butyl]amino]-18-oxo-octadecanoic acid of example 4.5.

Example 5.18: Compound 37

S{Beta-173}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys173]FGF21

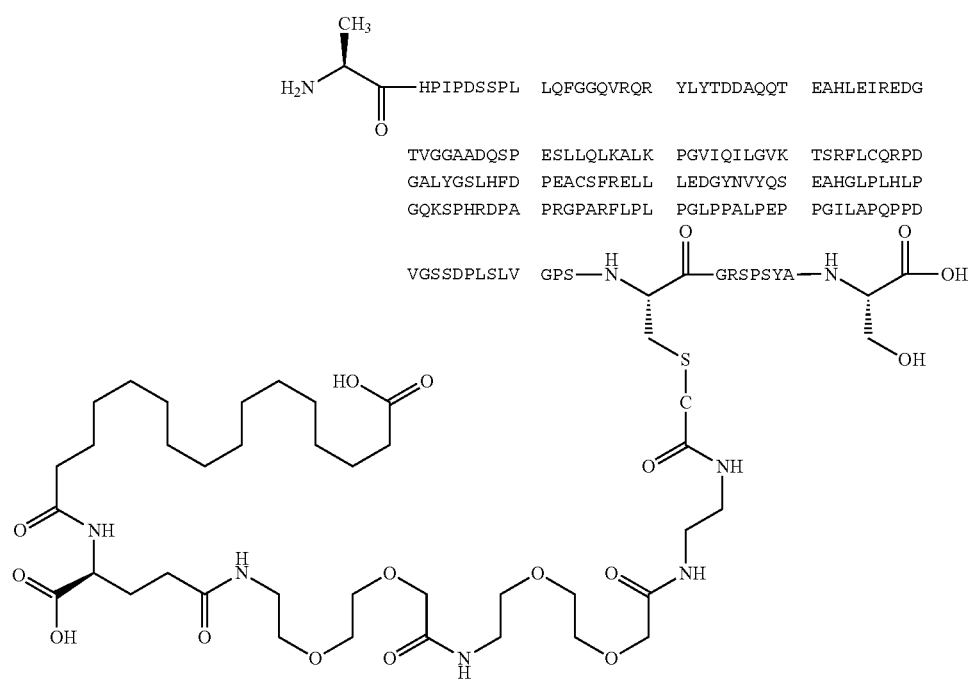

This compound is a derivative of the FGF21 analogue of SEQ ID NO:18 (see example 3) prepared by the method described under Example 5.1 using the reagent 15-{(S)-1-carboxy-3-[2-(2-{[2-(2-{[2-(2-bromoacetylamino)ethylcarbamoyl]methoxy}ethoxy)-ethylcarbamoyl]methoxy}ethoxy)ethylcarbamoyl]-propylcarbamoyl}pentadecanoic acid of Example 4.1.

LCMS method 3

Theoretical mass: 20238.8. Found: 20239.3

Example 5.19: Compound 38

S{Beta-174}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys174]FGF21

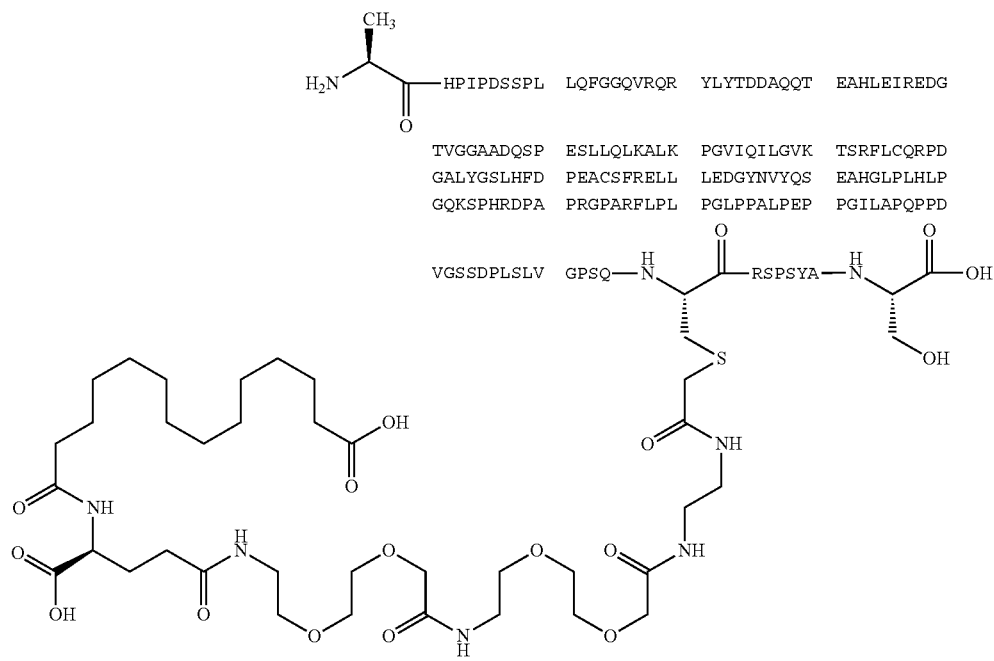

This compound is a derivative of the FGF21 analogue of SEQ ID NO:19 (see example 3) prepared by the method described under Example 5.1 using the reagent 13-{(S)-1-carboxy-3-[2-(2-{[2-(2-{[2-(2-bromoacetylamino)ethylcarbamoyl]methoxy}ethoxy)-ethylcarbamoyl]methoxy}ethoxy)ethylcarbamoyl]-propylcarbamoyl}tritadecanoic acid of Example 4.3.

LCMS method 1

Theoretical mass: 20281.9. Found: 20281.9

Example 5.20: Compound 39

18-[[(1 S)-4-[2-[2-[2-[2-[2-[2-(2-acetamidoethyl-amino)-2-oxo-ethoxy]ethoxy]ethylamino]-2-oxo-ethoxy]ethoxy]ethylamino]-1-carboxy-4-oxo-butyl]amino]-18-oxo-octadecanoic acid-Ala[Gln121,Leu168,Cys174]FGF21

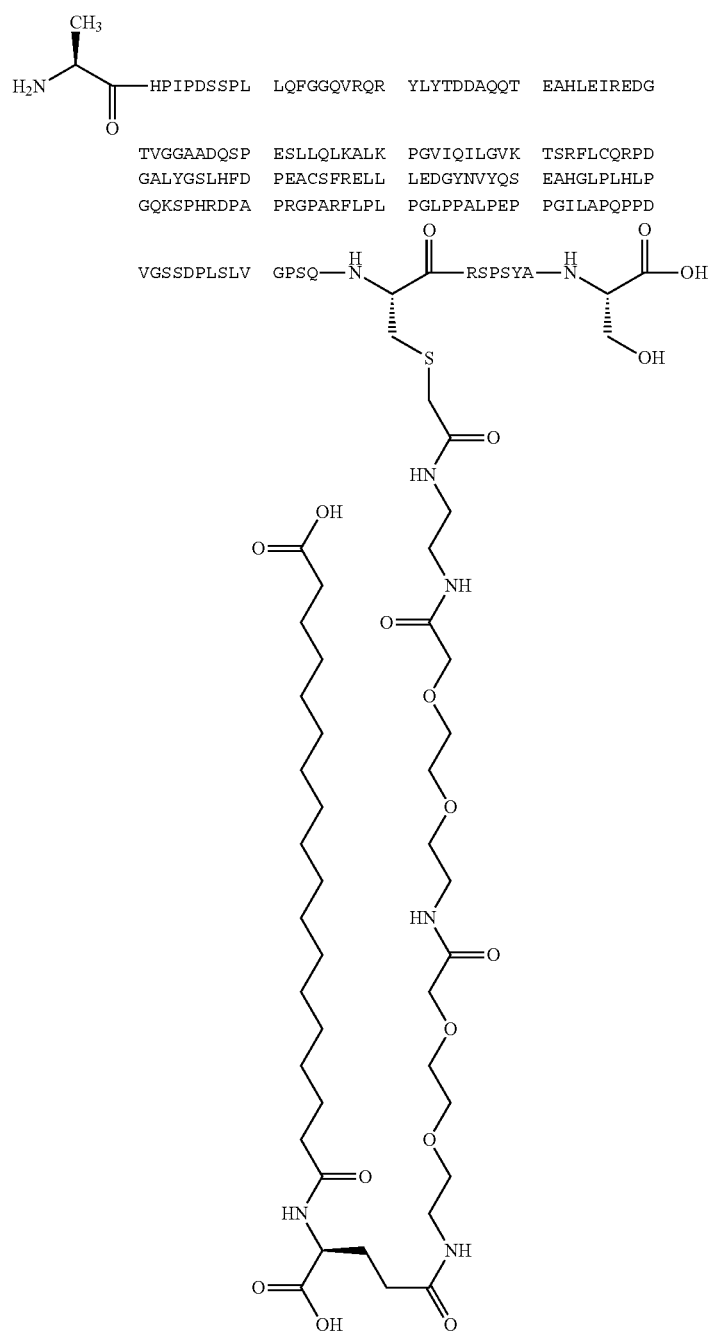

This compound is a derivative of the FGF21 analogue of SEQ ID NO: 19 (see example 3) prepared by the method described under Example 5.1 using the reagent 18-[[(1 S)-4-[2-[2-[2-[2-[2-[2-[(2-bromoacetyl)amino]ethyl-amino]-2-oxo-ethoxy]ethoxy]ethylamino]-2-oxo-ethoxy]ethoxy]ethylamino]-1-carboxy-4-oxo-butyl]amino]-18-oxo-octadecanoic acid of example 4.5

Example 5.21: Compound 40

16-[[(1 S)-4-[2-[2-[2-[2-[2-[2-(2-acetamidoethyl-amino)-2-oxo-ethoxy]ethoxy]ethylamino]-2-oxo-ethoxy]ethoxy]ethylamino]-1-carboxy-4-oxo-butyl]amino]-16-oxo-hexadecanoic acid-Ala[Gln121, Leu168,Cys174]FGF21

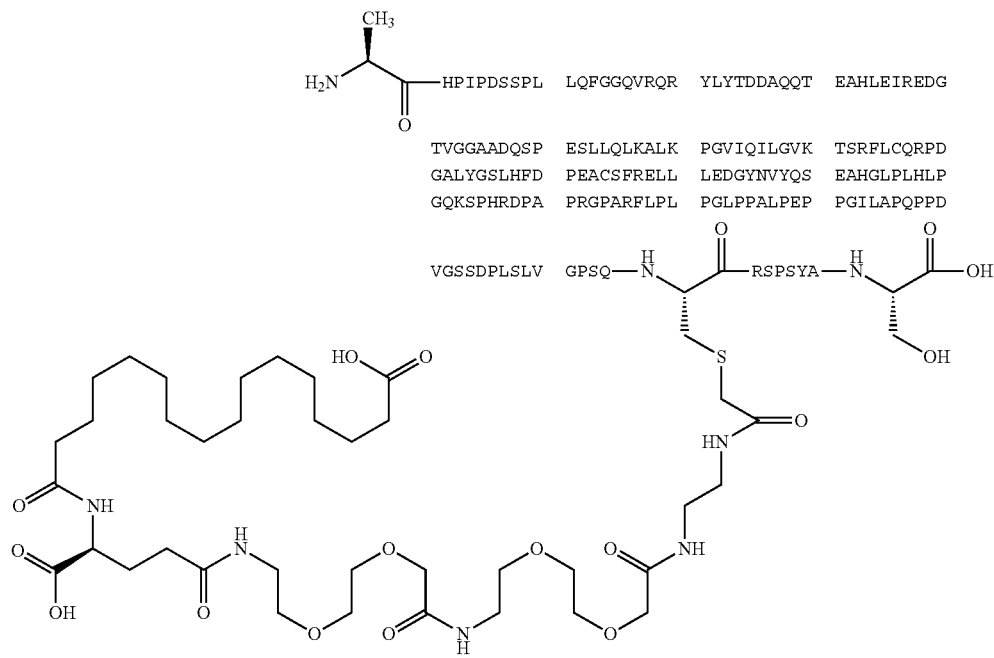

This compound is a derivative of the FGF21 analogue of SEQ ID NO: 19 (see example 3) prepared by the method described under Example 5.1 using the reagent 16-[[(1 S)-4-[2-[2-[2-[2-[2-[2-[(2-bromoacetyl)amino]ethyl-amino]-2-oxo-ethoxy]ethoxy]ethylamino]-2-oxo-ethoxy]ethoxy]ethylamino]-1-carboxy-4-oxo-butyl]amino]-16-oxo-hexadecanoic acid of example 4.1

Example 5.22: Compound 41

S{Beta-175}-[2-[2-[[2-[2-[2-[[2-[2-[2-[[(4S)-4-car-boxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys175]FGF21

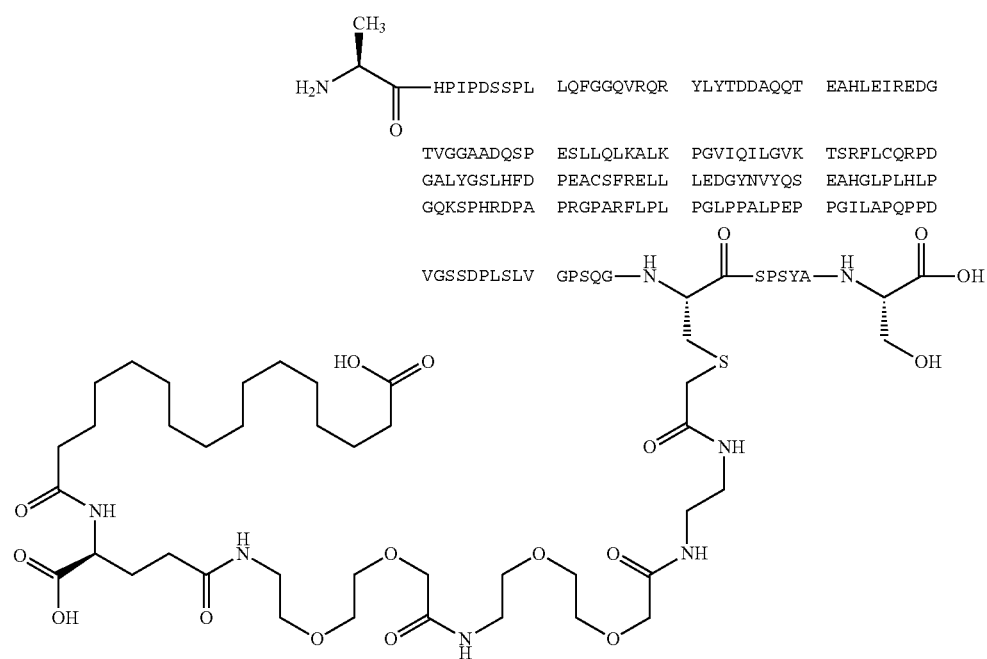

This compound is a derivative of the FGF21 analogue of SEQ ID NO:20 (see example 3) prepared by the method described under Example 5.1 using the reagent 15-{(S)-1-carboxy-3-[2-(2-{[2-(2-{[2-(2-bromoacetylamino)ethylcarbamoyl]methoxy}ethoxy)-ethylcarbamoyl]methoxy}ethoxy)ethylcarbamoyl]-propylcarbamoyl}pentadecanoic acid of Example 4.1.

LCMS method 3

Theoretical mass: 20210.8. Found: 20211.4

Example 5.23: Compound 42

S{Beta-176}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121, Leu168, Cys176]FGF21

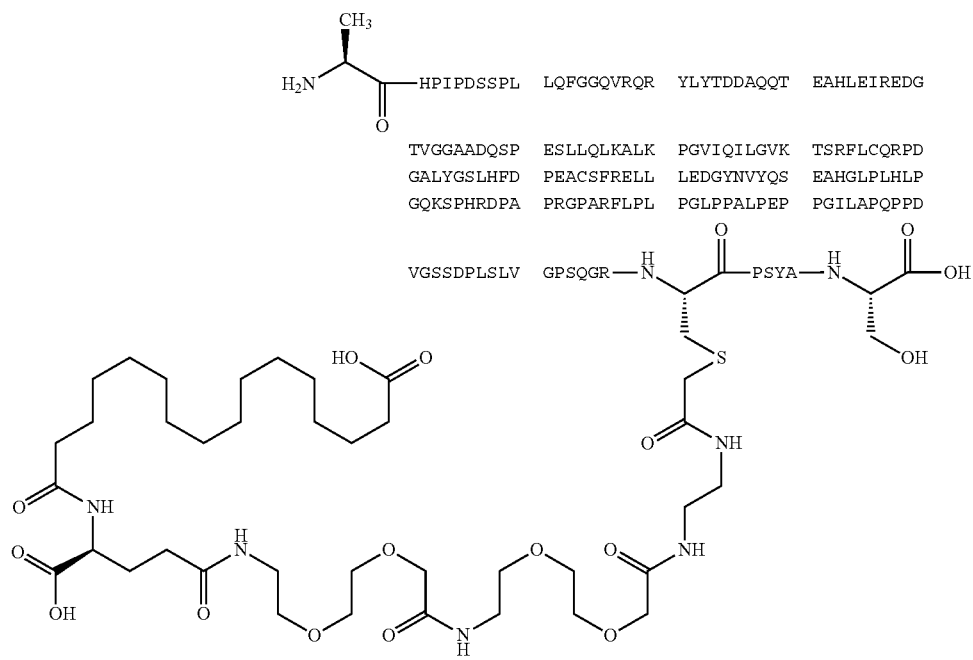

This compound is a derivative of the FGF21 analogue of SEQ ID NO:4 (see example 3) prepared by the method described under Example 5.1 using the reagent 15-{(S)-1-carboxy-3-[2-(2-{[2-(2-{[2-(2-bromoacetylamino)ethylcarbamoyl]methoxy}ethoxy)-ethylcarbamoyl]methoxy}ethoxy)ethylcarbamoyl]-propylcarbamoyl}pentadecanoic acid of Example 4.1.

LCMS method 3

Theoretical mass: 20279.9. Found: 20280.4

Example 5.24: Compound 43

4-[10-[[(1 S)-4-[2-[2-[2-[2-[2-[2-[[(1 S)-5-acet-amido-1-carboxy-pentyl]amino]-2-oxo-ethoxy]ethoxy]ethylamino]-2-oxo-ethoxy]ethoxy]ethylamino]-1-carboxy-4-oxo-butyl]amino]-10-oxo-decoxy]benzoic acid]-Ala[Gln121,Leu168,Cys180] FGF21

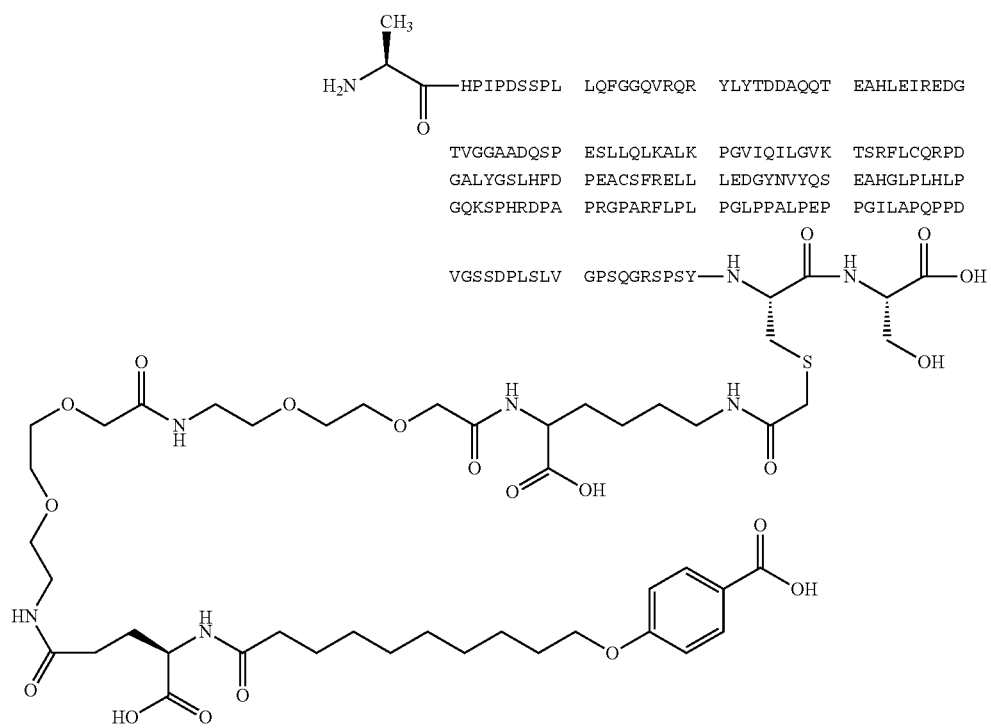

This compound is a derivative of the FGF21 analogue of SEQ ID NO:8 (see example 3) prepared by the method described under Example 5.1 using the reagent 4-[10-[[(1S)-4-[2-[2-[2-[2-[2-[2-[[(1 S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-10-oxo-decoxy]benzoic acid of Example 4.11.

Example 5.25: Compound 44

4-[10-[[4-[2-[2-[2-[2-[2-[2-[[(1 S)-5-acetamido-1-carboxy-pentyl]amino]-2-oxo-ethoxy]ethoxy]ethyl-amino]-2-oxo-ethoxy]ethoxy]ethylamino]-4-oxo-butyl]sulfonylamino]-10-oxo-decoxy]benzoic acid]-Ala[Gln121,Leu168,Cys180]FGF21

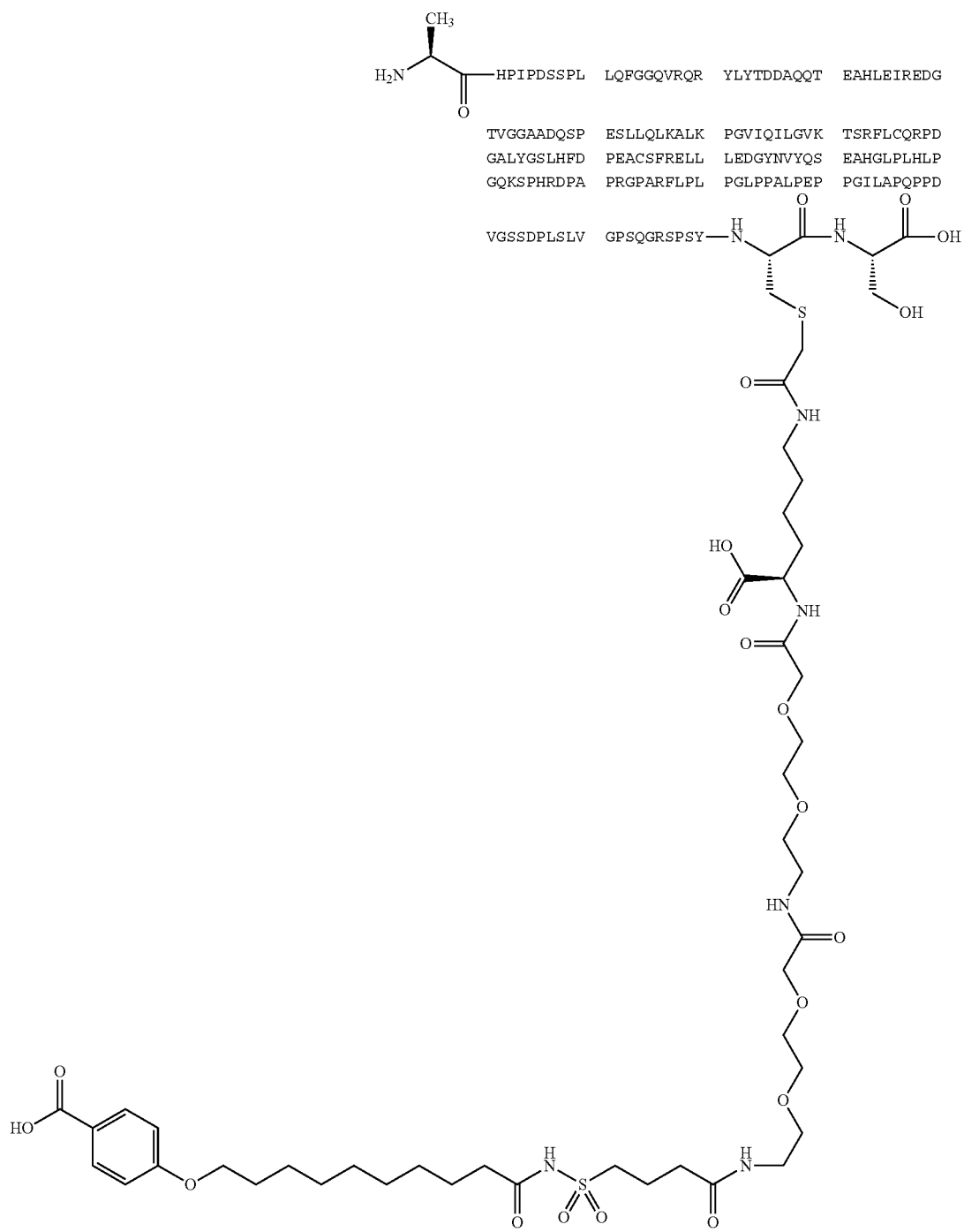

This compound is a derivative of the FGF21 analogue of SEQ ID NO:8 (see example 3) prepared by the method described under Example 5.1 using the reagent 4-[10-[[4-[2-[2-[2-[2-[2-[2-[[(1 S)-5-[(2-bromoacetyl)amino]-1-carboxy-pentyl]amino]-2-oxo-ethoxy]ethoxy]ethylamino]-2-oxo-ethoxy]ethoxy]ethylamino]-4-oxo-butyl]sulfonylamino]-10-oxo-decoxy]benzoic acid of Example 4.10.

Example 5.26: Compound 45

20-[[(1 S)-4-[[(1 S)-4-[2-[2-[2-[2-[2-[2-[[(1 S)-5-acetamido-1-carboxy-pentyl]amino]-2-oxo-ethoxy]ethoxy]ethylamino]-2-oxo-ethoxy]ethoxy]ethylamino]-1-carboxy-4-oxo-butyl]amino]-1-carboxy-4-oxo-butyl]amino]-20-oxo-icosanoic acid-Ala [Gln121,Leu168,Cys180]FGF21

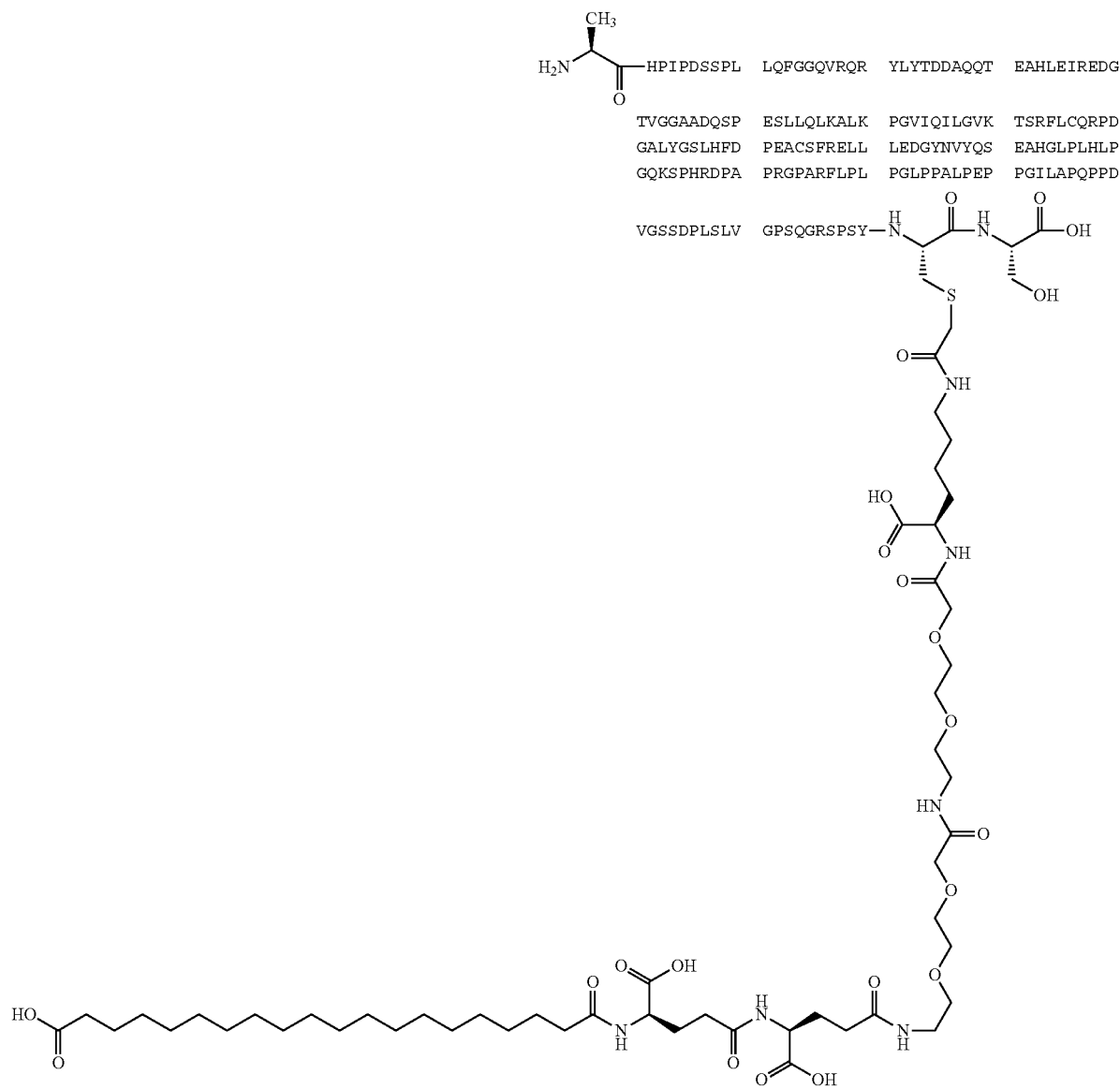

This compound is a derivative of the FGF21 analogue of SEQ ID NO:8 (see example 3) prepared by the method described under Example 5.1 using the reagent 20-[[(1 S)-4-[[(1 S)-4-[2-[2-[2-[2-[2-[2-[[(1 S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-1-carboxy-4-oxo-butyl]amino]-20-oxo-icosanoic acid of example 4.12.

Example 5.27: Compound 46

20-[[(1 S)-4-[2-[2-[2-[2-[2-[2-[[(1 S)-5-acetamido-1-carboxy-pentyl]amino]-2-oxo-ethoxy]ethoxy]ethylamino]-2-oxo-ethoxy]ethoxy]ethylamino]-1-carboxy-4-oxo-butyl]amino]-20-oxo-icosanoic acid-Ala[Gln121,Leu168,Cys180]FGF21

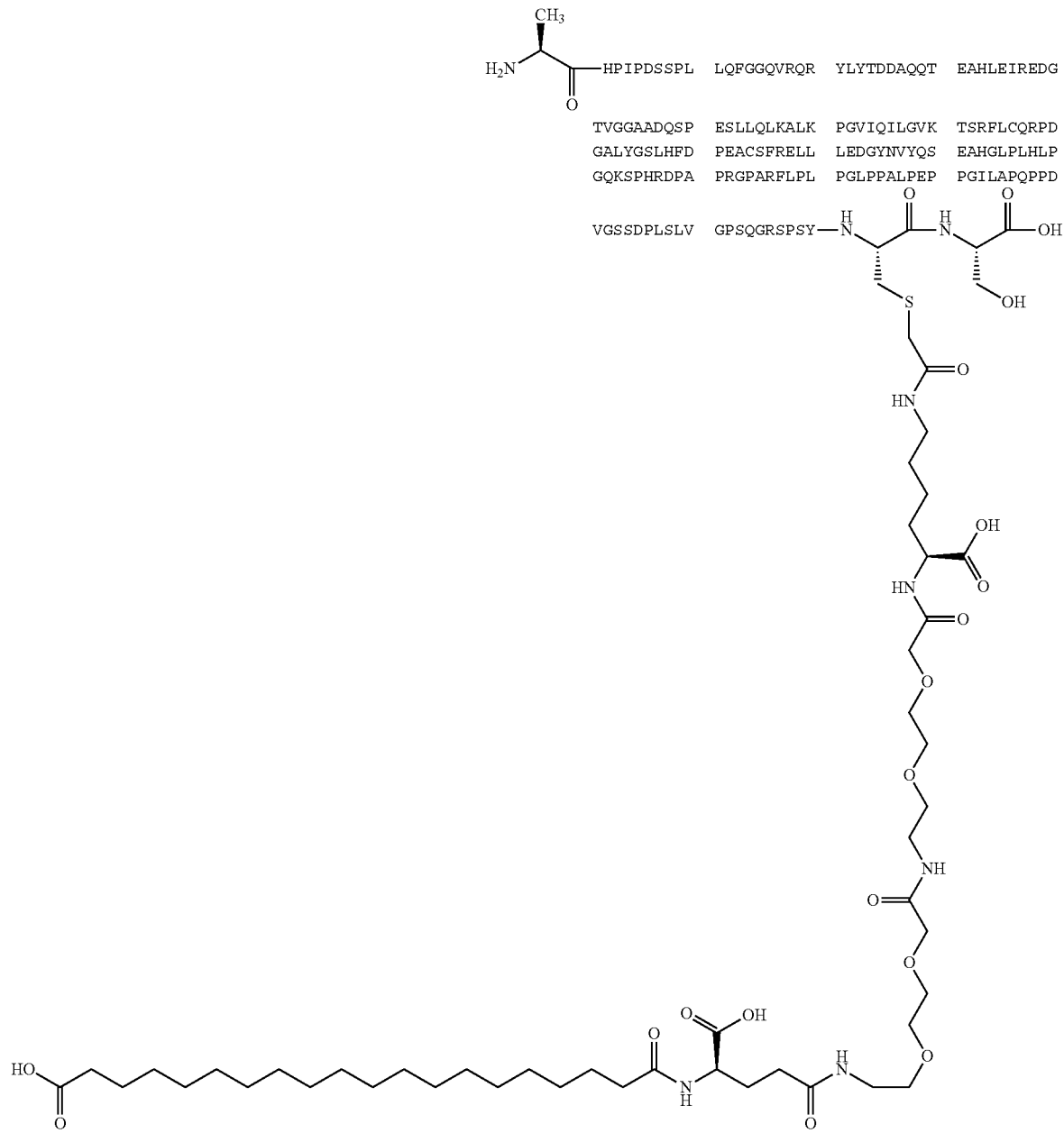

This compound is a derivative of the FGF21 analogue of SEQ ID NO:8 (see example 3) prepared by the method described under Example 5.1 using the reagent 20-[[(1 S)-4-[2-[2-[2-[2-[2-[2-[[(1 S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-20-oxo-icosanoic acid of example 4.13.

Example 5.28: Compound 47

(2S)-6-acetamido-2-[[2-[2-[2-[[2-[2-[2-[[(4S)-4-carboxy-4-(16-sulfohexadecanoylamino)butanoyl]amino]ethoxy]ethoxy]acetyl]amino]ethoxy]ethoxy]acetyl]amino]hexadecanoic acid-Ala[Gln121,Leu168,Cys180]FGF21

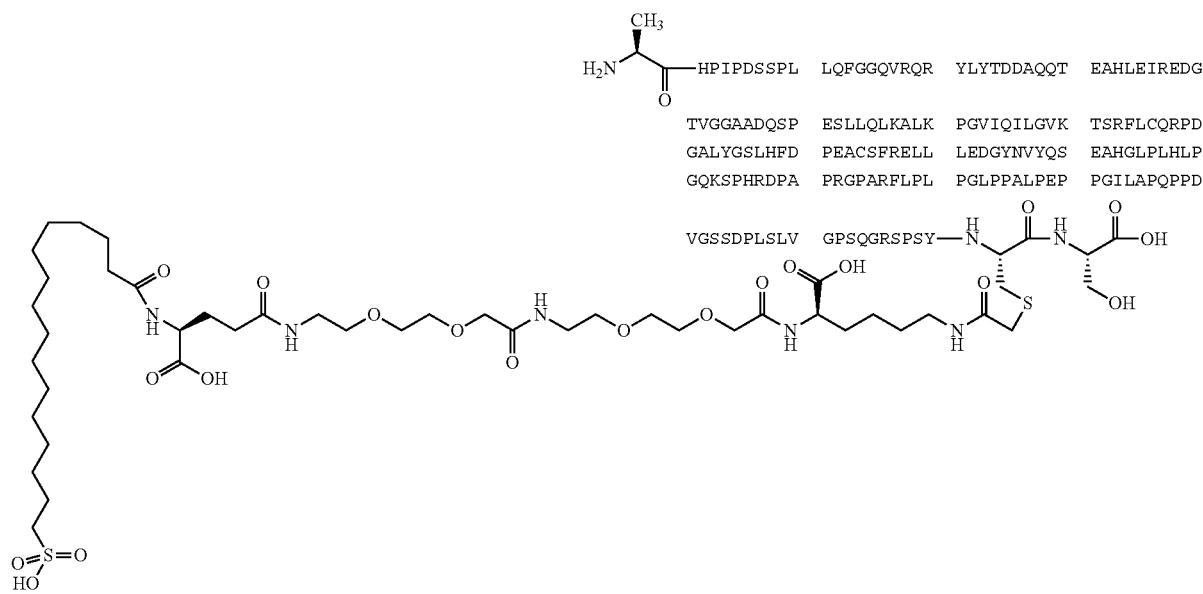

This compound is a derivative of the FGF21 analogue of SEQ ID NO:8 (see example 3) prepared by the method described under Example 5.1 using the reagent (2S)-6-[(2-bromoacetyl)amino]-2-[[2-[2-[2-[[2-[2-[2-[[(4S)-4-carboxy-4-(16-sulfohexadecanoylamino)butanoyl]amino]ethoxy]ethoxy]acetyl]amino]ethoxy]ethoxy]acetyl]amino]hexanoic acid of example 4.14.

Example 5.29: Compound 48

12-[[(1 S)-4-[2-[2-[2-[2-[2-[2-[[(1 S)-5-acetamido-1-carboxy-pentyl]amino]-2-oxo-ethoxy]ethoxy]ethylamino]-2-oxo-ethoxy]ethoxy]ethylamino]-1-carboxy-4-oxo-butyl]amino]-12-oxo-dodecanoic acid-Ala[Gln121,Leu168,Cys180]FGF21

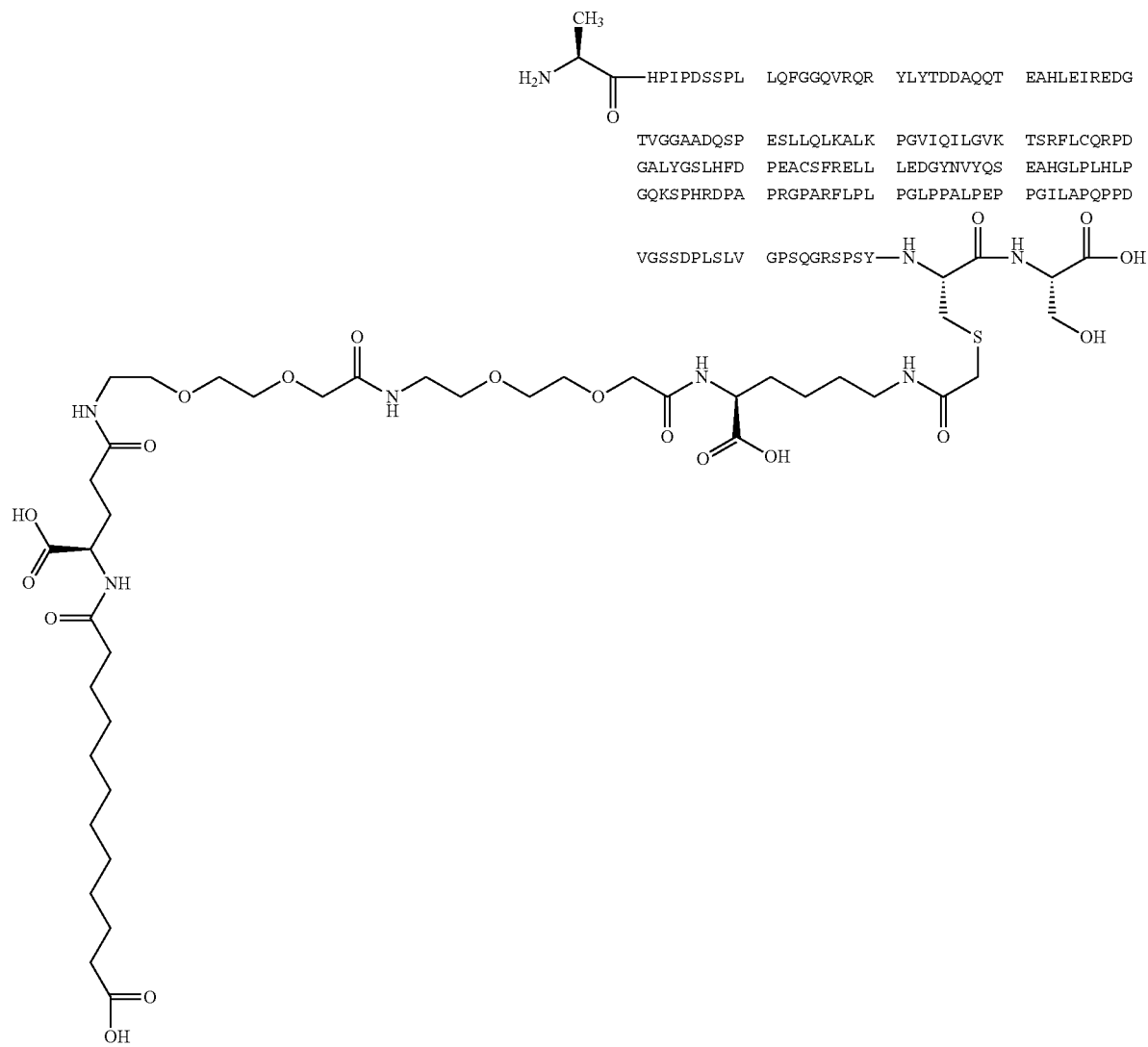

This compound is a derivative of the FGF21 analogue of SEQ ID NO:8 (see example 3) prepared by the method described under Example 5.1 using the reagent 12-[[(1 S)-4-[2-[2-[2-[2-[2-[2-[[(1 S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-12-oxo-dodecanoic acid of example 4.16.

Example 5.30: Compound 49

12-[[(1 S)-4-[[(1 S)-4-[2-[2-[2-[2-[2-[2-[[(1 S)-5-acetamido-1-carboxy-pentyl]amino]-2-oxo-ethoxy]ethoxy]ethylamino]-2-oxo-ethoxy]ethoxy]ethyl-amino]-1-carboxy-4-oxo-butyl]amino]-1-carboxy-4-oxo-butyl]amino]-12-oxo-dodecanoic acid-Ala[Gln121,Leu168,Cys180]FGF21

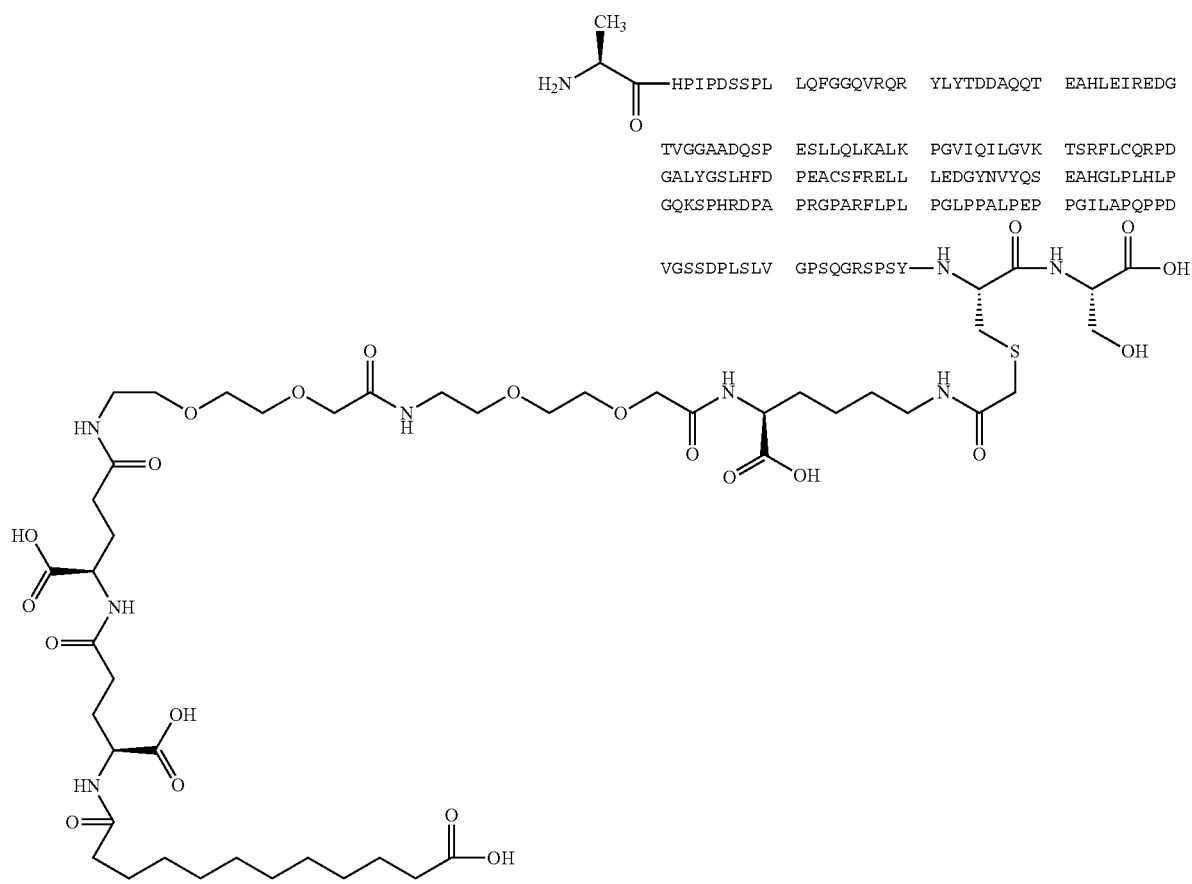

This compound is a derivative of the FGF21 analogue of SEQ ID NO:8 (see example 3) prepared by the method described under Example 5.1 using the reagent 12-[[(1 S)-4-[[(1 S)-4-[2-[2-[2-[2-[2-[2-[[(1 S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-1-carboxy-4-oxo-butyl]amino]-12-oxo-dodecanoic acid of example 4.15.

Example 5.31: Compound 50

20-[[4-[[(1 S)-4-[2-[2-[2-[2-[2-[2-[[(1 S)-5-[(2-acet-amido]-1-carboxy-pentyl]amino]-2-oxo- ethoxy]ethoxy]ethylamino]-2-oxo-ethoxy]ethoxy]ethyl-amino]-1-carboxy-4-oxo-butyl]carbamoyl]cyclohexyl]methylamino]-20-oxo-icosanoic acid-Ala[Gln121,Leu168,Cys180]FGF21

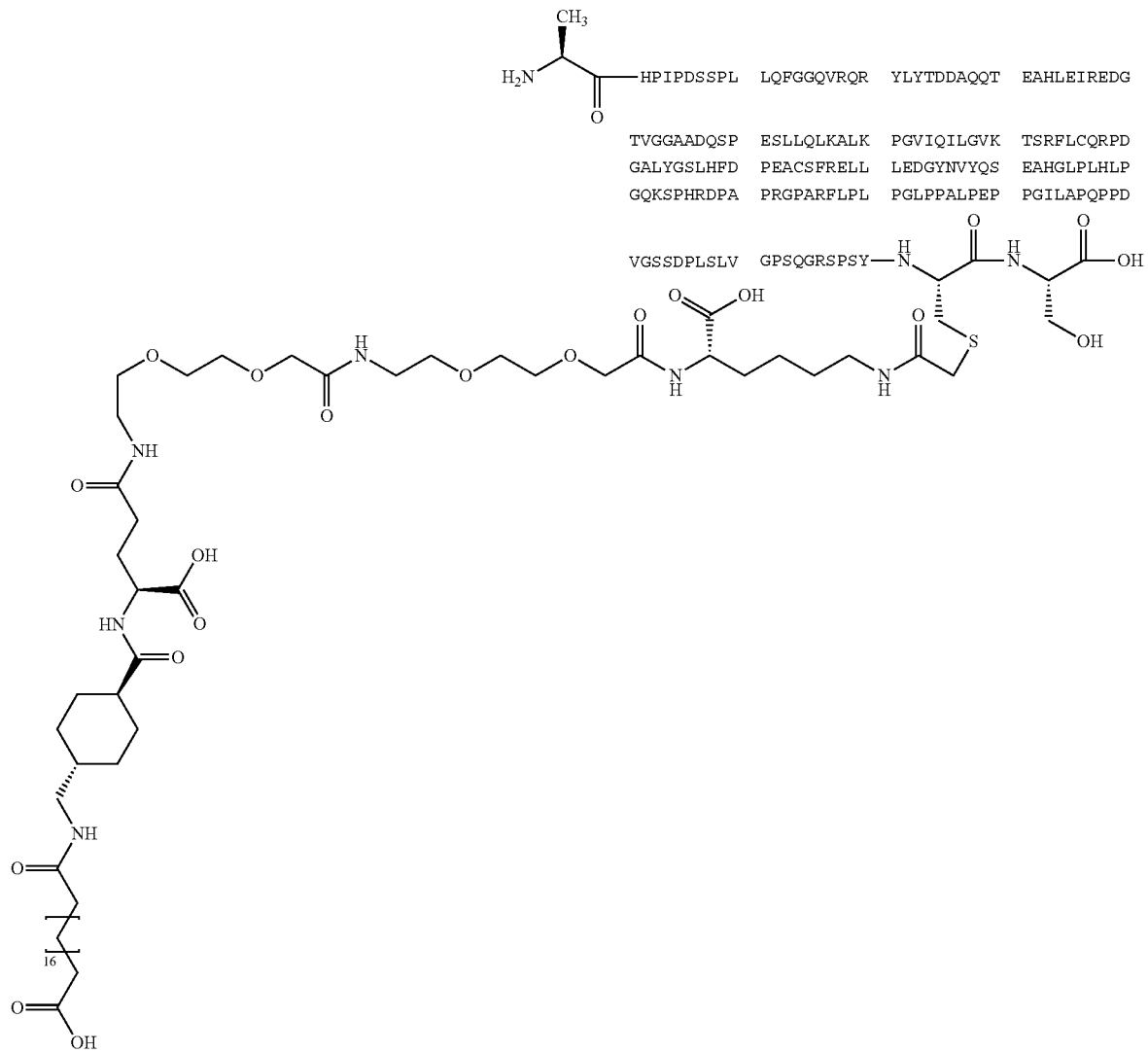

This compound is a derivative of the FGF21 analogue of SEQ ID NO:8 (see example 3) prepared by the method described under Example 5.1 using the reagent 20-[[4-[[(1 S)-4-[2-[2-[2-[2-[2-[2-[[(1 S)-5-[(2-bromoacetyl)amino]-1-carboxy-pentyl]amino]-2-oxo- ethoxy]ethoxy]ethylamino]-2-oxo-ethoxy]ethoxy]ethylamino]-1-carboxy-4-oxo-butyl]carbamoyl]cyclohexyl]methylamino]-20-oxo-icosanoic acid of example 4.17.

Example 5.32: Compound 51

16-[[4-[[(1 S)-4-[2-[2-[2-[2-[2-[2-(2-acetamidoethyl-amino)-2-oxo-ethoxy]ethoxy]ethylamino]-2-oxo-ethoxy]ethoxy]ethylamino]-1-carboxy-4-oxo-butyl]carbamoyl]cyclohexyl]methylamino]-16-oxo-hexadecanoic acid-Ala[Gln121,Leu168,Cys180] FGF21

5

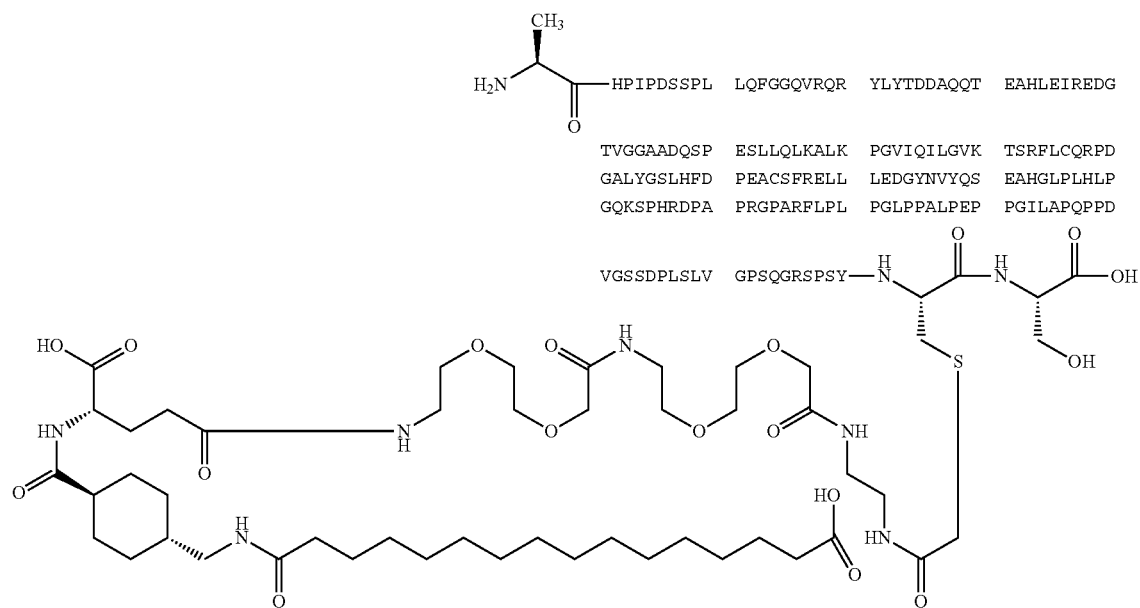

This compound is a derivative of the FGF21 analogue of SEQ ID NO:8 (see example 3) prepared by the method described under Example 5.1 using the reagent 16-[[4-[[(1 S)-4-[2-[2-[2-[2-[2-[2-[(2-bromoacetyl)amino]ethyl-amino]-2-oxo-ethoxy]ethoxy]ethylamino]-2-oxo-ethoxy]ethoxy]ethylamino]-1-carboxy-4-oxo-butyl]carbamoyl]cyclohexyl]methylamino]-16-oxo-hexadecanoic acid of example 4.7.

Example 5.33: Compound 52

16-[[4-[[(1 S)-4-[2-[2-[2-[2-[2-[2-[[(1 S)-5-[(2-acet-amido]-1-carboxy-pentyl]amino]-2-oxo- ethoxy]ethoxy]ethylamino]-2-oxo-ethoxy]ethoxy]ethyl-amino]-1-carboxy-4-oxo-butyl]carbamoyl]cyclohexyl]methylamino]-16-oxo-hexadecanoic acid-Ala[Gln121,Leu168,Cys180]FGF21

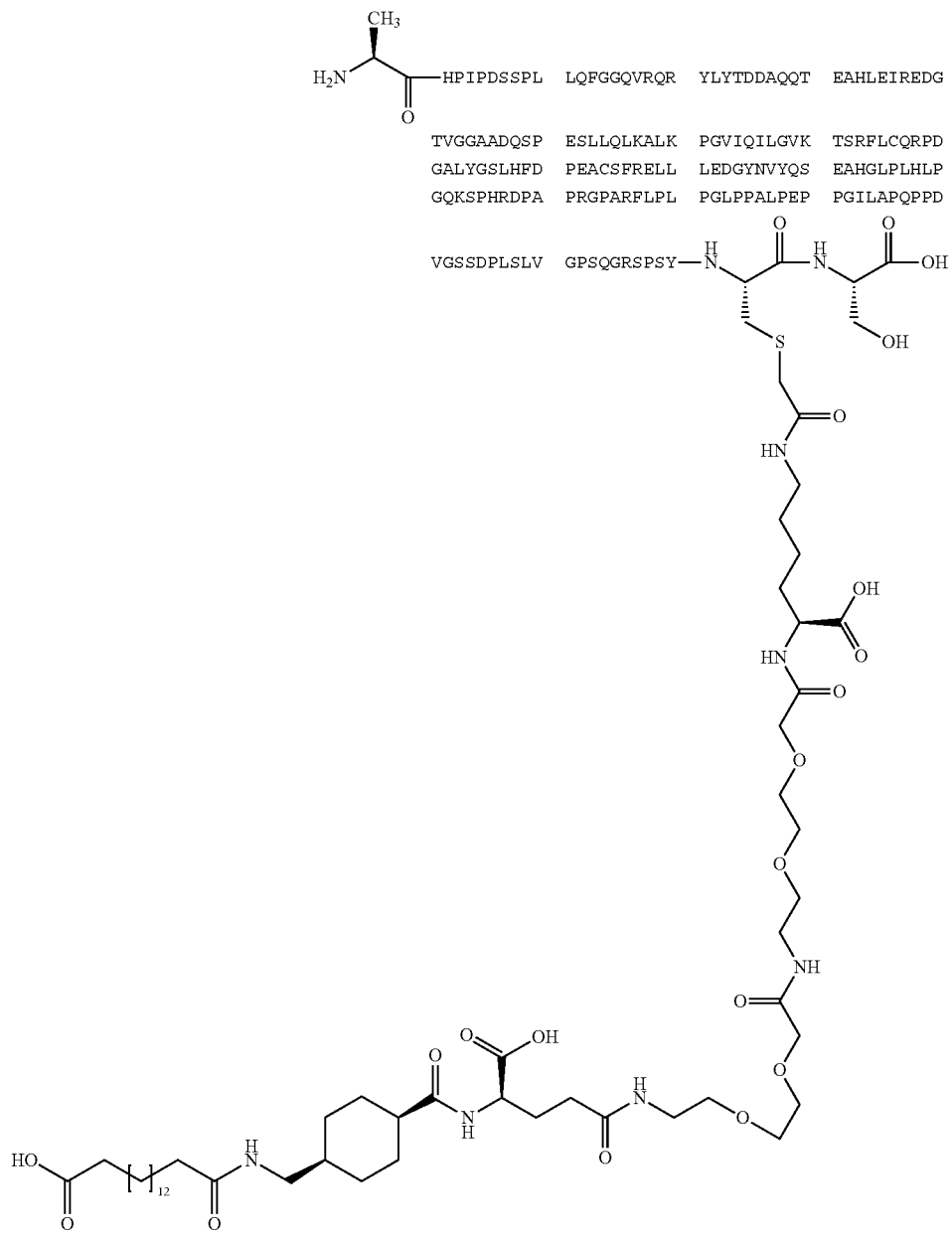

This compound is a derivative of the FGF21 analogue of SEQ ID NO:8 (see example 3) prepared by the method described under Example 5.1 using the reagent 16-[[4-[[(1 S)-4-[2-[2-[2-[2-[2-[2-[[(1 S)-5-[(2-bromoacetyl)amino]-1-carboxy-pentyl]amino]-2-oxo- ethoxy]ethoxy]ethylamino]-2-oxo-ethoxy]ethoxy]ethylamino]-1-carboxy-4-oxo-butyl] carbamoyl]cyclohexyl]methylamino]-16-oxo-hexadecanoic acid of example 4.9.

Example 5.34: Compound 53

18-[[4-[[(1 S)-4-[2-[2-[2-[2-[2-[2-[[(1 S)-5-[(2-acetamido]-1-carboxy-pentyl]amino]-2-oxo- ethoxy]ethoxy]ethylamino]-2-oxo-ethoxy]ethoxy]ethylamino]-1-carboxy-4-oxo-butyl]carbamoyl]cyclohexyl]methylamino]-8-oxo-octadecanoic acid-Ala[Gln121,Leu168,Cys180]FGF21

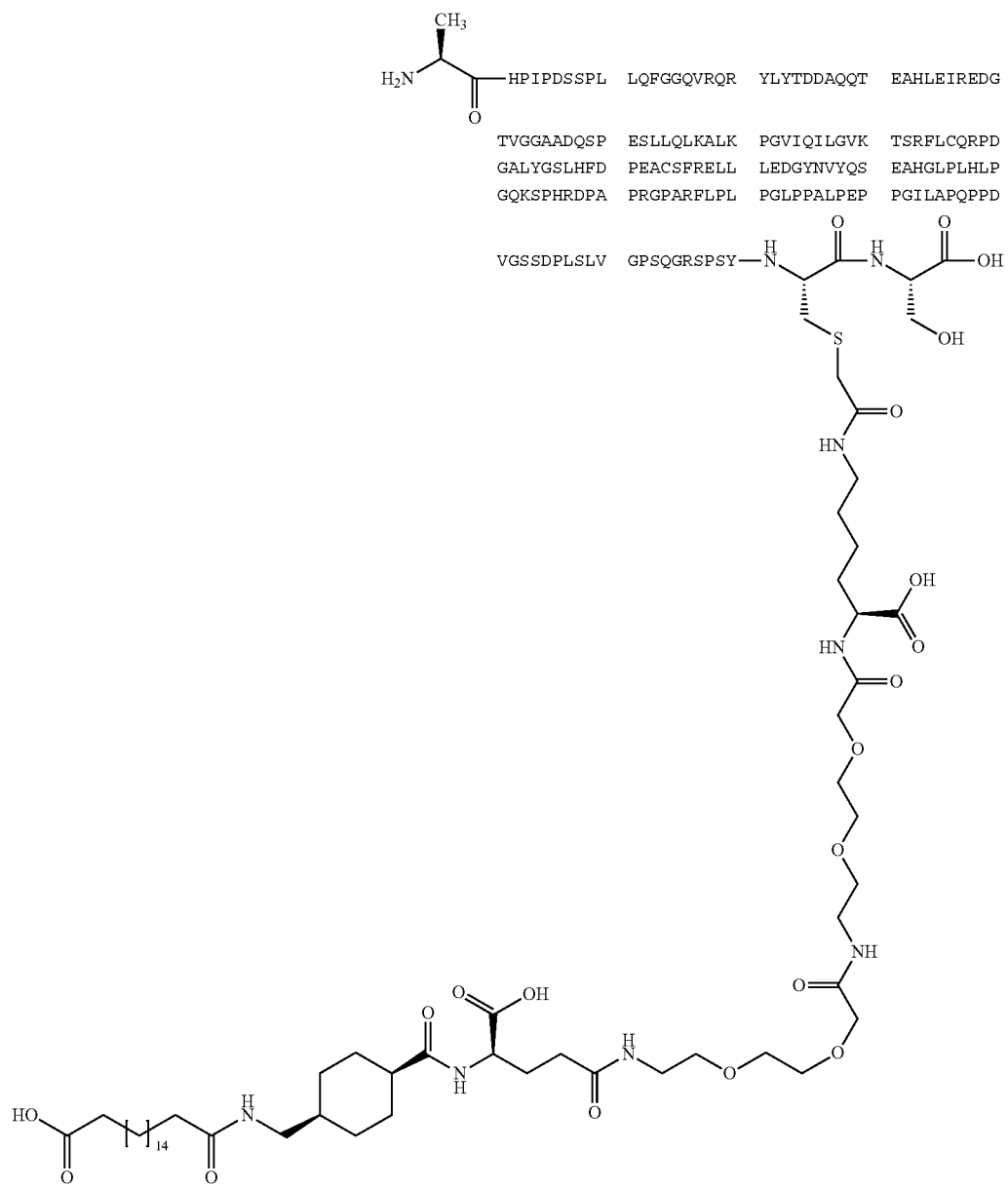

This compound is a derivative of the FGF21 analogue of SEQ ID NO:8 (see example 3) prepared by the method described under Example 5.1 using the reagent 18-[[4-[[(1 S)-4-[2-[2-[2-[2-[2-[2-[[(1 S)-5-[(2-bromoacetyl)amino]-1-carboxy-pentyl]amino]-2-oxo- ethoxy]ethoxy]ethylamino]-2-oxo-ethoxy]ethoxy]ethylamino]-1-carboxy-4-oxo-butyl]carbamoyl]cyclohexyl]methylamino]-18-oxo-octadecanoic acid of example 4.8.

Example 5.35: Compound 54

12-[[4-[[(1 S)-4-[2-[2-[2-[2-[2-[2-(2-acetamidoethyl-amino)-2-oxo-ethoxy]ethoxy]ethylamino]-2-oxo-ethoxy]ethoxy]ethylamino]-1-carboxy-4-oxo-butyl] carbamoyl]cyclohexyl]methylamino]-12-oxo-dodecanoic acid-Ala[Gln121,Leu168,Cys180] FGF21

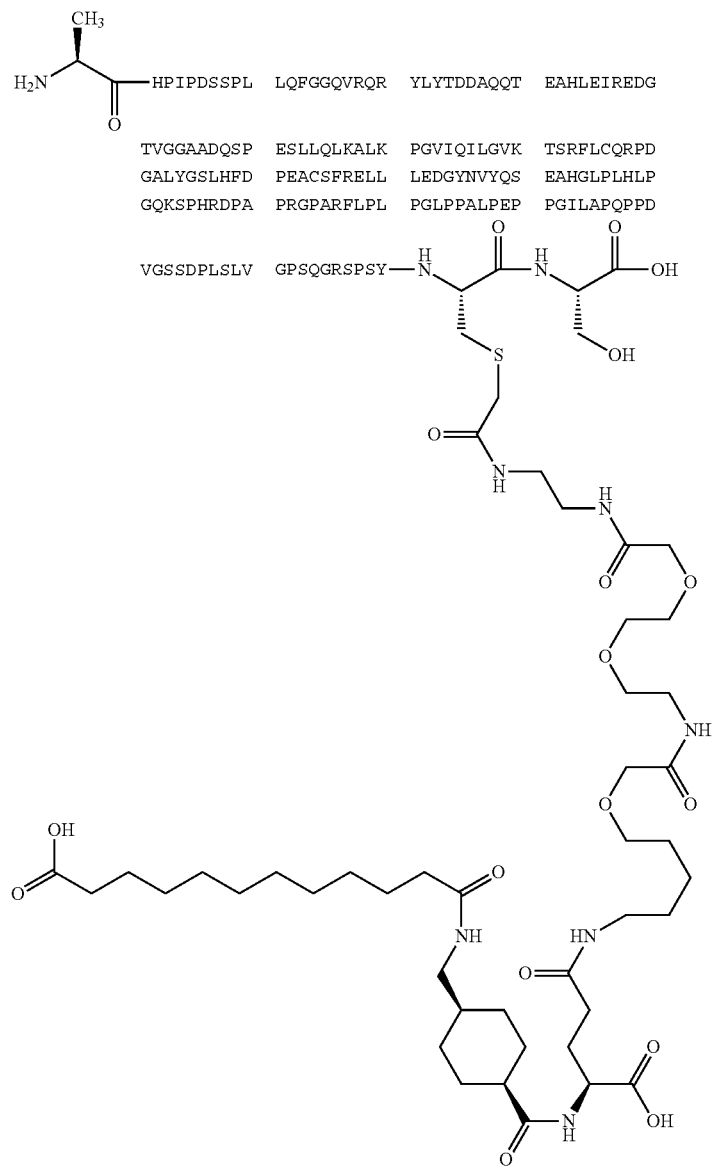

| | | | |
|---|---|---|---|
| HPIPDSSPL | LQFGGQVRQR | YLYTDDAQQT | EAHLEIREDG |
| TVGGAADQSP | ESLLQLKALK | PGVIQILGVK | TSRFLCQRPD |
| GALYGSLHFD | PEACSFRELL | LEDGYNVYQS | EAHGLPLHLP |
| GQKSPHRDPA | PRGPARFLPL | PGLPPALPEP | PGILAPQPPD |
| VGSSDPLSLV | GPSQGRSPSY | | |

This compound is a derivative of the FGF21 analogue of SEQ ID NO:8 (see example 3) prepared by the method described under Example 5.1 using the reagent 12-[[4-[[(1 S)-4-[2-[2-[2-[2-[2-[2-[(2-bromoacetyl)amino]ethyl-amino]-2-oxo-ethoxy]ethoxy]ethylamino]-2-oxo-ethoxy] ethoxy]ethylamino]-1-carboxy-4-oxo-butyl]carbamoyl]cy-clohexyl]methylamino]-12-oxo-dodecanoic acid of example 4.6.

Example 5.36: Compound 55

4-[10-[[(1 S)-4-[2-[2-[2-[2-[2-[2-[[(1 S)-5-acet-amido-1-carboxy-pentyl]amino]-2-oxo-ethoxy]ethoxy]ethylamino]-2-oxo-ethoxy]ethoxy]ethyl-amino]-1-carboxy-4-oxo-butyl]amino]-10-oxo-decoxy]benzoic acid]-Ala[Gln121,Leu168,Cys181] FGF21

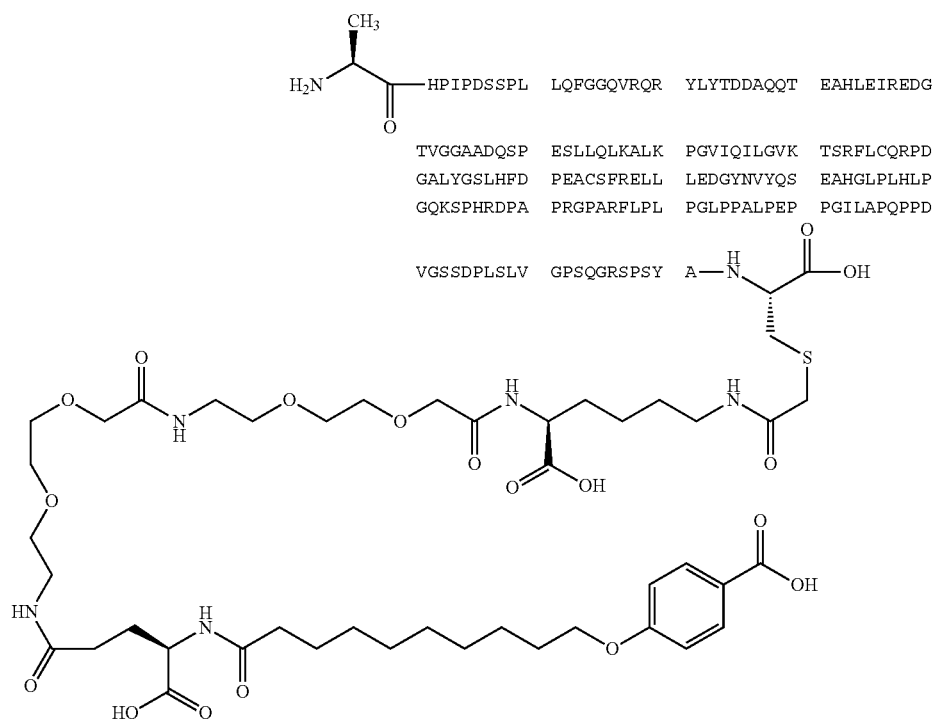

This compound is a derivative of the FGF21 analogue of SEQ ID NO:10 (see example 3) prepared by the method described under Example 5.1 using the reagent 4-[10-[[(1S)-4-[2-[2-[2-[2-[2-[2-[[(1 S)-5-[(2-bromoacetyl)amino]-1-carboxy-pentyl]amino]-2-oxo-ethoxy]ethoxy]ethylamino]-2-oxo-ethoxy]ethoxy]ethylamino]-1-carboxy-4-oxo-butyl]amino]-10-oxo-decoxy]benzoic acid of Example 4.11.

Example 5.37: Compound 56

4-[10-[[4-[2-[2-[2-[2-[2-[2-[[(1 S)-5-acetamido-1-carboxy-pentyl]amino]-2-oxo-ethoxy]ethoxy]ethyl-amino]-2-oxo-ethoxy]ethoxy]ethylamino]-4-oxo-butyl]sulfonylamino]-10-oxo-decoxy]benzoic acid-Ala[Gln121,Leu168,Cys181]FGF21 boxy-pentyl]amino]-2-oxo-ethoxy]ethoxy]ethylamino]-2-oxo-ethoxy]ethoxy]ethylamino]-4-oxo-butyl]sulfonylamino]-10-oxo-decoxy]benzoic acid of Example 4.10.

Pharmacological Methods

The utility of the FGF21 analogues or derivatives thereof of the present invention as pharmaceutically active agents in

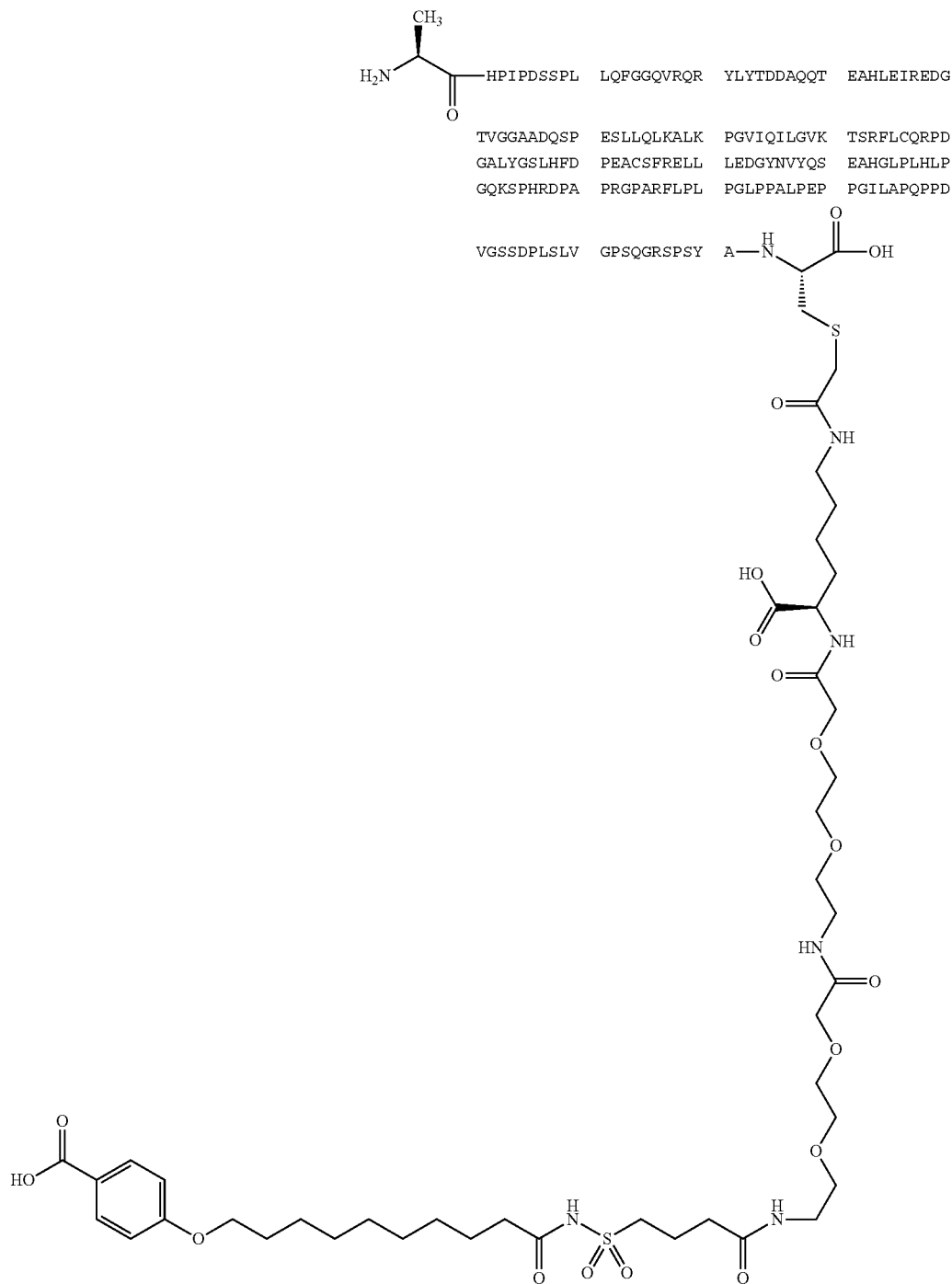

This compound is a derivative of the FGF21 analogue of SEQ ID NO:10 (see example 3) prepared by the method described under Example 5.1 using the reagent 4-[10-[[4-[2-[2-[2-[2-[2-[2-[[(1 S)-5-[(2-bromoacetyl)amino]-1-carthe reduction of weight gain and treatment of obesity and diabetes in mammals (such as humans) may be demonstrated by the activity of the FGF21 agonists in conventional assays and in the in vitro and in vivo assays described below.

Such assays also provide a means whereby the activities of the FGF21 compounds of this invention can be compared with the activities of known compounds.

Example 6: FGF Receptor Potency in an Erk Phosphorylation Assay in HEK293 Overexpressing Human BKL The purpose of this example is to test the activity, or potency, of the FGF21 derivatives in vitro. The in vitro potency is the measure of FGF receptor activation in a whole cell assay.

The potencies of the FGF21 derivatives of Example 5 were determined in HEK (Human Embryonic Kidney cells) overexpressing human beta-klotho (BKL) as described further below. In order to test the binding of the FGF21 derivatives to albumin, the assay was performed in the absence of serum albumin as well as in the presence of human serum albumin (HSA) (0.1% final assay concentration). An increase in EC50 value (decrease in potency) in the presence of serum albumin for FGF21 derivatives would indicate binding to serum albumin and represents a method to predict a protracted pharmacokinetic profile of the test substance in animal models. The results for FGF21 analogues are shown in table 2 and the results for the FGF21 derivatives are shown in table 3. MetFGF21 (SEQ ID NO:2) is included for reference.

Assay Principle

HEK293 cells endogenously express several FGF receptors, including FGFR1c, FGFR3c and FGFR4. These cells are unresponsive to FGF21 until transfected with the co-receptor beta-klotho (BKL). Activation of the FGF receptor/BKL complex leads to activation of the MAPK/ERK signalling pathway and phosphorylation of ERK. The level of phosphorylated ERK (pERK) at a given time point increases with increasing concentrations of FGF21. As described below the level of pERK is measured after 12 minutes of stimulation with a range of FGF21 analogue concentrations.

Assay Description

The HEK293/beta-klotho cells are seeded with 30.000 cells/well in 96 well plates in DMEM (BioWhittaker #BE12-604F/U1), supplemented with 10% FCS (Gibco #16140-071), 1% penicillin/streptomycin (Gibco #15140), 100 µg/ml Hygromycin B, (Calbiochem, #400052). Two days later and 2 hours before addition of compound the cell medium is exchanged with 100 µl basal medium (DMEM (BioWhittaker #BE12-604F/U1)). The FGF21 analogues are diluted in assay medium (DMEM (BioWhittaker #BE12-604F/U1) supplemented with 0.02% Tween20), warmed to 37° C., added to the cells (100 µl) and incubated at 37° C. for 12 minutes. The FGF21 derivatives were also tested in the presence of 0.1% HSA (Sigma-A1887). All medium is quickly removed and 50 µl lysis buffer is added pr. well. The plate is shaken for 5 minutes and the lysate is ready for measurement of pERK. pERK is measured in 384 well plates with the AlphaScreen SureFire kit (PerkinElmer #TGRES10K). This kit is based on ERK and pERK specific antibodies coupled to donor and acceptor beads. The presence of pERK will bring acceptor and donor beads in close proximity and a signal is generated that is read on EnVision. The data are analysed using GraphPad Prism and the potency of the FGF21 proteins is described as absolute $EC_{50}$ value.

TABLE 2A

Potency of FGF21 analogues in HEK293/BKL cells

| Compound | Compound name | EC50 (nM) |
|---|---|---|
| 1 | MetFGF21 | 1.8 |
| 2 | Ala[Gln121,Leu168]FGF21 | 2.0 |
| 3 | S{Beta-176}-2-aminoethylsulfanyl-Ala[Gln121,Leu168,Cys176]FGF21 | 227 |
| 4 | Ala[Gln121,Leu168,Cys177]FGF21 | 416 |
| 5 | S{Beta-178}-2-aminoethylsulfanyl-Ala[Gln121,Leu168,Cys178]FGF21 | 105 |
| 6 | S{Beta-179}-2-aminoethylsulfanyl-Ala[Gln121,Leu168,Cys179]FGF21 | 69 |
| 7 | S{Beta-180}-2-aminoethylsulfanyl-Ala[Gln121,Leu168,Cys180]FGF21 | 2.3 |
| 8 | S{Beta-180}-2-aminoethylsulfanyl-Ala[Gln121,Leu168,Cys180,des181]FGF21 | 20 |
| 9 | S{Beta-181}-2-aminoethylsulfanyl-Ala[Gln121,Leu168,Cys181]FGF21 | 27 |

As can be seen from the results in table 2, introduction of a cysteine in positions 176, 177, 178 or 179 dramatically decreases the potency as compared to MetFGF21. Surprisingly, however, the introduction of a cysteine in position 180 or in position 181 leads to no (180C) or modest (181C) reduction in potency as compared to MetFGF21. Compound 7, with a cysteine in position 180, displays a potency similar to both MetFGF21 and Compound 2 having the same amino acid changes as Compound 8, except for the cysteine in position 180.

The potency of Compound 9 with a cysteine in position 181 is only slightly decreased as compared to MetFGF21 and also to Compound 2 having the same amino acid changes as Compound 9, except for the cysteine in position 181.

TABLE 2B

Potency of further FGF21 analogues in HEK293/BKL cells

| Compound | Compound name | EC50 (nM) |
|---|---|---|
| 25 | Ala[Gln121,Cys167,Leu168,]FGF21 | 4 |
| 26 | Ala[Gln121,Cys168]FGF21 | 492 |
| 27 | Ala[Gln121,Leu168,Cys169]FGF21 | 22 |
| 28 | Ala[Gln121,Leu168,Cys170]FGF21 | 7 |
| 29 | Ala[Gln121,Leu168,Cys171]FGF21 | 8 |
| 30 | Ala[Gln121,Leu168,Cys172]FGF21 | 5 |
| 31 | Ala[Gln121,Leu168,Cys173]FGF21 | 4 |
| 32 | Ala[Gln121,Leu168,Cys174]FGF21 | 5 |
| 33 | Ala[Gln121,Leu168,Cys175]FGF21 | 11 |

It can be seen that compound #26 with a C168 amino acid substitution has decreased potency, while the analogues with a cysteine in position 167, 169, 170, 171, 172, 173, 174 and 175 surprising have potencies similar to MetFGF21.

TABLE 3A

Potency of FGF21 derivatives in HEK293/BKL cells in the absence or presence of 0.1% HSA.

| Compound | Protein backbone | Protractor element | EC50 (nM) | EC50 (0.1% HSA) (nM) |
|---|---|---|---|---|
| 11 | Ala[Gln121,Leu168,Cys178]FGF21 | C16 diacid | 167 | 137 |
| 12 | Ala[Gln121,Leu168,Cys179]FGF21 | C16 diacid | 107 | 134 |

TABLE 3A-continued

Potency of FGF21 derivatives in HEK293/BKL cells in the absence or presence of 0.1% HSA.

| Compound | Protein backbone | Protractor element | EC50 (nM) | EC50 (0.1% HSA) (nM) |
|---|---|---|---|---|
| 13 | Ala[Gln121,Leu168,Cys180]FGF21 | C12 diacid | 7 | 4 |
| 14 | Ala[Gln121,Leu168,Cys180]FGF21 | C14 diacid | 6 | 6 |
| 15 | Ala[Gln121,Leu168,Cys180]FGF21 | C16 diacid | 4 | 6 |
| 16 | Ala[Gln121,Leu168,Cys180]FGF21 | C18 diacid | 5 | 48 |
| 17 | Ala[Gln121,Leu168,Cys180]FGF21 | C20 diacid | 5 | 133 |
| 18 | Ala[Gln121,Leu168,Cys180,des181]FGF21 | C18 diacid | 8 | 20 |
| 19 | Ala[Gln121,Leu168,Cys181]FGF21 | C12 diacid | 154 | 137 |
| 20 | Ala[Gln121,Leu168,Cys181]FGF21 | C14 diacid | 58 | 41 |
| 21 | Ala[Gln121,Leu168,Cys181]FGF21 | C16 diacid | 55 | 72 |
| 22 | Ala[Gln121,Leu168,Cys181]FGF21 | C18 diacid | 42 | 170 |
| 23 | Ala[Gln121,Leu168,Cys181]FGF21 | C20 diacid | 58 | 434 |
| 24 | Met[Cys181]FGF21 | C18 diacid | 16 | 71 |

As can be seen from the results in table 3A, it was surprisingly found that the attachment of a side chain of the present invention to the cysteine in either of positions 178-181 does not lead to a decrease in potency as compared to the compounds without a side chain (see table 2). Compounds 11, 12, 15 and 21 all comprise an identical side chain wherein the protractor element is C16 diacid (Chem. 1a) (the linker elements are one Chem. 2 element, two Chem. 3a elements, and one Chem. 4a element). When comparing with the potencies of the corresponding FGF21 analogues (Compounds 5, 6, 7, and 9, see table 2), it can be seen that the potencies of these FGF21 derivatives are similar to the corresponding FGF analogues (i.e. having no side chain).

The effect on potency of compounds having protractor elements of varying fatty acid chain length was also explored. The potencies of the FGF derivatives with a cysteine in position 180 were similar for FGF21 derivatives having a C12 diacid, a C14 diacid, a C16 diacid or a C18 diacid as protractor element in the absence of HSA. The potencies of the FGF derivatives with a cysteine in position 181 were similar for FGF21 derivatives having a C14 diacid, a C16 diacid, a C18 diacid or a C20 diacid as protractor element in the absence of HSA.

Increasing the HSA concentration has no or modest effect on the potency of derivatives comprising a C12, C14 or C16 side chain, while the potency of compounds with a C18 or C20 side chain have reduced potency in the presence of 0.1% HAS.

As can be seen from table 3A, the increase of the EC50 value in the presence of 0.1% serum albumin as compared to the EC50 value without serum albumin for the FGF21 derivatives corresponds with the increasing length of the protractor. This corresponds well with an increased half-life for these FGF21 derivatives (see Example 8).

TABLE 3B

Potency of further FGF21 derivatives in HEK293/BKL cells in the absence or presence of 0.1% HSA.

| Compound | Protein backbone | Protractor element | EC50 (nM) | EC50 (0.1% HSA) (nM) |
|---|---|---|---|---|
| 34 | -1A, 121Q, 168C | C14 diacid | 667 | 4264 |
| 35 | -1A, 121Q, 168L, 169C | C16 diacid | 25 | 20 |
| 36 | -1A, 121Q, 168L, 170C | C18 diacid | 1 | 20 |
| 37 | -1A, 121Q, 168L, 173C | C16 diacid | 3 | 4 |
| 38 | -1A, 121Q, 168L, 174C | C14 diacid | 4 | 4 |
| 39 | -1A, 121Q, 168L, 174C | C18 diacid | 1 | 1 |
| 40 | -1A, 121Q, 168L, 174C | C16 diacid | 2 | 4 |
| 41 | -1A, 121Q, 168L, 175C | C16 diacid | 1 | 1 |
| 42 | -1A, 121Q, 168L, 176C | C16 diacid | 214 | 373 |

The potency of FGF21 derivatives with different FGF21 backbones as described above was further tested and it was found that derivatives with the cysteine in position 169, 170, 171, 172, 173, 174 and 175 all maintain potency when derivatised with a fatty acid protractor. It is noticed that derivatization in Cys169 reduces potency slightly.

TABLE 3C

Potency of further FGF21 derivatives in HEK293/BKL cells in the absence or presence of 0.1% HSA.

| Compound | Protein backbone | Protractor element | EC50 (nM) | EC50 (0.1% HSA) (nM) |
|---|---|---|---|---|
| 43 | -1A, 121Q, 168L, 180C | 4-COOH–PhO-C10 | 5.0 | 3 |
| 44 | -1A, 121Q, 168L, 180C | 4-COOH–PhO-C10 | 3.2 | 4 |
| 45 | -1A, 121Q, 168L, 180C | C20 diacid | 10.3 | 65.5 |
| 46 | -1A, 121Q, 168L, 180C | C20 diacid | 6.1 | 52.5 |
| 47 | -1A, 121Q, 168L, 180C | sulfonic acid-C16 | 4.2 | 7.1 |
| 48 | -1A, 121Q, 168L, 180C | C12 diacid | 8.4 | 3.4 |
| 50 | -1A, 121Q, 168L, 180C | C12 diacid | 7.9 | 6.1 |
| 50 | -1A, 121Q, 168L, 180C | C20 diacid | 4.0 | 35.5 |
| 51 | -1A, 121Q, 168L, 180C | C16 diacid | 3.5 | 3.2 |
| 52 | -1A, 121Q, 168L, 180C | C16 diacid | 4.0 | 2.1 |
| 53 | -1A, 121Q, 168L, 180C | C18 diacid | 4.0 | 14.0 |
| 54 | -1A, 121Q, 168L, 180C | C12 diacid | 4.0 | 4.7 |
| 55 | -1A, 121Q, 168L, 181C | 4-COOH–PhO-C10 | 26.4 | 138 |
| 56 | -1A, 121Q, 168L, 181C | 4-COOH–PhO-C10 | 24.7 | 132 |

To compare further protracting elements, different combinations of protractors and linkers were tested. All were conjugated to Cys180 or Cys181 and quite similar functionalities of the obtained FGF21 derivatives were observed demonstrating that a variety of protractor elements may be used when conjugated to an FGF21 Cys, such as Cys180 or Cys181.

Example 7: Glucose Uptake in 3T3-L1 Adipocytes

The C-terminal modified analogues were tested for their ability to increase glucose uptake in 3T3-L1 mouse adipocytes. The following assay was used for determining the biological activity, or potency, of FGF21 analogues and derivatives of the invention.

Assay Principle

The in vitro potency may also be determined in an assay with mouse 3T3-L1 adipocytes by testing the FGF21 analogues and derivatives for their ability to increase glucose uptake into adipocytes. Differentiated 3T3-L1 adipocytes endogenously express FGFR1c and BKL. The 3T3-L1 cells are unresponsive to FGF21 until after differentiated as differentiation lead to expression of the co-receptor BKL. Activation of the FGFR1 receptor/BKL complex increase the expression of glucose transporter 1 (GLUT1) and therefore FGF21 agonists will lead to an increased amount of glucose taken into the adipocytes in a dose responsive manner.

Assay Description

Mouse 3T3-L1 fibroblasts (e.g. available from ATCC, catalogue no. CL-173) were maintained in basal medium (DMEM (4500 mg/l Glucose) with 10% Fetal Bovine Serum (FBS) and 1% Penicillin/Streptomycin). The cells are not allowed to reach confluence and should be passed (transferred to new vials) before reaching approx. 60% of confluency (by visual inspection).

For the glucose uptake assay, cells were 15.000 cells/well in a 96 well plate (BIOCOAT), and when they reached confluency (high density, with a view to have differentiated adipose cells made), the medium was changed from basal medium to basal medium containing Troglitazone, IBMX, Dexamethasone (commercially available from, e.g., Sigma) and human insulin (commercially available from, e.g., Novo Nordisk A/S).

The cells were used 7-9, days after initiation of differentiation. The cells were stimulated with increasing concentrations (0-300 nM) of the FGF21 analogues or derivatives of the invention for 20 hours in basal medium. Before addition of 3H-deoxy-glucose (in what follows: the tracer) the cells were washed in warm (approximately 37° C.) assay buffer (PBS with 1 mM MgCl2 and 2 mM CaCl2), HEPES and 0.1% Human serum albumin) and the cells were incubated with the tracer for 1 hour. This incubation was terminated by washing twice in ice cold assay buffer. The cells were lysed with Triton X-100 and lysates transferred to a 96 wells plate, microscint-40 (commercially available from, e.g., Perkin Elmer) was added and amount of tracer counted in a TOP-counter (e.g. a Packard top-counter from Perkin Elmer). The EC50 and Emax of the FGF21 compound in question were calculated. The results which are shown in tables 4-5 below indicate the EC50 (potency) and Emax (efficacy) of the FGF21 analogues and derivatives, respectively.

TABLE 4

Glucose uptake in 3T3-L1 adipocytes of FGF21 analogues

| Compound | Compound name | Glucose uptake EC50 (nM) | Glucose uptake Emax (%) |
|---|---|---|---|
| 1 | MetFGF21 | 1.2 | 100 |
| 2 | Ala[Gln121,Leu168]FGF21 | 3.1 | 85 |
| 3 | S{Beta-176}-2-aminoethylsulfanyl-Ala[Gln121,Leu168,Cys176]FGF21 | 73 | 84 |
| 4 | Ala[Gln121,Leu168,Cys177]FGF21 | ND | ND |
| 5 | S{Beta-178}-2-aminoethylsulfanyl-Ala[Gln121,Leu168,Cys178]FGF21 | 50 | 69 |
| 6 | S{Beta-179}-2-aminoethylsulfanyl-Ala[Gln121,Leu168,Cys179]FGF21 | 25 | 77 |
| 7 | S{Beta-180}-2-aminoethylsulfanyl-Ala[Gln121,Leu168,Cys180]FGF21 | 2.6 | 102 |
| 8 | S{Beta-180}-2-aminoethylsulfanyl-Ala[Gln121,Leu168,Cys180, des181]FGF21 | 73 | 72 |
| 9 | S{Beta-181}-2-aminoethylsulfanyl-Ala[Gln121,Leu168,Cys181]FGF21 | 5.0 | 74 |

TABLE 5

Glucose uptake in 3T3-L1 adipocytes of FGF21 derivatives

| Compound | Protein backbone | Protractor element | Glucose uptake EC50 (nM) | Glucose uptake Emax (%) |
|---|---|---|---|---|
| 11 | Ala[Gln121,Leu168,Cys178]FGF21 | C16 diacid | 186 | 59 |
| 12 | Ala[Gln121,Leu168,Cys179]FGF21 | C16 diacid | 107 | 54 |
| 13 | Ala[Gln121,Leu168,Cys180]FGF21 | C12 diacid | 2.7 | 87 |
| 14 | Ala[Gln121,Leu168,Cys180]FGF21 | C14 diacid | 6.7 | 106 |
| 15 | Ala[Gln121,Leu168,Cys180]FGF21 | C16 diacid | 9.1 | 98 |
| 16 | Ala[Gln121,Leu168,Cys180]FGF21 | C18 diacid | 32 | 109 |
| 17 | Ala[Gln121,Leu168,Cys180]FGF21 | C20 diacid | 24 | 53 |
| 18 | Ala[Gln121,Leu168,Cys180, des181]FGF21 | C18 diacid | 8 | 71 |
| 19 | Ala[Gln121,Leu168,Cys181]FGF21 | C12 diacid | ND | ND |
| 20 | Ala[Gln121,Leu168,Cys181]FGF21 | C14 diacid | 7.2 | 55 |
| 21 | Ala[Gln121,Leu168,Cys181]FGF21 | C16 diacid | 31 | 61 |
| 22 | Ala[Gln121,Leu168,Cys181]FGF21 | C18 diacid | 56 | 73 |
| 23 | Ala[Gln121,Leu168,Cys181]FGF21 | C20 diacid | 410 | 57 |
| 24 | Met[Cys181]FGF21 | C18 diacid | 37 | — |

Due to the binding of the side chains of the FGF21 derivatives to albumin, the FGF21 derivatives (table 5) have lower potencies than the corresponding FGF21 analogues (table 4) due to the presence of serum and thereby albumin in the basal assay medium. The decrease in potency correlates with the length of the protractor element.

Example 8: Pharmacokinetic Study in Mini Pigs and Mice

The purpose of this study was to determine the protraction in vivo of the FGF21 derivatives after i.v. administration to mini pigs and mice, i.e. the prolongation of their time in the body and thereby their time of action. This was done in a pharmacokinetic (PK) study, where the terminal half-life of the analogue in question was determined. By terminal half-life is meant the time it takes to halve a certain plasma concentration in the terminal elimination phase.

Study in Mini Pigs

Female Göttingen mini pigs were obtained from Ellegaard Göttingen Minipigs (Dalmose, Denmark) approximately 7-14 months of age and weighing approximately 16-35 kg were used in the studies. The mini pigs were housed either individually (pigs with permanent catheters) or in a group and fed restrictedly once or twice daily with SDS mini pig diet (Special Diets Services, Essex, UK).

After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between successive dosing.

Intravenous injections (the volume corresponding to for example 0.050-0.125 ml/kg) of the compounds were given through one catheter or through the venflon, and blood was sampled at predefined time points for up till 11 days post dosing (preferably through the other catheter or by venipuncture).

Blood samples (for example 0.8 ml) were collected in EDTA (8 mM) coated tubes and then centrifuged at 4° C. and 1942G for 10 minutes. Blood samples were collected to adequately cover the full plasma concentration-time profile of the API. In example blood samples were collected at t=predose, 0.0833, 0.25, 0.5, 0.75, 1, 1.5, 2, 3, 4, 6, 8, 10, 24, 30, 48, 72, 96, 120, 144, 168, 192, 216, 240, 264 hours after dose.

Plasma was pipetted into Micronic tubes on dry ice, and kept at −20° C. until analysed for plasma concentration of the respective FGF-1 analogue using ELISA. Individual plasma concentration-time profiles were analyzed by a non-compartmental pharmacokinetic method in Phoenix v. 6.3 (Pharsight Inc., Mountain View, Calif., USA), or other relevant software for PK analysis, and the resulting terminal half-lives (harmonic mean) determined. The terminal half-life of the FGF21 derivatives is the arithmetic mean of two determinations with different dosages, as explained above.

Study in Mice

The pharmacokinetic profile of FGF21 analogues was tested in normal lean C57bl mice, n=2-3 (approximately 30 grams). FGF21 compounds were dosed as a single intravenous dose of 20 mg/kg (approximately 5 ml/kg).

The plasma levels of the FGF21 compounds were determined using Fibroblast Growth Factor-21 Human ELISA (available from BioVendor, catalogue no. RD191108200R). The PC based software, WinNonLin version 6.3 from Pharsight Corportion, Cary N.C., was used for the pharmacokinetic calculation. The results are given in table 6.

TABLE 6

Pharmacokinetic profiles of FGF21 analogues.

| Compound | Protein backbone | Protractor element | Half-life mice (hours) | Half-life mini pigs (hours) |
|---|---|---|---|---|
| 1 | MetFGF21 | — | 1 | 2 |
| 13 | Ala[Gln121,Leu168,Cys180]FGF21 | C12 diacid | 1 | ND |
| 14 | Ala[Gln121,Leu168,Cys180]FGF21 | C14 diacid | 1 | 3 |
| 15 | Ala[Gln121,Leu168,Cys180]FGF21 | C16 diacid | 3 | 23 |
| 16 | Ala[Gln121,Leu168,Cys180]FGF21 | C18 diacid | 12 | 70 |
| 17 | Ala[Gln121,Leu168,Cys180]FGF21 | C20 diacid | ND | ND |
| 18 | Ala[Gln121,Leu168,Cys180,des181]FGF21 | C18 diacid | ND | ND |
| 19 | Ala[Gln121,Leu168,Cys181]FGF21 | C12 diacid | 1 | |
| 20 | Ala[Gln121,Leu168,Cys181]FGF21 | C14 diacid | 3 | 2 |
| 21 | Ala[Gln121,Leu168,Cys181]FGF21 | C16 diacid | 4 | 25 |
| 22 | Ala[Gln121,Leu168,Cys181]FGF21 | C18 diacid | 14 | 85 |
| 23 | Ala[Gln121,Leu168,Cys181]FGF21 | C20 diacid | 19 | ND |
| 24 | Met[Cys181]FGF21 | C18 diacid | 12 | ND |

As can be seen from table 6, the plasma half-life increases with the length of the fatty acid chain of the protractor element in both mini pigs and mice.

Example 9: Body Weight Reduction in Lean Mice

In order to determine the in vivo potency of the FGF21 derivatives the effect on body weight was studied in lean C57BL mice after subcutaneous (s.c.) administration. It has previously been shown that the weight loss induced by FGF21 in lean mice is predictive of the effect in obese mice and therefore lean mice are considered a good screening model.

The compounds were administered s.c. 1 mg/kg either once (QD) or twice (BID) daily in 10 mM phosphate, 2% (w/vol) glycerol, 500 ppm (=0.05%) polysorbate 80, pH=8.15, (2 ml/kg) for 7 days (n=7-8). The respective vehicle treated groups (control) were treated with 10 mM phosphate, 2% (w/vol) glycerol, 500 ppm (=0.05%) polysorbate 80, pH=8.15, (2 ml/kg) s.c. twice daily for 7 days (n=6-8). Body weight was measured before dosing and again after 7 days treatment. The results can be seen in table 7.

TABLE 7

Change in body weight from baseline (percentage) from day 1 to 7

| Compound | Dosing | n/group | Mean Δ body weight (%) | SD Δ body weight (%) |
|---|---|---|---|---|
| Vehicle | BID | 8 | 2.84 | 2.65 |
| 1 | BID | 8 | −1.88** | 2.52 |
| 2 | BID | 8 | −1.98** | 3.33 |
| 14 | QD | 8 | 1.85 | 3.33 |
| 15 | QD | 8 | −4.48*** | 2.41 |
| 16 | QD | 8 | −10.59*** | 3.39 |
| 21 | QD | 8 | 0.18 | 2.12 |
| Vehicle | BID | 6 | 0.44 | 3.27 |
| 13 | BID | 8 | −2.04 | 1.30 |
| 14 | BID | 8 | −3.09* | 1.61 |
| 19 | BID | 7 | 0.04 | 1.11 |
| 20 | BID | 8 | −0.94 | 2.94 |

*p < 0.05,
**p < 0.01,
***p < 0.001

One-way ANOVA post hoc Dunnet's test comparing compound vs. respective vehicle, n = 6-8

The in vivo potency measured as loss of body weight of the FGF21 derivatives having the side chain in position 180 is higher than derivatives having the same side chain in position 181. The potency in vivo thus correlates with the in vitro potency. The effect on body weight reduction is dependent on plasma half-life. If plasma half-life is short then dosing twice daily increases the efficacy.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a FGF21 protein comprising an amino acid sequence, a protractor, and a linker;
   wherein the amino acid sequence is at least 95% identical to mature human FGF21 (SEQ ID NO:1) and comprises a Cys residue at a position corresponding to position 180 or position 181 of SEQ ID NO:1;
   wherein the protractor is attached to the Cys residue via the linker;
   wherein the protractor is selected from the group consisting of HOOC—$(CH_2)_x$—CO—*, HOOC-benzene-O—$(CH_2)_x$—CO—*, and HO—S(=O)$_2$—$(CH_2)_x$—CO—*;
   wherein x is an integer in the range of 8-18;
   wherein the linker comprises at least one of each of Chem. 2, Chem. 3, and Chem. 4;
   wherein Chem. 2 is selected from the group consisting of *—NH—CH(COOH)—$(CH_2)_m$—CO—*, *—NH—S(=O)$_2$—$(CH_2)_m$—CO—*, and *—NH—$(CH_2)_m$-cyclohexane-CO—*;
   wherein m is an integer in the range of 1-5;
   wherein Chem. 3 is *—NH—$(CH_2)_2$—[O—$(CH_2)_2$]$_k$—O—$[CH_2]_n$—CO—*;
   wherein k is an integer in the range of 1-5 and n is an integer in the range of 1-5;
   wherein Chem. 4 is *—NH—$(CH_2)_m$—NH—CO—$CH_2$—* or *—NH—CH(COOH)—$(CH_2)_m$—NH—CO—$CH_2$—*;
   wherein m is an integer in the range of 1-5;
   wherein Chem. 2, Chem. 3, and Chem. 4 are interconnected via amide bonds;
   wherein the linker is (i) connected at its *—NH end to the CO—* end of the protractor and (ii) at its $CH_2$—* end to the sulfur atom of the Cys residue;
   or a pharmaceutically acceptable salt, amide, or ester thereof.

2. The derivative according to claim 1, wherein the protractor is selected from the group consisting of HOOC—$(CH_2)_{16}$—CO—*, HOOC-benzene-O—$(CH_2)_9$—CO—*, and HO—S(=O)$_2$—$(CH_2)_{15}$—CO—*.

3. The derivative according to claim 1, wherein the protractor is HOOC—$(CH_2)_{16}$—CO—*.

4. The derivative according to claim 1, wherein Chem. 2 is selected from the group consisting of *—NH—CH(COOH)—$(CH_2)_2$—CO—*, *—NH—S(=O)$_2$—$(CH_2)_3$—CO—*, and *—NH—$CH_2$-cyclohexane-CO—*.

5. The derivative according to claim 1, wherein Chem. 3 is *—NH—$(CH_2)_2$—[O—$(CH_2)_2$]—O—$CH_2$—CO—*.

6. The derivative according to claim 1, wherein Chem. 4 is *—NH—$(CH_2)_2$—NH—CO—$CH_2$—* or *—NH—CH(COOH)—$(CH_2)_4$—NH—CO—$CH_2$—*.

7. The derivative according to claim 1, wherein the linker comprises at least one of *—NH—CH(COOH)—$(CH_2)_2$—CO—*, *—NH—$(CH_2)_2$—O—$(CH_2)_2$—O—$CH_2$—CO—*, and *—NH—$(CH_2)_2$—NH—CO—$CH_2$—*.

8. The derivative according to claim 1, wherein the derivative comprises an amino acid change compared to one or more of positions 121 and 168 of mature human FGF21 (SEQ ID NO:1).

9. The derivative according to claim 1, wherein the derivative comprises an addition of an Ala residue at a position corresponding to the N-terminal of mature human FGF21 (SEQ ID NO:1).

10. The derivative according to claim 1, wherein the derivative comprises one or both of 121Q and 168L.

11. The derivative according to claim 1, wherein the amino acid sequence is SEQ ID NO: 8 or SEQ ID NO: 10.

12. The derivative according to claim 1, wherein the derivative is selected from the group consisting of:
   S{Beta-180}-[2-[2-[[2-[2-[2-[[2-[2-[2-[[(4S)-4-carboxy-4-(11-carboxyundecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 13)

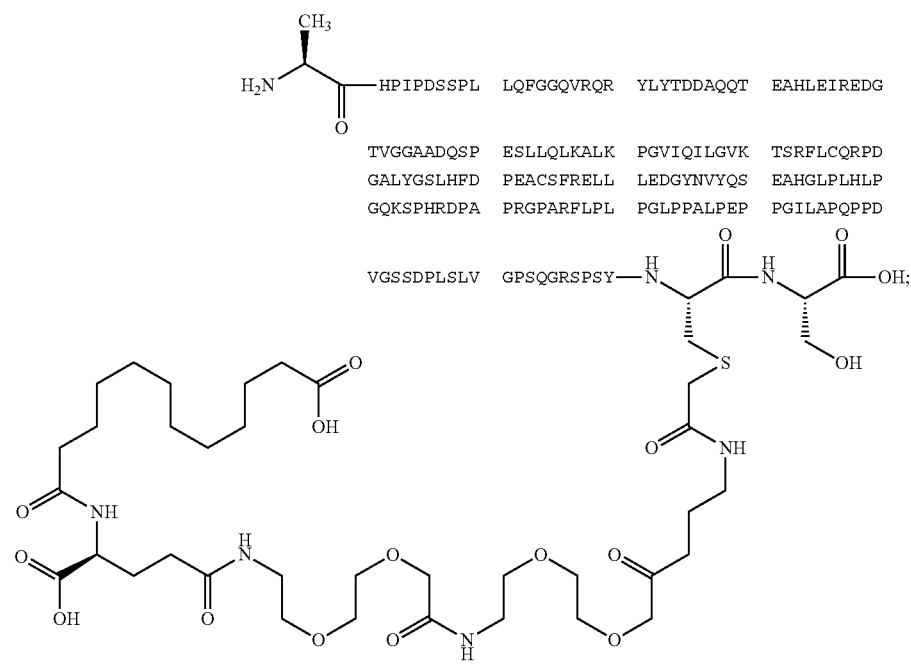

S{Beta-180}-[2-[2-[[2-[2-[2-[[2-[2-[2-[[(4S)-4-carboxy-
4-(13-carboxytridecanoyl-amino)butanoyl]amino]
ethoxy]ethoxy]acetyl]amino]ethoxy]ethoxy]acetyl]
amino]-ethylamino]-2-oxoethyl]-Ala[Gln121,Leu168,
Cys180]FGF21 (Compound 14)
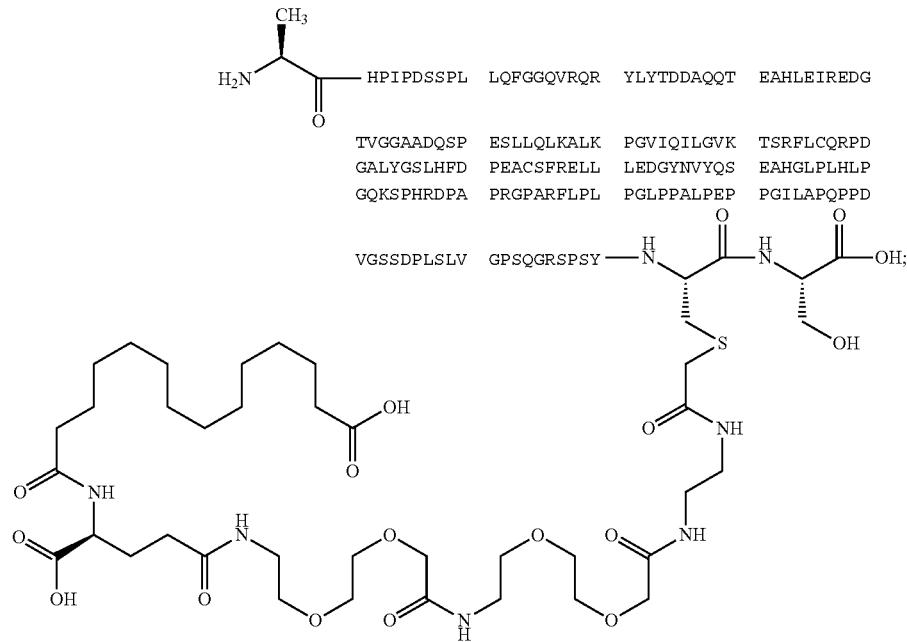
S{Beta-180}-[2-[2-[[2-[2-[2-[[2-[2-[2-[[(4S)-4-carboxy-
4-(15-carboxypentadecanoyl-amino)butanoyl]amino]
ethoxy]ethoxy]acetyl]amino]ethoxy]ethoxy]acetyl]
amino]-ethylamino]-2-oxoethyl]-Ala[Gln121, Leu168,
Cys180]FGF21 (Compound 15)
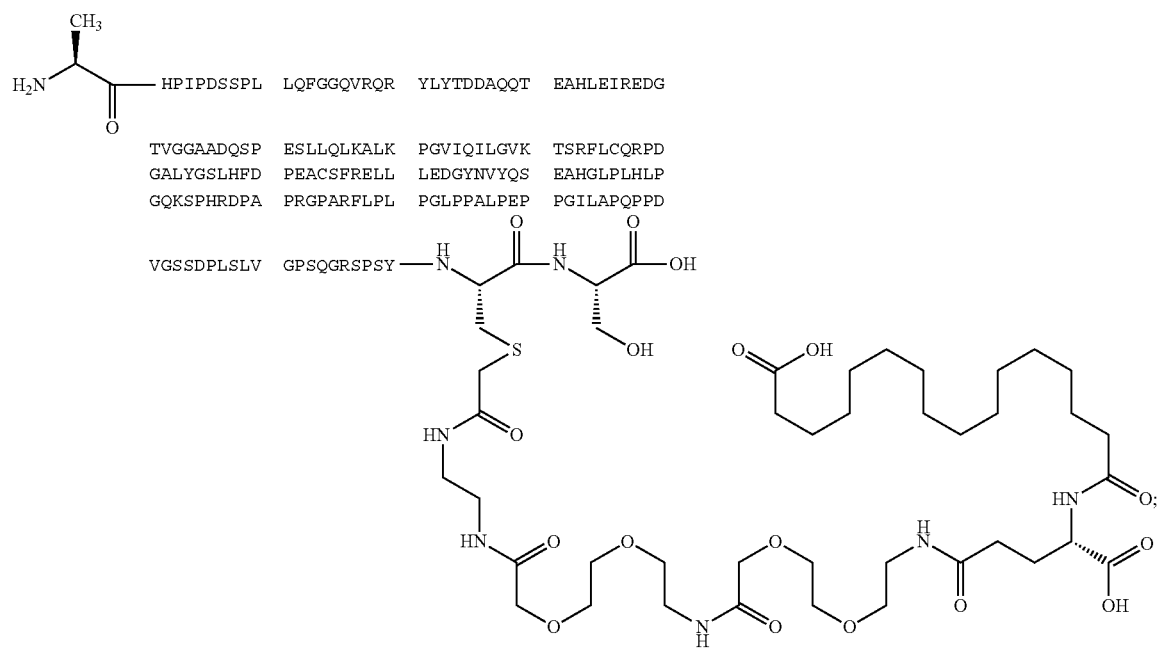

S{Beta-180}-[2-[2-[[2-[2-[2-[[2-[2-[2-[[(4S)-4-carboxy-
4-(17-carboxyheptadecanoyl-amino)butanoyl]amino]
ethoxy]ethoxy]acetyl]amino]ethoxy]ethoxy]acetyl]
amino]-ethylamino]-2-oxoethyl]-Ala[Gln121,Leu168,
Cys180]FGF21 (Compound 16)
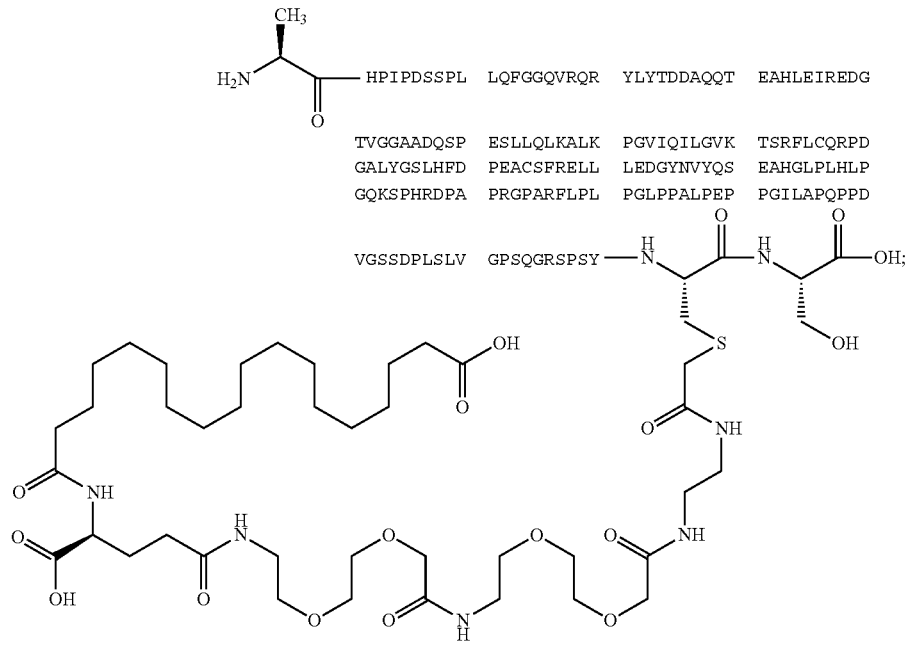
S{Beta-180}-[2-[2-[[2-[2-[2-[[2-[2-[2-[[(4S)-4-carboxy-
4-(19-carboxynonadecanoyl-amino)butanoyl]amino]
ethoxy]ethoxy]acetyl]amino]ethoxy]ethoxy]acetyl]
amino]-ethylamino]-2-oxoethyl]-Ala[Gln121, Leu168,
Cys180]FGF21 (Compound 17)
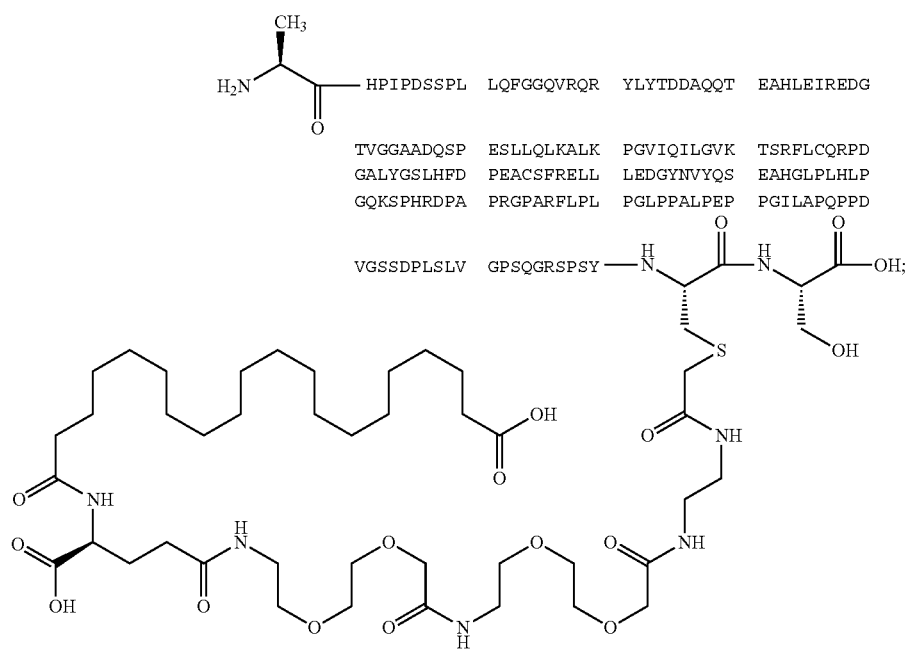

S{Beta-181}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 20)
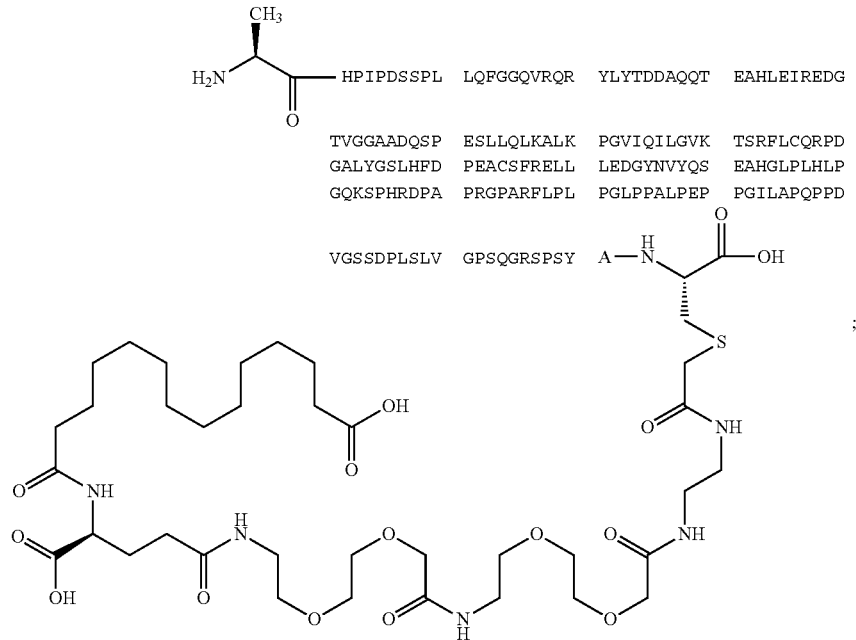
S{Beta-181}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 21)
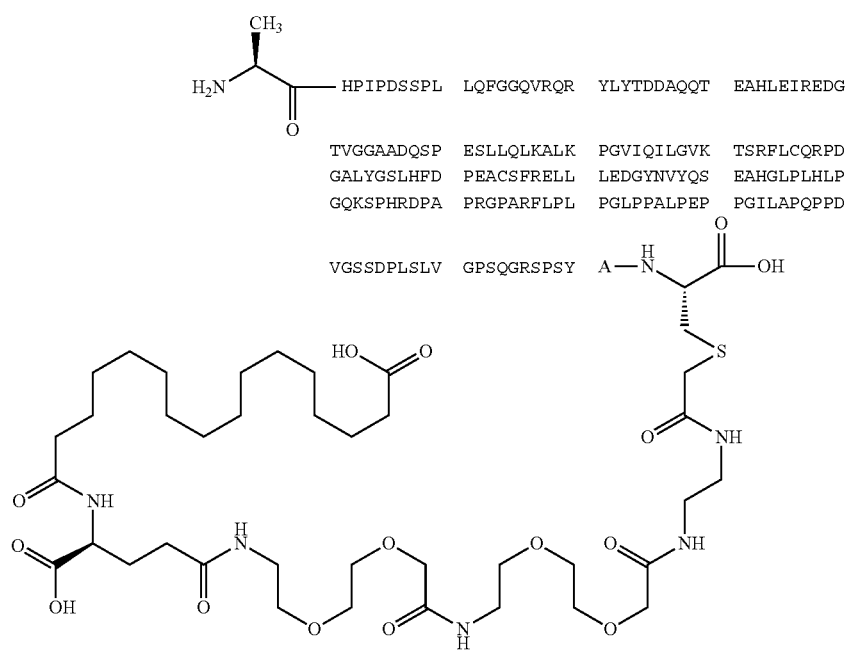

and
S{Beta-181}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 22)

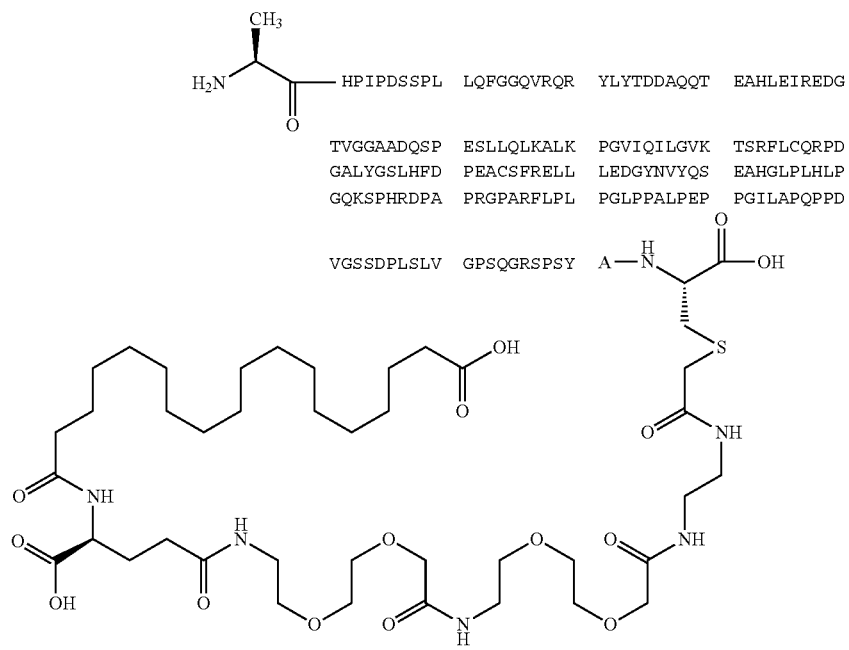

13. The derivative according to claim 12, wherein the derivative is S{Beta-180}-[2-[2-[[2-[2-[2-[[2-[2-[2-[[(4S)-4-carboxy-4-(1-carboxyundecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 13)

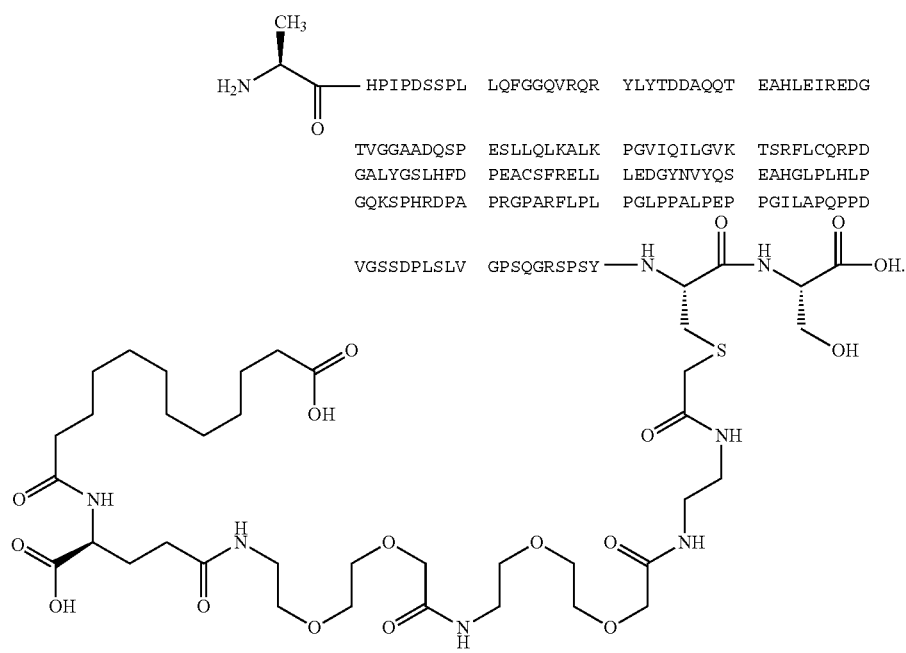

14. The derivative according to claim 12, wherein the derivative is S{Beta-180}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 14)

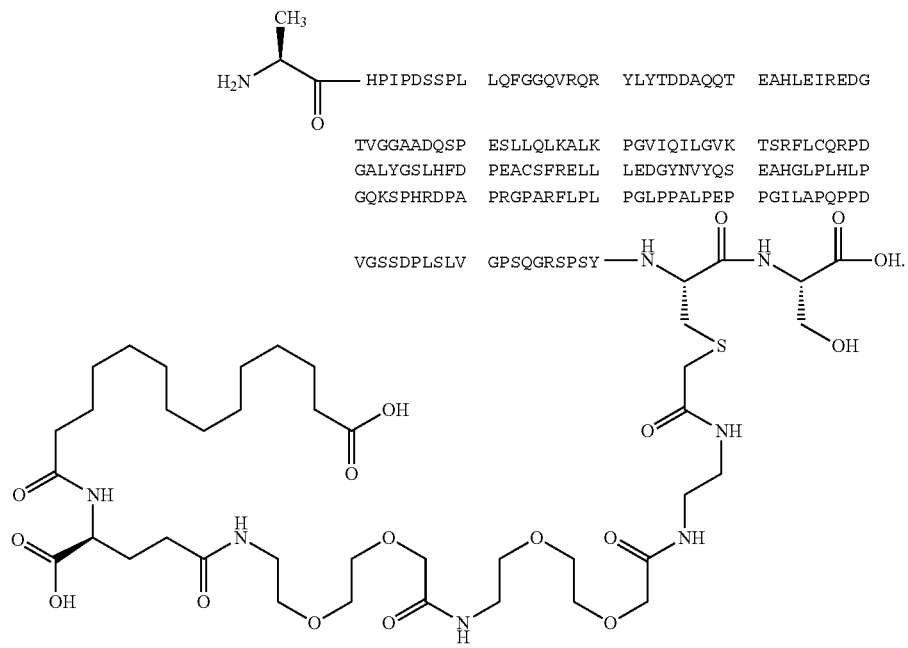

15. The derivative according to claim 12, wherein the derivative is S{Beta-180}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 15)

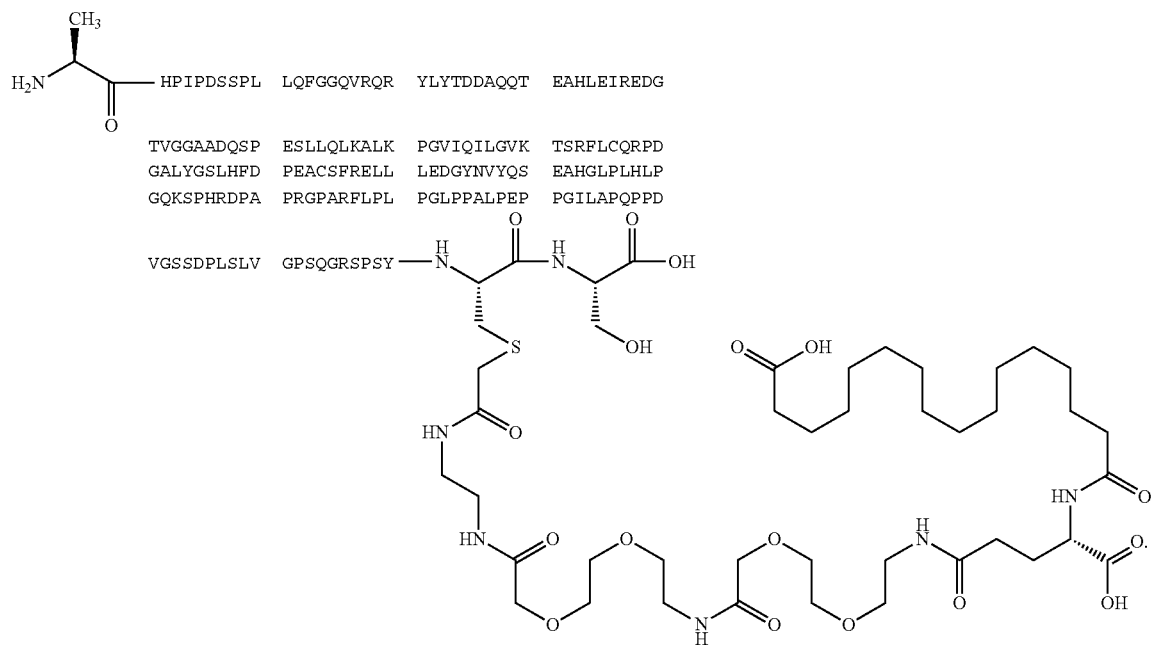

16. The derivative according to claim 12, wherein the derivative is S{Beta-180}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 16)

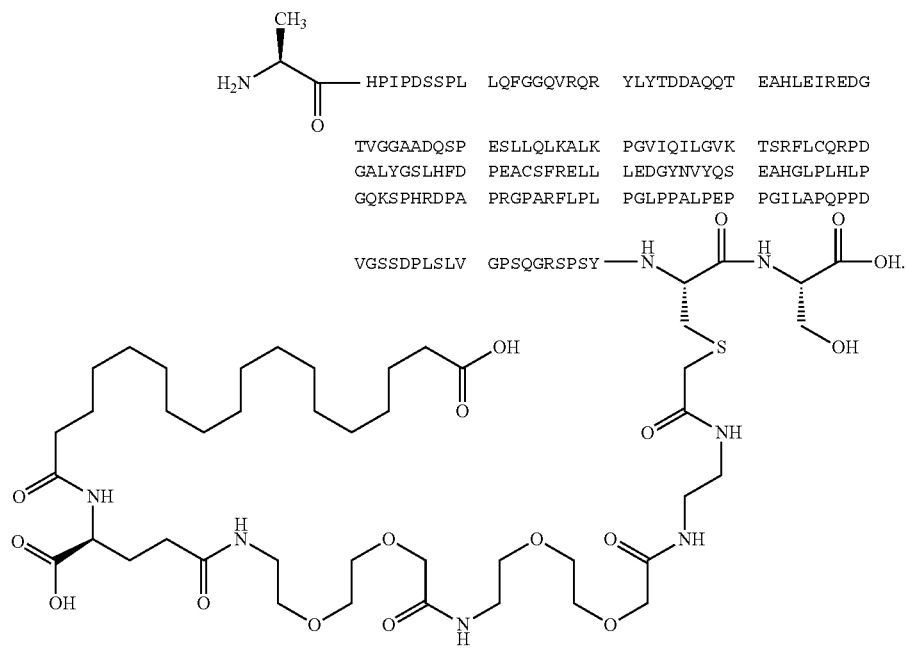

17. The derivative according to claim 12, wherein the derivative is S{Beta-180}-[2-[2-[[2-[2-[2-[[2-[2-[2-[[(4S)-4-carboxy-4-(19-carboxynonadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 17)

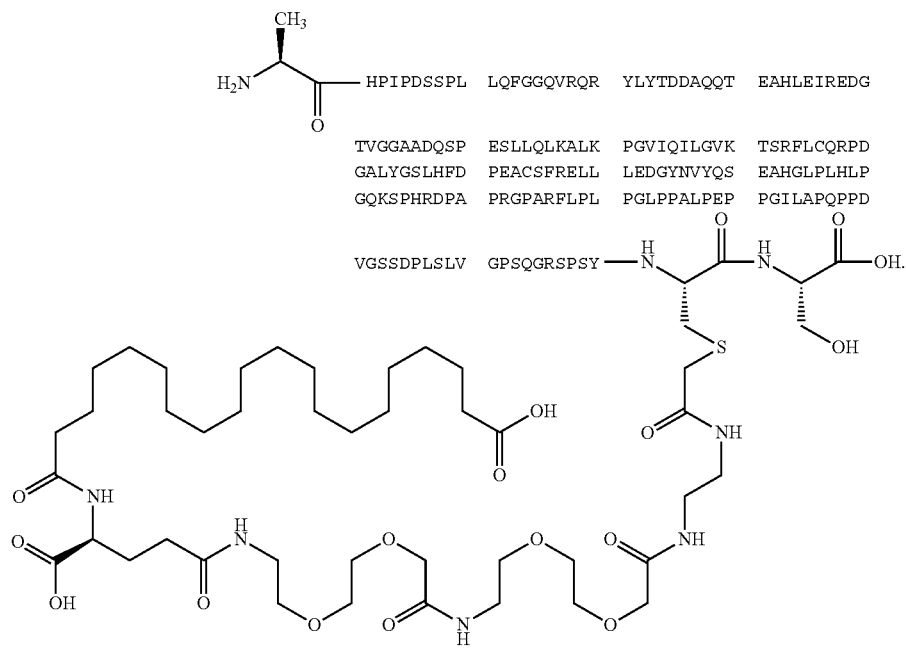

18. The derivative according to claim 12, wherein the derivative is S{Beta-181}-[2-[2-[[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 20)

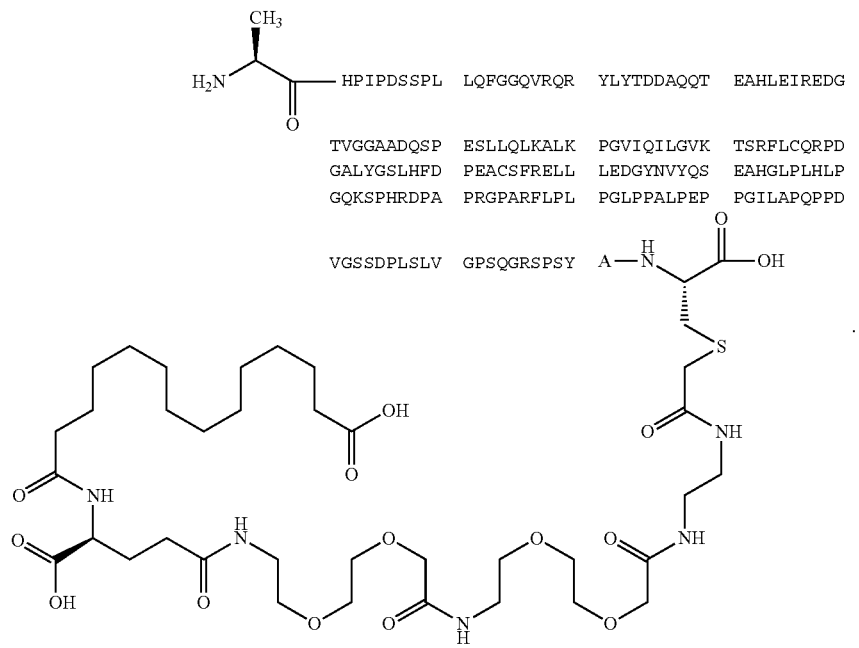

19. The derivative according to claim 12, wherein the derivative is S{Beta-181}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 21)

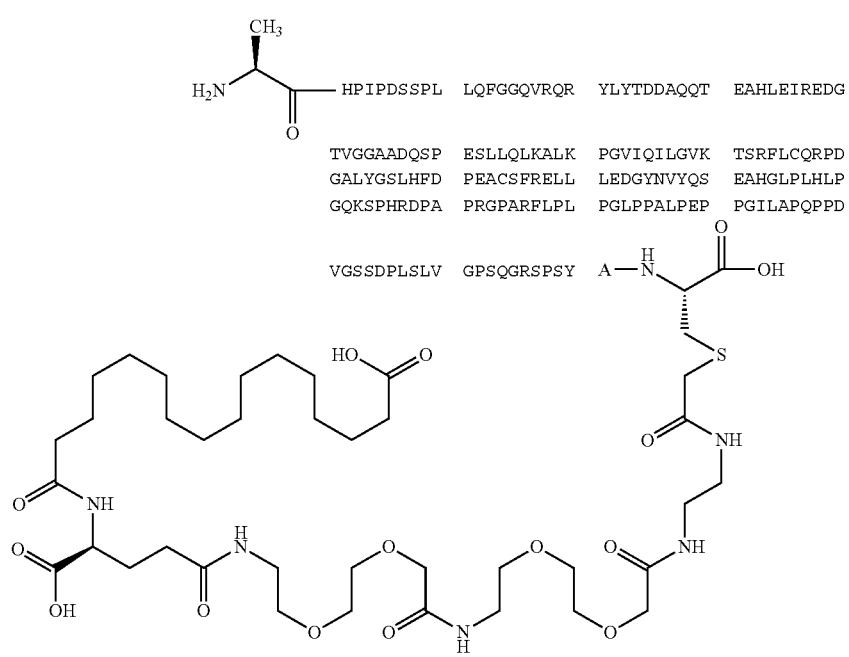

20. The derivative according to claim 12, wherein the derivative is S{Beta-181}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys181]FGF21 (Compound 22)
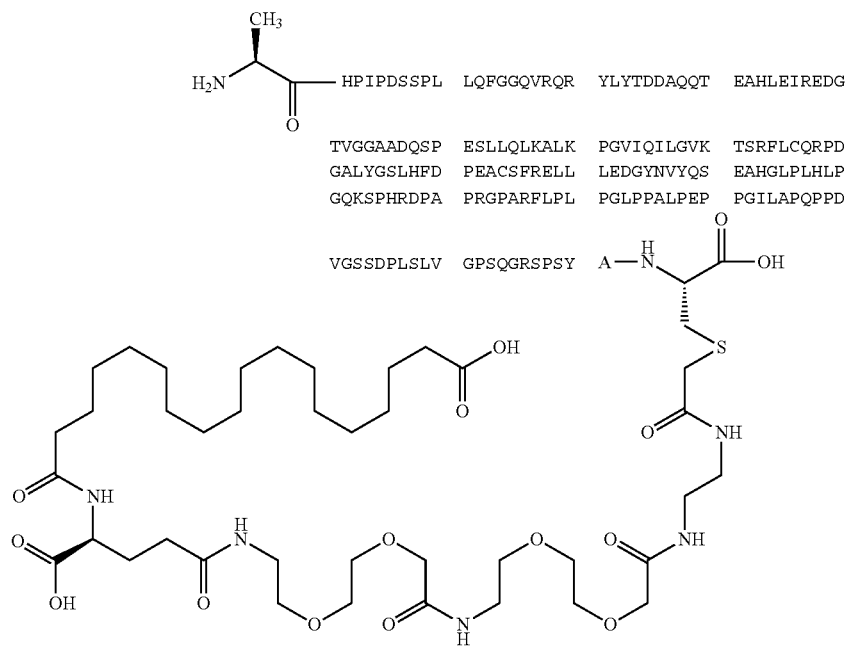
* * * * *

UNITED STATES PATENT AND TRADEMARK OFFICE
CERTIFICATE OF CORRECTION

PATENT NO. : 9,744,213 B2  
APPLICATION NO. : 15/453617  
DATED : August 29, 2017  
INVENTOR(S) : Birgit Wieczorek et al.

Page 1 of 1

It is certified that error appears in the above-identified patent and that said Letters Patent is hereby corrected as shown below:

In the Claims

At Column 179, Claim 13, please make the following change:
"The derivative according to claim 12, wherein the derivative is S{Beta-180}-[2-[2-[[2-[2-[2-[[2-[2-[2-[[(4S)-4-carboxy-4-(11-carboxyundecanoyl-amino)butanoyl]amino]ethoxy]ethoxy]acetyl]amino]ethoxy]ethoxy]acetyl]amino]-ethylamino]-2-oxoethyl]-Ala[Gln121,Leu168,Cys180]FGF21 (Compound 13) ..."

Signed and Sealed this  
Eighth Day of January, 2019

Andrei Iancu  
*Director of the United States Patent and Trademark Office*